(12) United States Patent
Slamon et al.

(10) Patent No.: US 12,403,202 B2
(45) Date of Patent: Sep. 2, 2025

(54) DOSAGE OF CLAUDIN-6 CONJUGATES FOR CANCER TREATMENT

(71) Applicant: The Regents of the University of California, Oakland, CA (US)

(72) Inventors: Dennis Slamon, Los Angeles, CA (US); Neil A. O'Brien, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 18/674,612

(22) Filed: May 24, 2024

(65) Prior Publication Data
US 2024/0390511 A1    Nov. 28, 2024

Related U.S. Application Data

(60) Provisional application No. 63/468,817, filed on May 25, 2023.

(51) Int. Cl.
A61K 47/68    (2017.01)
A61P 35/00    (2006.01)

(52) U.S. Cl.
CPC .......... *A61K 47/6849* (2017.08); *A61P 35/00* (2018.01)

(58) Field of Classification Search
CPC .......... A61K 47/6849; A61K 47/68031; A61K 47/6851; A61P 35/00; C07K 2317/77; C07K 16/28
See application file for complete search history.

(56) References Cited

U.S. PATENT DOCUMENTS

| | | |
|---|---|---|
| 9,718,886 B2 | 8/2017 | Sahin et al. |
| 12,065,489 B2 | 8/2024 | Conklin et al. |
| 2010/0111852 A1 | 5/2010 | Yoshida |
| 2016/0272711 A1 | 9/2016 | Sahin et al. |
| 2017/0015720 A1 | 1/2017 | Sahin et al. |
| 2020/0291111 A1 | 9/2020 | Conklin et al. |
| 2022/0162299 A1 | 5/2022 | Conklin et al. |
| 2022/0177583 A1 | 6/2022 | Conklin et al. |
| 2023/0049752 A1 | 2/2023 | Conklin et al. |

FOREIGN PATENT DOCUMENTS

| | | | |
|---|---|---|---|
| CA | 2775373 | A1 | 5/2011 |
| CA | 2786940 | A1 | 9/2011 |
| CA | 2928671 | A1 | 5/2015 |
| EP | 3747465 | A1 | 12/2020 |
| WO | WO-2009/087978 | A1 | 7/2009 |
| WO | WO-2012/003956 | A1 | 1/2012 |
| WO | WO-2012/156018 | A1 | 11/2012 |
| WO | WO-2014/075697 | A1 | 5/2014 |
| WO | WO-2014/075788 | A1 | 5/2014 |
| WO | WO-2015/014870 | A1 | 2/2015 |
| WO | WO-2015/069794 | A9 | 5/2015 |
| WO | WO-2017/096163 | A1 | 6/2017 |
| WO | WO-2019/056023 | A2 | 3/2019 |
| WO | WO 2020/191342 | * | 9/2020 ............. C07K 16/30 |
| WO | WO-2020/191342 | A1 | 9/2020 |
| WO | WO-2020/191344 | A1 | 9/2020 |
| WO | WO-2024/243561 | A1 | 11/2024 |

OTHER PUBLICATIONS

Sun et al. (Bioconjugate Chem., 16: 1282-1290, 2005).*
Li et al. (MABS, 12(1): 1-12, 2019).*
Konecky et al. (Annals of Oncology, vol. 34, Issue S2, Abstract, 2023).*
Konecky et al. (American Society of Clinical Oncology, Poster Session 3082, 2023).*
International Preliminary Report on Patentability for PCT/US2024/031113.*
First in Human Study of TORL-1-23 in Participants with Advanced Cancer (ClinicalTrials.gov ID NCT05103683).*
Almagro et al., "Humanization of antibodies", Frontiers in Bioscience 2008; 13: 1619-33.
Arabzadeh et al., "Role of the Cldn6 Cytoplasmic Tail Domain in Membrane Targeting and Epidermal Differentiation In Vivo," Molecular and Cellular Biology, 26(15); 5876-5887 (2006).
Extended European Search Report for EP Application No. 18857242.4 dated Jun. 28, 2022.

(Continued)

*Primary Examiner* — Nelson B Moseley, II
(74) *Attorney, Agent, or Firm* — Foley Hoag LLP; Janine S. Ladislaw

(57) ABSTRACT

Described herein are methods for inhibiting a solid tumor expressing claudin-6 in a human subject, comprising administering to the human subject an effective amount of a composition comprising conjugates of a CLDN6-specific antigen-binding protein covalently bound to heterologous moieties comprising structural formula (I):

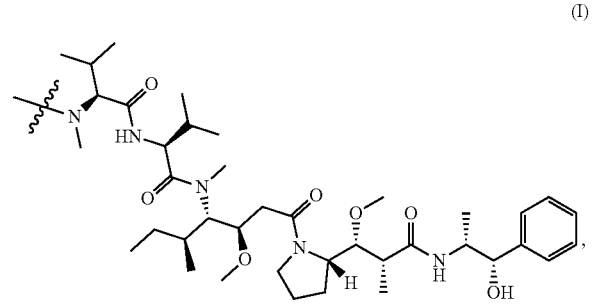

wherein
a first plurality of the conjugates are bound to four heterologous moieties comprising structural formula (I);
at least about 95% of the first plurality of conjugates are structurally homogenous; and
the effective amount is in a range of about
1.0 mg of conjugate/kg weight of the subject to 10 mg of conjugate/kg weight of the subject.

27 Claims, 10 Drawing Sheets

Specification includes a Sequence Listing.

(56) References Cited

OTHER PUBLICATIONS

Extended European Search Report for EP Application No. 20772537.5 dated Oct. 27, 2022.
Extended European Search Report for EP Application No. 20772686.0 dated Oct. 27, 2022.
International Preliminary Report on Patentability for International Application No. PCT/US2020/023981 dated Sep. 16, 2021.
International Preliminary Report on Patentability for International Application No. PCT/US2020/023986 notification mailed Sep. 30, 2021.
International Search Report and Written Opinion for International Application No. PCT/US2018/051610 mailed Apr. 15, 2019.
International Search Report and Written Opinion for International Application No. PCT/US2020/023981 dated Jun. 15, 2020.
International Search Report and Written Opinion for International Application No. PCT/US2020/023986 dated Jun. 15, 2020.
Li et al., "Clinical pharmacology of vc-MMAE antibody-drug conjugates in cancer patients: learning from eight first-in-human Phase 1 studies", MAbs. 12(1). Taylor & Francis, (2020).
McDermott., "Development and characterization of an anti-Claudin-6 (CLDN6) Antibody-Drug Conjugate for the treatment of CLDN6 positive cancer", UCLA, 30 slides, (2022).
Notice of Allowance for U.S. Appl. No. 17/846,900 dated Apr. 10, 2024.
Rudikoff et al., Single amino acid substitution altering antigen-binding specificity, PNAS, USA, 1982, 79: 1979-1983.
Screnci et al., "Antibody specificity against highly conserved membrane protein Claudin 6 driven by single atomic contact point", Iscience 25.12 (2022).
Sukuzi et al., "Therapeutic antitumor efficacy of monoclonal antibody against Claudin-4 for pancreatic and ovarian cancers", Cancer Science 100(9): 1623-1630 (2009).
Winkler et al., "Molecular Determinants of the Interaction between Clostridium perfringens Enterotoxin Fragments and Claudi n-3", Journal of Biological Chemistry 284(28): 18863-18872 (2009).
International Search Report and Written Opinion for International Application No. PCT/US24/31113 dated Sep. 12, 2024.
U.S. Appl. No. 16/648,428, Abandoned.
U.S. Appl. No. 17/719,609, Abandoned.
U.S. Appl. No. 18/545,890, Published.
U.S. Appl. No. 17/441,157, Abandoned.
U.S. Appl. No. 17/846,900, Granted.
U.S. Appl. No. 18/792,232, Pending.
U.S. Appl. No. 17/441,183, Published.

\* cited by examiner

DOSAGE OF CLAUDIN-6 CONJUGATES FOR CANCER TREATMENT

CROSS-REFERENCE TO RELATED APPLICATIONS

This application claims the benefit of U.S. Provisional Application No. 63/468,817, filed on May 25, 2023, the entire contents of which are incorporated herein in their entirety by this reference.

REFERENCE TO ELECTRONIC SEQUENCE LISTING

The application contains a Sequence Listing which has been submitted electronically in XML format and is hereby incorporated by reference in its entirety. Said XML copy, created on May 23, 2024, is named "UCL-00525.xml" and is 839,728 bytes in size. The sequence listing contained in this XML file is part of the specification and is hereby incorporated by reference herein in its entirety.

BACKGROUND

Claudin-6

Claudin-6 (CLDN6) is a member of the claudin family that consists of 27 four-transmembrane domain proteins located at the tight junctions between epithelial cells where they play a critical role in barrier function. CLDN6 expression in non-cancerous tissues is limited to tissues involved in the early stages of development, while it has been reported to be aberrantly expressed in various cancer types including ovarian, gastric, embryonic, pediatric, and endometrial cancer.

CLDN6 is expressed in a significant portion of ovarian, endometrioid, and testicular cancers as well as in a subset of non-small cell lung carcinomas using The Cancer Genome Atlas (TCGA) dataset. Analysis of cancer cell lines revealed CLDN6-positive cell lines within the ovarian, lung, endometrial, and bladder cancer. No notable expression of CLDN6 was detected in normal tissue.

Ovarian Cancer

Ovarian cancer accounts for more deaths than any other cancer of the female reproductive system. The overall 5-year relative survival rate is 49.1%.

Generally, ovarian cancers also include fallopian tube and peritoneal cancers as they are closely related and treated the same way. The most common type of ovarian cancer is epithelial carcinoma, which accounts for 85% to 90% of ovarian cancers. Rarer forms of ovarian cancer include germ cell malignancies and sex cord stromal tumors.

The majority of women are diagnosed with advanced stages of ovarian cancer, and approximately 80% of these patients will have tumor progression or recurrent disease after initial treatment. Ovarian cancer that recurs within 6 months of platinum-based chemotherapy is categorized as platinum-resistant, while ovarian cancer that recurs more than 6 months after platinum-based chemotherapy is platinum-sensitive. Patients with platinum-resistant ovarian cancer typically undergo additional treatment with single agents, such as pegylated liposomal doxorubicin (PLD), topotecan, gemcitabine, and weekly paclitaxel, but the objective response rates (ORR) for these agents are low (10-15%) and the duration of response (DOR) is short (4 months).

In addition to the single agents, bevacizumab in combination with chemotherapy and poly(adenosine diphosphate [ADP]-ribose polymerase (PARP) inhibitors have been studied in the treatment of advanced ovarian cancer. However, these treatments also present issues. While bevacizumab in combination showed increased progression free survival (PFS) in clinical trials, it is unclear whether this PFS is clinically significant and will lead to improvements in quality of life or overall survival (OS). Bevacizumab has also raised concerns regarding gastrointestinal (GI) toxicity. PARP inhibitors, such as olaparib and niraparib, are administered as maintenance therapy in patients with BRCA mutations, which represents a low percentage of patients (about 17% of patients in high serous subset of ovarian cancer).

Ovarian cancer patients eventually progress on all available treatments and thus, additional therapies to prolong survival are needed. Platinum-resistant advanced ovarian cancer remains an area of unmet need.

Non-Small Cell Lung Cancer

Lung cancer is the second most common cancer and by far the leading cause of cancer deaths, accounting for almost 25% of cancer deaths. The 5-year relative survival rate is 21.7%. Cigarette smoking is the most important risk factor, accounting for 85% to 90% of lung cancers. However, the risk of developing lung cancer is associated with the extent of smoking and exposure to other carcinogenic factors, such as asbestos.

Lung cancer is made up of two different types: non-small cell lung cancer (NSCLC) and small cell lung cancer. NSCLC makes up the majority of cases in about 85% of patients. The different classifications of NSCLC include adenocarcinoma (approximately 40% of lung cancers), squamous cell carcinoma (25% to 30% of lung cancers), large cell carcinoma (5% to 10% of lung cancers), and NSCLC—not otherwise specified (NOS).

Systemic therapy for advanced NSCLC is selected according to the presence of specific biomarkers. Molecular alterations that predict response to treatment (e.g., epidermal growth factor receptor [EGFR] mutations, anaplastic lymphoma kinase [ALK] rearrangements, ROS1 rearrangements, and BRAF V600E mutations) are present in approximately 30% of patients with NSCLC. Targeted therapy for these alterations improves progression-free survival compared with cytotoxic chemotherapy. Recently inhibitors of KRAS G12C have demonstrated antitumor activity and sotorasib has been approved. For patients without biomarkers indicating susceptibility to specific targeted treatments, immune checkpoint inhibitor-containing regimens either as monotherapy or in combination with chemotherapy are superior to chemotherapy alone.

Despite numerous advances in NSCLC over the past decade with targeted therapies and immunotherapies, resistance is common and the development of new therapeutics is needed.

There exists a need for CLDN6-targeted therapeutics for treating cancer, such as ovarian cancer and NSCLC, in humans.

SUMMARY

In certain embodiments, the disclosure relates to a method for inhibiting a solid tumor expressing claudin-6 in a human subject, comprising administering to the human subject an effective amount of a composition comprising conjugates of a CLDN6-specific antigen-binding protein covalently bound to heterologous moieties comprising structural formula (I):

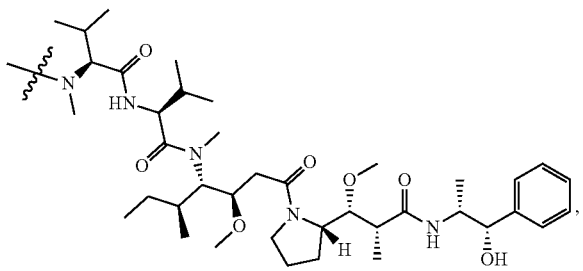

wherein
- a first plurality of the conjugates are bound to about four heterologous moieties comprising structural formula (I);
- at least about 95% of the first plurality of conjugates are structurally homogenous; and
- the effective amount is in a range of about
  - 1.7 mg/kg to 6 mg/kg;
  - 2.0 mg/kg to 6 mg/kg; or
  - 2.4 mg/kg to 6 mg/kg.

In certain embodiments, the disclosure relates to any of the methods disclosed herein, wherein the CLDN6-specific antigen-binding protein comprises an antibody that binds CLDN6 or antigen-binding fragment thereof comprising:
(i) HC CDR1 having a sequence GFTFSNYW (SEQ ID NO: 23);
(ii) HC CDR2 having a sequence IRLKSDNYAT (SEQ ID NO: 24),
(iii) HC CDR3 having a sequence XDGPPSGX (SEQ ID NO: 457), wherein X at position 1 is N and X at position 8 is S, T, A, C, or Y,
(iv) LC CDR1 having a sequence ENIYSY (SEQ ID NO: 20),
(v) LC CDR2 having a sequence NAK (SEQ ID NO: 21), and
(vi) LC CDR3 having a sequence QHHYTVPWT (SEQ ID NO: 22).

DETAILED DESCRIPTION

Overview

Figure 1A:
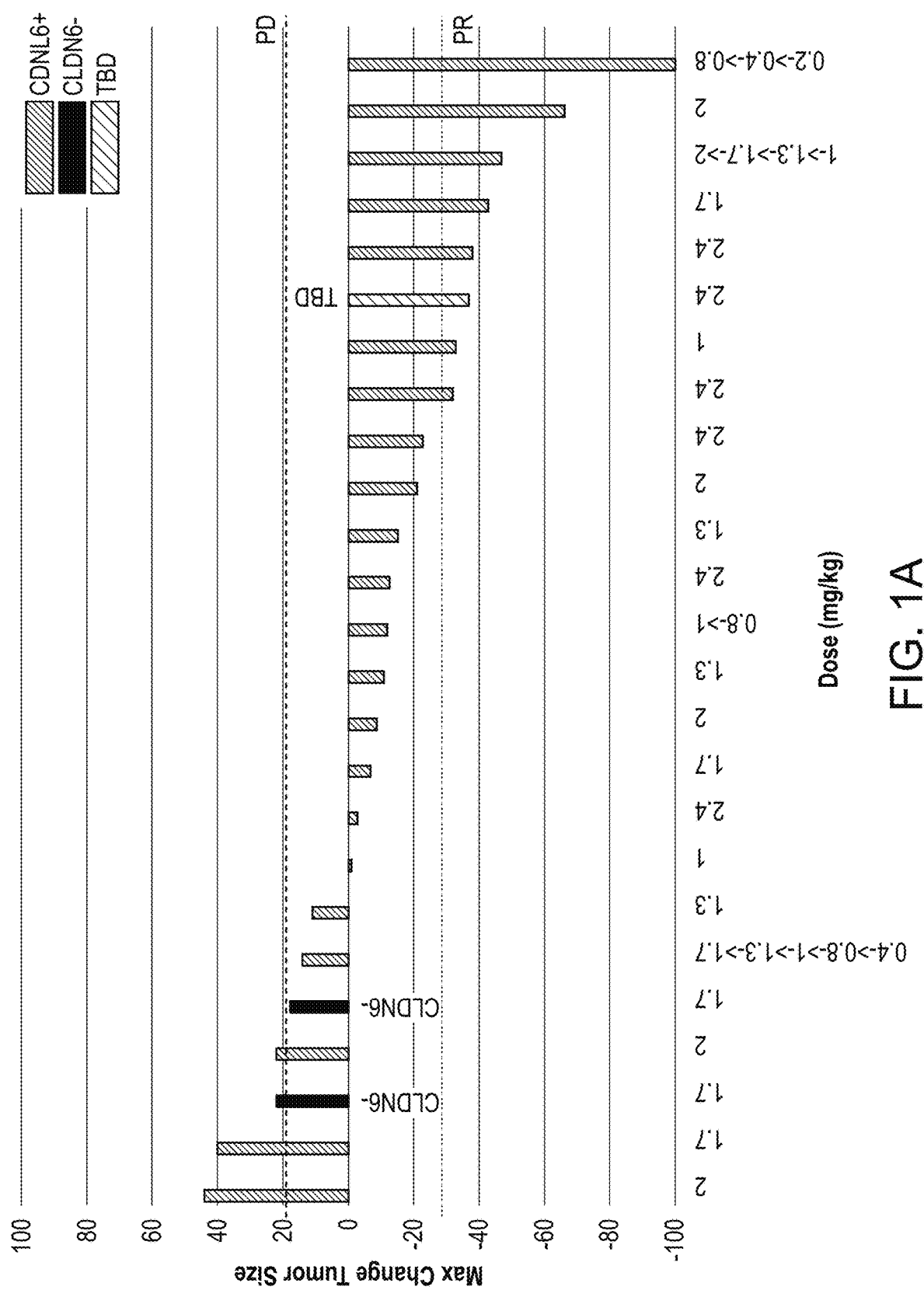
FIG. 1A is a bar graph showing tumor response (max change in tumor size by RECIST 1.1) at dose levels 0.2 to 2.4 mg/kg of TORL-1-23 in humans

Described herein are methods for inhibiting a solid tumor expressing claudin-6 in a human subject, comprising administering to the human subject an effective amount of a composition comprising conjugates of a CLDN6-specific antigen-binding protein covalently bound to heterologous moieties comprising structural formula (I):

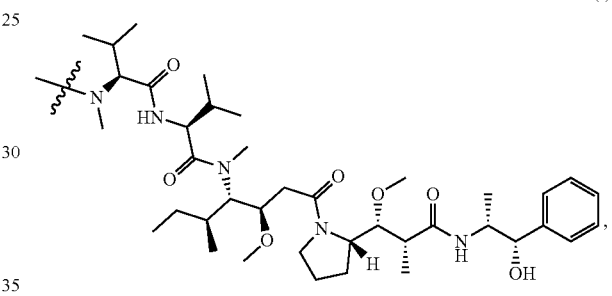

wherein
- a first plurality of the conjugates are bound to about four heterologous moieties comprising structural formula (I);
- at least 95% of the first plurality of conjugates are structurally homogenous; and
- the effective amount is in the range of about 1.0 mg conjugate/kg weight of the subject to about 10 mg conjugate/kg weight of the subject.

As used herein, the term "about" when used before a numerical designation, e.g., temperature, time, amount, concentration, and such other, including a range, indicates approximations which may vary by plus or minus (+/−) 5%, 4%, 3%, 2% or 1%.

In certain embodiments, the solid tumor is ovarian cancer, primary peritoneal cancer, fallopian tube cancer, non-small cell lung cancer, or testicular cancer.

In certain embodiments, after administration, the human subject does not experience peripheral neuropathy of grade 3 or higher severity, does not experience alopecia of grade 3 or higher severity, does not experience fatigue of grade 3 or higher severity, does not experience nausea, vomiting or anorexia of grade 3 or higher severity, or does not experience constipation of grade 3 or higher severity, or the human subject does not experience any combination of two or more of these adverse events. In certain embodiments, after administration, the human subject does not experience peripheral neuropathy of grade 3 or higher severity. In certain embodiments, after administration, the human subject does not experience alopecia of grade 3 or higher severity. In certain embodiments, after administration, the human subject does not experience fatigue of grade 3 or higher severity. In certain embodiments, after administration, the human subject does not experience nausea, vomiting or anorexia of grade 3 or higher severity. In certain embodiments, after administration, the human subject does not experience constipation of grade 3 or higher severity. For purposes of this disclosure, widely accepted criteria for documentation and classification of adverse events will be utilized (i.e., National Cancer Institute (NCI) Common Terminology Criteria for Adverse Events (CTCAE) Version 5.0). For example, a "grade 3" adverse event may be a severe or medically significant adverse event that is not immediately life-threatening, but which requires hospitalization. Grade 3 adverse events may limit a patient's ability to bathe, dress or undress, feed himself or herself, use the toilet, or take medication.

In certain embodiments, after administration, treatment-related grade 3 or higher severity peripheral neuropathy occurs in less than 30% of patients treated, treatment-related grade 3 or higher severity alopecia occurs in less than 30% of patients treated, or treatment-related grade 3 or higher severity nausea, vomiting or anorexia occurs in less than 30% of patients treated, or any combination of two or more of these treatment-related adverse events occurs in less than 30% of patients treated. Preferably, after administration, treatment-related grade 3 or higher severity peripheral neuropathy occurs in less than 20% of patients treated, treatment-related grade 3 or higher severity alopecia occurs in less than 20% of patients treated, or treatment-related grade 3 or higher severity nausea, vomiting or anorexia occurs in less than 20% of patients treated, or any combination of two or more of these treatment-related adverse events occurs in less than 20% of patients treated. More preferably, after administration, treatment-related grade 3 or higher severity peripheral neuropathy occurs in less than 10% of patients treated, treatment-related grade 3 or higher severity alopecia occurs in less than 10% of patients treated, or treatment-related grade 3 or higher severity nausea, vomiting or anorexia occurs in less than 10% of patients treated, or any combination of two or more of these treatment-related adverse events occurs in less than 10% of patients treated. In certain embodiments, after administration, no human subject experiences an adverse event of grade 3 or higher severity.

In certain embodiments, after administration, the human subject does not experience any adverse event of grade 3 or higher severity.

In certain embodiments, after administration, the human subject does not experience peripheral neuropathy of grade 2 or higher severity, does not experience alopecia of grade 2 or higher severity, does not experience fatigue of grade 2 or higher severity, does not experience nausea, vomiting or anorexia of grade 2 or higher severity, or does not experience constipation of grade 2 or higher severity, or the human subject does not experience any combination of two or more of these adverse events. In certain embodiments, after administration, the human subject does not experience peripheral neuropathy of grade 2 or higher severity. In certain embodiments, after administration, the human subject does not experience alopecia of grade 2 or higher severity. In certain embodiments, after administration, the human subject does not experience fatigue of grade 2 or higher severity. In certain embodiments, after administration, the human subject does not experience nausea, vomiting or anorexia of grade 2 or higher severity. In certain embodiments, after administration, the human subject does not experience constipation of grade 2 or higher severity. For purposes of this disclosure, widely accepted criteria for documentation and classification of adverse events will be utilized (i.e., National Cancer Institute (NCI) Common Terminology Criteria for Adverse Events (CTCAE) Version 5.0). For example, a "grade 2" adverse event is an adverse event of moderate severity, which limits age-appropriate instrumental activities of daily life, such as preparing meals, shopping for groceries or clothes, using the telephone, or managing money. Minimal, local or noninvasive intervention may be indicated for a subject experiencing a grade 2 adverse event.

In certain embodiments, after administration, treatment-related grade 2 or higher severity peripheral neuropathy occurs in less than 40% of patients treated, treatment-related grade 2 or higher severity alopecia occurs in less than 40% of patients treated, or treatment-related grade 2 or higher severity nausea, vomiting or anorexia occurs in less than 40% of patients treated, or any combination of two or more of these treatment-related adverse events occurs in less than 40% of patients treated. In some embodiments, after administration, treatment-related grade 2 or higher severity peripheral neuropathy occurs in less than 30% of patients treated, treatment-related grade 2 or higher severity alopecia occurs in less than 30% of patients treated, or treatment-related grade 2 or higher severity nausea, vomiting or anorexia occurs in less than 30% of patients treated, or any combination of two or more of these treatment-related adverse events occurs in less than 30% of patients treated. Preferably, after administration, treatment-related grade 2 or higher severity peripheral neuropathy occurs in less than 20% of patients treated, treatment-related grade 2 or higher severity alopecia occurs in less than 20% of patients treated, or treatment-related grade 2 or higher severity nausea, vomiting or anorexia occurs in less than 20% of patients treated, or any combination of two or more of these treatment-related adverse events occurs in less than 20% of patients treated. More preferably, after administration, treatment-related grade 2 or higher severity peripheral neuropathy occurs in less than 10% of patients treated, treatment-related grade 2 or higher severity alopecia occurs in less than 10% of patients treated, or treatment-related grade 2 or higher severity nausea, vomiting or anorexia occurs in less than 10% of patients treated, or any combination of two or more of these treatment-related adverse events occurs in less than 10% of patients treated.

In other embodiments, after administration, the human subject does not experience any adverse event of grade 2 or higher severity.

Use

The conjugates of the present disclosure are useful for inhibiting tumor growth. Without being bound to a particular theory, the inhibiting action of the conjugates provided herein allow such entities to be useful in methods of treating cancer.

In some embodiments, the method provides that prior to administration of CLDN6 conjugates of the present disclosure to the human subject, a hematopoietic protein such as a colony stimulating factor (CSF) such as granulocyte-colony stimulating factor (G-CSF) or granulocyte macrophage-CSF (GM-CSF) is administered to the subject. In some embodiments, G-CSF pre-treatment is preferred.

Accordingly, provided herein are methods of inhibiting tumor growth in a subject and methods of reducing tumor size in a subject. In various embodiments, the methods comprise administering to the subject the pharmaceutical composition of the present disclosure in an amount effective for inhibiting tumor growth or reducing tumor size in the subject. In various aspects, the growth of an ovarian tumor, melanoma tumor, bladder tumor, or endometrial tumor is inhibited. In various aspects, the size of an ovarian tumor, melanoma tumor, bladder tumor, or endometrial tumor is reduced.

As used herein, the term "inhibit" or "reduce" and words stemming therefrom may not be a 100% or complete inhibition or reduction. Rather, there are varying degrees of inhibition or reduction of which one of ordinary skill in the art recognizes as having a potential benefit or therapeutic effect. In this respect, the antigen-binding proteins of the present disclosure may inhibit tumor growth or reduce tumor size to any amount or level. In various embodiments, the inhibition provided by the methods of the present disclosure is at least or about a 10% inhibition (e.g., at least or about a 20% inhibition, at least or about a 30% inhibition, at least or about a 40% inhibition, at least or about a 50% inhibition, at least or about a 60% inhibition, at least or about a 70% inhibition, at least or about a 80% inhibition, at least or about a 90% inhibition, at least or about a 95% inhibition, at least or about a 98% inhibition). In various embodiments, the reduction provided by the methods of the present disclosure is at least or about a 10% reduction (e.g., at least or about a 20% reduction, at least or about a 30% reduction, at least or about a 40% reduction, at least or about a 50% reduction, at least or about a 60% reduction, at least or about a 70% reduction, at least or about a 80% reduction, at least or about a 90% reduction, at least or about a 95% reduction, at least or about a 98% reduction).

Additionally provided herein are methods of treating a subject with cancer, e.g., CLDN6-expressing cancer. In various embodiments, the method comprises administering to the subject the pharmaceutical composition of the present disclosure in an amount effective for treating the cancer in the subject.

In particular aspects, the cancer is selected from the group consisting of: head and neck, ovarian, cervical, bladder and oesophageal cancers, pancreatic, gastrointestinal cancer, gastric, breast, endometrial and colorectal cancers, hepatocellular carcinoma, glioblastoma, bladder, lung cancer, e.g., non-small cell lung cancer (NSCLC), bronchioloalveolar carcinoma. In various aspects, the cancer is ovarian cancer, melanoma, bladder cancer, lung cancer, liver cancer, endometrial cancer. In various aspects, the cancer is any cancer characterized by moderate to high expression of CLDN6.

As used herein, the term "treat," as well as words related thereto, do not necessarily imply 100% or complete treatment. Rather, there are varying degrees of treatment of which one of ordinary skill in the art recognizes as having a potential benefit or therapeutic effect. In this respect, the methods of treating cancer of the present disclosure can provide any amount or any level of treatment. Furthermore, the treatment provided by the method of the present disclosure can include treatment of one or more conditions or symptoms or signs of the cancer being treated. Also, the treatment provided by the methods of the present disclosure can encompass slowing the progression of the cancer. For example, the methods can treat cancer by virtue of enhancing the T cell activity or an immune response against the cancer, reducing tumor or cancer growth, reducing metastasis of tumor cells, increasing cell death of tumor or cancer cells, and the like. In various aspects, the methods treat by way of delaying the onset or recurrence of the cancer by at least 1 day, 2 days, 4 days, 6 days, 8 days, 10 days, 15 days, 30 days, two months, 3 months, 4 months, 6 months, 1 year, 2 years, 3 years, 4 years, or more. In various aspects, the methods treat by way increasing the survival of the subject.

Dosages

The active agents of the disclosure are believed to be useful in methods of inhibiting tumor growth, as well as other methods, as further described herein, including methods of treating cancer. For purposes of the disclosure, the amount or dose of the active agent administered should be sufficient to effect, e.g., a therapeutic response, in the human subject over a reasonable time frame.

For example, the dose of the active agent of the present disclosure can be about 1.0 to about 10 mg/kg body weight of the subject being treated, from about 1.0 to about 6.0 mg/kg, from about 1.0 to about 5.0 mg/kg, from about 1.0 to about 4.0 mg/kg, or from about 1.0 to about 3.0 mg/kg.

Additionally, in another example, the dose can be about 1.7 to about 6.0 mg/kg body weight of the subject, from about 1.7 to about 5.0 mg/kg, from about 1.7 to about 4.0 mg/kg, from about 1.7 to about 3.0 mg/kg, or from about 1.7 to about 2.0 mg/kg.

In certain examples, the dose can be about 1.7 to about 5.0 mg/kg body weight of the subject, from about 1.7 to about 4.0 mg/kg, or from about 1.7 to about 3.0 mg/kg.

In yet another example, the dose can be about 2.0 to about 10.0 mg/kg body weight of the subject, from about 2.0 to about 6.0 mg/kg, from about 2.0 to about 5.0 mg/kg, from about 2.0 to about 4.0 mg/kg, or from about 2.0 to about 3.0 mg/kg.

In some examples, example, the dose can be about 2.0 to about 6.0 mg/kg body weight of the subject, from about 2.0 to about 5.0 mg/kg, from about 2.0 to about 4.0 mg/kg, or from about 2.0 to about 3.0 mg/kg.

In certain examples, example, the dose can be about 2.0 to about 5.0 mg/kg body weight of the subject, from about 2.0 to about 4.0 mg/kg, or from about 2.0 to about 3.0 mg/kg.

In further examples, the dose can be about 2.4 to about 10.0 mg/kg body weight of the subject, from about 2.4 to about 6.0 mg/kg, from about 2.4 to about 5.0 mg/kg, from about 2.4 to about 4.0 mg/kg, or from about 2.4 to about 3.0 mg/kg.

In some examples, the dose can be about 2.4 to about 6.0 mg/kg body weight of the subject, from about 2.4 to about 5.0 mg/kg, from about 2.4 to about 4.0 mg/kg, or from about 2.4 to about 3.0 mg/kg.

In certain examples, the dose can be about 2.4 to about 5.0 mg/kg body weight of the subject, from about 2.4 to about 4.0 mg/kg, or from about 2.4 to about 3.0 mg/kg.

In further examples, the dose can be about 3.0 to about 5.0 mg/kg body weight of the subject, from about 3.0 to about 4.0 mg/kg, or from about 3.0 to about 3.6 mg/kg.

Conjugates and Conjugation

The present disclosure relates to antigen-binding proteins attached, linked or conjugated to a second moiety (e.g., a heterologous moiety) comprising structural formula (I):

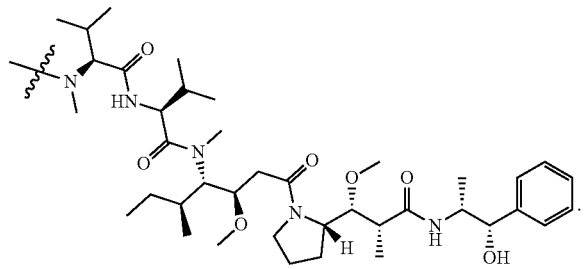

Accordingly, the present disclosure provides a conjugate comprising an antigen-binding protein and a heterologous moiety and compositions thereof.

The heterologous moiety comprising structural formula (I) derives from monomethyl auristatin E (MMAE), which has the following structural formula:

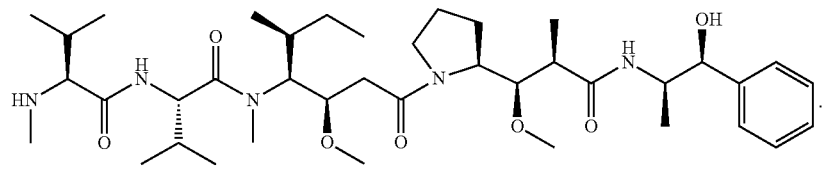 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@@H](NC)C(C)C)C(C)C]

IUPAC name: (S)—N-((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-N,3-dimethyl-2-((S)-3-methyl-2-(methylamino)butanamido)butanamide MMAE, or desmethyl-auristatin E, is a synthetic antineoplastic agent. It is a potent antimitotic drug that inhibits cell division by blocking the polymerization of tubulin.

In certain embodiments, the heterologous moiety (e.g., MMAE) is conjugated to an antigen-binding protein via a linker. In some such embodiments, the linker comprises a peptide having Valine-Citrulline (Val-Cit). In some embodiments, the linker comprises Valine-citrulline coupled with a self-immolative ρ-aminobenzyl (PAB) group, collectively referred to as Val-Cit-PAB. Accordingly, in some embodiments, a conjugate of the present disclosure comprises an antigen-binding protein, Val-Cit-PAB, and MMAE. In preferred embodiments, an antigen-binding protein is conjugated to at least one MMAE, wherein each MMAE is conjugated to the antigen-binding protein via Val-Cit-PAB.

In certain embodiments, the heterologous moiety has structural formula (II):

the HAR ranges from about 1 to about 15, about 1 to about 10, about 1 to about 9, about 1 to about 8, about 1 to about 7, about 1 to about 6, about 1 to about 5, about 1 to about 4, about 1 to about 3, or about 1 to about 2. In some embodiments, the HAR ranges from about 2 to about 10, about 2 to about 9, about 2 to about 8, about 2 to about 7, about 2 to about 6, about 2 to about 5, about 2 to about 4 or about 2 to about 3. In other embodiments, the HAR is about 2, about 2.5, about 3, about 4, about 5, or about 6. In some embodiments, the HAR ranges from about 2 to about 4. The HAR may be characterized by conventional means such as mass spectrometry, UV/Vis spectroscopy, ELISA assay, and/or HPLC. In some embodiments, the HAR is about 3.0, about 3.1, about 3.2, about 3.3, about 3.4, about 3.5, about 3.6, about 3.7, about 3.8, about 3.9, about 4, about 4.1, about 4.2, about 4.3, about 4.4, about 4.5, about 4.6, about 4.7, about 4.8, about 4.9, or about 5.0.

In some embodiments, the invention provides a composition comprising structurally "homogeneous" conjugates, wherein the substantial percentage of the antigen-binding proteins are conjugated to a defined number of heterologous moieties at the same specific sites of the antigen-binding protein. In some embodiments, the structurally homogeneous conjugates comprise the HAR of about 1, about 2, about 3, about 4, about 5, about 6, about 7, about 8, about 9, or about 10. In some embodiments, the structurally homogeneous conjugates comprise the HAR of about 2, about 4, about 6, or about 8. In preferred embodiments, the (II)

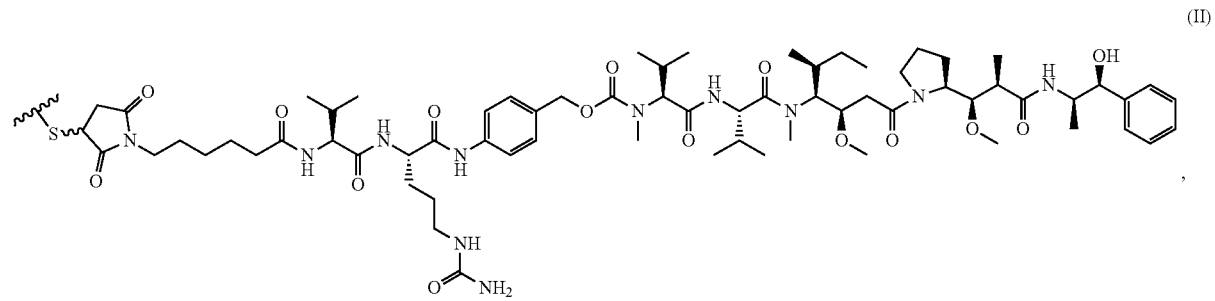 [SMILES: *SC1CC(=O)N(CCCCCC(=O)N[C@H](C(=O)N[C@@H](CCCNC(N)=O)C(=O)Nc2ccc(COC(=O)N(C)[C@H](C(=O)N[C@H](C(=O)N(C)[C@@H]([C@@H](C)CC)[C@@H](CC(=O)N3CCC[C@H]3[C@H](OC)[C@@H](C)C(=O)N[C@H](C)[C@@H](O)c3ccccc3)OC)C(C)C)C(C)C)cc2)C(C)C)C1=O]

wherein

is a covalent thiol bond to the antigen-binding protein. The heterologous moiety having structural formula (II) is called vedotin using International Nonproprietary Names (INN) nomenclature.

The heterologous moiety-to-antigen-binding protein ratio (HAR) represents the number of a heterologous moiety linked per antigen-binding molecule. In some embodiments, structurally homogeneous conjugates comprise the HAR of about 4. In other preferred embodiments, the structurally homogeneous conjugates comprise the HAR of about 2. In some embodiments, the structurally homogeneous conjugates comprise the HAR of about 3.0, about 3.1, about 3.2, about 3.3, about 3.4, about 3.5, about 3.6, about 3.7, about 3.8, about 3.9, about 4, about 4.1, about 4.2, about 4.3, about 4.4, about 4.5, about 4.6, about 4.7, about 4.8, about 4.9, or about 5.0. In some embodiments, the structurally homogeneous conjugates comprise greater than or equal to about 85, 86, 87, 88, 89, 90, 91, 92, 93, 94, 95, 96, 97, 98, 99, or 100 percent conjugates with the defined HAR. In some embodiments, the structurally homogeneous conjugates comprise about 85, 86, 87, 88, 89, 90, 91, 92, 93, 94, 95, 96, 97, 98, 99, or 100 percent conjugates with the defined HAR. In some embodiments, the structurally homogeneous conjugates comprise at least about 85, 86, 87, 88, 89, 90, 91, 92, 93, 94, 95, 96, 97, 98, 99, or 100 percent conjugates with the defined HAR. In some embodiments, the homogeneity of the structurally homogeneous conjugates is determined by a chromatogram, e.g., HPLC or any suitable chromatography. In some embodiments, the chromatogram is a HIC chromatogram. In some embodiments, homogeneity of the homogeneous conjugates is determined, or further determined, by protease or tryptic digestion followed by liquid chromatography and tandem mass spectroscopy (e.g., nanoLC-MS/MS) analysis (Farràs et al. (2020) MAbs:12(1): 1702262). The structurally homogeneous conjugate may be generated by a site-specific conjugation.

In some embodiments, the heterologous moiety is conjugated to the antigen-binding protein (e.g., antibody) in a site-specific manner. Various site-specific conjugation methods are known in the art, e.g., thiomab or TDC or conjugation at an unpaired cysteine residue or conjugation after reduction of interchain sulfide bonds (WO2020/164561; Junutula et al. (2008) *Nat. Biotechnol.* 26:925-932; Dimasi et al. (2017) *Mol. Pharm.* 14:1501-1516; Shen et al. (2012) *Nat. Biotechnol.* 30:184-9); thiol bridge linker (Behrens et al. (2015) *Mol. Pharm.* 12:3986-98); conjugation at glutamine using a transglutaminase (Dennler et al. (2013) *Methods Mol. Bio.* 1045:205-15; Dennler et al. (2014) *Bioconjug Chem.* 25:569-78); conjugation at engineered unnatural amino acid residues (Axup et al. (2012) *Proc Natl Acad Sci U.S.A.* 104-16101-6; Tian et al. (2014) *Proc Natl Acad Sci U.S.A.* 111:1766-71; VanBrunt et al. (2015) *Bioconjug Chem* 26:2249-60; Zimmerman et al. (2014) *Bioconjug Chem* 25:351-61); selenocysteine conjugation (Li et al. (2017) *Cell Chem Biol* 24:433-442); glycan-mediated conjugation (Okeley et al. (2013) *Bioconjug Chem* 24:1650-5); conjugation at galactose or GalNAc analogues (Ramakrishnan and Qasba (2002) *J Biol Chem* 277:20833-9; van Geel et al. (2015) *Bioconjug Chem* 26:2233-42); via glycan engineering (Zhou et al. (2014) *Bioconjug Chem* 25:510-20; Tang et al. (2017) *Nat Protoc* 12:1702-1721); via a short peptide tag, such as engineering a glutamine tag or sortase A-mediated transpeptidation (Strop et al. (2013) *Chem Biol* 20:161-7; Beerli et al. (2015) *PLoS One* 10:e0131177); and via an aldehyde tag (Wu et al. (2009) *Proc Natl Acad Sci U.S.A.* 106:3000-5).

Antigen-Binding Proteins

Provided herein are methods of using antigen-binding proteins, such as antibodies, that bind to Claudin-6 (CLDN6) in ADCs for use in treating cancer.

As used herein, the term "antibody" refers to a protein having a conventional immunoglobulin format, comprising heavy and light chains, and comprising variable and constant regions. For example, an antibody may be an IgG which is a "Y-shaped" structure of two identical pairs of polypeptide chains, each pair having one "light" (typically having a molecular weight of about 25 kDa) and one "heavy" chain (typically having a molecular weight of about 50-70 kDa). An antibody has a variable region and a constant region. In IgG formats, the variable region is generally about 100-110 or more amino acids, comprises three complementarity determining regions (CDRs), is primarily responsible for antigen recognition, and substantially varies among other antibodies that bind to different antigens. The constant region allows the antibody to recruit cells and molecules of the immune system. The variable region is made of the N-terminal regions of each light chain and heavy chain, while the constant region is made of the C-terminal portions of each of the heavy and light chains. (Janeway et al., "Structure of the Antibody Molecule and the Immunoglobulin Genes", Immunobiology: The Immune System in Health and Disease, 4$^{th}$ ed. Elsevier Science Ltd./Garland Publishing, (1999)).

The general structure and properties of CDRs of antibodies have been described in the art. Briefly, in an antibody scaffold, the CDRs are embedded within a framework in the heavy and light chain variable region where they constitute the regions largely responsible for antigen binding and recognition. A variable region typically comprises at least three heavy or light chain CDRs (Kabat et al., 1991, Sequences of Proteins of Immunological Interest, Public Health Service N.I.H., Bethesda, Md.; see also Chothia and Lesk, 1987, J. Mol. Biol. 196:901-917; Chothia et al., 1989, Nature 342: 877-883), within a framework region (designated framework regions 1-4, FR1, FR2, FR3, and FR4, by Kabat et al., 1991; see also Chothia and Lesk, 1987, supra).

Antibodies can comprise any constant region known in the art. Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4. IgM has subclasses, including, but not limited to, IgM1 and IgM2. Embodiments of the present disclosure include all such classes or isotypes of antibodies. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant regions, e.g., a human alpha-, delta-, epsilon-, gamma-, or mu-type heavy chain constant region. Accordingly, in various embodiments, the antibody is an antibody of isotype IgA, IgD, IgE, IgG, or IgM, including any one of IgG1, IgG2, IgG3 or IgG4. In various aspects, the antibody comprises a constant region comprising one or more amino acid modifications, relative to the naturally-occurring counterpart, in order to improve half-life/stability or to render the antibody more suitable for expression/manufacturability. In various instances, the antibody comprises a constant region wherein the C-terminal Lys residue that is present in the naturally-occurring counterpart is removed or clipped.

The antibody can be a monoclonal antibody. In some embodiments, the antibody comprises a sequence that is substantially similar to a naturally-occurring antibody produced by a mammal, e.g., mouse, rabbit, goat, horse, chicken, hamster, human, and the like. In this regard, the antibody can be considered as a mammalian antibody, e.g., a mouse antibody, rabbit antibody, goat antibody, horse antibody, chicken antibody, hamster antibody, human antibody, and the like. In certain aspects, the antibody is a chimeric antibody or a humanized antibody. The term "chimeric antibody" refers to an antibody containing domains from two or more different antibodies. A chimeric antibody can, for example, contain the constant domains from one species and the variable domains from a second, or more generally, can contain stretches of amino acid sequence from at least two species. A chimeric antibody also can contain domains of two or more different antibodies within the same species. The term "humanized" when used in relation to antibodies refers to antibodies having at least CDR regions from a non-human source which are engineered to have a structure and immunological function more similar to true human antibodies than the original source antibodies. For example, humanizing can involve grafting a CDR from a non-human antibody, such as a mouse antibody, into a human antibody. Humanizing also can involve select amino acid substitutions to make a non-human sequence more similar to a human sequence. Information, including sequence information for human antibody heavy and light chain constant regions is publicly available through the Uniprot database as well as other databases well-known to those in the field of antibody engineering and production. For example, the IgG2 constant region is available from the Uniprot database as Uniprot number P01859, incorporated herein by reference.

An antibody can be cleaved into fragments by enzymes, such as, e.g., papain and pepsin. Papain cleaves an antibody to produce two Fab fragments and a single Fc fragment. Pepsin cleaves an antibody to produce a F(ab')$_2$ fragment and a pFc' fragment.

In various embodiments, an anti-CLDN6 antibody is selected from the group consisting of a human antibody, a humanized antibody, a chimeric antibody, a monoclonal antibody, a recombinant antibody, an IgG1 antibody, an IgG2 antibody, an IgG3 antibody, and an IgG4 antibody.

CLDN6 and Epitopes

In various aspects, the CLDN6 is a human CLDN6 having the amino acid sequence of:

```
                                            (SEQ ID NO: 202)
MASAGMQILGVVLTLLGWVNGLVSCALPMWKVTAFIGNSIVVAQVVWEG

LWMSCVVQSTGQMQCKVYDSLLALPQDLQAARALCVIALLVALFGLLVY

LAGAKCTTCVEEKDSKARLVLTSGIVFVISGVLTLIPVCWTAHAXIRDF

YNPLVAEAQKRELGASLYLGWAASGLLLLGGGLLCCTCPSGGSQGPSHY

MARYSTSAPAISRGPSEYPTKNYV, wherein X is Ile or Val.
```

In various aspects, the human CLDN6 comprises the amino acid sequence of any one of SEQ ID NOs: 1, 178, and 200-202.

In various aspects, the antigen-binding proteins of the present disclosure bind to an epitope within an amino acid sequence of CLDN6. In various aspects, CLDN6 is a human CLDN6 and the antigen-binding proteins of the present disclosure bind to an epitope within an amino acid sequence of human CLDN6, e.g., SEQ ID NOs: 1, 178, and 200-202. By "epitope" is meant the region of or within CLDN6 which is bound by the antigen-binding protein. In some embodiments, the epitope is a linear epitope. "Linear epitope" refers to the region of or within the CLDN6 which is bound by the antigen-binding protein and which region is composed of contiguous amino acids of the amino acid sequence of the CLDN6. The amino acids of a linear epitope are adjacent to each other in the primary structure of the CLDN6. Accordingly, a linear epitope is a fragment or portion of the amino acid sequence of the antigen, i.e., CLDN6. In other various embodiments, the epitope is a conformational or structural epitope. By "conformational epitope" or "structural epitope" is meant an epitope which is composed of amino acids which are located in close proximity to one another only when the CLDN6 is in its properly folded state. Unlike linear epitopes, the amino acids of a conformational or structural epitope are not adjacent to each other in the primary structure (i.e., amino acid sequence) of the CLDN6. A conformational or structural epitope is not made of contiguous amino acids of the amino acid sequence of the antigen (CLDN6).

In various aspects, the epitope is located within the extracellular domain (ECD) of CLDN6, e.g., human CLDN6. In various aspects, the antigen binding protein binds to Extracellular Loop 2 (EL2) of the ECD of CLDN6 having the amino acid sequence of WTAHAIIRDFYNPL-VAEAQKREL (SEQ ID NO: 2). In various aspects, the epitope to which the antigen-binding protein binds is within SEQ ID NO: 2. In various aspects, the antigen-binding protein of the present disclosure binds to an N-terminal portion of SEQ ID NO: 2, e.g., TAHAIIRDFYNPL (SEQ ID NO: 3). In various aspects, the antigen-binding protein of the present disclosure binds to a C-terminal portion of SEQ ID NO: 2, e.g., LVAEAQKREL (SEQ ID NO: 4). In various instances, the antigen-binding protein of the present disclosure binds to EL2, but not to Extracellular Loop 1 (EL1) of CLDN6. In various aspects, the epitope(s) to which the antigen binding proteins of the present disclosure bind to is different from the epitope bound by an anti-CLDN6 antibody comprising a light chain variable region comprising the sequence of SEQ ID NO: 185 and a heavy chain variable region comprising the sequence of SEQ ID NO: 186. In various aspects, the epitope(s) to which the antigen binding proteins of the present disclosure bind to is different from the epitope bound by an anti-CLDN6 antibody comprising a light chain variable region comprising the sequence of SEQ ID NO: 181 and a heavy chain variable region comprising the sequence of SEQ ID NO: 182.

In various aspects, the antigen-binding proteins bind to human CLDN6 and a non-human CLDN6. In various instances, the non-human CLDN6 is a CLDN6 of chimpanzee, Rhesus monkey, dog, cow, mouse, rat, zebrafish, or frog. In various instances, the antigen-binding proteins bind to human CLDN6 and mouse CLDN6.

Affinity and Avidity

The antigen-binding proteins provided herein bind to CLDN6 in a non-covalent and reversible manner. In various embodiments, the binding strength of the antigen-binding protein to CLDN6 may be described in terms of its affinity, a measure of the strength of interaction between the binding site of the antigen-binding protein and the epitope. In various aspects, the antigen-binding proteins provided herein have high-affinity for CLDN6 and thus will bind a greater amount of CLDN6 in a shorter period of time than low-affinity antigen-binding proteins. In various aspects, the antigen-binding protein has an equilibrium association constant, $K_A$, which is at least $10^5$ M$^{-1}$, at least $10^6$ M$^{-1}$, at least $10^7$ M$^{-1}$, at least $10^8$ M$^{-1}$, at least $10^9$ M$^{-1}$, or at least $10^{10}$ M$^{-1}$. As understood by the artisan of ordinary skill, $K_A$ can be influenced by factors including pH, temperature and buffer composition.

In various embodiments, the binding strength of the antigen-binding protein to CLDN6 may be described in terms of its sensitivity. $K_D$ is the equilibrium dissociation constant, a ratio of $k_{off}/k_{on}$, between the antigen-binding protein and CLDN6. $K_D$ and $K_A$ are inversely related. The $K_D$ value relates to the concentration of the antigen-binding protein (the amount of antigen-binding protein needed for a particular experiment) and so the lower the $K_D$ value (lower concentration) the higher the affinity of the antigen-binding protein. In various aspects, the binding strength of the antigen-binding protein to CLDN6 may be described in terms of $K_D$. In various aspects, the $K_D$ of the antigen-binding proteins provided herein is about $10^{-1}$ M, about $10^{-2}$ M, about $10^{-3}$ M, about $10^{-4}$ M, about $10^{-5}$ M, about $10^{-6}$ M, or less. In various aspects, the $K_D$ of the antigen-binding proteins provided herein is micromolar, nanomolar, picomolar or femtomolar. In various aspects, the $K_D$ of the antigen-binding proteins provided herein is within a range of about $10^{-4}$ M to $10^{-6}$ M, or $10^{-7}$ M to $10^{-9}$ M, or $10^{-10}$ M to $10^{-12}$ M, or $10^{-13}$ M to $10^{-15}$ M. In various aspects, the $K_D$ of the antigen-binding proteins provided herein is within a range of about $1.0 \times 10^{-12}$ M to about $1.0 \times 10^{-8}$ M. In various aspects, the $K_D$ of the antigen-binding proteins is within a range of about $1.0 \times 10^{-11}$ M to about $1.0 \times 10^{-9}$ M.

In various aspects, the affinity of the antigen-binding proteins are measured or ranked using a flow cytometry- or Fluorescence-Activated Cell Sorting (FACS)-based assay. Flow cytometry-based binding assays are known in the art. See, e.g., Cedeno-Arias et al., Sci Pharm 79(3): 569-581 (2011); Rathanaswami et al., Analytical Biochem 373: 52-60 (2008); and Geuijen et al., J Immunol Methods 302(1-2): 68-77 (2005). In various aspects, the affinity of the antigen-binding proteins are measured or ranked using a competition assay as described in Trikha et al., Int J Cancer 110: 326-335 (2004) and Tam et al., Circulation 98(11): 1085-1091 (1998), as well as below. See section titled "Competition Assays" below. In Trikh et al., cells that express the antigen were used in a radioassay. The binding of $^{125}$I-labeled antigen-binding protein (e.g., antibody) to the cell surface antigen is measured with the cells in suspension. In various aspects, the relative affinity of a CLDN6 antibody is determined via a FACS-based assay in which different concentrations of a CLDN6 antibody conjugated to a fluorophore are incubated with cells expressing CLDN6 and the fluorescence emitted (which is a direct measure of antibody-antigen binding) is determined. A curve plotting the fluorescence for each dose or concentration is made. The max value is the lowest concentration at which the fluorescence plateaus or reaches a maximum, which is when binding saturation occurs. Half of the max value is considered an EC50 or an IC50 and the antibody with the lowest EC50/IC50 is considered as having the highest affinity relative to other antibodies tested in the same manner.

In various aspects, the $IC_{50}$ value, as determined in a competitive binding inhibition assay, approximates the $K_D$ of the antigen-binding protein. In various instances, as discussed below, the competition assay is a FACS-based assay carried out with a reference antibody, fluorophore-conjugated secondary antibody, and cells which express CLDN6. In various aspects, the cells are genetically-engineered to overexpress CLDN6. In some aspects, the cells are HEK293T cells transduced with a viral vector to express CLDN6. In alternative aspects, the cells endogenously express CLDN6. Before the FACS-based assay is carried out, in some aspects, the cells which endogenously express CLDN6 are pre-determined as low CLDN6-expressing cells or high CLDN6-expressing cells. In some aspects, the cells are cancer or tumor cells. In various aspects, the cells are cells from a cell line, e.g., an ovarian cell line, endometrial cell line, bladder cell line, lung cell line, gastrointestinal (GI) cell line, liver cell line, lung cell line, and the like. In various aspects, the cells which endogenously express CLDN6 as selected from the group consisting of OVCA429 ovarian cells, ARK2 endometrial cells, OAW28 ovarian cells, UMUC-4 bladder cells, PEO14 ovarian cells, OV177 ovarian cells, H1693 lung cells, MKN7 upper GI cells, OV-90 ovarian cells, HUH-7 liver cells, JHOS-4 ovarian cells, H1435 lung cells, and NUGC3 upper GI cells. In various aspects, the antigen-binding protein inhibits the binding interaction between human CLDN6 expressed by the cells and the reference antibody, which reference antibody is known to bind to CLDN6 but is not an antigen-binding protein of the present disclosure. In various instances, the antigen-binding proteins of the present disclosure compete with the reference antibody for binding to human CLDN6 and thereby reduce the amount of human CLDN6 bound to the reference antibody as determined by an in vitro competitive binding assay. In various aspects, the antigen-binding proteins of the present disclosure inhibit the binding interaction between human CLDN6 and the reference antibody and the inhibition is characterized by an $IC_{50}$. In various aspects, the antigen-binding proteins exhibit an $IC_{50}$ of less than about 2500 nM for inhibiting the binding interaction between human CLDN6 and the reference antibody. In various aspects, the antigen-binding proteins exhibit an $IC_{50}$ of less than about 2000 nM, less than about 1500 nM, less than about 1000 nM, less than about 900 nM, less than about 800 nM, less than about 700 nM, less than about 600 nM, less than about 500 nM, less than about 400 nM, less than about 300 nM, less than about 200 nM, or less than about 100 nM. In various aspects, the antigen-binding proteins exhibit an $IC_{50}$ of less than about 90 nM, less than about 80 nM, less than about 70 nM, less than about 60 nM, less than about 50 nM, less than about 40 nM, less than about 30 nM, less than about 20 nM, or less than about 10 nM. In various instances, the antigen binding proteins of the present disclosure compete against a reference antibody known to bind to CLDN6 (which reference antibody is different from any of the antigen-binding proteins of the present disclosure) for binding to CLDN6. See further description under Competition assays.

Avidity gives a measure of the overall strength of an antibody-antigen complex. It is dependent on three major parameters: affinity of the antigen-binding protein for the epitope, valency of both the antigen-binding protein and CLDN6, and structural arrangement of the parts that interact. The greater an antigen-binding protein's valency (number of antigen binding sites), the greater the amount of antigen (CLDN6) it can bind. In various aspects, the antigen-binding proteins have a strong avidity for CLDN6. In various aspects, the antigen-binding proteins are multivalent. In various aspects, the antigen-binding proteins are bivalent. In various instances, the antigen antigen-binding proteins are monovalent.

Cross-Reactivity

In various embodiments, the antibodies of the present disclosure bind to CLDN6 and do not bind to any other member of the CLDN family, e.g., do not cross-react with any other member of the CLDN family. In various instances, the antibodies of the present disclosure are CLDN-6 specific. In various embodiments, the antibodies of the present disclosure have a selectivity for CLDN6 which is at least 10-fold, 5-fold, 4-fold, 3-fold, 2-fold greater than the selectivity of the antibodies for CLDN3, CLDN4, CLDN9, or a combination thereof. In various embodiments, the antibodies of the present disclosure have a selectivity for CLDN6 which is at least 10-fold, 5-fold, 4-fold, 3-fold, 2-fold greater than the selectivity of the antibodies for each of CLDN3, CLDN4, and CLDN9. Selectivity may be based on the $K_D$ exhibited by the antibodies for CLDN6, or a CLDN family member, wherein the $K_D$ may be determined by techniques known in the art, e.g., surface plasmon resonance, FACS-based affinity assays.

In various aspects, the antibodies of the present disclosure bind to CLDN6 and do not bind to any of Claudin3 (CLDN3), Claudin4 (CLDN4), and Claudin9 (CLDN9). In various aspects, the antibodies do not bind to any of CLDN3, CLDN4, and CLDN9 and exhibit an $IC_{50}$ of less than about 1200 nM (e.g., less than about 1000 nM, less than about 750 nM, less than about 500 nM, less than about 250 nM) in a FACS-based assay with OVCA429 cells endogenously expressing CLDN6. In various aspects, the antibodies do not bind to any of CLDN3, CLDN4, and CLDN9 and the concentration at which 50% of binding saturation is achieved with OVCA429 cells endogenously expressing CLDN6 is less than about 1200 nM (e.g., less than about 1000 nM, less than about 750 nM, less than about 500 nM, less than about 250 nM). In various aspects, the antibodies exhibit at least a 5-fold selectivity for CLDN 6 greater than that for CLDN3, CLDN4, and CLDN9 and the concentration at which 50% of binding saturation is achieved with OVCA429 cells endogenously expressing CLDN6 is less than about 1200 nM (e.g., less than about 1000 nM, less than about 750 nM, less than about 500 nM, less than about 250 nM). In various aspects, the antibodies exhibit an IC50 of less than about 1200 nM (e.g., less than about 1000 nM, less than about 750 nM, less than about 500 nM, less than about 250 nM) for CLDN6 artificial and endogenous models and exhibit a greater than about 5-fold ratio separating CLDN6 IC50s from CLDN3, CLDN4 and/or CLDN9. In various instances, the antibodies exhibit an IC50 of less than about 1200 nM (e.g., less than about 1000 nM, less than about 750 nM, less than about 500 nM, less than about 250 nM) for CLDN6 and exhibit an IC50 for any one of CLDN3, CLDN4, and CLDN9 at least 5-fold greater than the IC50.

Competition Assays

In various embodiments, the antigen-binding protein inhibits a binding interaction between human CLDN6 and a reference antibody, which reference antibody is known to bind to CLDN6 but is not an antigen-binding protein of the present disclosure. In various instances, the antigen-binding proteins of the present disclosure compete with the reference antibody for binding to human CLDN6 and thereby reduce the amount of human CLDN6 bound to the reference antibody as determined by an in vitro competitive binding assay. In various embodiments, the reference antibody binds to an epitope within the amino acid sequence of the extracellular domain of human CLDN6, optionally, within EL2 or EL1. In various aspects, the reference antibody comprises a light chain variable sequence encoded by SEQ ID NO: 179, and a heavy chain variable sequence encoded by SEQ ID NO: 180. In various aspects, the reference antibody comprises a light chain variable sequence of SEQ ID NO: 181, and a heavy chain variable sequence of SEQ ID NO: 182. In various aspects, the antigen-binding proteins of the present disclosure inhibit the binding interaction between human CLDN6 and the reference antibody and the inhibition is characterized by an $IC_{50}$. In various aspects, the antigen-binding proteins exhibit an $IC_{50}$ of less than about 2500 nM for inhibiting the binding interaction between human CLDN6 and the reference antibody. In various aspects, the antigen-binding proteins exhibit an $IC_{50}$ of less than about 2000 nM, less than about 1500 nM, less than about 1000 nM, less than about 900 nM, less than about 800 nM, less than about 700 nM, less than about 600 nM, less than about 500 nM, less than about 400 nM, less than about 300 nM, less than about 200 nM, or less than about 100 nM. In various aspects, the antigen-binding proteins exhibit an $IC_{50}$ of less than about 90 nM, less than about 80 nM, less than about 70 nM, less than about 60 nM, less than about 50 nM, less than about 40 nM, less than about 30 nM, less than about 20 nM, or less than about 10 nM.

In various instances, the antigen-binding proteins of the present disclosure compete with the reference antibody for binding to human CLDN6 and thereby reduce the amount of human CLDN6 bound to the reference antibody as determined by an in vitro competitive binding assay. In various aspects, the in vitro competitive binding assay is a FACS-based assay in which the fluorescence of a fluorophore-conjugated secondary antibody which binds to the Fc of the reference antibody is measured in the absence or presence of a particular amount of the antigen-binding protein of the present disclosure. In various aspects, the FACS-based assay is carried out with the reference antibody, fluorophore-conjugated secondary antibody and cells which express CLDN6. In various aspects, the cells are genetically-engineered to overexpress CLDN6. In some aspects, the cells are HEK293T cells transduced with a viral vector to express CLDN6. In alternative aspects, the cells endogenously express CLDN6. Before the FACS-based assay is carried out, in some aspects, the cells which endogenously express CLDN6 are pre-determined as low CLDN6-expressing cells or high CLDN6-expressing cells. In some aspects, the cells are cancer or tumor cells. In various aspects, the cells are cells from a cell line, e.g., an ovarian cell line, endometrial cell line, bladder cell line, lung cell line, gastrointestinal (GI) cell line, liver cell line, lung cell line, and the like. In various aspects, the cells which endogenously express CLDN6 as selected from the group consisting of OVCA429 ovarian cells, ARK2 endometrial cells, OAW28 ovarian cells, UMUC-4 bladder cells, PEO14 ovarian cells, OV177 ovarian cells, H1693 lung cells, MKN7 upper GI cells, OV-90 ovarian cells, HUH-7 liver cells, JHOS-4 ovarian cells, H1435 lung cells, and NUGC3 upper GI cells. In various instances, the antigen binding proteins of the present disclosure bind to CLDN6 endogenously expressed by one or more of ARK2 cells, OVCA429 cells, LS513 cells, or MCF7 cells with high affinity. In various aspects, the antigen binding proteins exhibit an $IC_{50}$ of less than about 3000 nM as determined in a FACS-based competitive binding inhibition assay using one or more of ARK2 cells, OVCA429 cells, LS513 cells, or MCF7 cells. In various aspects, the antigen binding proteins exhibit an $IC_{50}$ of less than about 2500 nM, less than about 2000 nM, less than about 1750 nM, less than about 1500 nM, less than about 1250 nM, less than about 1000 nM, less than about 750 nM, or less than about 500 nM, as determined in a FACS-based competitive binding inhibition assay using one or more of ARK2 cells, OVCA429 cells, LS513 cells, or MCF7 cells. In various aspects, the antigen binding proteins exhibit an $IC_{50}$ of less than about 400 nM, less than about 300 nM, less than about 200 nM, less than about 100 nM, less than about 75 nM, less than about 50 nM, less than about 25 nM, or less than about 10 nM, as determined in a FACS-based competitive binding inhibition assay using one or more of ARK2 cells, OVCA429 cells, LS513 cells, or MCF7 cells.

Other binding assays, e.g., competitive binding assays or competition assays, which test the ability of an antibody to compete with a second antibody for binding to an antigen, or to an epitope thereof, are known in the art. See, e.g., Trikha et al., Int J Cancer 110: 326-335 (2004); Tam et al., Circulation 98(11): 1085-1091 (1998). U.S. Patent Application Publication No. US20140178905, Chand et al., Biologicals 46: 168-171 (2017); Liu et al., Anal Biochem 525: 89-91 (2017); and Goolia et al., J Vet Diagn Invest 29(2): 250-253 (2017). Also, other methods of comparing two antibodies are known in the art, and include, for example, surface plasmon resonance (SPR). SPR can be used to determine the binding constants of the antibody and second antibody and the two binding constants can be compared.

Methods of Antibody Production and Related Methods

Suitable methods of making antibodies are known in the art. For instance, standard hybridoma methods for producing antibodies are described in, e.g., Harlow and Lane (eds.), Antibodies: A Laboratory Manual, CSH Press (1988), and CA. Janeway et al. (eds.), Immunobiology, 5$^{th}$ Ed., Garland Publishing, New York, NY (2001)). In certain embodiments, methods of producing antibodies and conjugates for use in the methods disclosed herein are described in US2022372134, US2022040321, and US2023049752, each of which is incorporated herein by reference in its entirety.

Depending on the host species, various adjuvants can be used to increase the immunological response leading to greater antibody production by the host. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and Corynebacterium parvum are potentially useful human adjuvants.

Other methods of antibody production are summarized in Table 1.

TABLE 1

| Technique | Various references |
| --- | --- |
| EBV-hybridoma methods and Bacteriophage vector expression systems | Haskard and Archer, J. Immunol. Methods, 74(2), 361-67 (1984), Roder et al., Methods Enzymol., 121, 140-67 (1986), and Huse et al., Science, 246, 1275-81 (1989)). |
| methods of producing antibodies in non-human animals | U.S. Pat. Nos. 5,545,806, and 5,714,352, and U.S. patent application publication No. 2002/0197266 |
| inducing in vivo production in the lymphocyte population or by screening recombinant immunoglobulin libraries or panels of highly specific binding reagents | Orlandi et al (Proc Natl Acad Sci 86: 3833-3837; 1989), and Winter G and Milstein C (Nature 349: 293-299, 1991). |
| methods of producing recombinant proteins | "Protein production and purification" Nat Methods 5(2): 135-146 (2008). |
| Phage display | Janeway et al., supra, Huse et al., supra, and U.S. Pat. No. 6,265,150). Related methods also are described in U.S. Pat. No. 5,403,484; U.S. Pat. No. 5,571,698; U.S. Pat. No. 5,837,500 U.S. Pat. No. 5,702,892. The techinques described in U.S. Pat. No. 5,780,279; U.S. Pat. No. 5,821,047; U.S. Pat. No. 5,824,520; U.S. Pat. No. 5,855,885; U.S. Pat. No. 5,858,657; U.S. Pat. No. 5,871,907; U.S. Pat. No. 5,969,108; U.S. Pat. No. 6,057,098; and U.S. Pat. No. 6,225,447 |
| Antibodies can be produced by transgenic mice | U.S. Pat. Nos. 5,545,806 and 5,569,825, and Janeway et al., supra. |

Methods of testing antibodies for the ability to bind to the epitope of CLDN6 regardless of how the antibodies are produced are known in the art and include any antibody-antigen binding assay, such as, for example, radioimmunoassay (RIA), ELISA, Western blot, immunoprecipitation, SPR, and competitive inhibition assays (see, e.g., Janeway et al., infra, and U.S. Patent Application Publication No. 2002/0197266, and the above section relating to competition assays).

Sequences/Structure

CLND6 binding proteins are known in the art. For example, US2022372134 and US2023049752, each of which is hereby incorporated by reference in its entirety, describe CLDN6 binding proteins. CLDN6 antigen binding proteins are also described in US20220168438, US20200261594, US20220168440, US20220125943 (for example, SEQ ID NOS: 19, 21, 23, and 25 from this publication), US2020339677 (for example, SEQ ID NOS: 34-41 and FIGS. 25-26 from this publication), US2021179730 (for example, SEQ ID NOS: 34-41, FIGS. 25-26 from this publication), US2021079113, US2020385460 (for example, SEQ ID NOS: 3-12 from this publication), US2020399370, US2022306711, US2022162302 (for example, SEQ ID NOS: 40-45 from this publication), US2019309067, and WO2022187275 (for example, SEQ ID NOS: 1-4 and 23-31 from this publication), each of which is hereby incorporated by reference in its entirety. Sequences are listed with SEQ ID NOS in the Sequence Listing. Provided herein are antigen-binding proteins comprising (a) a heavy chain (HC) complementarity-determining region (CDR) 1 amino acid sequence set forth in Table A or a sequence selected from the group consisting of: SEQ ID NOs: 11, 17, 23, 29, 35, 41, 47, 53, 59, 65, 71, 107, 125, and 131, or a variant sequence thereof which differs by only one or two amino acids or which has at least or about 70% (e.g., at least about 80%, at least about 85%, at least about 90%, at least about 95%) sequence identity; (b) an HC CDR2 amino acid sequence set forth in Table A or a sequence selected from the group consisting of: SEQ ID NOs: 12, 18, 24, 30, 36, 42, 48, 54, 60, 66, 72, 108, 126, and 132, or a variant sequence thereof which differs by only one or two amino acids or which has at least or about 70% (e.g., at least about 80%, at least about 85%, at least about 90%, at least about 95%) sequence identity; (c) an HC CDR3 amino acid sequence set forth in Table A or a sequence selected from the group consisting of: SEQ ID NOs: 13, 19, 25, 31, 37, 43, 49, 55, 61, 67, 73, 109, 127, and 133, or a variant sequence thereof which differs by only one or two amino acids or which has at least or about 70% (e.g., at least about 80%, at least about 85%, at least about 90%, at least about 95%) sequence identity; (d) a light chain (LC) CDR1 amino acid sequence set forth in Table A or a sequence selected from the group consisting of: SEQ ID NOs: 8, 14, 20, 32, 38, 44, 50, 56, 62, 68, 104, 122, and 128, or a variant sequence thereof which differs by only one or two amino acids or which has at least or about 70% (e.g., at least about 80%, at least about 85%, at least about 90%, at least about 95%) sequence identity; (e) an LC CDR2 amino acid sequence set forth in Table A or a sequence selected from the group consisting of: SEQ ID NOs: 9, 15, 21, 27, 33, 39, 45, 51, 57, 63, 69, 105, 123, and 129, or a variant sequence thereof which differs by only one or two amino acids or which has at least or about 70% (e.g., at least about 80%, at least about 85%, at least about 90%, at least about 95%) sequence identity; (f) an LC CDR3 amino acid sequence set forth in Table A or a sequence selected from the group consisting of: SEQ ID NOs: 10, 16, 22, 28, 34, 40, 46, 52, 58, 64, 70, 106, 124, and 130, or a variant sequence thereof which differs by only one or two amino acids or which has at least or about 70% (e.g., at least about 80%, at least about 85%, at least about 90%, at least about 95%) sequence identity; or (g) a combination of any two or more of (a)-(f).

TABLE A

|      | LC CDR1 | LC CDR2 | LC CDR3 | HC CDR1 | HC CDR2 | HC CDR3 |
|------|---------|---------|---------|---------|---------|---------|
| AB1  | 8       | 9       | 10      | 11      | 12      | 13      |
| AB2  | 14      | 15      | 16      | 17      | 18      | 19      |
| AB3  | 20      | 21      | 22      | 23      | 24      | 25      |
| AB4  | 26      | 27      | 28      | 29      | 30      | 31      |
| AB5  | 32      | 33      | 34      | 35      | 36      | 37      |
| AB6  | 38      | 39      | 40      | 41      | 42      | 43      |
| AB7  | 44      | 45      | 46      | 47      | 48      | 49      |
| AB8  | 50      | 51      | 52      | 53      | 54      | 55      |
| AB9  | 56      | 57      | 58      | 59      | 60      | 61      |
| AB10 | 62      | 63      | 64      | 65      | 66      | 67      |
| AB11 | 68      | 69      | 70      | 71      | 72      | 73      |
| AB17 | 104     | 105     | 106     | 107     | 108     | 109     |
| AB20 | 122     | 123     | 124     | 125     | 126     | 127     |
| AB21 | 128     | 129     | 130     | 131     | 132     | 133     |
| AB-D1 | Dx4    | Dx5     | Dx6     | Dx1     | Dx2     | Dx3     |
| AB-D2 | Dx10   | Dx11    | Dx12    | Dx7     | Dx8     | Dx9     |
| AB-D3 | Dx16   | Dx17    | Dx18    | Dx13    | Dx14    | Dx15    |
| AB-D4 | Dx22   | Dx23    | Dx24    | Dx19    | Dx20    | Dx21    |

SEQ ID NOs:

Dx1 (SEQ ID NO: 514):
Gly Tyr Thr Phe Thr Glu Tyr Thr Met His

Dx2 (SEQ ID NO: 515):
Gly Val Asn Pro Asn Ser Gly Asp Thr Ser

Dx3 (SEQ ID NO: 516):
Pro Gly Gly Tyr Asp Val Gly Tyr Tyr Ala Met Asp
Tyr

Dx4 (SEQ ID NO: 517):
Arg Ala Ser Gln Asp Ile Asn Asn Tyr Leu Asn

Dx5 (SEQ ID NO: 518):
Phe Thr Ser Arg Leu His Ser

Dx6 (SEQ ID NO: 519):
Gln Gln Gly Tyr Pro Leu Pro Trp Thr

Dx7 (SEQ ID NO: 520):
Gly Tyr Thr Phe Thr Glu Tyr Thr Met His

Dx8 (SEQ ID NO: 521):
Gly Val Asn Pro Asn Ser Gly Asp Thr Ser

Dx9 (SEQ ID NO: 522):
Pro Gly Gly Tyr Asp Val Gly Tyr Tyr Ala Met Asp
Tyr

Dx10 (SEQ ID NO: 523):
Arg Ala Ser Gln Asp Ile Asn Asn Tyr Leu Asn

Dx11 (SEQ ID NO: 524):
Ser Thr Ser Arg Leu His Ser

Dx12 (SEQ ID NO: 525):
Gln Gln Gly Tyr Pro Leu Pro Trp Thr

Dx13 (SEQ ID NO: 526):
Gly Tyr Thr Phe Thr Glu Tyr Thr Met His

Dx14 (SEQ ID NO: 527):
Gly Val Asn Pro Asn Ser Gly Asp Thr Ser

Dx15 (SEQ ID NO: 528):
Pro Gly Gly Tyr Asp Val Gly Tyr Tyr Ala Met Asp
Tyr

Dx16 (SEQ ID NO: 529):
Arg Ala Ser Gln Asp Ile Asn Asn Tyr Leu Asn

Dx17 (SEQ ID NO: 530):
Phe Thr Ser Arg Leu His Ser

Dx18 (SEQ ID NO: 531):
Gln Gln Gly Tyr Pro Leu Pro Trp Thr

Dx19 (SEQ ID NO: 532):
Gly Tyr Thr Phe Thr Glu Tyr Thr Met His

Dx20 (SEQ ID NO: 533):
Gly Val Asn Pro Asn Ser Gly Asp Thr Ser

Dx21 (SEQ ID NO: 534):
Pro Gly Gly Tyr Asp Val Gly Tyr Tyr Ala Met Asp
Tyr

Dx22 (SEQ ID NO: 535):
Arg Ala Ser Gln Asp Ile Asn Asn Tyr Leu Asn

Dx23 (SEQ ID NO: 536):
Ser Thr Ser Arg Leu His Ser

Dx24 (SEQ ID NO: 537):
Gln Gln Gly Tyr Pro Leu Pro Trp Thr

In various aspects, the antigen-binding protein comprises a LC CDR1 amino acid sequence, a LC CDR2 amino acid sequence, and a LC CDR3 amino acid sequence set forth in Table A and at least 1 or 2 of the HC CDR amino acid sequences set forth in Table A. In various aspects, the antigen-binding protein comprises a HC CDR1 amino acid sequence, a HC CDR2 amino acid sequence, and a HC CDR3 amino acid sequence set forth in Table A and at least 1 or 2 of the LC CDR amino acid sequences set forth in Table A.

In various embodiments, the antigen-binding protein comprises at least 3, 4, or 5 of the amino acid sequences designated by the SEQ ID NOs: in a single row of Table A. In various embodiments, the antigen-binding protein comprises each of the LC CDR amino acid sequences designated by the SEQ ID NOs: of a single row of Table A and at least 1 or 2 of the HC CDR amino acid sequences designated by the SEQ ID NOs: in of a single row of Table A. In various embodiments, the antigen-binding protein comprises each of the HC CDR amino acid sequences designated by the SEQ ID NOs: of a single row of Table A and at least 1 or 2 of the LC CDR amino acid sequences designated by the SEQ ID NOs: of a single row of Table A. In various embodiments, the antigen-binding protein comprises all 6 of the CDR amino acid sequences designated by the SEQ ID NOs: of a single row of Table A. In various embodiments, the antigen-binding protein comprises six CDR amino acid sequences selected from the group consisting of: SEQ ID NOs: 50-55; SEQ ID NOs: 122-127; SEQ ID NOs: 26-31; SEQ ID NOs: 128-133; SEQ ID NOs: 38-43; SEQ ID NOs: 62-67; SEQ ID NOs: 44-49; SEQ ID NOs: 104-109; SEQ ID NOs: 56-61; SEQ ID NOs: 32-37; SEQ ID NOs: 8-13; SEQ ID NOs: 68-73; SEQ ID NOs: 14-19; and SEQ ID NOs: 20-25.

In various instances, the amino acid sequences of Table A are separated by at least one or more (e.g., at least 2, 3, 4, 5, 6, 7, 8, 9, 10, or more) intervening amino acid(s). In various instances, there are about 10 to about 20 amino acids between the sequences of the LC CDR1 and the LC CDR2 and about 25 to about 40 amino acids between the sequences of the LC CDR2 and the LC CDR3. In various instances, there are about 14 to about 16 amino acids between the sequences of the LC CDR1 and the LC CDR2 and about 30 to about 35 amino acids between the sequences of LC CDR2 and the LC CDR3. In various instances, there are about 10 to about 20 amino acids between the sequences of the HC CDR1 and HC CDR2 and about 25 to about 40 amino acids between the sequences of the HC CDR2 and the HC CDR3. In various instances, there are about 14 to about 16 amino acids between the sequences of the HC CDR1 and HC CDR2 and about 30 to about 35 amino acids between the sequences of the HC CDR2 and HC CDR3.

In various embodiments, the antigen-binding protein comprises (a) a heavy chain variable region amino acid sequence set forth in in Table B or a sequence selected from the group consisting of: SEQ ID NOs: 135, 137, 139, 141, 143, 145, 147, 149, 151, 153, 155, 167, 173, and 175, or a variant sequence thereof which differs by only one or two amino acids or which has at least or about 70% (e.g., at least about 80%, at least about 85%, at least about 90%, at least about 95%) sequence identity; or (b) a light chain variable region amino acid sequence set forth in Table B or a sequence selected from the group consisting of: SEQ ID NOs: 134, 136, 138, 140, 142, 144, 146, 148, 150, 152, 154, 166, 172, 174, and 176, or a variant sequence thereof which differs by only one or two amino acids or which has at least or about 70% (e.g., at least about 80%, at least about 85%, at least about 90%, at least about 95%) sequence identity; or (c) both (a) and (b).

TABLE B

|  | Light Chain Variable Region | Heavy Chain Variable Region |
| --- | --- | --- |
| AB1 | 134 | 135 |
| AB2 | 136 | 137 |
| AB3 | 138 | 139 |
| AB4 | 140 | 141 |
| AB5 | 142 | 143 |
| AB6 | 144 | 145 |
| AB7 | 146 | 147 |
| AB8 | 148 | 149 |
| AB9 | 150 | 151 |
| AB10 | 152 | 153 |
| AB11 | 154 | 155 |
| AB17 | 166 | 167 |
| AB20 | 172 | 173 |
| AB21 | 174 | 175 |

In various embodiments, the antigen-binding protein comprises a pair of amino acid sequences selected from the group consisting of: SEQ ID NOs: 148 and 149; SEQ ID NOs: 172 and 173; SEQ ID NOs: 140 and 141; SEQ ID NOs: 174 and 175; SEQ ID NOs: 144 and 145; SEQ ID NOs: 152 and 153; SEQ ID NOs: 146 and 147; SEQ ID NOs: 166 and 167; SEQ ID NOs: 150 and 151; SEQ ID NOs: 142 and 143; SEQ ID NOs: 164 and 165; SEQ ID NOs: 162 and 163; SEQ ID NOs: 134 and 135; SEQ ID NOs: 154 and 155; SEQ ID NOs: 136 and 137; and SEQ ID NOs: 138 and 139.

In various aspects, the antigen-binding protein comprises an amino acid sequence which is similar to an above-referenced amino acid sequence, yet the antigen-binding protein substantially retains its biological function, e.g., its ability to bind to human CLDN6, reduce tumor growth, inhibit tumor growth, and/or treat cancer.

In various aspects, the antigen-binding protein comprises an amino acid sequence which differs by only 1, 2, 3, 4, 5, 6, or more amino acids, relative to the above-referenced amino acid sequence(s). In various aspects, the antigen-binding protein comprises a variant sequence of the referenced sequence, which variant sequence differs by only one or two amino acids, relative to the referenced sequence. In various aspects, the antigen-binding protein comprising one or more amino acid substitutions that occur outside of the CDRs, e.g., the one or more amino acid substitutions occur within the framework region(s) of the heavy or light chain. In various aspects, the antigen-binding protein comprising one or more amino acid substitutions yet the antigen-binding protein retains the amino acid sequences of the six CDRs. In various aspects, the antigen-binding protein comprises an amino acid sequence having only 1, 2, 3, 4, 5, 6, or more conservative amino acid substitutions, relative to the above-referenced amino acid sequence(s). As used herein, the term "conservative amino acid substitution" refers to the substitution of one amino acid with another amino acid having similar properties, e.g., size, charge, hydrophobicity, hydrophilicity, and/or aromaticity, and includes exchanges within one of the following five groups:

I. Small aliphatic, nonpolar or slightly polar residues:
   Ala, Ser, Thr, Pro, Gly;
II. Polar, negatively charged residues and their amides and esters:
   Asp, Asn, Glu, Gln, cysteic acid and homocysteic acid;
III. Polar, positively charged residues:
   His, Arg, Lys; Ornithine (Orn)
IV. Large, aliphatic, nonpolar residues:
   Met, Leu, Ile, Val, Cys, Norleucine (Nle), homocysteine
V. Large, aromatic residues:
   Phe, Tyr, Trp, acetyl phenylalanine In various aspects, the conservative amino acid substitution is an exchange within one of the following groups of amino acids:

I. aliphatic amino acids: Gly, Ala, Val, Leu, Ile
II. non-aromatic amino acids comprising a side chain hydroxyl: Ser, Thr
III. amino acids comprising a sulfur side chain: Cys, Met
IV: amino acids comprising a side chain aromatic ring: Phe, Tyr, Trp
V: acidic amino acid: Glu; Asp
VI: basic amino acid: Arg; Lys
VII: amino acid comprising a side chain amide: Gln, Asn
VIII: amino acid comprising a side chain imidazole: His, alpha-dimethyl imidiazole acetic acid (DMIA)
IX: imino acid: Pro, 4-hydroxy-Pro, 4-amino-Pro In various aspects, the antigen-binding protein comprises an amino acid sequence which has greater than or about 30%, greater than or about 50%, or greater than or about 70% sequence identity to the above-referenced amino acid sequence. In various aspects, the antigen-binding protein comprises an amino acid sequence which has at least 30%, at least 40%, at least 50%, at least 60%, at least 70%, at least 80%, at least 85%, at least 90% or has greater than 90% sequence identity to the above-referenced amino acid sequence. In various aspects, the antigen-binding protein comprises an amino acid sequence that has at least 70%, at least 80%, at least 85%, at least 90% or has greater than 90% sequence identity along the full-length of the above-referenced amino acid sequence. In various aspects, the antigen-binding protein comprises an amino acid sequence having at least 95%, 96%, 97%, 98% or 99% sequence identity along the full-length of the above-referenced amino acid sequence.

In various aspects, the antigen-binding protein comprises a variant sequence of the referenced sequence, which variant sequence has at least or about 70% sequence identity, relative to the above-referenced sequence. In various aspects, the antigen-binding protein comprises a variant sequence of the referenced sequence, which variant sequence has at least or about 80% sequence identity, relative to the above-referenced sequence. In various aspects, the antigen-binding protein comprises a variant sequence of the referenced sequence, which variant sequence has at least or about 90% sequence identity, relative to the above-referenced sequence. In various aspects, the antigen-binding protein comprises a variant sequence of the referenced sequence, which variant sequence has at least or about 95% sequence identity, relative to the above-referenced sequence.

In various embodiments, the antigen-binding protein comprises one, two, three, four, or five sequences of the SEQ ID NOs. in a single row of Table A and at least one variant sequence having at least or about 70% (e.g., at least about 80%, at least about 85%, at least about 90%, at least about 95%) sequence identity to any of SEQ ID NOs: 8-133. In various embodiments, the antigen-binding protein comprises one, two, three, four, or five sequences of a set of sequences selected from: SEQ ID NOs: 50-55; SEQ ID NOs: 122-127; SEQ ID NOs: 26-31; SEQ ID NOs: 128-133; SEQ ID NOs: 38-43; SEQ ID NOs: 62-67; SEQ ID NOs: 44-49; SEQ ID NOs: 104-109; SEQ ID NOs: 56-61; SEQ ID NOs: 32-37; SEQ ID NOs: 8-13; SEQ ID NOs: 68-73; SEQ ID NOs: 14-19; and SEQ ID NOs: 20-25, wherein the antigen-binding protein further comprises at least one variant sequence having at least or about 70% (e.g., at least about 80%, at least about 85%, at least about 90%, at least about 95%) sequence identity to at least one of the sequences of the set.

In various embodiments, the antigen-binding protein comprises a pair of variant sequences having at least or about 70% (e.g., at least about 80%, at least about 85%, at least about 90%, at least about 95%) sequence identity to any of SEQ ID NOs: 134-155 and 166-167 and 172-175. In various instances, the antigen binding protein comprises a pair of variant sequences which have at least or about 70% (e.g., at least about 80%, at least about 85%, at least about 90%, at least about 95%) sequence identity to SEQ ID NOs: 148 and 149; SEQ ID NOs: 172 and 173; SEQ ID NOs: 140 and 141; SEQ ID NOs: 174 and 175; SEQ ID NOs: 144 and 145; SEQ ID NOs: 152 and 153; SEQ ID NOs: 166 and 167; SEQ ID NOs: 150 and 151; SEQ ID NOs: 142 and 143; SEQ ID NOs: 134 and 135; SEQ ID NOs: 154 and 155; SEQ ID NOs: 136 and 137; and SEQ ID NOs: 138 and 139. In various embodiments, the antigen-binding protein comprises a pair of sequences: one sequence of Table B and another sequence which is a variant sequence having at least or about 70% (e.g., at least about 80%, at least about 85%, at least about 90%, at least about 95%) sequence identity to any of SEQ ID NOs: 134-155 and 166-167 and 172-175. In various embodiments, the antigen-binding protein comprises a pair of sequences: one sequence selected from SEQ ID NOs: 148 and 149; SEQ ID NOs: 172 and 173; SEQ ID NOs: 140 and 141; SEQ ID NOs: 174 and 175; SEQ ID NOs: 144 and 145; SEQ ID NOs: 152 and 153; SEQ ID NOs: 146 and 147; SEQ ID NOs: 166 and 167; SEQ ID NOs: 150 and 151; SEQ ID NOs: 142 and 143; SEQ ID NOs: 134 and 135; SEQ ID NOs: 154 and 155; SEQ ID NOs: 136 and 137; and SEQ ID NOs: 138 and 139, and another sequence which is a variant sequence having at least or about 70% (e.g., at least about 80%, at least about 85%, at least about 90%, at least about 95%) sequence identity to a sequence above. For instance, in various aspects, the antigen-binding protein comprises a sequences of SEQ ID NO: 134 and the antigen-binding protein further comprises a variant sequence having at least or about 70% (e.g., at least about 80%, at least about 85%, at least about 90%, at least about 95%) sequence identity to SEQ ID NO 135.

In various instances, the antigen-binding protein comprises an amino acid sequence of an above-referenced amino acid sequence with one or more amino acid substitutions to reduce or eliminate reactive amino acids to decrease or prevent unwanted side chain reactions. For instance, the antigen-binding protein comprises an amino acid sequence of an above-referenced amino acid sequence with one or more (i) Trp residues substituted with His, Tyr, or Phe; (ii) Asn residues substituted with Gln, Ser, Ala, or Asp; (iii) Asp residues occurring immediately before a Pro residue substituted with Ala, Ser, or Glu, (iv) Asn residues substituted with Gln, Ser, or Ala; and/or (v) Cys residues substituted with Tyr, Ser, or Ala. In various aspects, the antigen-binding protein comprises an amino acid sequence of an above-referenced amino acid sequence with an amino acid substitution predicted to have greater binding affinity, greater stability, or other positive attribute, based on SHM events or based on statistical analyses of a multitude of other similar antibody sequences. In some aspects, the antigen-binding protein comprises (a) an HC CDR1 amino acid sequence set forth in Table A1 or a sequence selected from the group consisting of: SEQ ID NOs: 452, 455, 461, 465, and 71, or a variant sequence thereof which differs by only one or two amino acids or which has at least or about 70% (e.g., at least about 80%, at least about 85%, at least about 90%, at least about 95%) sequence identity; (b) an HC CDR2 amino acid sequence set forth in Table A1 or a sequence selected from the group consisting of: SEQ ID NOs: 475, 456, 462, 466, and 468; or a variant sequence thereof which differs by only one or two amino acids or which has at least or about 70% (e.g., at least about 80%, at least about 85%, at least about 90%, at least about 95%) sequence identity; (c) an HC CDR3 amino acid sequence set forth in Table A1 or a sequence selected from the group consisting of: SEQ ID NOs: 453, 457, 463, 467, and 469; or a variant sequence thereof which differs by only one or two amino acids or which has at least or about 70% (e.g., at least about 80%, at least about 85%, at least about 90%, at least about 95%) sequence identity; (d) a LC CDR1 amino acid sequence set forth in Table A1 or a sequence selected from the group consisting of: SEQ ID NOs: 449, 476, 458, 464, and 68; or a variant sequence thereof which differs by only one or two amino acids or which has at least or about 70% (e.g., at least about 80%, at least about 85%, at least about 90%, at least about 95%) sequence identity; (e) an LC CDR2 amino acid sequence set forth in Table A1 or a sequence selected from the group consisting of: SEQ ID NOs: 450, 477, 459, 57, and 69; or a variant sequence thereof which differs by only one or two amino acids or which has at least or about 70% (e.g., at least about 80%, at least about 85%, at least about 90%, at least about 95%) sequence identity; (f) an LC CDR3 amino acid sequence set forth in Table A1 or a sequence selected from the group consisting of: SEQ ID NOs: 451, 454, 460, 58, and 70, or a variant sequence thereof which differs by only one or two amino acids or which has at least or about 70% (e.g., at least about 80%, at least about 85%, at least about 90%, at least about 95%) sequence identity or (g) a combination of any two or more of (a)-(f).

TABLE A1

|       | LC CDR1 | LC CDR2 | LC CDR3 | HC CDR1 | HC CDR2 | HC CDR3 |
|-------|---------|---------|---------|---------|---------|---------|
| AB1*  | 449     | 450     | 451     | 452     | 475     | 453     |
| AB3*  | 476     | 477     | 454     | 455     | 456     | 457     |
| AB4*  | 458     | 459     | 460     | 461     | 462     | 463     |
| AB9*  | 464     | 57      | 58      | 465     | 466     | 467     |
| AB11* | 68      | 69      | 70      | 71      | 468     | 469     |

In some aspects, the HC CDR1 comprises Gly immediately N-terminal of SEQ ID NO: 452 and, optionally, in some aspects, the HC CDR1 comprises MX immediately C-terminal of SEQ ID NO: 452, wherein X is H, N, or S. In various aspects, the HC CDR3 comprises Ala immediately N-terminal of SEQ ID NO: 453. In various aspects, the LC CDR1 further comprises TAS immediately N-terminal of SEQ ID NO: 449, and, optionally, XH immediately C-terminal of SEQ ID NO: 449, wherein X is H, S, Y, or Q. In some aspects, as described below, the first amino acid of SEQ ID NO: 449 is S or Q. In some aspects, as described below, the first amino acid of SEQ ID NO: 451 is S or Q.

In various aspects, the HC CDR1 comprises Gly immediately N-terminal of SEQ ID NO: 455, and, optionally, in various aspects, the HC CDR1 comprises MX immediately C-terminal of SEQ ID NO: 455, wherein X is N, S, or H. In some aspects, HC CDR2 comprises Gln immediately N-terminal of SEQ ID NO: SEQ ID NO: 456, and optionally H immediately C-terminal of SEQ ID NO: 456. In various aspects, the LC CDR1 comprises RIS immediately N-terminal of SEQ ID NO: 476, and optionally, comprises LA immediately C-terminal of SEQ ID NO: 476. In various aspects, the LC CDR2 comprises XLVE immediately C-terminal of SEQ ID NO: 477, wherein X is I or S.

In various aspects, the HC CDR1 comprises MH immediately C-terminal of SEQ ID NO: 461. In various aspects, the HC CDR2 comprises Tyr immediately N-terminal of SEQ ID NO: 462, and optionally, TH immediately C-terminal of SEQ ID NO: 462. In exemplary aspects, the HC CDR3 does not include the first two amino acids of SEQ ID NO: 463. In various aspects, the LC CDR1 comprises RSS immediately N-terminal of SEQ ID NO: 458, and optionally, LN immediately C-terminal of SEQ ID NO: 458. In various aspects, the LC CDR2 comprises XRFS immediately C-terminal of SEQ ID NO: 459, wherein X is Q, S, A, or D.

In various aspects, the HC CDR1 comprises MH immediately C-terminal of SEQ ID NO: 465. In various aspects, the HC CDR2 comprises YI immediately N-terminal of SEQ ID NO: 466, and optionally, Xaa immediately C-terminal of SEQ ID NO: 466, wherein Xaa is N, S, Q, or A. In various aspects, the LC CDR1 comprises LAS immediately N-terminal of SEQ ID NO: 464, and optionally, LA immediately C-terminal of SEQ ID NO: 464. In various aspects, the LC CDR2 comprises SLAD immediately C-terminal of SEQ ID NO: 57.

In various aspects, the HC CDR1 comprises MH immediately C-terminal of SEQ ID NO: 71. In various aspects, the HC CDR2 comprises Tyr immediately N-terminal of SEQ ID NO: 468 and optionally IY immediately C-terminal of SEQ ID NO: 468. In various aspects, the LC CDR1 comprises RAS immediately N-terminal of SEQ ID NO: 68, and optionally SYIH immediately C-terminal to SEQ 68. In various aspects, the LC CDR2 comprises XLES immediately C-terminal to SEQ ID NO: 69, wherein X is N, Q, S, A, or D.

In various aspects, the antigen-binding protein comprises a LC CDR1 amino acid sequence, a LC CDR2 amino acid sequence, and a LC CDR3 amino acid sequence set forth in Table A1 and at least 1 or 2 of the HC CDR amino acid sequences set forth in Table A1. In various aspects, the antigen-binding protein comprises a HC CDR1 amino acid sequence, a HC CDR2 amino acid sequence, and a HC CDR3 amino acid sequence set forth in Table A1 and at least 1 or 2 of the LC CDR amino acid sequences set forth in Table A1.

In various embodiments, the antigen-binding protein comprises at least 3, 4, or 5 of the amino acid sequences designated by the SEQ ID NOs: in a single row of Table A1. In various embodiments, the antigen-binding protein comprises each of the LC CDR amino acid sequences designated by the SEQ ID NOs: of a single row of Table A1 and at least 1 or 2 of the HC CDR amino acid sequences designated by the SEQ ID NOs: in of a single row of Table A1. In various embodiments, the antigen-binding protein comprises each of the HC CDR amino acid sequences designated by the SEQ ID NOs: of a single row of Table A1 and at least 1 or 2 of the LC CDR amino acid sequences designated by the SEQ ID NOs: of a single row of Table A1. In various embodiments, the antigen-binding protein comprises all 6 of the CDR amino acid sequences designated by the SEQ ID NOs: of a single row of Table A1. In various embodiments, the antigen-binding protein comprises six CDR amino acid sequences selected from the group consisting of: (a) SEQ ID NOs: 449-453 and 475; (b) SEQ ID NOs: 476-477, 454-457; (c) SEQ ID NOs: 458-463; (d) SEQ ID NOs: 57, 58, 464-467; and (e) SEQ ID NOs: 68-71 and 468-469.

In various instances, the amino acid sequences of Table A1 are separated by at least one or more (e.g., at least 2, 3, 4, 5, 6, 7, 8, 9, 10, or more) intervening amino acid(s). In various instances, there are about 10 to about 20 amino acids between the sequences of the LC CDR1 and the LC CDR2 and about 25 to about 40 amino acids between the sequences of the LC CDR2 and the LC CDR3. In various instances, there are about 14 to about 16 amino acids between the sequences of the LC CDR1 and the LC CDR2 and about 30 to about 35 amino acids between the sequences of LC CDR2 and the LC CDR3. In various instances, there are about 10 to about 20 amino acids between the sequences of the HC CDR1 and HC CDR2 and about 25 to about 40 amino acids between the sequences of the HC CDR2 and the HC CDR3. In various instances, there are about 14 to about 16 amino acids between the sequences of the HC CDR1 and HC CDR2 and about 30 to about 35 amino acids between the sequences of the HC CDR2 and HC CDR3.

In various embodiments, the antigen-binding protein comprises (a) a heavy chain variable region amino acid sequence set forth in in Table B1 or a sequence selected from the group consisting of: SEQ ID NO: 478, 480, 482, 486, and 488, or a variant sequence thereof which differs by only one or two amino acids or which has at least or about 70% (e.g., at least about 80%, at least about 85%, at least about 90%, at least about 95%) sequence identity; or (b) a light chain variable region amino acid sequence set forth in Table B1 or a sequence selected from the group consisting of: SEQ ID NO: 479, 481, 483, 487, and 489, or a variant sequence thereof which differs by only one or two amino acids or which has at least or about 70% (e.g., at least about 80%, at least about 85%, at least about 90%, at least about 95%) sequence identity; or (c) both (a) and (b).

TABLE B1

|  | HC variable | LC variable |
| --- | --- | --- |
| AB1* | 478 | 479 |
| AB3* | 480 | 481 |
| AB4* | 482 | 483 |
| AB9* | 488 | 489 |
| AB11* | 486 | 487 |

In various embodiments, the antigen-binding protein comprises a pair of amino acid sequences selected from the group consisting of: (a) SEQ ID NO: 478 and 479; (b) SEQ ID NO: 480 and 481; (c) SEQ ID NO: 482 and 483; (d) SEQ ID NO: 486 and 487; and (e) SEQ ID NO: 488 and 489. In various aspects, the antigen-binding protein comprises a variant sequence of a sequence having a SEQ ID NO: listed in Table B1 which differs by only one or two amino acids or which has at least or about 70% (e.g., at least about 80%, at least about 85%, at least about 90%, at least about 95%) sequence identity, wherein the different amino acid(s) occur(s) at the positions described below in "Humanized Antibodies".

Humanized Antibodies

In various aspects, the antigen-binding protein is a humanized version of an antigen binding protein described in Table A, Table A1, Table B, or Table B1.

Humanized AB1

In various aspects, the antigen-binding protein is a humanized version of AB1 as set forth in Table B or B1 with one or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35) amino acid substitutions in the heavy chain variable region at one or more of the following positions: 5, 8, 11, 12, 13, 20, 31, 33, 35, 38, 40, 48, 50, 55, 57, 59, 61, 65, 66, 67, 68, 70, 72, 74, 76, 79, 80, 82, 87, 90, 91, 98, 101, and 116. In various instances, the antigen-binding protein comprises an amino acid sequence of SEQ ID NO: 428. In various aspects, the antigen-binding protein is a humanized version of AB1 as set forth in Table B or B1 with one or more amino acid substitutions in the heavy chain variable region at one or more (e.g., 1, 2, 3, 4, 5, 6, 7, 8, 9, 10, 11, or 12) of the following positions: 20, 31, 35, 48, 50, 59, 67, 70, 74, 79, 98, 101. In various instances, the antigen-binding protein comprises an amino acid sequence of SEQ ID NO: 429. In various aspects, the amino acids at the above-recited positions are selected from the amino acids according to the table below:

| Position | Amino acids | Position | Amino acids | Position | Amino acids |
| --- | --- | --- | --- | --- | --- |
| 5 | Q, V | 8 | A, G | 11 | L, V |
| 12 | A, K | 13 | R, K | 20 | M, V |
| 31 | S, T, V, D | 33 | Y, T | 35 | H, N, S |
| 38 | K, R | 40 | R, A | 48 | I, M |
| 50 | F, V, T, Y, I | 55 | G, S | 57 | S, Y |
| 59 | D, E, N, S | 61 | N, A | 65 | K, Q |
| 66 | D, G | 67 | R, Q, N, K | 68 | T, V |
| 70 | L, M | 72 | R, A | 74 | K, T |
|  |  | 79 | V, D, S, A | 82 | Q, E |
| 87 | T, R | 91 | S, T | 98 | N, Q, H, D, R |
| 101 | Y | 76 | ST | 116 | A, S |

In various aspects, the antigen-binding protein is a humanized version of AB1 as set forth in Table B or B1 with one or more amino acid substitutions in the light chain variable region at one or more e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41) of the following positions: 1, 3, 4, 9, 10, 11, 15, 17, 21, 24, 27, 29, 32, 34, 35, 43, 44, 48, 51, 52, 53, 54, 55, 56, 61, 67, 71, 72, 73, 79, 80, 81, 84, 90, 92, 93, 94, 95, 96, 101, 107. In various instances, the antigen-binding protein comprises an amino acid sequence of SEQ ID NO: 430. In various aspects, the antigen-binding protein is a humanized version of AB1 as set forth in Table B or B1 with one or more amino acid substitutions in the light chain variable region at one or more (e.g., 1, 2, 3, 4, 5, 6, 7, 8, 9, 11, 12, or 13) of the following positions: 4, 21, 32, 34, 48, 51, 53, 61, 67, 79, 84, 91, and 93. In various instances, the antigen-binding protein comprises an amino acid sequence of SEQ ID NO: 431. In various aspects, the amino acids at the above-recited positions are selected from the amino acids according to the table below:

| Position | Amino acids | Position | Amino acids | Position | Amino acids |
| --- | --- | --- | --- | --- | --- |
| 1 | Q, D | 3 | V, Q | 4 | L, M |
| 9 | A, S | 10 | I, S | 11 | M, L |
| 15 | L, V | 17 | E, D | 21 | M, I |
| 24 | T, R | 27 | S, Q | 32 | T, V, F, D, S |
| 34 | F, L | 35 | H, S, Y, Q, N | 43 | S, K |
| 44 | S, A | 48 | W, L | 51 | S, T, Q, A |
| 52 | T, A | 53 | S, T, D, Q | 54 | N, S |
|  |  | 56 | A, Q | 61 | R, Q, S, D, |
| 67 | A, S, T, G | 71 | S, D | 72 | Y, F |
| 73 | S, T | 79 | M, L | 80 | E, Q |
| 81 | A, P | 84 | A, F | 90 | H, Q |
| 91 | Q, H, S | 93 | H, Q, S, Y | 94 | R, S |
| 97 | L, P | 101 | A, Q | 107 | L, I |
| 29 | V, I | 92 | Y, S | 95 | S, T |

Humanized AB3

In various aspects, the antigen-binding protein is a humanized version of AB3 as set forth in Table B or B1 with one or more amino acid substitutions in the heavy chain variable region at one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, or 33) of the following positions: 3, 5, 18, 19, 23, 31, 33, 35, 40, 42, 49, 50, 52, 53, 54, 55, 56, 57, 58, 59, 61, 64, 76, 79, 80, 81, 87, 94, 95, 99, 106, 112, 114. In various instances, the antigen-binding protein comprises an amino acid sequence of SEQ ID NO: 432. In various aspects, the antigen-binding protein is a humanized version of AB3 as set forth in Table B or B1 with one or more amino acid substitutions in the heavy chain variable region at one or more (e.g., 1, 2, 3, 4, 5, 6, or 7) of the following positions: 31, 35, 50, 55, 79, 99, 106. In various instances, the antigen-binding protein comprises an amino acid sequence of SEQ ID NO: 433. In various aspects, the amino acids at the above-recited positions are selected from the amino acids according to the table below:

| Position | Amino acids | Position | Amino acids | Position | Amino acids |
|---|---|---|---|---|---|
| 3 | K, Q | 5 | E, L | 18 | M, L |
| 19 | K, R | 23 | V, A | 31 | N, S, R |
| 33 | W, A | 35 | N, S, H | 40 | S, A |
| 42 | E, G | 49 | A, S | 50 | Q, S, N, H, A |
|  |  | 52 | R, S | 53 | L, G |
| 54 | K, S | 55 | S, N, T, A, G | 56 | D, G |
|  |  |  |  | 59 | A, S |
| 61 | H, Y | 64 | E, D | 76 | D, N |
| 79 | R, N, Q, D, S | 80 | S, T | 81 | V, L |
| 87 | N, S | 94 | G, A | 95 | T, V, I |
| 99 | N, D, T, K, A | 106 | C, Y, A, S, T | 112 | T, L |
| 114 | I, T |  |  |  |  |

In various aspects, the antigen-binding protein is a humanized version of AB3 as set forth in Table B or B1 with one or more amino acid substitutions in the light chain variable region at one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, or 29) of the following positions: 9, 17, 18, 25, 27, 28, 30, 34, 40, 43, 45, 48, 50, 52, 53, 55, 56, 70, 72, 74, 76, 84, 85, 90, 91, 93, 94, 97, and 100. In various instances, the antigen-binding protein comprises an amino acid sequence of SEQ ID NO: 434. In various aspects, the antigen-binding protein is a humanized version of AB3 as set forth in Table B or B1 with one or more amino acid substitutions in the light chain variable region at one or more (e.g., 1, 2, 3, 4, 5, 6, 7, 8, or 9) of the following positions: 25, 34, 48, 53, 55, 84, 85, 90, and 93. In various instances, the antigen-binding protein comprises an amino acid sequence of SEQ ID NO: 435. In various aspects, the amino acids at the above-recited positions are selected from the amino acids according to the table below:

| Position | Amino acids | Position | Amino acids | Position | Amino acids |
|---|---|---|---|---|---|
| 9 | A, S | 17 | E, D | 18 | T, R |
| 25 | I, V, L, T, A | 34 | A, S, N | 40 | Q, P |
| 43 | S, A | 45 | Q, K | 48 | V, I |
| 53 | I, V, L, T, S | 55 | V, T, L, A, Q | 70 | Q, D |
| 72 | S, T | 74 | K, T | 76 | N, S |
| 84 | G, A | 85 | N, Q, S, T | 90 | H, Q, S, T |
| 93 | T, S, N, G | 100 | G, Q | 27 | E, Q |
| 28 | N, S | 30 | Y, S | 50 | N, A |
| 52 | K, S | 56 | E, S | 91 | H, S |
| 94 | V, T | 97 | T, P |  |  |

Humanized AB4

In various aspects, the antigen-binding protein is a humanized version of AB4 as set forth in Table B or B1 with one or more amino acid substitutions in the heavy chain variable region at one or more (e.g., 1, 2, 3, 4, 5, 6, 7, 8, 9, 10, 11, 12, 13, 14, 15, 16, 17, 18, 20, 21, 22, 23, 24, 25, 26, 27, 28, 29, 30, 31, 32, 33, 34, 35, or 36 of the following positions: 5, 11, 12, 13, 20, 29, 31, 33, 37, 38, 40, 45, 48, 50, 55, 56, 57, 59, 61, 62, 65, 66, 67, 68, 70, 72, 74, 76, 79, 82, 84, 87, 91, 97, 101, 117. In various instances, the antigen-binding protein comprises an amino acid sequence of SEQ ID NO: 436. In various aspects, the antigen-binding protein is a humanized version of AB4 as set forth in Table B or B1 with one or more amino acid substitutions in the heavy chain variable region at one or more (e.g., 1, 2, 3, 4, 5, 6, 7, 8, 9, 10, 11, 12, 13, 14, 15, 16, 17, 18, or 19) of the following positions: 20, 29, 31, 37, 45, 48, 56, 59, 61, 62, 65, 66, 68, 70, 74, 79, 84, 97, and 101. In various instances, the antigen-binding protein comprises an amino acid sequence of SEQ ID NO: 437. In various aspects, the amino acids at the above-recited positions are selected from the amino acids according to the table below:

| Position | Amino acids | Position | Amino acids | Position | Amino acids |
|---|---|---|---|---|---|
| 5 | Q, V | 11 | L, V | 12 | A, K |
| 13 | R, K | 20 | M, V | 33 | T, Y |
| 37 | I, V, F, Y | 38 | K, R | 40 | R, A |
| 45 | Q, L, V, T, N | 48 | I, M | 50 | Y, I |
| 55 | S, G | 56 | T, G, S, V, D | 57 | Y, S |
| 59 | H, K, S, Q, N | 61 | I, A, N, F, Y, V | 62 | K, Q |
| 65 | K, Q | 66 | D, G | 67 | K, R |
| 68 | A, V | 70 | L, M | 72 | A, R |
| 74 | T, K | 76 | S, T | 79 | A, V |
| 82 | Q, E | 84 | R, S, Q, D | 87 | T, R |
| 91 | S, T | 97 | S, A, T, V | 101 | L, V, F |
| 117 | A, S | 29 | F, Y, S, T | 31 | S, T, Y, D |

In various aspects, the antigen-binding protein is a humanized version of AB4 as set forth in Table B or B1 with one or more amino acid substitutions in the light chain variable region at one or more (e.g., 1, 2, 3, 4, 5, 6, 7, 8, 9, 10, 11, 12, 13, 14, 15, 16, 17, 18, 19, 20, 21, 22, 23, or 24) of the following positions: 7, 14, 17, 18, 31, 33, 39, 41, 42, 44, 50, 51, 55, 57, 60, 81, 88, 92, 94, 95, 96, 99, 100, 105. In various instances, the antigen-binding protein comprises an amino acid sequence of SEQ ID NO: 438. In various aspects, the antigen-binding protein is a humanized version of AB4 as set forth in Table B or B1 with one or more amino acid substitutions in the light chain variable region at one or more (e.g., 1, 2, 3, 4, 5, 6, or 7) of the following positions: 33, 39, 55, 57, 81, 95, and 96. In various instances, the antigen-binding protein comprises an amino acid sequence of SEQ ID NO: 439. In various aspects, the amino acids at the above-recited positions are selected from the amino acids according to the table below:

| Position | Amino acids | Position | Amino acids | Position | Amino acids |
|---|---|---|---|---|---|
| 7 | T, S | 14 | S, T | 17 | D, Q |
| 18 | Q, P | 31 | Y, H | 33 | D, N, E, Q |
| 39 | H, N, Q, D | 41 | F, Y | 42 | L, Q |
| 44 | K, R | 50 | K, R | 51 | R, L |
| 55 | K, R, Q | 57 | S, T, V | 60 | D, F |
| 81 | R, S, N, D | 88 | L, V | 92 | F, Y |
| 94 | M, S | 95 | Q, H, T | 96 | S, T, G, D |
| 99 | W, V | 105 | G, Q |  |  |

Humanized AB9

In various aspects, the antigen-binding protein is a humanized version of AB9 as set forth in Table B or B1 with one or more amino acid substitutions in the heavy chain variable region at one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, or 29) of the following positions: 1, 5, 9, 11, 12, 20, 38, 40, 41, 43, 44, 48, 61, 63, 65, 67, 69, 70, 72, 73, 74, 76, 79, 84, 87, 91, 93, 112, and 113. In various instances, the antigen-binding protein comprises an amino acid sequence of SEQ ID NO: 444. In various aspects, the amino acids at the above-recited positions are selected from the amino acids according to the table below:

| Position | Amino acids | Position | Amino acids | Position | Amino acids |
|---|---|---|---|---|---|
| 1 | E, Q | 5 | Q, V | 9 | P, A |
| 11 | L, V | 12 | V, K | 20 | M, V |
| 38 | K R, | 40 | S, A | 41 | H, P |
| 43 | K Q | 44 | S, G | 48 | I, M |
| 61 | N, A | 63 | N, K | 65 | K, Q |
| 67 | K, R | 69 | A, V | 70 | L, M |
| 72 | V, R | 73 | N, D | 74 | K, T |
| 76 | S, T | 79 | A, V | 84 | R, S |
| 87 | T, R | 91 | S, T | 93 | A, V |
| 112 | T, L | 113 | L, V | | |

In various aspects, the antigen-binding protein is a humanized version of AB9 as set forth in Table B or B1 with one or more amino acid substitutions in the light chain variable region at one or more (e.g., 1, 2, 3, 4, 5, 6, 7, 8, 9, 10, 11, 12, 13, 14, or 15) of the following positions: 9, 11, 15, 17, 18, 43, 45, 70, 72, 73, 74, 80, 84, 85, and 100. In various instances, the antigen-binding protein comprises an amino acid sequence of SEQ ID NO: 445. In various aspects, the amino acids at the above-recited positions are selected from the amino acids according to the table below:

| Position | Amino acids | Position | Amino acids | Position | Amino acids |
|---|---|---|---|---|---|
| 9 | A, S | 11 | Q, L | 15 | L, V |
| 17 | E, D | 18 | S, R | 43 | S, A |
| 45 | Q, K | 70 | R, D | 72 | S, T |
| 73 | F, L | 74 | K, R | 80 | A, P |
| 84 | V, A | 85 | S, T | 100 | G, Q |

Humanized AB11

In various aspects, the antigen-binding protein is a humanized version of AB11 as set forth in Table B or B1 with one or more amino acid substitutions in the heavy chain variable region at one or more (e.g., 1, 2, 3, 4, 5, 6, 7, 8, 9, 10, 11, 12, 13, 14, or 15) of the following positions: 1, 15, 18, 19, 42, 49, 63, 75, 76, 78, 80, 84, 88, and 93. In various instances, the antigen-binding protein comprises an amino acid sequence of SEQ ID NO: 446. In various aspects, the amino acids at the above-recited positions are selected from the amino acids according to the table below:

| Position | Amino acids | Position | Amino acids | Position | Amino acids |
|---|---|---|---|---|---|
| 1 | D, E | 15 | R, G | 18 | R, L |
| 19 | K, R | 42 | E, G | 49 | A, S |
| 63 | T, S | 75 | P, A | 76 | T, K |
| 78 | T, S | 80 | F, Y | 84 | T, N |
| 88 | S, A | 93 | M, V | | |

In various aspects, the antigen-binding protein is a humanized version of AB11 as set forth in Table B or B1 with one or more amino acid substitutions in the light chain variable region at one or more (e.g., 1, 2, 3, 4, 5, 6, 7, 8, 9, 10, 11, 12, 13, 14, or 15) of the following positions: 4, 9, 17, 22, 64, 78, 80, 81, 82, 83, 84, 87, 89, 104, and 110, optionally, one or more of the following positions: 4, 82, 110. In various instances, the antigen-binding protein comprises an amino acid sequence of SEQ ID NO: 447 or 448. In various aspects, the amino acids at the above-recited positions are selected from the amino acids according to the table below:

| Position | Amino acids | Position | Amino acids | Position | Amino acids |
|---|---|---|---|---|---|
| 4 | L, M | 9 | A, D | 17 | Q, E |
| 22 | S, N | 64 | A, D | 78 | N, T |
| 80 | H, S | 81 | P, S | 82 | V, L |
| 83 | E, Q | 84 | E, A | 87 | A, V |
| 89 | T, V | 104 | A, Q | 110 | L, I |

In various embodiments, the antigen-binding protein comprises (a) a heavy chain variable region amino acid sequence set forth in in Table C or a sequence selected from the group consisting of: 376-379, 384-387, 391-396, 403-408, 412, 413, and 422-427 or a variant sequence thereof which differs by only one or two amino acids or which has at least or about 70%, or about 80%, or about 85%, or about 90%, or about 95% sequence identity; or (b) a light chain variable region amino acid sequence set forth in Table C or a sequence selected from the group consisting of: 380-383, 388-390, 397-402, 409-411, 414, 415, or a variant sequence thereof which differs by only one or two amino acids or which has at least or about 70%, or about 80%, or about 85%, or about 90%, or about 95% sequence identity; or (c) both (a) and (b).

TABLE C

| | Humanized Light Chain Variable Region | Humanized Heavy Chain Variable Region |
|---|---|---|
| AB1 | 380, 381, 382, 383 | 376, 377, 378, 379 |
| AB3 | 388, 389, 390 | 384, 385, 386, 387, 422 |
| AB4 | 397, 398, 399, 400, 401, 402 | 391, 392, 392, 394, 395, 396, 423, 424, 425, 426, 427 |
| AB9 | 409, 410, 411, | 403, 404, 405, 406, 407, 408 |
| AB11 | 414, 415 | 412, 413 |

In various embodiments, the humanized antigen-binding protein comprises a pair of amino acid sequences as shown in Table D. Further embodiments include CLDN6-specific antigen-binding proteins comprising CDRs1-3 from a heavy chain variable region shown in Table D; and CDRs1-3 from a light chain variable region shown in Table D. In a preferred embodiment, the CLDN6-specific antigen-binding protein comprises (i) CDRs1-3 from a heavy chain variable region comprising the amino acid sequence set forth in SEQ ID NO: 387; and (ii) CDRs1-3 from a light chain variable region comprising the amino acid sequence set forth in SEQ ID NO: 389 of Table D.

TABLE D

| Humanized AB | HC | LC |
|---|---|---|
| 1-1 | 376 | 380 |
| 1-2 | 377 | 380 |
| 1-3 | 377 | 381 |
| 1-4 | 377 | 382 |
| 1-5 | 377 | 383 |
| 1-6 | 378 | 381 |
| 1-7 | 378 | 382 |
| 1-8 | 378 | 383 |
| 1-9 | 379 | 381 |
| 1-10 | 379 | 382 |
| 1-11 | 379 | 383 |
| 3-1 | 384 | 388 |
| 3-2 | 385 | 388 |
| 3-3 | 385 | 389 |
| 3-4 | 386 | 388 |
| 3-5 | 386 | 389 |
| 3-6 | 387 | 388 |
| 3-7 | 387 | 389 |

TABLE D-continued

| Humanized AB | HC | LC |
|---|---|---|
| 3-9 | 422 | 389 |
| 4-1 | 391 | 397 |
| 4-2 | 392 | 397 |
| 4-3 | 392 | 398 |
| 4-4 | 393 | 398 |
| 4-5 | 394 | 398 |
| 4-6 | 395 | 398 |
| 4-7 | 396 | 398 |
| 4-8 | 423 | 398 |
| 4-9 | 424 | 398 |
| 4-10 | 425 | 398 |
| 4-11 | 426 | 398 |
| 4-12 | 427 | 398 |
| 9-1 | 403 | 409 |
| 9-2 | 404 | 409 |
| 9-3 | 405 | 410 |
| 9-4 | 405 | 411 |
| 9-5 | 406 | 410 |
| 9-6 | 406 | 411 |
| 9-7 | 407 | 410 |
| 9-8 | 407 | 411 |
| 9-9 | 408 | 410 |
| 9-10 | 408 | 411 |
| 11-1 | 412 | 414 |
| 11-2 | 413 | 414 |
| 11-3 | 413 | 415 |

In various embodiments, the antigen-binding protein comprises a pair of variant sequences, each having at least or about 70% (e.g., at least about 80%, at least about 85%, at least about 90%, at least about 95%) sequence identity to a SEQ ID NO listed in Table C. In various embodiments, the antigen-binding protein comprises a pair of sequences: one sequence selected from a SEQ ID NO: listed in Table C and another sequence which is a variant sequence having at least or about 70% (e.g., at least about 80%, at least about 85%, at least about 90%, at least about 95%) sequence identity to a sequence having a SEQ ID NO: listed in Table D a sequence having a SEQ ID NO: listed in Table C.

In various embodiments, the antigen-binding protein comprises a pair of sequences: one sequence selected from a SEQ ID NO listed in Table D, and another sequence which is a variant sequence having at least or about 70% (e.g., at least about 80%, at least about 85%, at least about 90%, at least about 95%) sequence identity to a sequence having a SEQ ID NO listed in Table D. For instance, in various aspects, the antigen-binding protein comprises a sequences of SEQ ID NO: 387 and the antigen-binding protein further comprises a variant sequence having at least or about 70% (e.g., at least about 80%, at least about 85%, at least about 90%, at least about 95%) sequence identity to SEQ ID NO 389.

In various instances, the antigen-binding protein is a humanized antigen-binding protein as set forth in Table D with one or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35) amino acid substitutions in the heavy chain (HC) variable region or in the light chain (LC) variable region, or in both. In exemplary aspects, the antigen-binding protein is a humanized antigen-binding protein of AB1-11 with one or more amino acid substitutions in the HC variable region, the LC variable region, or both. In exemplary aspects, the antigen-binding protein comprises a HC of SEQ ID NO: 379 with 1, 2, 3, 4, or 5 amino acid substitutions. In exemplary aspects, the antigen-binding protein comprises a HC CDR1 of SEQ ID NO: 504, a HC CDR2 of SEQ ID NO: 505, a HC CDR3 of SEQ ID NO: 506, or a combination thereof. In exemplary instances, the antigen-binding protein comprises a HC of SEQ ID NO: 503. In some aspects, the antigen-binding protein comprises a HC of any one of SEQ ID NOs: 496-501. In various instances, the light chain variable region comprises a LC CDR1 of SEQ ID NO: 449, a LC CDR2 of SEQ ID NO: 450, a LC CDR3 of SEQ ID NO: 451, or a combination thereof. In some aspects, the antigen-binding protein comprises a LC of any one of SEQ ID NOs: 380-383, and 479. In exemplary instances, the antigen-binding protein comprises a LC of SEQ ID NO: 383. In exemplary aspects, the antigen-binding protein is a humanized antigen-binding protein of AB3-7 with one or more amino acid substitutions in the HC variable region, the LC variable region, or both. In exemplary aspects, the antigen-binding protein comprises a HC of SEQ ID NO: 387 with 1, 2, 3, 4, 5, or 6 amino acid substitutions. In exemplary aspects, the antigen-binding protein comprises a HC CDR1 of SEQ ID NO: 507, a HC CDR2 of SEQ ID NO: 508, a HC CDR3 of SEQ ID NO: 509, or a combination thereof. In exemplary instances, the antigen-binding protein comprises a HC of SEQ ID NO: 502. In some aspects, the antigen-binding protein comprises a HC of any one of SEQ ID NOs: 490-495. In various instances, the light chain variable region comprises a LC CDR1 of SEQ ID NO: 476, a LC CDR2 of SEQ ID NO: 477, a LC CDR3 of SEQ ID NO: 454, or a combination thereof. In some aspects, the antigen-binding protein comprises a LC of any one of SEQ ID NOs: 388-390, and 481. In exemplary instances, the antigen-binding protein comprises a LC of SEQ ID NO: 389. In exemplary aspects, the antigen-binding protein is a humanized antigen-binding protein of AB3 with one or more amino acid substitutions in the HC variable region, the LC variable region, or both. In exemplary aspects, the antigen-binding protein comprises a HC of SEQ ID NO: 139 with 1, 2, 3, 4, or 5 (or more) amino acid substitutions. In some aspects, the antigen-binding protein comprises a HC of any one of SEQ ID NOs: 510 In exemplary aspects, the antigen-binding protein comprises a HC of SEQ ID NO: 138 with 1, 2, 3, 4, or 5 (or more) amino acid substitutions. In some aspects, the antigen-binding protein comprises a HC of any one of SEQ ID NOs: 511. In exemplary aspects, the antigen-binding protein is a humanized antigen-binding protein of AB1 with one or more amino acid substitutions in the HC variable region, the LC variable region, or both. In exemplary aspects, the antigen-binding protein comprises a HC of SEQ ID NO: 135 with 1, 2, 3, 4, or 5 (or more) amino acid substitutions. In some aspects, the antigen-binding protein comprises a HC of any one of SEQ ID NOs: 513. In exemplary aspects, the antigen-binding protein comprises a HC of SEQ ID NO: 134 with 1, 2, 3, 4, or 5 (or more) amino acid substitutions. In some aspects, the antigen-binding protein comprises a HC of any one of SEQ ID NOs: 512. In some aspects, the antigen-binding protein comprises a HC sequence of SEQ ID NO: 512 with 1, 2, 3, 4, or 5 (or more) amino acid substitutions.

Compositions, Pharmaceutical Compositions and Formulations

Compositions comprising an antigen-binding protein as presently disclosed are provided herein.

In some aspects, the composition comprises agents which enhance the chemico-physico features of the antigen-binding protein, e.g., via stabilizing the antigen-binding protein at certain temperatures, e.g., room temperature, increasing shelf life, reducing degradation, e.g., oxidation protease mediated degradation, increasing half-life of the antigen-binding protein, etc. In some aspects, the composition comprises any of the agents disclosed herein as a heterologous moiety, optionally in admixture with the antigen-binding proteins of the present disclosure or conjugated to the antigen-binding proteins.

In various aspects of the present disclosure, the composition additionally comprises a pharmaceutically acceptable carrier, diluents, or excipient. In some embodiments, the conjugate as presently disclosed (hereinafter referred to as "active agent") is formulated into a pharmaceutical composition comprising the active agent, along with a pharmaceutically acceptable carrier, diluent, or excipient. In this regard, the present disclosure further provides pharmaceutical compositions comprising an active agent which is intended for administration to a subject, e.g., a mammal.

In some embodiments, the active agent is present in the pharmaceutical composition at a purity level suitable for administration to a patient. In some embodiments, the active agent has a purity level of at least about 90%, about 91%, about 92%, about 93%, about 94%, about 95%, about 96%, about 97%, about 98% or about 99%, and a pharmaceutically acceptable diluent, carrier or excipient. In some embodiments, the compositions contain an active agent at a concentration of about 0.001 to about 30.0 mg/ml.

In various aspects, the pharmaceutical compositions comprise a pharmaceutically acceptable carrier. As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

The pharmaceutical composition can comprise any pharmaceutically acceptable ingredients, including, for example, acidifying agents, additives, adsorbents, aerosol propellants, air displacement agents, alkalizing agents, anticaking agents, anticoagulants, antimicrobial preservatives, antioxidants, antiseptics, bases, binders, buffering agents, chelating agents, coating agents, coloring agents, desiccants, detergents, diluents, disinfectants, disintegrants, dispersing agents, dissolution enhancing agents, dyes, emollients, emulsifying agents, emulsion stabilizers, fillers, film forming agents, flavor enhancers, flavoring agents, flow enhancers, gelling agents, granulating agents, humectants, lubricants, mucoadhesives, ointment bases, ointments, oleaginous vehicles, organic bases, pastille bases, pigments, plasticizers, polishing agents, preservatives, sequestering agents, skin penetrants, solubilizing agents, solvents, stabilizing agents, suppository bases, surface active agents, surfactants, suspending agents, sweetening agents, therapeutic agents, thickening agents, tonicity agents, toxicity agents, viscosity-increasing agents, water-absorbing agents, water-miscible cosolvents, water softeners, or wetting agents. See, e.g., the *Handbook of Pharmaceutical Excipients*, Third Edition, A. H. Kibbe (Pharmaceutical Press, London, UK, 2000), which is incorporated by reference in its entirety. *Remington's Pharmaceutical Sciences*, Sixteenth Edition, E. W. Martin (Mack Publishing Co., Easton, Pa., 1980), which is incorporated by reference in its entirety.

In various aspects, the pharmaceutical composition comprises formulation materials that are nontoxic to recipients at the dosages and concentrations employed. In specific embodiments, pharmaceutical compositions comprising an active agent and one or more pharmaceutically acceptable salts; polyols; surfactants; osmotic balancing agents; tonicity agents; anti-oxidants; antibiotics; antimycotics; bulking agents; lyoprotectants; anti-foaming agents; chelating agents; preservatives; colorants; analgesics; or additional pharmaceutical agents. In various aspects, the pharmaceutical composition comprises one or more polyols and/or one or more surfactants, optionally, in addition to one or more excipients, including but not limited to, pharmaceutically acceptable salts; osmotic balancing agents (tonicity agents); anti-oxidants; antibiotics; antimycotics; bulking agents; lyoprotectants; anti-foaming agents; chelating agents; preservatives; colorants; and analgesics.

In certain embodiments, the pharmaceutical composition can contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates, glutamate or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20 or polysorbate 80 (PS80), triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. See, REMINGTON'S PHARMACEUTICAL SCIENCES, 18" Edition, (A. R. Genrmo, ed.), 1990, Mack Publishing Company.

The pharmaceutical compositions can be formulated to achieve a physiologically compatible pH. In some embodiments, the pH of the pharmaceutical composition can be for example between about 4 or about 5 and about 8.0 or about 4.5 and about 7.5 or about 5.0 to about 7.5. In various embodiments, the pH of the pharmaceutical composition is between 5.5 and 7.5.

Routes of Administration

With regard to the present disclosure, the active agent, or pharmaceutical composition comprising the same, can be administered to the subject via any suitable route of administration. For example, the active agent can be administered to a subject via parenteral administration, such as, for example, intravenous infusion or subcutaneous injection.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The term, "parenteral" means not through the alimentary canal but by some other route such as subcutaneous, intramuscular, intraspinal, or intravenous. The active agent of the present disclosure can be administered with a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-153-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations in some embodiments contain from about 0.5% to about 25% by weight of the active agent of the present disclosure in solution. Preservatives and buffers can be used. In order to minimize or eliminate irritation at the site of injection, such compositions can contain one or more nonionic surfactants having a hydrophile-lipophile balance (HLB) of from about 12 to about 17. The quantity of surfactant in such formulations will typically range from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations in some aspects are presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions in some aspects are prepared from sterile powders, granules, and tablets of the kind previously described.

Injectable formulations are in accordance with the present disclosure. The requirements for effective pharmaceutical carriers for injectable compositions are well-known to those of ordinary skill in the art (see, e.g., *Pharmaceutics and Pharmacy Practice*, J. B. Lippincott Company, Philadelphia, PA, Banker and Chalmers, eds., pages 238-250 (1982), and *ASHP Handbook on Injectable Drugs*, Toissel, 4th ed., pages 622-630 (1986)). Injectable formulations suitable for subcutaneous administration may be co-formulated with hyaluronidase (U.S. Pat. No. 9,084,743).

Kits

In some embodiments, the antigen-binding proteins of the present disclosure are provided in a kit. In various aspects, the kit comprises the ADC as a unit dose. For purposes herein "unit dose" refers to a discrete amount dispersed in a suitable carrier. In various aspects, the unit dose is the amount sufficient to provide a subject with a desired effect, e.g., inhibition of tumor growth, reduction of tumor size, treatment of cancer. Accordingly, provided herein are kits comprising an ADC of the present disclosure optionally provided in unit doses. In various aspects, the kit comprises several unit doses, e.g., a week or month supply of unit doses, optionally, each of which is individually packaged or otherwise separated from other unit doses. In some embodiments, the components of the kit/unit dose are packaged with instructions for administration to a patient. In some embodiments, the kit comprises one or more devices for administration to a patient, e.g., a needle and syringe, and the like. In some aspects, the ADC of the present disclosure is pre-packaged in a ready to use form, e.g., a syringe, an intravenous bag, etc. In some aspects, the kit further comprises other therapeutic or diagnostic agents or pharmaceutically acceptable carriers (e.g., solvents, buffers, diluents, etc.), including any of those described herein.

Various Embodiments

In certain embodiments, the disclosure relates to a method for inhibiting a solid tumor expressing claudin-6 in a human subject, comprising administering to the human subject an effective amount of a composition comprising conjugates of a CLDN6-specific antigen-binding protein covalently bound to heterologous moieties comprising structural formula (I):

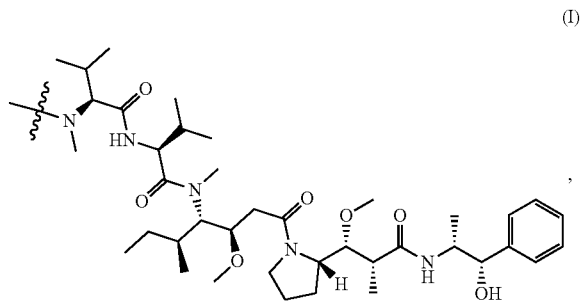 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

(I)

wherein
a first plurality of the conjugates are bound to four heterologous moieties comprising structural formula (I);
at least about 95% of the first plurality of conjugates are structurally homogenous; and
the effective amount is in a range of about
  1.7 mg/kg to 6 mg/kg;
  2.0 mg/kg to 6 mg/kg; or
  2.4 mg/kg to 6 mg/kg.

In certain embodiments, the disclosure relates to any of the methods disclosed herein, wherein at a $C_{max}$ after administration, the percent of unbound circulating MMAE in serum is less than about 0.01% (w/v) thereby reducing toxicity in the subject and inhibiting the solid tumor. In certain embodiments, the percent of free MMAE is less than about 0.009% at $C_{max}$. In certain embodiments, the percent of free MMAE is less than about 0.008% at $C_{max}$. In certain embodiments, the percent of free MMAE is less than about 0.007% at $C_{max}$. In certain embodiments, the percent of free MMAE is less than about 0.006% at $C_{max}$. In certain embodiments, the percent of free MMAE is less than about 0.005% at $C_{max}$. In certain embodiments, the percent of free MMAE is less than about 0.004% at $C_{max}$. In certain embodiments, the percent of free MMAE is less than about 0.003% at $C_{max}$. In certain embodiments, the percent of free MMAE is less than about 0.0000010% at $C_{max}$. In certain embodiments, the percent of free MMAE is less than about 0.0000009% at $C_{max}$. In certain embodiments, the percent of free MMAE is less than about 0.0000008% at $C_{max}$. In certain embodiments, the percent of free MMAE is less than about 0.0000007% at $C_{max}$. In certain embodiments, the percent of free MMAE is less than about 0.0000006% at $C_{max}$. In certain embodiments, the percent of free MMAE is less than about 0.0000005% at $C_{max}$. In certain embodiments, the percent of free MMAE is less than about 0.0000004% at $C_{max}$. In certain embodiments, the percent of free MMAE is less than about 0.0000003% at $C_{max}$. In certain embodiments, the $C_{max}$ of the percent of free MMAE is determined after a single dose in cycle 1. In a separate embodiment, the $C_{max}$ of the percent of free MMAE is determined in cycle 3 after three separate administrations, three weeks apart of the composition comprising the conjugates of a CLDN6-specific antigen-binding protein covalently bound to heterologous moieties. In certain embodiments, the conjugate is an anti-CLDN6-specific antibody conjugated to a chemotherapeutic or cytotoxic agent. In certain embodiments, the conjugate is TORL-1-23.

In certain embodiments, the disclosure relates to any of the methods disclosed herein, wherein at a $C_{max}$ after administration, the unbound circulating MMAE in serum is less than about 5 ng/mL, thereby reducing toxicity in the subject and inhibiting the solid tumor. In certain embodiments, the free MMAE is less than about 4 ng/mL at $C_{max}$. In certain embodiments, the free MMAE is less than about 3 ng/mL at $C_{max}$. In certain embodiments, the free MMAE is less than about 2 ng/mL at $C_{max}$. In certain embodiments, the free MMAE is less than about 1 ng/mL at $C_{max}$. In certain embodiments, the free MMAE is less than about 0.5 ng/mL at $C_{max}$. In certain embodiments, the free MMAE is less than about 0.15 ng/mL at $C_{max}$. In certain embodiments, the free MMAE is less than about 0.12 ng/mL at $C_{max}$.

In certain embodiments, the disclosure relates to any of the methods disclosed herein, wherein at a $C_{max}$ after administration, the unbound circulating MMAE in serum is less than about 10 ng/mL, thereby reducing toxicity in the subject and inhibiting the solid tumor. In certain embodiments, the free MMAE is less than about 9 ng/mL at $C_{max}$. In certain embodiments, the free MMAE is less than about 8 ng/mL at $C_{max}$. In certain embodiments, the free MMAE is less than about 7 ng/mL at $C_{max}$. In certain embodiments, the free MMAE is less than about 6 ng/mL at $C_{max}$. In certain embodiments, the free MMAE is less than about 5 ng/mL at $C_{max}$. In certain embodiments, the free MMAE is less than about 4 ng/mL at $C_{max}$. In certain embodiments, the free MMAE is less than about 3 ng/mL at $C_{max}$.

In certain embodiments, the administration is a single dose administration of the conjugate at a dose between about 1.7 mg/kg to 6.0 mg/kg, inclusive. In certain embodiments, the administration is a single dose administration of the conjugate at a dose between about 1.7 mg/kg to 3.0 mg/kg, inclusive. In certain embodiments, the $C_{max}$ of the percent free MMAE is determined after administration of a single dose in cycle 1. In a separate embodiment, the $C_{max}$ of the percent free MMAE is determined in cycle 3 after three separate administrations, three weeks apart of the composition comprising the conjugates of a CLDN6-specific antigen-binding protein covalently bound to heterologous moieties. In certain embodiments, the administration is a single dose of the conjugate between at about 1.7 mg/kg to 3.0 mg/kg, inclusive. In certain embodiments, the conjugate is an anti-CLDN6-specific antibody conjugated to a chemotherapeutic or cytotoxic agent. In certain embodiments, the conjugate is TORL-1-23.

In certain embodiments, the disclosure relates to any of the methods disclosed herein, wherein at a dose normalized $C_{max}$ value for the unbound (free) circulating MMAE is less than about 35 pg/mL free MMAE per mg of the conjugate after administration of the conjugate, thereby reducing toxicity in the subject and inhibiting the solid tumor. In certain embodiments, the dose normalized $C_{max}$ value for free MMAE is less than about 30 pg/mL per mg of the conjugate. In certain embodiments the dose normalized $C_{max}$ value for free MMAE is less than about 25 pg/mL per mg of the conjugate. In certain embodiments, the dose normalized $C_{max}$ value for free MMAE is less than about 20 pg/mL per mg of the conjugate. In certain embodiments, the dose normalized $C_{max}$ value for free MMAE is less than about 15 pg/mL per mg of the conjugate. In certain embodiments, the dose normalized $C_{max}$ value for free MMAE is less than about 10 pg/mL per mg of the conjugate. In certain embodiments, the dose normalized $C_{max}$ is determined from the $C_{max}$ measured after a single administration of the conjugate. In certain embodiments, the dose normalized $C_{max}$ is determined from the $C_{max}$ measure after three administrations of the same dose with each dose separated by a three-week interval. In certain embodiments, the conjugate is an anti-CLDN6-specific antibody conjugated to a chemotherapeutic or cytotoxic agent. In certain embodiments, the conjugate is TORL-1-23.

In certain embodiments, the disclosure relates to any of the methods disclosed herein, wherein at a $C_{max}$ after first administration of 3.0 mg/kg the conjugate, the unbound circulating MMAE in serum is less than about 2.6 ng/mL, thereby reducing toxicity in the subject and inhibiting the solid tumor.

In certain embodiments, the disclosure relates to any of the methods disclosed herein, wherein at a $C_{max}$ after first administration of 2.4 mg/kg of the conjugate, the unbound circulating MMAE in serum is about 4.1±2.1 ng/mL, thereby reducing toxicity in the subject and inhibiting the solid tumor.

In certain embodiments, the disclosure relates to any of the methods disclosed herein, wherein at a $C_{max}$ after first administration of 2.0 mg/kg of the conjugate, the unbound circulating MMAE in serum is about 3.7±1.6 ng/mL, thereby reducing toxicity in the subject and inhibiting the solid tumor.

In certain embodiments, the disclosure relates to any of the methods disclosed herein, wherein at a $C_{max}$ after first administration of 1.7 mg/kg of the conjugate, the unbound circulating MMAE in serum is about 2.7±1.9 ng/mL, thereby reducing toxicity in the subject and inhibiting the solid tumor. In certain embodiments, the conjugate is an anti-CLDN6-specific antibody conjugated to a chemotherapeutic or cytotoxic agent. In certain embodiments, the conjugate is TORL-1-23.

In certain embodiments, the disclosure relates to any of the methods disclosed herein, wherein at a cycle 3 $C_{max}$ after three administrations of 1.7 mg/kg of the conjugate, the unbound circulating MMAE in serum is about 1.4±0.8 ng/mL, wherein the conjugate is administered once every three weeks and cycle 3 starts at the 3$^{rd}$ administration of the conjugate, thereby reducing toxicity in the subject and inhibiting the solid tumor. In certain embodiments, the conjugate is an anti-CLDN6-specific antibody conjugated to a chemotherapeutic or cytotoxic agent. In certain embodiments, the conjugate is TORL-1-23.

In certain embodiments, the disclosure relates to any of the methods disclosed herein, wherein the solid tumor is an ovarian tumor.

In certain embodiments, the disclosure relates to any of the methods disclosed herein, wherein the solid tumor is a bladder tumor.

In certain embodiments, the disclosure relates to any of the methods disclosed herein, wherein the solid tumor is a testicular tumor.

In certain embodiments, the disclosure relates to any of the methods disclosed herein, wherein the solid tumor is an endometrial tumor.

In certain embodiments, the disclosure relates to any of the methods disclosed herein, wherein the solid tumor is non-small cell lung cancer.

In certain embodiments, the disclosure relates to any of the methods disclosed herein, wherein the solid tumor is primary peritoneal cancer.

In certain embodiments, the disclosure relates to any of the methods disclosed herein, wherein the solid tumor is fallopian tube cancer.

In certain embodiments, the disclosure relates to any of the methods disclosed herein, wherein, after administration, the human subject does not experience peripheral neuropathy of grade 3 or higher severity, does not experience alopecia of grade 3 or higher severity, does not experience fatigue of grade 3 or higher severity, does not experience nausea, vomiting or anorexia of grade 3 or higher severity, or does not experience constipation of grade 3 or higher severity. In certain embodiments, the disclosure relates to any of the methods disclosed herein, wherein, after administration, the human subject does not experience any adverse event of grade 3 or higher severity.

In certain embodiments, the disclosure relates to any of the methods disclosed herein, wherein the effective amount is about 1.7 mg/kg to 5 mg/kg, 1.7 mg/kg to 4 mg/kg, or 1.7 mg/kg to 3 mg/kg. In certain embodiments, the disclosure relates to any of the methods disclosed herein, wherein the effective amount is about 2.0 mg/kg to 5 mg/kg, 2.0 mg/kg to 4 mg/kg or 2.0 mg/kg to 3 mg/kg. In certain embodiments, the disclosure relates to any of the methods disclosed herein, wherein the effective amount is about 2.4 mg/kg to 5 mg/kg, 2.4 mg/kg to 4 mg/kg or 2.4 mg/kg to 3 mg/kg. In certain embodiments, the disclosure relates to any of the methods disclosed herein, wherein the effective amount is about 1.7 mg/kg. In certain embodiments, the disclosure relates to any of the methods disclosed herein, wherein the effective amount is about 2.0 mg/kg. In certain embodiments, the disclosure relates to any of the methods disclosed herein, wherein the effective amount is about 2.4 mg/kg. In certain embodiments, the disclosure relates to any of the methods disclosed herein, wherein the effective amount is about 3.0 mg/kg. In certain embodiments, the disclosure relates to any of the methods disclosed herein, wherein the effective amount is about 4 mg/kg. In certain embodiments, the disclosure relates to any of the methods disclosed herein, wherein the effective amount is about 5 mg/kg.

In certain embodiments, the disclosure relates to any of the methods disclosed herein, wherein the effective amount of the composition is administered once every 1-4 weeks, for example once every 2-4 weeks, preferably once every 3 weeks.

In certain embodiments, the disclosure relates to any of the methods disclosed herein, wherein the composition is administered intravenously.

In certain embodiments, the disclosure relates to any of the methods disclosed herein, wherein the effective amount of the composition is administered over a time period from about 20 minutes to about 40 minutes, preferably over a time period of about 30 minutes.

In certain embodiments, the disclosure relates to any of the methods disclosed herein, wherein the human subject achieves a partial response.

In certain embodiments, the disclosure relates to any of the methods disclosed herein, wherein the human subject achieves a complete response.

In certain embodiments, the disclosure relates to any of the methods disclosed herein, wherein the composition further comprises a glutamate-sodium hydroxide buffer, sucrose, and polysorbate 80 (PS80).

In certain embodiments, the disclosure relates to any of the methods disclosed herein, wherein the composition further comprises dextrose and water.

In certain embodiments, the disclosure relates to any of the methods disclosed herein, wherein the composition further comprises sodium chloride and water.

In certain embodiments, the disclosure relates to any of the methods disclosed herein, wherein the average number of heterologous moieties per CLDN6-specific antigen-binding protein in the composition is about 3.5 to about 4, for example, about 3.6 to about 3.9, preferably about 3.7 to about 3.8. In certain embodiments, the disclosure relates to any of the methods disclosed herein, wherein the average number of heterologous moieties per CLDN6-specific antigen-binding protein in the composition is about 3.8 to about 3.9. In certain embodiments, the disclosure relates to any of the methods disclosed herein, wherein the average number of heterologous moieties per CLDN6-specific antigen-binding protein in the composition is at least 3.8.

In certain embodiments, the disclosure relates to any of the methods disclosed herein, wherein, in the first plurality of conjugates, the heterologous moieties are covalently conjugated at unpaired cysteine residues of the CLDN6-specific antigen-binding protein.

In certain embodiments, the disclosure relates to any of the methods disclosed herein, wherein, in the first plurality of conjugates, the heterologous moieties are covalently conjugated at cysteine residues resulting from cleavage of the heavy chain-light chain interchain disulfide bonds of the CLDN6-specific antigen-binding protein.

In certain embodiments, the disclosure relates to any of the methods disclosed herein, wherein about 95%, about 96%, about 97%, or about 98% of the first plurality of conjugates are structurally homogenous.

In certain embodiments, the disclosure relates to any of the methods disclosed herein, wherein a second plurality of the conjugates are bound to eight heterologous moieties comprising structural formula (I).

In certain embodiments, the disclosure relates to any of the methods disclosed herein, wherein a third plurality of the conjugates are bound to two heterologous moieties comprising structural formula (I).

In certain embodiments, the disclosure relates to any of the methods disclosed herein, wherein a fourth plurality of the conjugates are bound to six heterologous moieties comprising structural formula (I).

In certain embodiments, the disclosure relates to any of the methods disclosed herein, wherein the heterologous moiety comprising structural formula (I) has structural formula (II):

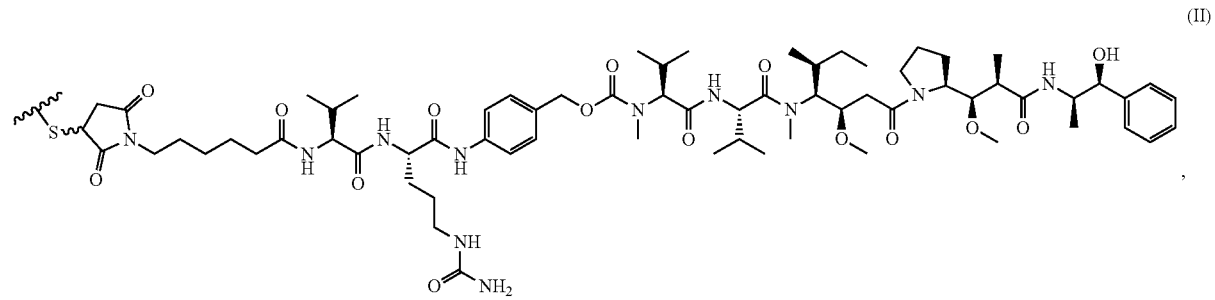 [SMILES: *SC1CC(=O)N(CCCCCC(=O)N[C@H](C(=O)N[C@@H](CCCNC(N)=O)C(=O)Nc2ccc(COC(=O)N(C)[C@H](C(=O)N[C@H](C(=O)N(C)[C@@H]([C@@H](C)CC)[C@@H](CC(=O)N3CCC[C@H]3[C@H](OC)[C@@H](C)C(=O)N[C@H](C)[C@@H](O)c3ccccc3)OC)C(C)C)C(C)C)cc2)C(C)C)C1=O]

(II)

wherein

is a covalent thiol bond to the CLDN6-specific antigen-binding protein.

In certain embodiments, the disclosure relates to any of the methods disclosed herein, wherein the subject has not received prior treatment for the solid tumor.

In certain embodiments, the disclosure relates to any of the methods disclosed herein, wherein the subject has received at least one prior treatment for the solid tumor. In certain embodiments, the disclosure relates to any of the methods disclosed herein, wherein the subject has received at least two prior treatments for the solid tumor. In certain embodiments, the disclosure relates to any of the methods disclosed herein, wherein the subject has received at least three prior treatments for the solid tumor. In certain embodiments, the disclosure relates to any of the methods disclosed herein, wherein the subject has received at least four prior treatments for the solid tumor.

In certain embodiments, the disclosure relates to any of the methods disclosed herein, wherein the CLDN6-specific antigen-binding protein is selected from a group consisting of:
(a) a heavy chain CDR1 amino acid sequence set forth in Table A or Table A1, or a variant sequence thereof which differs by only one or two amino acids;
(b) a heavy chain CDR2 amino acid sequence set forth in Table A or Table A1, or a variant sequence thereof which differs by only one or two amino acids;
(c) a heavy chain CDR3 amino acid sequence set forth in Table A or Table A1, or a variant sequence thereof which differs by only one or two amino acids;
(d) a light chain CDR1 amino acid sequence set forth in Table A or Table A1, or a variant sequence thereof which differs by only one or two amino acids;
(e) a light chain CDR2 amino acid sequence set forth in Table A or Table A1, or a variant sequence thereof which differs by only one or two amino acids;
(f) a light chain CDR3 amino acid sequence set forth in Table A or Table A1, or a variant sequence thereof which differs by only one or two amino acids; or a combination of any two or more of (a)-(f).

In certain embodiments, the disclosure relates to any of the methods disclosed herein, wherein the CLDN6-specific antigen-binding protein comprises a heavy chain CDR amino sequence selected from the group consisting of: SEQ ID NOs: 23, 24, 25, 455, 456, 457, and a variant sequence thereof which differs by only one or two amino acids.

In certain embodiments, the disclosure relates to any of the methods disclosed herein, wherein the CLDN6-specific antigen-binding protein comprises a light chain CDR amino sequence selected from the group consisting of: SEQ ID NOs: 20, 21, 22, 476, 477, 454, and a variant sequence thereof which differs by only one or two amino acids.

In certain embodiments, the disclosure relates to any of the methods disclosed herein, wherein the CLDN6-specific antigen-binding protein comprises an antibody that binds CLDN6 or antigen-binding fragment thereof comprising:
(a) a heavy chain CDR1 amino acid sequence set forth in SEQ ID NOs: 23 or 455, or a variant sequence thereof which differs by only one or two amino acids;
(b) a heavy chain CDR2 amino acid sequence set forth in SEQ ID NOs: 24 or 456, or a variant sequence thereof which differs by only one or two amino acids;
(c) a heavy chain CDR3 amino acid sequence set forth in SEQ ID NOs: 25 or 457, or a variant sequence thereof which differs by only one or two amino acids;
(d) a light chain CDR1 amino acid sequence set forth in SEQ ID NOs:20 or 476, or a variant sequence thereof which differs by only one or two amino acids;
(e) a light chain CDR2 amino acid sequence set forth in SEQ ID NOs:21 or 477, or a variant sequence thereof which differs by only one or two amino acids;
(f) a light chain CDR3 amino acid sequence set forth in SEQ ID NOs:22 or 454, or a variant sequence thereof which differs by only one or two amino acids; or
a combination of any two or more of (a)-(f).

In certain embodiments, the disclosure relates to any of the methods disclosed herein, wherein the CLDN6-specific antigen-binding protein comprises an antibody that binds CLDN6 or antigen-binding fragment thereof comprising:
the heavy chain (HC) CDR1-3 amino acid sequences of SEQ ID NOs: 23, 24, and 25, and the light chain (LC) CDR1-3 amino acid sequences of SEQ ID NOs: 20, 21, and 22; or
the heavy chain (HC) CDR1-3 amino acid sequences of SEQ ID NOs: 455, 456, and 457, and the light chain (LC) CDR1-3 amino acid sequences of SEQ ID NOs: 476, 477, and 454.

Additionally, the disclosure includes conjugates of a CLDN6-specific antigen-binding protein covalently bound to heterologous moieties comprising structural formula (I):

(I)

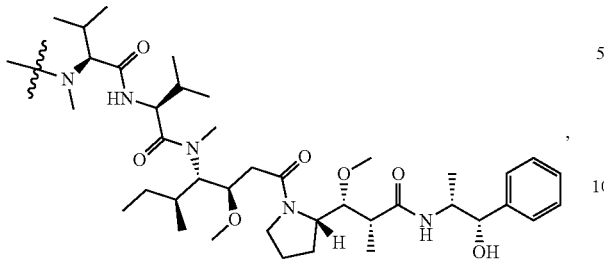

wherein
a first plurality of the conjugates are bound to four heterologous moieties comprising structural formula (I);
at least about 95% of the first plurality of conjugates are structurally homogenous; and
the effective amount is in a range of about
1.7 mg/kg to 6 mg/kg;
2.0 mg/kg to 6 mg/kg; or
2.4 mg/kg to 6 mg/kg for use in treating cancer.

In further embodiments, the disclosure relates to any of the methods disclosed herein, wherein the CLDN6-specific antigen-binding protein of the conjugates comprises an antibody that binds CLDN6 or antigen-binding fragment thereof comprising:
(i) HC CDR1 having a sequence GFTFSNYW (SEQ ID NO: 23);
(ii) HC CDR2 having a sequence IRLKSDNYAT (SEQ ID NO: 24),
(iii) HC CDR3 having a sequence XDGPPSGX (SEQ ID NO: 457), wherein X at position 1 is N and X at position 8 is S, T, A, C, or Y,
(iv) LC CDR1 having a sequence ENIYSY (SEQ ID NO: 20),
(v) LC CDR2 having a sequence NAK (SEQ ID NO: 21), and
(vi) LC CDR3 having a sequence QHHYTVPWT (SEQ ID NO: 22).

TORL-1-23 (also referred to as CLDN6-23-ADC) is an antibody drug conjugate comprising an antibody that binds CLDN6 comprising:
(i) HC CDR1 having a sequence GFTFSNYW (SEQ ID NO: 23);
(ii) HC CDR2 having a sequence IRLKSDNYAT (SEQ ID NO: 24),
(iii) HC CDR3 having a sequence XDGPPSGX (SEQ ID NO: 457), wherein X at position 1 is N and X at position 8 is S,
(iv) LC CDR1 having a sequence ENIYSY (SEQ ID NO: 20),
(v) LC CDR2 having a sequence NAK (SEQ ID NO: 21), and
(vi) LC CDR3 having a sequence QHHYTVPWT (SEQ ID NO: 22),
wherein the antibody is conjugated to about four molecules of MMAE, each via a linker comprising Val-Cit-PAB.

Additional Exemplary Embodiments

1. A method for inhibiting a solid tumor expressing claudin-6 (CLDN6) in a human subject, comprising administering to the human subject an effective amount of a composition comprising conjugates of a CLDN6-specific antigen-binding protein covalently bound to heterologous moieties comprising structural formula (I):

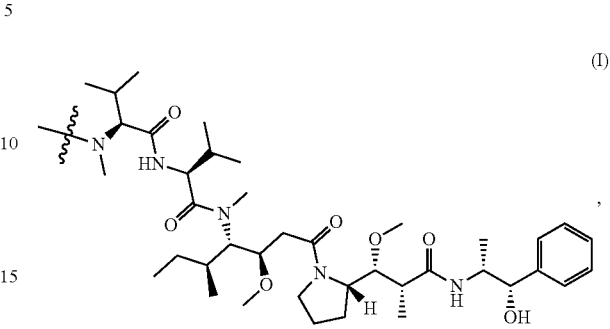

wherein
a first plurality of the conjugates are bound to four heterologous moieties comprising structural formula (I);
at least about 95% of the first plurality of conjugates are structurally homogenous; and
the effective amount is in a range of about
1.7 mg/kg to 6 mg/kg;
2.0 mg/kg to 6 mg/kg; or
2.4 mg/kg to 6 mg/kg.
2. The method of 1, wherein at a $C_{max}$ after administration, the percent of unbound circulating MMAE in serum is less than about 0.01% (w/v), thereby reducing toxicity in the subject and inhibiting the solid tumor.
3. The method of 2, wherein the percent of unbound circulating MMAE is less than about 0.009% (w/v) at $C_{max}$.
4. The method of 3, wherein the percent of unbound circulating MMAE is less than about 0.008% (w/v) at $C_{max}$.
5. The method of 4, wherein the percent of unbound circulating MMAE is less than about 0.007% (w/v) at $C_{max}$.
6. The method of 5, wherein the percent of unbound circulating MMAE is less than about 0.006% (w/v) at $C_{max}$.
7. The method of 6, wherein the percent of unbound circulating MMAE is less than about 0.005% (w/v) at $C_{max}$.
8. The method of 7, wherein the percent of unbound circulating MMAE is less than about 0.004% (w/v) at $C_{max}$.
9. The method of 8, wherein the percent of unbound circulating MMAE is less than about 0.003% (w/v) at $C_{max}$.
10. The method of 1, wherein at a $C_{max}$ after administration, the unbound circulating MMAE in serum is less than about 9 ng/mL, thereby reducing toxicity in the subject and inhibiting the solid tumor.
11. The method of 10, wherein the unbound circulating MMAE is less than about 8 ng/mL at $C_{max}$.
12. The method of 11, wherein the unbound circulating MMAE is less than about 7 ng/mL at $C_{max}$.
13. The method of 12, wherein the unbound circulating MMAE is less than about 6 ng/mL at $C_{max}$.
14. The method of 13, wherein the unbound circulating MMAE is less than about 5 ng/mL at $C_{max}$.
15. The method of 14, wherein the unbound circulating MMAE is less than about 4 ng/mL at $C_{max}$.

16. The method of 15, wherein the unbound circulating MMAE is less than about 3 ng/mL at $C_{max}$.
17. The method of 1, wherein a dose normalized $C_{max}$ value for the unbound circulating MMAE is less than about 35 pg/mL per mg of the conjugate after administration of the conjugate, thereby reducing toxicity in the subject and inhibiting the solid tumor.
18. The method of 17, wherein the dose normalized $C_{max}$ value for unbound circulating MMAE is less than about 30 pg/mL per mg of the conjugate.
19. The method of 18, wherein the dose normalized $C_{max}$ value for unbound circulating MMAE is less than about 25 pg/mL per mg of the conjugate.
20. The method of 19, wherein the dose normalized $C_{max}$ value for unbound circulating MMAE is less than about 20 pg/mL per mg of the conjugate.
21. The method of 20, wherein the dose normalized $C_{max}$ value for unbound circulating MMAE is less than about 15 pg/mL per mg of the conjugate.
22. The method of 21, wherein the dose normalized $C_{max}$ value for unbound circulating MMAE is less than about 10 pg/mL per mg of the conjugate.
23. The method of 1, wherein at a $C_{max}$ after first administration of 3.0 mg/kg of the conjugate, the unbound circulating MMAE in serum is about 2.6 ng/mL, thereby reducing toxicity in the subject and inhibiting the solid tumor.
24. The method of 1, wherein at a $C_{max}$ after first administration of 2.4 mg/kg of the conjugate, the unbound circulating MMAE in serum is about 4.1±2.1 ng/mL, thereby reducing toxicity in the subject and inhibiting the solid tumor.
25. The method of 1, wherein at a $C_{max}$ after first administration of 2.0 mg/kg of the conjugate, the unbound circulating MMAE in serum is about 3.7±1.6 ng/mL, thereby reducing toxicity in the subject and inhibiting the solid tumor.
26. The method of 1, wherein at a $C_{max}$ after first administration of 1.7 mg/kg of the conjugate, the unbound circulating MMAE in serum is about 2.7±1.9 ng/mL, thereby reducing toxicity in the subject and inhibiting the solid tumor.
27. The method of 1, wherein cycle 3 $C_{max}$ after three administrations of 1.7 mg/kg of the conjugate, the unbound circulating MMAE in serum is about 1.4±0.8 ng/mL, wherein the conjugate is administered once every three weeks and cycle 3 starts at the $3^{rd}$ administration of the conjugate, thereby reducing toxicity in the subject and inhibiting the solid tumor.
28. The method of any one of 1-27, wherein the solid tumor is an ovarian tumor.
29. The method of any one of 1-27, wherein the solid tumor is a bladder tumor.
30. The method of any one of 1-27, wherein the solid tumor is a testicular tumor.
31. The method of any one of 1-27, wherein the solid tumor is an endometrial tumor.
32. The method of any one of 1-27, wherein the solid tumor is non-small cell lung cancer.
33. The method of any one of 1-27, wherein the solid tumor is primary peritoneal cancer.
34. The method of any one of 1-27, wherein the solid tumor is fallopian tube cancer.
35. The method of any one of 1-34, wherein, after administration, the human subject does not experience peripheral neuropathy of grade 3 or higher severity, does not experience alopecia of grade 3 or higher severity, does not experience fatigue of grade 3 or higher severity, does not experience nausea, vomiting or anorexia of grade 3 or higher severity, or does not experience constipation of grade 3 or higher severity.
36. The method of any one of 1-35, wherein, after administration, the human subject does not experience any adverse event of grade 3 or higher severity.
37. The method of any one of 1-36, wherein the effective amount is about 1.7 mg/kg to 5 mg/kg, 1.7 mg/kg to 4 mg/kg, or 1.7 mg/kg to 3 mg/kg.
38. The method of any one of 1-36, wherein the effective amount is about 2.0 mg/kg to 5 mg/kg, 2.0 mg/kg to 4 mg/kg or 2.0 mg/kg to 3 mg/kg.
39. The method of any one of 1-36, wherein the effective amount is about 2.4 mg/kg to 5 mg/kg, 2.4 mg/kg to 4 mg/kg or 2.4 mg/kg to 3 mg/kg.
40. The method of any one of 1-36, wherein the effective amount is about 1.7 mg/kg.
41. The method of any one of 1-36, wherein the effective amount is about 2.0 mg/kg.
42. The method of any one of 1-36, wherein the effective amount is about 2.4 mg/kg.
43. The method of any one of 1-36, wherein the effective amount is about 3.0 mg/kg.
44. The method of any one of 1-36, wherein the effective amount is about 3.6 mg/kg.
45. The method of any one of 1-36, wherein the effective amount is about 4 mg/kg.
46. The method of any one of 1-45, wherein the effective amount of the composition is administered once every 1-4 weeks, for example once every 2-4 weeks, preferably once every 3 weeks.
47. The method of any one of 1-46, wherein the composition is administered intravenously.
48. The method of any one of 1-47, wherein the effective amount of the composition is administered over a time period from about 20 minutes to about 40 minutes, preferably over a time period of about 30 minutes.
49. The method of any one of 1-48, wherein the human subject achieves a partial response.
50. The method of any one of 1-48, wherein the human subject achieves a complete response.
51. The method of any one of 1-50, wherein the composition further comprises a glutamate-sodium hydroxide buffer, sucrose, and polysorbate 80 (PS80).
52. The method of any one of 1-51, wherein the composition further comprises dextrose and water.
53. The method of any one of 1-51, wherein the composition further comprises sodium chloride and water.
54. The method of any one of 1-53, wherein the average number of heterologous moieties per CLDN6-specific antigen-binding protein in the composition is about 3.5 to about 4, for example, about 3.6 to about 3.9, preferably about 3.7 to about 3.8.
55. The method of any one of 1-54, wherein, in the first plurality of conjugates, the heterologous moieties are covalently conjugated at unpaired cysteine residues of the CLDN6-specific antigen-binding protein.
56. The method of any one of 1-54, wherein, in the first plurality of conjugates, the heterologous moieties are covalently conjugated at cysteine residues resulting from cleavage of the heavy chain-light chain interchain disulfide bonds of the CLDN6-specific antigen-binding protein.
57. The method of any one of 1-56, wherein about 95%, about 96%, about 97%, or about 98% of the first plurality of conjugates are structurally homogenous.

58. The method of any one of 1-57, wherein the heterologous moiety comprising structural formula (I) has structural formula (II):

(II)

wherein is a covalent thiol bond to the CLDN6-specific antigen-binding protein.

59. The method of any one of 1-58, wherein the subject has not received prior treatment for the solid tumor.
60. The method of any one of 1-58, wherein the subject has received at least one prior treatment for the solid tumor.
61. The method of any one of 1-58, wherein the subject has received at least two prior treatments for the solid tumor.
62. The method of any one of 1-58, wherein the subject has received at least three prior treatments for the solid tumor.
63. The method of any one of 1-58, wherein the subject has received at least four prior treatments for the solid tumor.
64. The method of anyone of 1-63, wherein the effective amount is in the range of 3.0 mg/kg to 3.6 mg/kg.
65. The method of any one of 1-64, wherein prior to administering to the human subject an effective amount of the composition, the human subject is administered an effective amount of a G-CSF.
66. The method of any one of 1-65, wherein the CLDN6-specific antigen-binding protein is selected from a group consisting of:
   (a) a heavy chain CDR1 amino acid sequence set forth in Table A or Table A1, or a variant sequence thereof which differs by only one or two amino acids;
   (b) a heavy chain CDR2 amino acid sequence set forth in Table A or Table A1, or a variant sequence thereof which differs by only one or two amino acids;
   (c) a heavy chain CDR3 amino acid sequence set forth in Table A or Table A1, or a variant sequence thereof which differs by only one or two amino acids;
   (d) a light chain CDR1 amino acid sequence set forth in Table A or Table A1, or a variant sequence thereof which differs by only one or two amino acids;
   (e) a light chain CDR2 amino acid sequence set forth in Table A or Table A1, or a variant sequence thereof which differs by only one or two amino acids;
   (f) a light chain CDR3 amino acid sequence set forth in Table A or Table A1, or a variant sequence thereof which differs by only one or two amino acids; or
   a combination of any two or more of (a)-(f).
67. The method of 66, wherein the CLDN6-specific antigen-binding protein comprises an antibody that binds CLDN6 or antigen-binding fragment thereof comprising:
   (a) the heavy chain (HC) CDR1-3 amino acid sequences of SEQ ID NOs: 23, 24, and 25, and the light chain (LC) CDR1-3 amino acid sequences of SEQ ID NOs: 20, 21, and 22; or
   (b) the heavy chain (HC) CDR1-3 amino acid sequences of SEQ ID NOs: 455, 456, and 457, and the light chain (LC) CDR1-3 amino acid sequences of SEQ ID NOs: 476, 477, and 454.
68. The method of any one of 1-67, wherein the CLDN6-specific antigen-binding protein comprises an antibody that binds CLDN6 or antigen-binding fragment thereof comprising:
   (i) HC CDR1 having a sequence GFTFSNYW (SEQ ID NO: 23);
   (ii) HC CDR2 having a sequence IRLKSDNYAT (SEQ ID NO: 24),
   (iii) HC CDR3 having a sequence XDGPPSGX (SEQ ID NO: 457), wherein X at position 1 is N and X at position 8 is S, T, A, C, or Y,
   (iv) LC CDR1 having a sequence ENIYSY (SEQ ID NO: 20),
   (v) LC CDR2 having a sequence NAK (SEQ ID NO: 21), and
   (vi) LC CDR3 having a sequence QHHYTVPWT (SEQ ID NO: 22).
69. The method of 68, wherein the CLDN6-specific antigen-binding protein comprises: HC CDR3 having a sequence XDGPPSGX (SEQ ID NO: 457), wherein X at position 1 is N and X at position 8 is S.
70. The method of any one of 1-67, wherein the CLDN6-specific antigen-binding protein comprises an antibody that binds CLDN6 or antigen-binding fragment thereof comprising:
   (i) CDRs1-3 from a heavy chain variable region comprising the amino acid sequence set forth in SEQ ID NO: 387; and
   (ii) CDRs1-3 from a light chain variable region comprising the amino acid sequence set forth in SEQ ID NO: 389.
71. A conjugate of a CLDN6-specific antigen-binding protein covalently bound to heterologous moieties comprising structural formula (I):

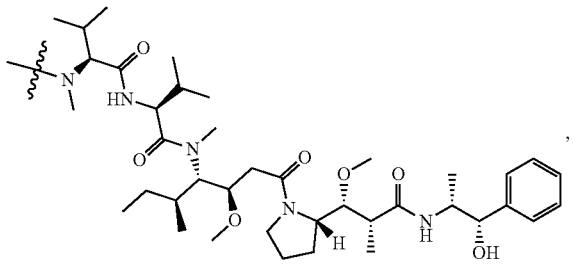

wherein
a first plurality of the conjugates are bound to four heterologous moieties comprising structural formula (I);
at least about 95% of the first plurality of conjugates are structurally homogenous; and
the effective amount is in a range of about
  1.7 mg/kg to 6 mg/kg;
  2.0 mg/kg to 6 mg/kg; or
  2.4 mg/kg to 6 mg/kg for use in treating cancer.

SEQUENCES

The following sequences were part of the Sequence Listing filed as Appendix 3 in the U.S. Application No. 63/468,817 to which this application claims priority. These sequences are less than 4 amino acids or 10 base pairs in length, and do not meet the length requirements of ST. 26, paragraph 7.

| Sequence | SEQ ID NO |
|---|---|
| Ser Thr Ser | 9 |
| Asn Ala Lys | 15 |
| Asn Ala Lys | 21 |
| Lys Val Ser | 27 |
| Lys Val Ser | 33 |
| Trp Ala Ser | 39 |
| Ser Thr Ser | 45 |
| Lys Val Ser | 51 |
| Ala Ala Ala | 57 |
| Lys Val Ser | 63 |
| Leu Ala Ser | 69 |
| Ser Thr Ser | 75 |
| Arg Thr Ser | 81 |
| Ala Ala Ser | 87 |
| Trp Ala Ser | 93 |
| Ala Ala Ser | 99 |
| Ser Thr Ser | 105 |
| Trp Ala Ser | 111 |
| Trp Ala Ser | 117 |
| Lys Val Ser | 123 |
| Ser Thr Ser | 129 |
| agcacatcc | 209 |
| aatgcaaaa | 215 |
| aatgcaaaa | 221 |
| aaagtttcc | 227 |
| aaagtttcc | 233 |
| tgggcatcc | 239 |
| agcacatcc | 245 |
| aaagtttcc | 251 |
| gctgcagcc | 257 |
| aaagtttcc | 263 |
| cttgcatcc | 269 |
| tccacatcc | 275 |
| aggacatcc | 281 |
| gctgcatcc | 287 |
| tgggcatcc | 293 |
| gctgcatcc | 299 |
| agcacatcc | 305 |
| tgggcatcc | 311 |
| tgggcatcc | 317 |

-continued

SEQ ID NO: 323
aaagtttcc

SEQ ID NO: 329
tccacatcc

SEQ ID NO: 450
Xaa Thr Xaa, wherein Xaa at position 1 is S, T,
Q, or A, and Xaa at position 3 is S, T, D, or Q.

SEQ ID NO: 459
Xaa Val Xaa, wherein Xaa at position 1 is K, Q,
or R, and Xaa at position 3 is S, T, or V.

SEQ ID NO: 471
Xaa Ala Ser, wherein Xaa at position 1 is H, Y,
F, or W.

SEQ ID NO: 477
Xaa Ala Lys, wherein Xaa at position 1 is Q, S,
A, D, or N.

EXAMPLES

The following examples are given merely to illustrate the present disclosure and not in any way to limit its scope.

Example 1

This example describes administration of a CLDN6 ADC for treatment of cancer in humans.
Participant Inclusion Criteria
1. Female or male ≥18 years of age willing and able to provide informed consent
2. Disease Type:
   For Part 1:
      Histologically or cytologically confirmed diagnosis of advanced (unresectable) or metastatic solid tumor malignancy that was not responsive to accepted standard therapies or for which there was no standard therapy
   For Part 2 Cohort 2A:
      Histologically or cytologically confirmed diagnosis of advanced (unresectable) or metastatic ovarian, primary peritoneal, or fallopian tube cancer
      Patient's tumor must be positive for claudin 6 expression as defined by the claudin 6 reference laboratory assay, an IHC assay.
      Patients must have platinum-resistant disease (defined as progression within 6 months from completion of a minimum of four cycles of platinum-containing therapy). Note: This should be calculated from the date of the last administered dose of platinum therapy to the date of the radiographic imaging showing progression. Patients who are platinum-refractory during front-line treatment are excluded.
      Patients must have received at least 1 but no more than 4 prior systemic lines of anticancer therapy, and for whom single-agent therapy is appropriate as the next line of treatment:
         a. Adjuvant±neoadjuvant considered one line of therapy
         b. Maintenance therapy (e.g., bevacizumab, PARP inhibitors) will be considered as part of the preceding line of therapy (ie, not counted independently)
         c. Therapy changed due to toxicity in the absence of progression will be considered as part of the same line (i.e., not counted independently)
         d. Hormonal therapy will not be counted as a separate line of therapy.
   For Part 2 Cohort 2B:
      Histologically or cytologically confirmed diagnosis of advanced (unresectable) or metastatic solid tumor malignancy that is not responsive to accepted standard therapies or for which there is no standard therapy
      Patient's tumor must be positive for claudin 6 expression as defined by the claudin 6 reference laboratory assay.
   For Part 2 Cohort 2C:
      Histologically confirmed diagnosis of advanced (unresectable) or metastatic NSCLC that has progressed on or following treatment with platinum-based regimens and PD1 or PDL1 inhibitor containing regimens and EGFR TKI containing regimen for EGFRmu NSCLC and ALK inhibitor regimen for ALK translocated NSCLC and KRAS G12C inhibitor for KRASG12Cmu NSCLC
      Patient's tumor must be positive for claudin 6 expression as defined by the claudin 6 reference laboratory assay
3. Measurable disease, per RECIST v1.1
4. Eastern Cooperative Oncology Group (ECOG) performance status 0-1
5. Able to tolerate intravenous blood sampling for PK, had no known intolerance or hypersensitivity to IMP or excipients, and able to comply with study requirements
6. Adequate organ function, based on the following laboratory values, as shown in Table 2.

TABLE 2

Adequate organ function criteria.

| System | Laboratory Value |
|---|---|
| Hematological | |
| ANC | ≥1,500/mcL |
| Platelets | ≥100,000/mcL without transfusion within 4 weeks of first dose |
| Hemoglobin | ≥8 g/dL |
| Renal | |
| Measured or Cockcroft and Gault equation calculated creatinine clearance | ≥30 mL/min |
| Hepatic | |
| Serum total bilirubin | ≤1.5 × ULN (participants with known Gilbert disease who have serum bilirubin level ≤3 × ULN may be enrolled) |
| AST (SGOT) and ALT (SGPT) | ≤3 × ULN |
| Albumin | ≥2 g/dL |
| Cardiac | |
| ECG | 12-Lead ECG with normal tracing or non-clinically significant changes that do not require medical intervention and QTcF interval ≤470 msec and without history of Torsades des Pointes or other symptomatic QTc abnormality. |

ALT = alanine aminotransferase;
ANC = absolute neutrophil count;
AST = aspartate aminotransferase;
ECG = electrocardiogram;
QTc = corrected QT interval;
QTcF = QT interval corrected by Friderica's formula;
ULN = upper limit of normal 7. Female participants of childbearing potential must have a negative urine or serum pregnancy test within 72 hours before starting study drug treatment. If the urine test is positive or cannot be confirmed as negative, a serum pregnancy test will be required. The serum pregnancy test must be negative for the participant to be eligible, and participants must agree to use a highly effective birth control method from the time of the first study drug treatment through 90 days after the last study drug treatment, or be of nonchildbearing potential. Highly effective birth control method is defined as combined (estrogen and progestogen containing) hormonal contraception (e.g., oral, intravaginal, transdermal), progestin-only hormonal contraception associated with inhibition of ovulation (e.g., oral, injectable, implantable, intrauterine device [IUD], intrauterine hormone-releasing system [IUS]), bilateral tubal occlusion, vasectomized partner, or sexual abstinence. Abstinence refers to 'true abstinence,' which means it is in line with the preferred and usual lifestyle of the patient. Periodic abstinence (e.g., calendar, ovulation, symptothermal, post-ovulation methods), declaration of abstinence for the duration of exposure to study treatment, and withdrawal are not acceptable methods of contraception. Nonchildbearing potential is defined as follows:
   a. ≥45 years of age and has not had menses for >1 year
   b. Participants who have been amenorrhoeic for <2 years without history of a hysterectomy and oophorectomy must have a follicle stimulating hormone (FSH) value in the postmenopausal range upon screening evaluation
   c. Post-hysterectomy, post-bilateral oophorectomy, or post-tube ligation. Documented hysterectomy or oophorectomy must be confirmed with medical records of the actual procedure or confirmed by an ultrasound. Tubal ligation must be confirmed with medical records of the actual procedure.
8. Female and male participants must agree not to donate eggs or sperm, respectively, from the first study-drug treatment through 90 days after the last study drug treatment.
9. Female participants must agree to not breastfeed from the first dose of study treatment through 90 days after the last dose of study treatment.
10. Male participants must use a condom when having sex with a pregnant woman and when having sex with a woman of childbearing potential from the time of the first study-drug treatment through 4 months after the last study drug treatment. Withdrawal (coitus interruptus) and/or use of a spermicide without a condom are not acceptable methods of contraception or fetal protection. Effective contraception should be considered for a non-pregnant female partner of childbearing potential. Male participants are advised to have semen samples frozen before initiation of TORL-1-23 administration given the potential risk to male fertility.

Participant Exclusion Criteria
1. Has not recovered [recovery is defined as NCI CTCAE, version 5.0, grade ≤1] from the acute toxicities of previous therapy, except treatment-related alopecia or laboratory abnormalities otherwise meeting eligibility requirements
2. For Cohort 2A
   a. Patients with low-grade, borderline ovarian tumors or non-epithelial ovarian cancers
   b. Patients with primary platinum-refractory ovarian, primary peritoneal or fallopian tube cancer, defined as disease that did not respond to or has progressed within 3 months of the last dose of first line platinum-containing chemotherapy
3. Received prior chemotherapeutic, investigational, radiotherapy, or other therapies for the treatment of cancer within 14 days with small molecule and within 28 days with biologic before the first dose of TORL-1-23. There is no waiting period required for stereotactic radiosurgery (SRS).
4. Progressive or symptomatic brain metastases. Brain metastases that have been radiated, are asymptomatic, and on a stable or decreasing dose of steroids are allowed. Leptomeningeal disease is excluded.
5. Grade 2 or greater peripheral neuropathy
6. Participants must not be considered a poor medical risk due to a serious, uncontrolled medical disorder, nonmalignant systemic disease, or active, uncontrolled infection. Examples include, but are not limited to, uncontrolled major seizure disorder, unstable spinal cord compression, superior vena cava syndrome, or any psychiatric disorder that prohibits obtaining informed consent.
7. History of significant cardiac disease:
   Congestive heart failure >New York Heart Association (NYHA) class 2 within last year
   Unstable angina (angina symptoms at rest), new-onset angina (begun within the last 3 months)
   Myocardial infarction less than 6 months before start of study drug
   Anti-arrhythmic therapy (beta blockers are permitted)
   Any unstable ischemic disease or untreated arrhythmia
8. Known history of myelodysplastic syndrome (MDS) or acute myeloid leukemia (AML)
9. History of another cancer within 3 years before Day 1 of study treatment, with the exception of basal or squamous cell carcinoma of the skin that has been definitively treated. Participants with malignancies with a low risk of recurrence, including appropriately treated ductal carcinoma in situ (DCIS) of the breast and prostate cancer with a Gleason score less than or equal to 6, are not excluded.
10. Uncontrolled infection; active, clinically serious infections (>CTCAE grade 2)
11. Participants with seizure disorder requiring medication
12. Participants must not be pregnant or breastfeeding
13. Known hypersensitivity or intolerance to any of the study drugs, study drug classes, or excipients in the formulation
14. History of having an allogeneic bone marrow or organ transplant
15. Any condition (concurrent disease, infection, or comorbidity) that interferes with ability to participate in the study, causes undue risk, or complicates the interpretation of safety data, in the opinion of the Investigator.
16. Participants who are taking any drugs that are strong inducers and/or strong inhibitors of CYP3A4 enzymes
17. Participants who are taking any drugs that are inhibitors of P-glycoprotein (P-gp)

Administration and Monitoring Protocols

The drug product of TORL-1-23 is a sterile, colorless to slightly yellow, clear to slightly opalescent liquid that is essentially free of visible particles and was supplied in a 10 mL glass vial with a flip-off seal (cap) over a 20 mm rubber stopper. Each vial contained 40 mg of TORL-1-23. Drug product was formulated at a target concentration of 10 mg/mL in 20 mM Glutamate-NaOH buffer, 8% (w/v) Sucrose, 0.02% (w/v) PS80, pH 5.2. Transfer and dilution to an intravenous (IV) bag was required prior to IV infusion.

The appropriate volume of TORL-1-23 for injection was transferred to a non-PVC IV infusion bag containing USP grade 5% Dextrose Injection or 0.9% Sodium Chloride Injection. The final concentration of the prepared TORL-1-23 dosing solution in 5% Dextrose was ≥0.1 mg/mL and ≤4 mg/mL. If diluting into 0.9% Sodium Chloride, the final concentration of the prepared TORL-1-23 was ≥0.2 mg/mL and ≤4 mg/mL Dosing was based on participant weight. The investigational product will be administered at mg/kg doses based on the participant's actual body weight at baseline. The dose was adjusted if the participant's weight changed by ≥10% from their baseline weight.

The investigational product was administered through a dedicated IV line with a 0.22 micron in-line filter.

TORL-1-23 was administered as a 30 minute IV infusion once every 3 weeks on 21-day cycles (±3 days after Cycle 1). See description of Parts 1 and 2 below for specific treatment group descriptions.

Participants were continuously monitored for AEs throughout the duration of the study. Complete safety assessments (physical examination, vital sign measurements, 12-lead ECGs, and clinical laboratory tests) were performed periodically at baseline, on-treatment, and at follow-up. Widely accepted criteria for documentation and classification of adverse events were utilized [i.e., National Cancer Institute (NCI) Common Terminology Criteria for Adverse Events (CTCAE) Version 5.0].

Participants experiencing Grade 3 possibly related toxicity or intolerable Grade 2 toxicity despite optimal supportive care had their treatment interrupted until resolution to ≤Grade 1 (except for alopecia, fatigue, or peripheral neuropathy). Upon adequate recovery, treatment was resumed at the next lowest dose level.

Tumor assessments by Response Evaluation Criteria in Solid Tumors (RECIST) v1.1 were performed at Screening, and every 6 to 9 weeks after Cycle 1 Day 1 in the first year and at least every 12 weeks (±4 weeks) thereafter or as clinically indicated until disease progression or withdrawal from the study. PK parameters were determined for TORL-1-23 during Cycle 1.

Safety Follow-up Period: Participants were followed for ongoing and new adverse events for 28 days after the last investigational medicinal product (IMP) administration, or until all drug-related toxicities resolved or were deemed stable, whichever was later.

Survival Follow-up Period: All participants will be followed at least every 3 months (±1 month) for up to 2 years for survival and new systemic anticancer treatment. Participants who do not return to the site should be contacted by telephone every 3 months as an alternative.

Part 1: Dose Escalation

The starting dose level was 0.2 mg/kg IV infusion once every 3 weeks.

In order to reduce the number of participants who were treated at sub-therapeutic dose levels while ensuring a risk mitigated starting dose and dose escalation, dose finding was conducted according to an accelerated titration design by Simon et al. (1997). During the accelerated phase, sequential cohorts of 1 participant each using 100% dose increments were evaluated for 21 days or until the first instance of DLT or first course CTCAE Grade 2 or greater possibly related toxicity. At dose levels above 0.8 mg/kg (2 dose doublings from the starting dose) or with a DLT or first course Grade 2 or greater possibly related AE, the accelerated phase of dose finding reverted to a standard 3+3 dose escalation design using ~33% or less dose increments between all subsequent dose cohorts.

At each dose level in the standard 3+3 escalation phase, at least 3 participants were or will be treated (unless DLT is observed in the first 2 participants at a dose level). If a DLT is observed in 1 of the initial 3 treated participants at a dose level in the standard 3+3 dose escalation phase, 3 additional participants were or will be enrolled and treated at the same dose level. If no further DLT is observed, the next dose level may be opened using a ~33% or less dose increment. Subsequent dose levels may not be opened until all participants entered at the current dose level have been treated and observed for at least one complete 21-day cycle and the number of participants with DLTs in their 4-week cycle has been determined. Dose escalation continued and will continue, as tolerated, until 6.0 mg/kg, DLT is observed in at least 2 of the 3 to 6 participants treated at that dose level, or potentially at a lower dose if the MTD has been reached.

The treatment groups for the cohorts are listed in Table 3 based on this information.

TABLE 3

Monotherapy Dose Escalation - Part 1

| Cohort | TORL-1-23 Dose |
|---|---|
| P1-1 | 0.2 mg/kg iv infusion once every 3 weeks |
| P1-2 | 0.4 mg/kg iv infusion once every 3 weeks |
| P1-3 | 0.8 mg/kg iv infusion once every 3 weeks |
| P1-4 | 1.0 mg/kg iv infusion once every 3 weeks |
| P1-5 | 1.3 mg/kg iv infusion once every 3 weeks |
| P1-6 | 1.7 mg/kg iv infusion once every 3 weeks |
| P1-7 | 2.0 mg/kg iv infusion once every 3 weeks |
| P1-8 | 2.4 mg/kg iv infusion once every 3 weeks |
| P1-9 | 3.0 mg/kg iv infusion once every 3 weeks |
| P1-10 | 4.0 mg/kg iv infusion once every 3 weeks |
| P1-11 | 5.0 mg/kg iv infusion once every 3 weeks |
| P1-12 | 6.0 mg/kg iv infusion once every 3 weeks |

[a]100% dose escalations between cohorts until dose level exceeded 0.8 mg/kg every 3 weeks (2 dose doublings from the starting dose) or a DLT or Grade 2 possibly related toxicities are observed during Cycle 1, at which point dose escalation reverted to ~33% or less dose increments between cohorts until MTD was reached and RP2D was declared.

DLT was defined as any of the following events as classified according to NCI CTCAE, version 5.0, which are not clearly due to underlying disease or extraneous causes (regardless of investigator attribution) and occur during the first 21 days of Cycle 1:

Any death not clearly due to underlying disease or extraneous causes
≥Grade 4 hematologic toxicity
≥Grade 3 febrile neutropenia
≥Grade 3 thrombocytopenia with bleeding
≥Grade 3 non-hematologic toxicity except:
  untreated diarrhea, nausea, vomiting, constipation, pain, and rash which only become DLTs if the AE persists for ≥72 hours despite adequate treatment
  fatigue which only becomes DLT if persists ≥1 week
  electrolyte abnormality which only become DLT if lasts >72 hours, unless the patient has clinical symptoms, in which case all grade 3+ electrolyte abnormality regardless of duration should count as a DLT amylase or lipase elevations which only becomes DLT if associated with symptoms or clinical manifestations of pancreatitis for participants with hepatic metastases, aspartate aminotransferase (AST) or alanine aminotransferase (ALT) elevations which only become DLT if AST or ALT >8× upper limit of normal (ULN) or AST or ALT >5×ULN for ≥14 days AEs that are cases of Hy's law (e.g., ALT or AST >3×ULN and total bilirubin [TBILI]>2×ULN without initial findings of cholestasis [elevated serum alkaline phosphatase (ALP)])

Inability to begin Cycle 2 for >14 days due to TORL-1-23-related toxicity

Results

To date, 25 participants have been enrolled in this study and treated across 8 dose levels, ranging from 0.2 to 2.4 mg/kg IV every 3 weeks. 95% of patients had received at least 3 prior lines of treatment in the metastatic setting. Table 4 shows the demographics of the 25 participants.

TABLE 4

Demographics of Phase 1 Clinical Trial Participants

| Dose, mg/kg | 0.2 | 0.4 | 0.8 | 1 | 1.3 | 1.7 | 2 | 2.4 | Total |
|---|---|---|---|---|---|---|---|---|---|
| N | 1 | 1 | 1 | 3 | 3 | 5[a] | 5[a] | 6[a] | 25 |
| Age, years (range) | 56 | 44 | 57 | 50 (30-69) | 55 (48-70) | 62 (52-66) | 51 (27-65) | 66 (59-74) | 61 (27-74) |
| Gender, male/female | 0/1 | 1/0 | 0/1 | 1/2 | 0/3 | 0/5 | 1/4 | 0/6 | 3/22 |
| Cancer type, n | | | | | | | | | |
| Ovarian | 1 | 0 | 1 | 2 | 3 | 4 | 4 | 4 | 19 |
| Testicular | 0 | 1 | 0 | 1 | 0 | 0 | 1 | 0 | 3 |
| Endometrial | 0 | 0 | 0 | 0 | 0 | 1 | 0 | 2 | 3 |
| Median number of prior treatments (range) | 6 | 3 | 10 | 5 (1-9) | 6 (6-7) | 5 (3-7) | 6 (3-9) | 4 (1-6) | 5 (1-10) |
| CLDN6 Positive by IHC n/N | 1/1 | 1/1 | 1/1 | 3/3 | 3/3 | 3/5 | 5/5 | 5/6 | 22/25 |

[a]Cohort expanded to further characterize and guide dose selection

No dose-limiting toxicities (DLTs) have been reported. The most common treatment-related adverse events were grade 1 peripheral neuropathy (n=3), grade 1 alopecia (n=3), grade 1/2 fatigue (n=5), grade 1 anemia (n=2), grade 3 anemia (n=2), and grade 1/2 nausea (n=3), as shown in Table 5.

TABLE 5

Treatment Related Adverse Events Occurring in 10% or Greater

| Preferred Term | | 0.2 mg/kg N = 1; n(%) | 0.4 mg/kg N = 1; n(%) | 0.8 mg/kg N = 1; n(%) | 1 mg/kg N = 3; n(%) | 1.3 mg/kg N = 3; n(%) | 1.7 mg/kg N = 5; n(%) | 2 mg/kg N = 5; n(%) | 2.4 mg/kg N = 6; n(%) | Total N = 25 n(%) |
|---|---|---|---|---|---|---|---|---|---|---|
| Patients with any TRAE | | 1 (100) | 1 (100) | 1 (100) | 2 (66) | 1 (33) | 3 (60) | 2 (40) | 3 (50) | 14 (56) |
| Alopecia | All Grades | 1 (100) | 0 | 0 | 0 | 0 | 0 | 1 (20) | 1 (17) | 3 (12) |
| | Gr 1 | 1 (100) | 0 | 0 | 0 | 0 | 0 | 1 (20) | 1 (17) | 3 (12) |
| | Gr 2 | 0 | 0 | 0 | 0 | 0 | 0 | 0 | 0 | 0 |
| | Gr 3 | 0 | 0 | 0 | 0 | 0 | 0 | 0 | 0 | 0 |
| Anaemia | All Grades | 0 | 0 | 0 | 1 (33) | 0 | 1 (20) | 0 | 2 (33) | 4 (16) |
| | Gr 1 | 0 | 0 | 0 | 0 | 0 | 1 (20) | 0 | 1 (17) | 2 (8) |
| | Gr 2 | 0 | 0 | 0 | 0 | 0 | 0 | 0 | 0 | 0 |
| | Gr 3 | 0 | 0 | 0 | 1 (33) | 0 | 0 | 0 | 1 (17) | 1 (4) |
| Fatigue | All Grades | 0 | 0 | 1 (100) | 1 (33) | 0 | 3 (60) | 0 | 0 | 5 (20) |
| | Gr 1 | 0 | 0 | 1 (100) | 1 (33) | 0 | 1 (20) | 0 | 0 | 3 (12) |
| | Gr 2 | 0 | 0 | 0 | 0 | 0 | 2 (40) | 0 | 0 | 2 (8) |
| | Gr 3 | 0 | 0 | 0 | 0 | 0 | 0 | 0 | 0 | 0 |
| Nausea | All Grades | 0 | 0 | 0 | 0 | 0 | 0 | 0 | 1 (17) | 1 (4) |
| | Gr 1 | 0 | 0 | 0 | 0 | 0 | 1 (20) | 0 | 1 (17) | 1 (4) |
| | Gr 2 | 0 | 0 | 0 | 0 | 0 | 1 (20) | 0 | 0 | 1 (4) |
| | Gr 3 | 0 | 0 | 0 | 0 | 0 | 0 | 0 | 0 | 0 |

TABLE 5-continued

Treatment Related Adverse Events Occurring in 10% or Greater

| Preferred Term | | 0.2 mg/kg N = 1; n(%) | 0.4 mg/kg N = 1; n(%) | 0.8 mg/kg N = 1; n(%) | 1 mg/kg N = 3; n(%) | 1.3 mg/kg N = 3; n(%) | 1.7 mg/kg N = 5; n(%) | 2 mg/kg N = 5; n(%) | 2.4 mg/kg N = 6; n(%) | Total N = 25 n(%) |
|---|---|---|---|---|---|---|---|---|---|---|
| Neuropathy peripheral | All Grades | 0 | 1 (100) | 1 (100) | 1 (33) | 0 | 0 | 0 | 0 | 3 (12) |
| | Gr 1 | 0 | 1 (100) | 1 (100) | 1 (33) | 0 | 0 | 0 | 0 | 3 (12) |
| | Gr 2 | 0 | 0 | 0 | 0 | 0 | 0 | 0 | 0 | 0 |
| | Gr 3 | 0 | 0 | 0 | 0 | 0 | 0 | 0 | 0 | 0 |
| Dose Limiting Toxicities (DLT) | | | | | | | | | | |
| DLT | All | 0 | 0 | 0 | 0 | 0 | 0 | 0 | 0 | 0 |

Grade 4 Lymphocyte count decreased (n = 1), Grade 5 Pneumonia (n = 1).
Datacut 3 May 2023 Dose Levels 0.2 to 2.4 mg/kg No dose reductions or delays for toxicity were required. Preliminary PK data demonstrate sustained exposure of TORL-1-23 over the dosing interval and low levels of free MMAE.

Confirmed partial responses (PR) were observed in 7/25 evaluable participants, including in 6/19 subjects with platinum-resistant/refractory ovarian cancer across all dose levels, with 3/4 patients at the 2.4 mg/kg dose level achieving a PR. Separately, 1/3 patients with metastatic CLDN6 positive testicular cancer achieved a PR; this patient previously was treated with 4 prior lines of treatment. This participant initially received 1 mg/kg and was subsequently escalated to 1.3 mg/kg; the participant remains in response in Cycle 11 and is currently being treated with 1.7 mg/kg.

Figure 1B:
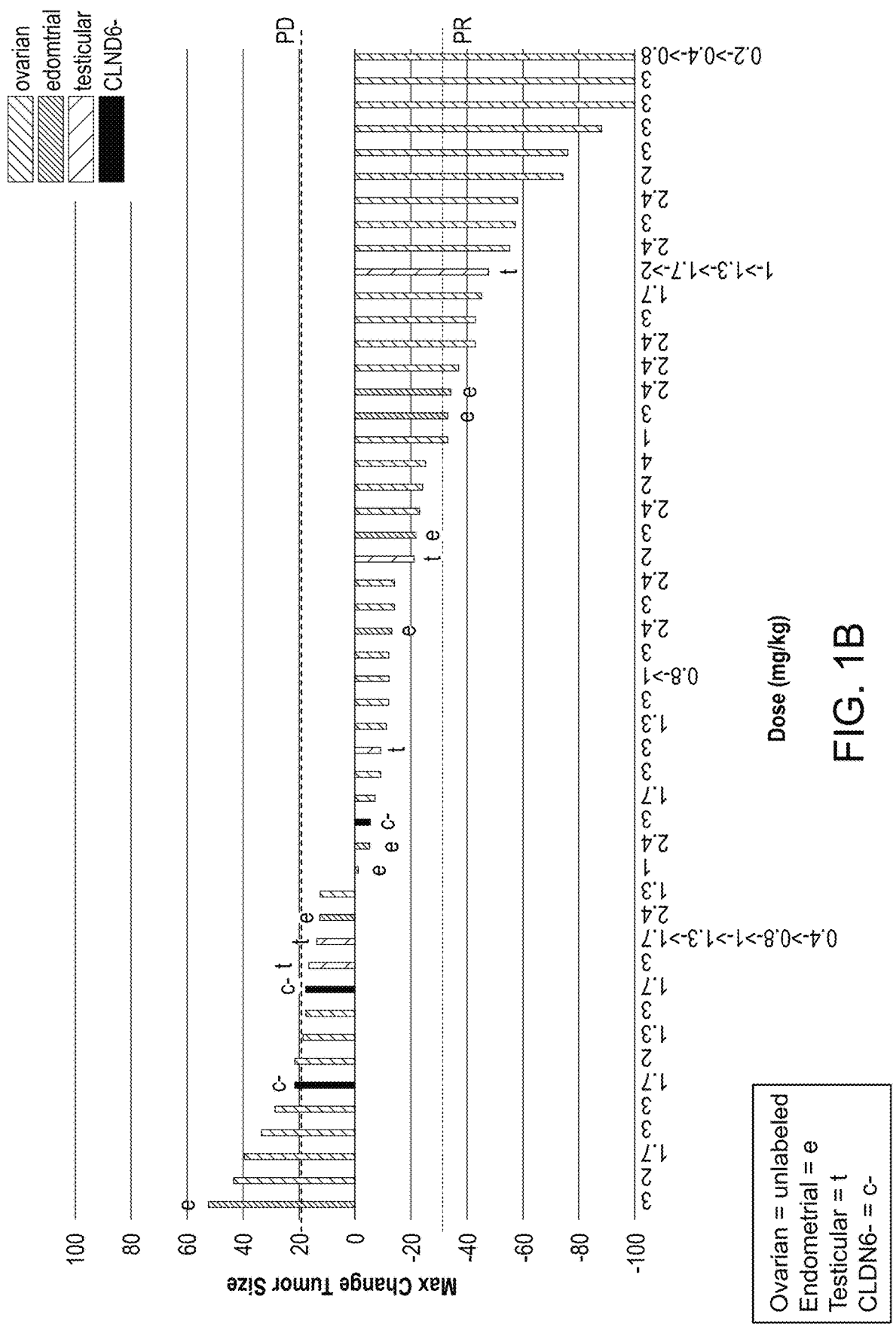
FIG. 1B shows dose levels 0.2 to 3.0 mg/kg of TORL-1-23 in humans.
Figure 2A:
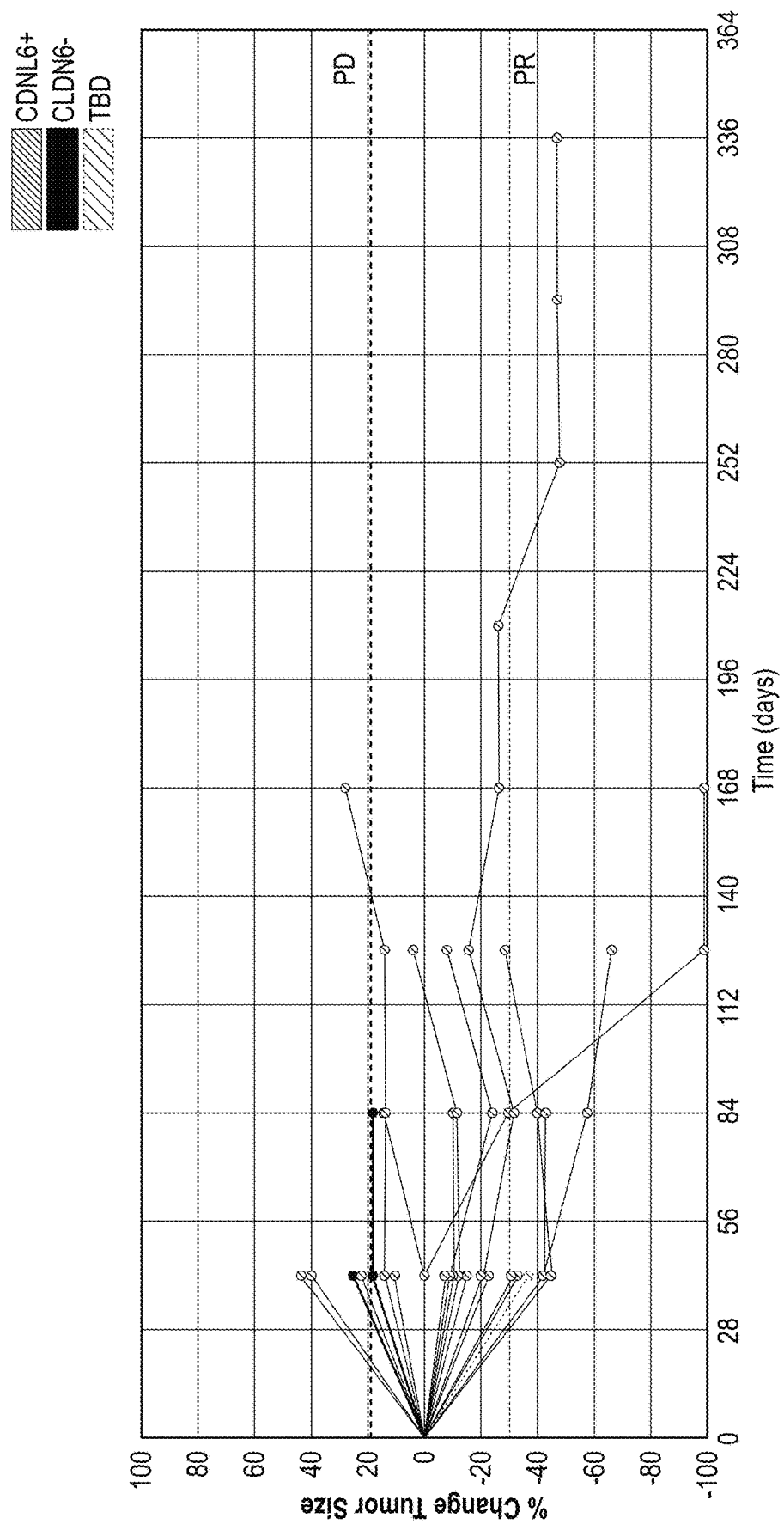
FIG. 2A is a graph showing change in tumor size over time at dose levels 0.2 to 2.4 mg/kg of TORL-1-23 in humans
Figure 2B:
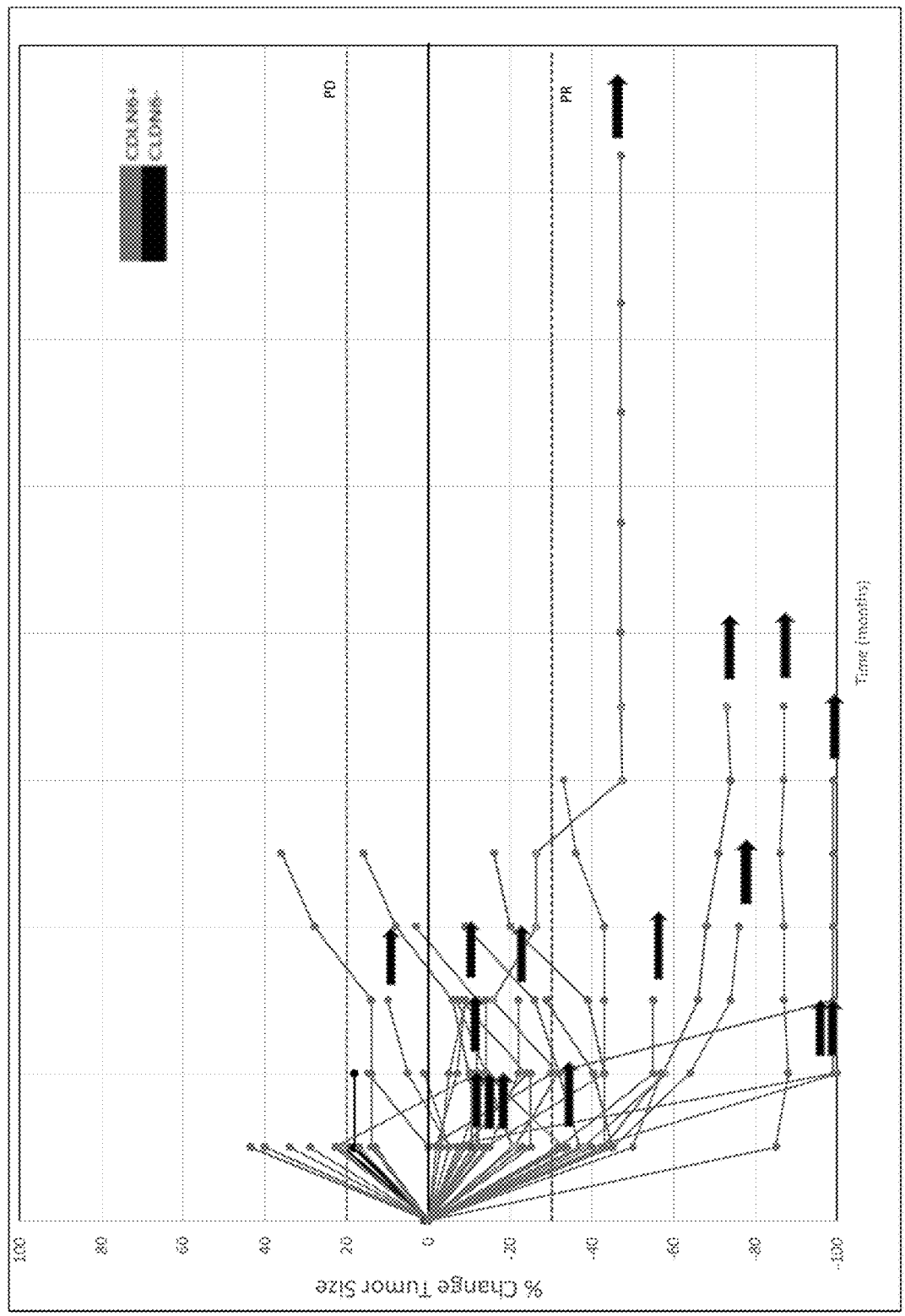
FIG. 2B shows tumor size over time at dose levels 0.2 to 3.0 mg/kg of TORL-1-23 in humans.

Change in tumor size as a function of dose is shown in FIG. 1 with threshold for disease progression indicated by a dash line labeled as "PD" and partial response indicated by a dash line labeled as "PR." TBD indicates CLDN6 status to be determined. Change in tumor size over time is shown in FIG. 2.

Blood was collected in all participants for TORL-1-23 serum PK assessment. Pre-dose PK samples were collected within 1 hour prior to infusion on Cycle 1 Day 1 and within 30 minutes prior to all subsequent pre-dose timepoints.

Validated analytical methods were used to analyze serum concentration of TORL-1-23 total antibody (conjugated and unconjugated) and MMAE-conjugated TORL-1-23 antibody and unconjugated (free) circulating MMAE.

Dose-finding is ongoing to identify the maximum tolerated dose (MTD) and doses for evaluation in expansion cohorts of the target populations. Exposure response modeling of available safety and serum MMAE data indicate that doses of up to 6.0 mg/kg may be tolerated.

Part 2: Recommended Phase 2 Dose Expansion Cohorts

Once doses have been identified in Part 1 as potential RP2D, expansion cohorts of up to 20 participants each will be enrolled at each potential RP2D to characterize the safety, tolerability, and PK at the RP2D in participants with advanced claudin 6 IHC positive ovarian cancer (Cohort 2A), in participants with claudin 6 positive advanced solid cancer (Cohort 2B), and in participants with claudin 6 positive advanced NSCLC (Cohort 2C). In Cohort 2A, participants must have platinum-resistant disease, defined as completing 4 or more cycles of platinum-based therapy and progressing within 6 months of last platinum-based therapy. Participants must have received at least 1 but no more than 4 prior systemic lines of anticancer therapy and for whom single-agent therapy is appropriate at the next line of treatment. In Cohort 2B, participants must have advanced (unresectable) or metastatic solid tumor malignancy that is not responsive to accepted standard therapies or for which there is no standard therapy. In Cohort 2C, advanced (unresectable) or metastatic NSCLC that has progressed on or following treatment with platinum-based regimens and PD1 or PDL1 inhibitor containing regimens and EGFR TKI containing regimen for EGFRmu NSCLC and ALK inhibitor regimen for ALK translocated NSCLC and KRAS G12C inhibitor for KRASG12Cmu NSCLC.

Example 2

This example describes the preclinical efficacy of a conjugate used in the claimed methods.

CLDN6-23-ADC selectively binds to CLDN6, versus other CLDN family members, inhibits the proliferation of CLDN6+ cancer cells in vitro, and is rapidly internalized in CLDN6+ cells. Robust tumor regressions were observed in multiple CLDN6+ xenograft models and tumor inhibition led to markedly enhanced survival of mice with CLDN6+ PDX tumors or CLDN6+ cancer cells from established human cancer cell lines following treatment with CLDN6-23-ADC.

IHC assessment of cancer tissue microarrays demonstrate elevated levels of CLDN6 in 29% of ovarian epithelial carcinomas. Approximately 45% of high-grade serous ovarian carcinomas and 11% of endometrial carcinomas are positive for the target (for additional preclinical efficacy data of CLDN6-23-ADC, see McDermott et al. (2023) Clin. Cancer Res. 29(11):2131-2143).

Figure 3:
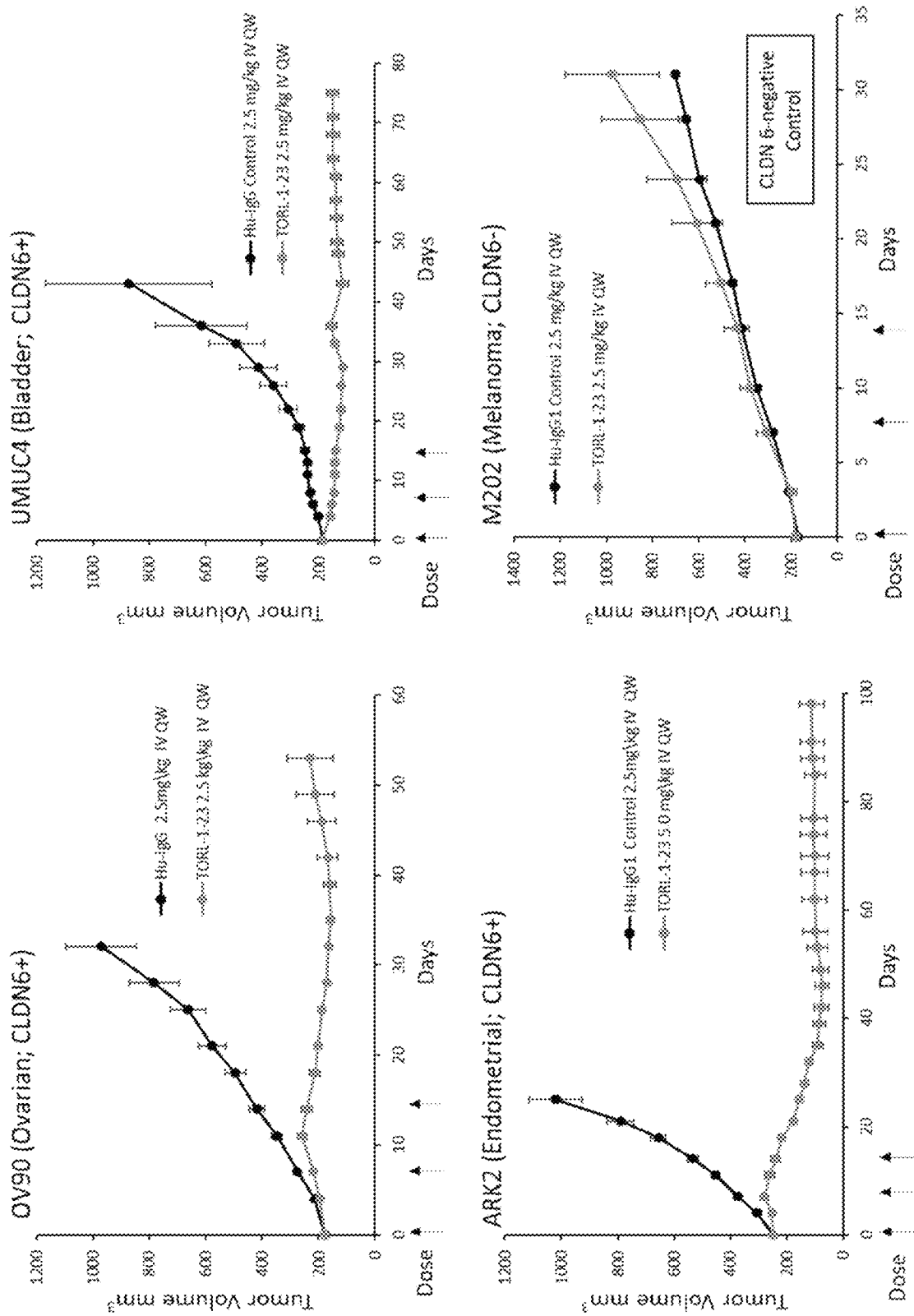
FIG. 3 is a collection of line graphs assessing anti-tumor activity of TORL-1-23 administered intravenously once weekly at either 2.5 or 5.0 mg/kg in human cancer murine xenograft models with CLDN6-positive ovarian (OV90), bladder (UMUC4) or endometrial (ARK2) cancer or CLDN6-negative melanoma (M202) cancer.
Figure 4A:
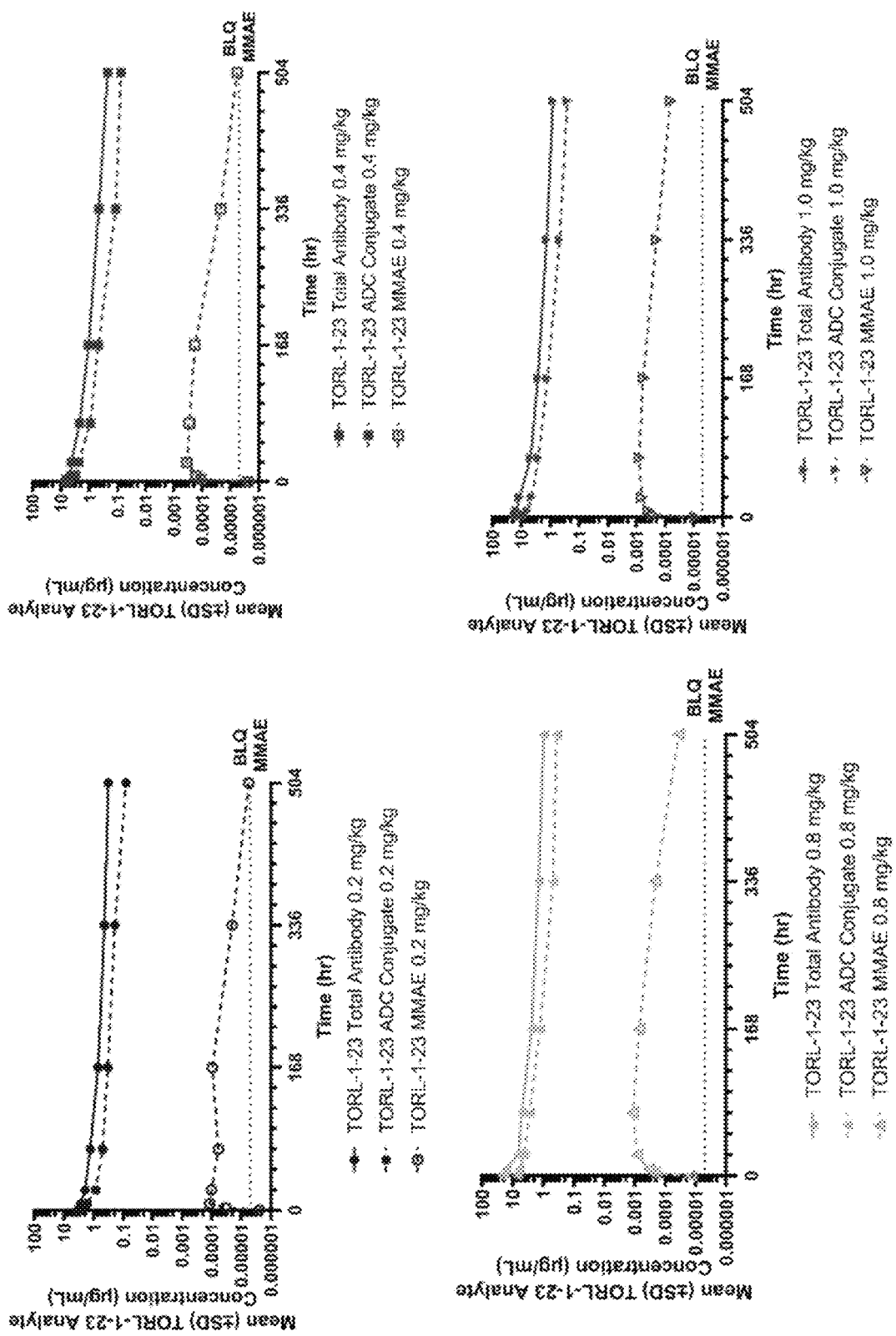
FIGS. 4A and 4A continued are a collection of line graphs showing mean plasma concentrations of TORL-1-23 total antibody (conjugated and unconjugated to four MMAEs), TORL-1-23 (comprising 4 MMAEs), and unconjugated (or free) MMAE following TORL-1-23 administration every 3 weeks at doses of 0.2, 0.4, 0.8, 1.0, 1.3, 1.7, 2.0, and 2.4 mg/kg for cycle 1.
Figure 4A:
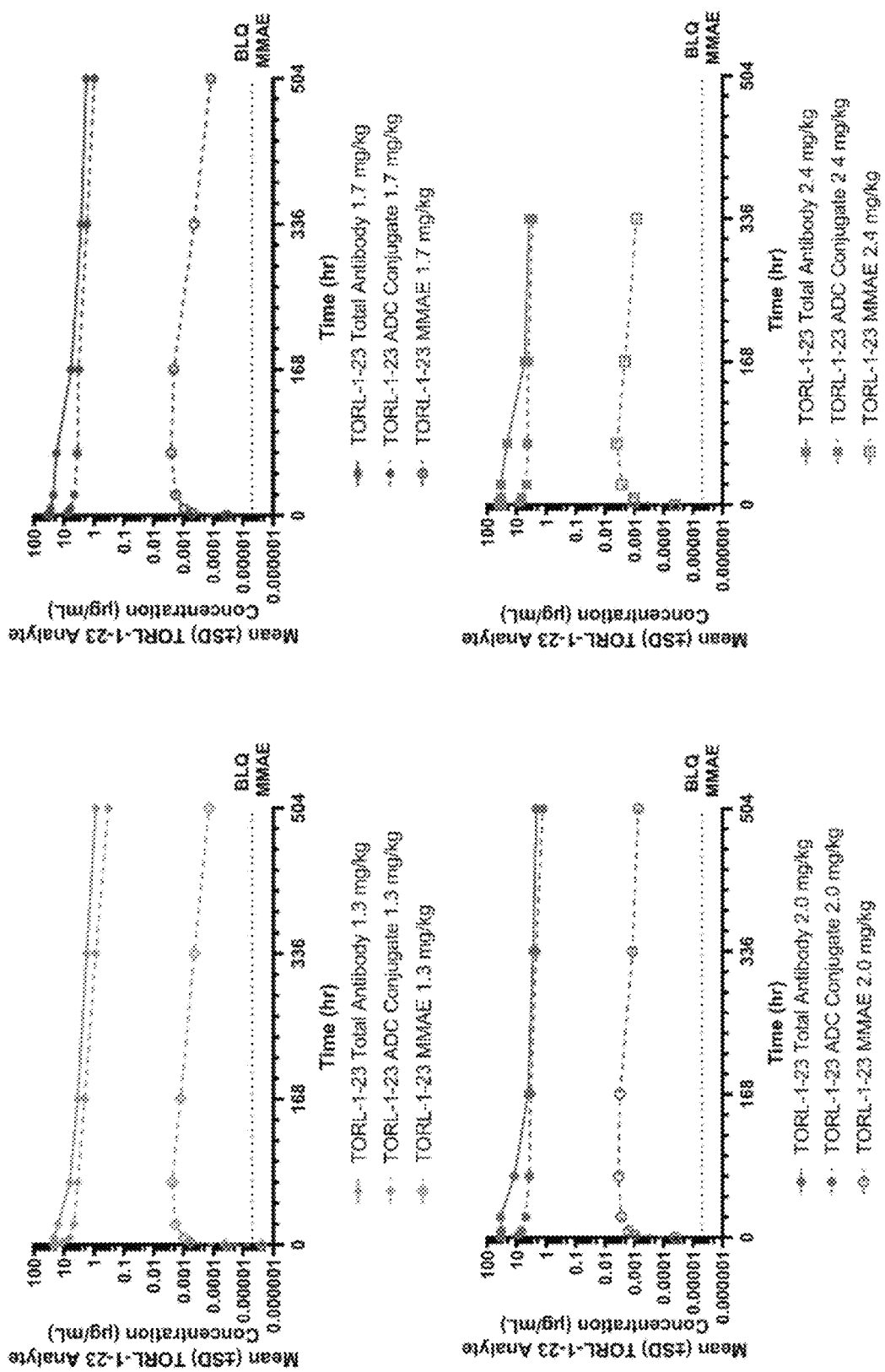
Figure 4B:
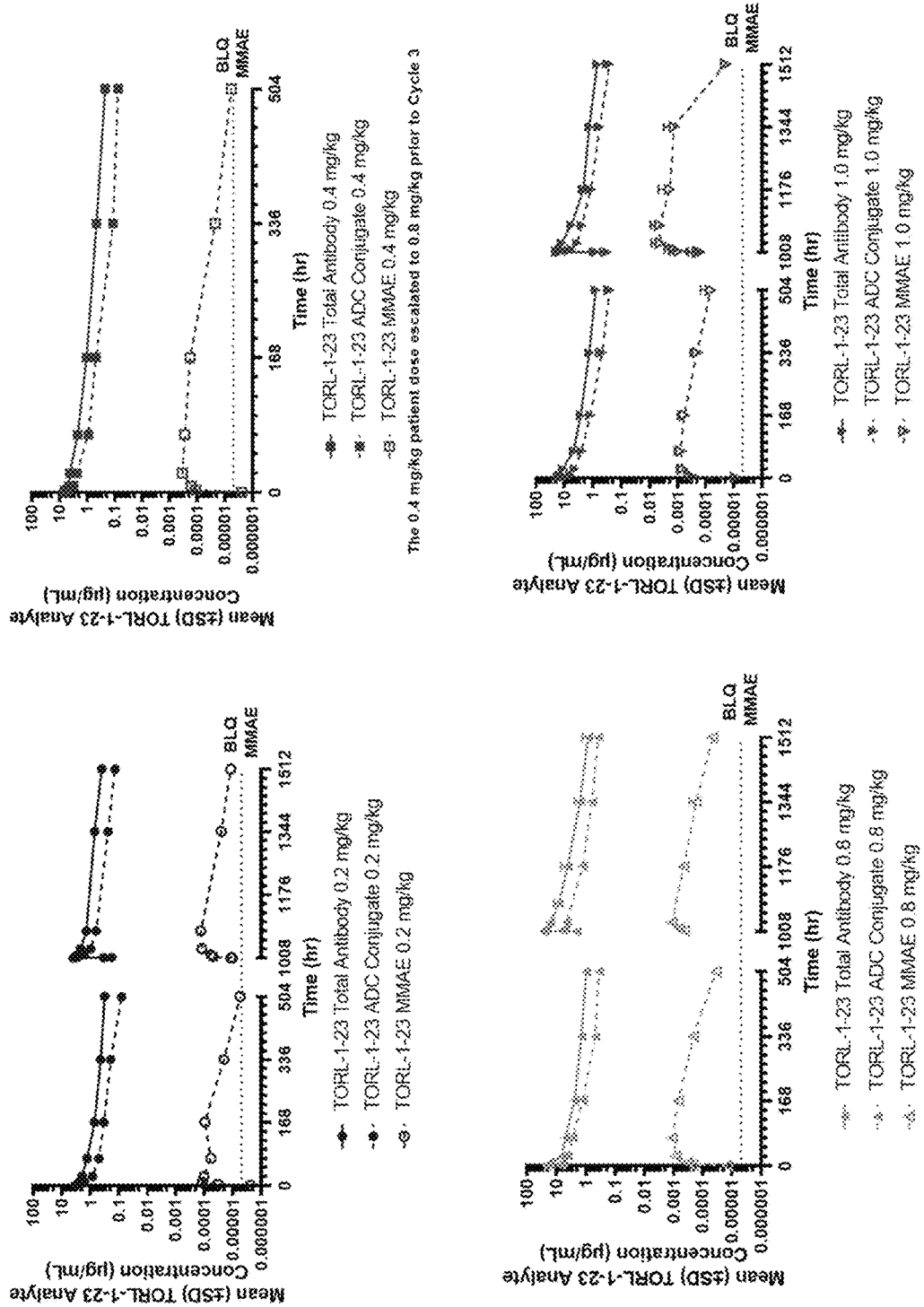
FIGS. 4B and 4B continued are a collection of line graphs showing mean plasma concentrations of TORL-1-23 total antibody (conjugated and unconjugated to four MMAEs), TORL-1-23 (comprising 4 MMAEs), and unconjugated (or free) MMAE following TORL-1-23 administration every 3 weeks at doses of 0.2, 0.4, 0.8, 1.0, 1.3, 1.7, 2.0, 2.4, and 3.0 mg/kg for cycles 1 and 3.
Figure 4B:
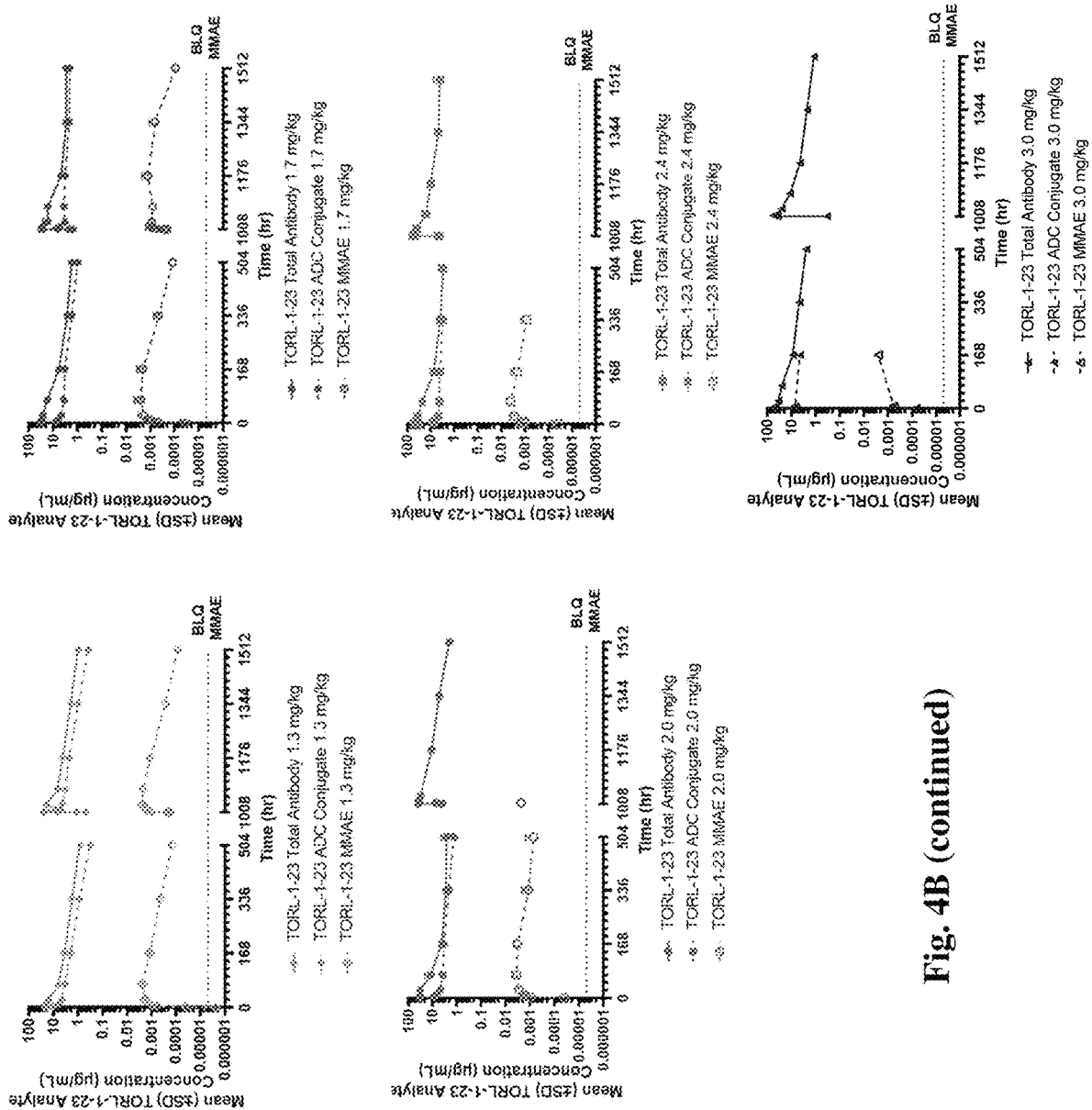

Anti-tumor activity of TORL-1-23 is shown in FIG. 3. Weekly intravenous administration of TORL-1-23 (upward pointing arrow) for three weeks to mice with CLDN6-positive human cancer xenografts from ovarian (OV90) or bladder cancer (UMUC4) at 2.5 mg/kg or endometrial cancer (ARK2) at 5.0 mg/kg resulted in inhibition of tumor growth and reduction in tumor volume that persists substantially beyond the last administered dose (e.g., more than 83 days for ARK2 xenografts in FIG. 3). Specificity of TORL-1-23 anti-tumor activity for CLDN6-positive cancer is demonstrated by a lack of anti-tumor activity on CLDN6-negative human melanoma cancer xenografts (M202) similarly treated with TORL-1-23 at 2.5 mg/kg. Human IgG1 (Hu-IgG1) administered intravenously once a week for three weeks at 2.5 mg/kg served as a negative control.

Example 3

This example compares the PK properties of conjugates used in the claimed methods to other ADCs having the same linker-heterologous moiety.

An anti-CLDN6 antibody drug conjugate, TORL-1-23, was administered at doses between 0.2 mg/kg to 3.0 mg/kg every 3 weeks to cancer patients participating in phase 1 clinical trial study to determine safety that included a dose-escalation component and cohort expansion to help characterize and guide potential recommended phase 2 dose (RP2D).

Results of the preliminary analyses of the measured PK values are presented herein.

TORL-1-23 Total Antibody Preliminary Analysis

FIG. 4 shows graphs of measured TORL-1-23 total antibody concentration (conjugated and unconjugated), TORL-1-23 concentration, and unconjugated (or free) MMAE following administration of TORL-1-23 preparation to cancer patients participating in the Phase 1 clinical trial and dosed at 0.2 to 2.4 mg/kg (0.2, 0.4, 0.8, 1.0, 1.3, 1.7, 2.0, or 2.4 mg/kg) at cycle 1 (0-504 hrs). The TORL-1-23 is an anti-CLDN6 antibody conjugated to 4 MMAEs per antibody. As can be seen in the graphs, the serum concentrations of TORL-1-23 total antibody (both ADC and free antibody combined) was higher than the serum concentration of TORL-1-23.

Preliminary analyses showed that TORL-1-23 total antibody $C_{max}$ increased in a nearly dose proportional manner between doses of 0.2 and 3.0 mg/kg. Further, TORL-1-23 total antibody $AUC_{0-168\ h}$ and $AUC_{0-504\ h}$ increased in a nearly dose proportional manner between doses of 0.2 and 2.4 mg/kg and was slightly less than dose proportional between 2.4 and 3.0 mg/kg.

Minimal to no accumulation in $C_{max}$, $AUC_{0-168\ h}$, and $AUC_{0-504\ h}$ was observed at doses of 0.2, 1, 1.3, 1.7, 2.0, 2.4, and 3 mg/kg for TORL-1-23 total antibody. However, significant accumulation in $AUC_{0-168\ h}$, but not in $C_{max}$ or $AUC_{0-504\ h}$, was observed only at a dose of 0.8 mg/kg for a cohort with n=1 in cycle 3.

Preliminary assessments of TORL-1-23 total antibody accumulation based on $C_{max}$, $AUC_{0-168\ h}$, and $AUC_{0-504\ h}$ values showed in general minimal to no accumulation of total antibody at cycle 3 based on a three-week dosing interval and comparing to cycle 1 values. No significant difference in cycle 3 $C_{max}$ to cycle 1 $C_{max}$ ratio was observed for doses between 0.2 and 3.0 mg with the $C_{max}$ ratios ranging between 0.87 and 1.19. Similarly, when analyzing total antibody accumulation based on $AUC_{0-168\ h}$ and $AUC_{0-504\ h}$, minimal to no accumulation in $AUC_{0-168\ h}$ and $AUC_{0-504\ h}$ were observed at doses of 0.2, 1, 1.3, 1.7, 2.0, 2.4, and 3 mg/kg for TORL-1-23 total antibody at cycle 3 compared to cycle 1. However, for a dose of 0.8 mg/kg and a cohort of n=1, despite significant accumulation in $AUC_{0-168\ h}$ observed at cycle 3, no significant accumulation in $C_{max}$ or $AUC_{0-504\ h}$ was observed at a dose of 0.8 mg/kg. Thus, in general, there is no significant accumulation of TORL-1-23 total antibody at a three-week dosing interval for a range of doses from 0.2 to 3 mg/kg every three weeks.

The mean half-life of TORL-1-23 total antibody for cycle 1 ranged from 136 to 290 hours, while the mean half-life of TORL-1-23 total antibody is slightly lower for cycle 3 ranging from 121 to 280 hours.

TORL-1-23 Preliminary Analysis

Preliminary analysis of the TORL-1-23 concentrations showed that the MMAE-conjugated anti-CLDN6 antibody had a lower serum concentrations than the serum concentrations determined for TORL-1-23 total antibody (see FIG. 4, where the solid line corresponds to total antibody and the dashed line underneath and closest to the solid line corresponds to ADC).

Like TORL-1-23 total antibody, the TORL-1-23 $C_{max}$ increased in a nearly dose proportional manner between doses of 0.2 and 3.0 mg/kg. TORL-1-23 $AUC_{0-506\ h}$ increased in a nearly dose proportional manner between 0.2 and 2.4 mg/kg. Note that data was only available up to 168-hour post-dose for 3.0 mg/kg (n=1), such that the $AUC_{0-504\ h}$ is an extrapolation.

Preliminary assessments of the Cm and $AUC_{0-504\ h}$ values at cycle 1 and cycle 3 showed, in general, minimal to no accumulation in $C_{max}$ or $AUC_{0-504\ h}$ at doses of 0.2, 0.8, 1.0, 1.3, and 1.7 mg/kg for TORL-1-23. Data for cycle 3 were not yet available for other dose levels at the time of analysis.

The mean half-life of TORL-1-23 total antibody for cycle 1 ranged from 127 to 387 hours.

Unconjugated MMAE Preliminary Analysis

Preliminary analysis of unconjugated or free MMAE in the serum showed an increase in a nearly dose proportional manner between doses of 0.2 and 2.4 mg/kg (see FIG. 4, open symbols connected by a dash line). Similarly, the $AUC_{0-504\ h}$ of unconjugated MMAE increased in a nearly dose proportional manner between doses of 0.2 and 2.4 mg/kg. Minimal to no accumulation in $C_{max}$ or $AUC_{0-504\ h}$ was observed at doses of 0.2, 0.8, 1.3, and 1.7 mg/kg for the unconjugated or free MMAE. Significant accumulation in $C_{max}$ and $AUC_{0-504\ h}$ was observed at a dose of 1.0 mg/kg.

The mean half-life of the unconjugated or free MMAE for cycle 1 ranged from 68.1 to 131 hours.

Figure 5:
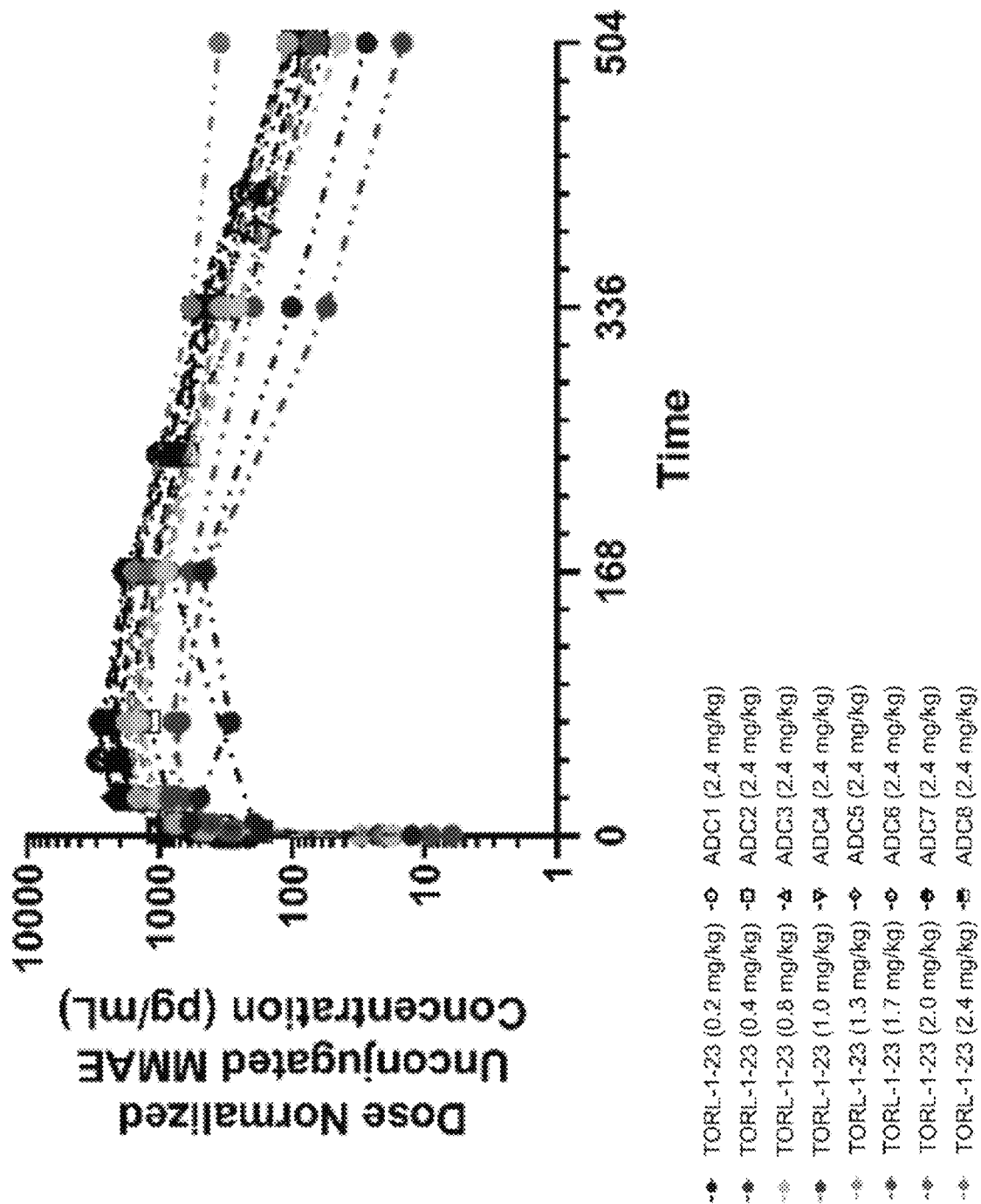
FIG. 5 is a line graph showing dose normalized unconjugated MMAE concentrations after a single administration of 0.2, 0.4, 0.8, 1.0, 1.3, 1.7, 2.0, and 2.4 mg/kg of TORL-1-23 (filled circles) or after a single administration of 2.4 mg/kg dose of eight other leading ADCs, ADC1-ADC8, which have undergone phase 1 clinical trial (filled symbols).

Unexpected Advantage of TORL-1-23 Over Other ADCs with MMAE Attached by a Valine-Citrulline Linker Compared to eight other ADCs, ADC1 to ADC8, which have undergone phase 1 clinical trial in which the therapeutic antibody is a humanized IgG1 ADC conjugated to MMAE through a valine-citrulline linker with 4 MMAE conjugates per antibody (average HAR=~3.5; Li et al., 2020, MAbs 12(1):1699768), the dose normalized free MMAE concentration following a single dose, systemic exposure to TORL-1-23 is about 3× lower than expected compared to other clinically tested MMAE-containing ADCs, as shown in FIG. 5. Following administration of a single 2.4 mg/kg dose of either TORL-1-23 or eight other ADCs described by Li et al. (2020), the percent MMAE $AUC_{inf}$ (=(MMAE $AUC_{inf}$/total antibody $AUC_{inf}$)×100) is 0.011% MMAE $AUC_{inf}$ for TORL 1-23 ADC (0.011%), which is lower than those observed for ADC1 to ADC8 described by Li et al. (2020) with the percent MMAE $AUC_{inf}$ ranging from 0.012% to 0.039% (mean of 0.025% for ADC1 to ADC8; median of 0.025% for ADC1 to ADC8). Similar to the finding with the dose normalized free MMAE concentration analysis, the percent MMAE $AUC_{inf}$ following a single 2.4 mg/kg dose ADC administration is about 2.3-fold lower for TORL-1-23 than expected compared to other clinically tested MMAE-containing ADCs. TORL-1-23 provides an unexpected advantage over an average ADC as exemplified from the analysis of eight leading ADCs conjugated to 4 MMAEs through valine-citrulline linkers (Li et al., 2020) in reducing overall exposure to unconjugated MMAE by about 2 to 3-fold. The risk of an adverse event associated with general exposure to circulating unconjugated MMAE is significantly much less than other antibodies similarly conjugated to MMAEs through valine-citrulline linkers.

INCORPORATION BY REFERENCE

All references, including publications, patent applications, and patents, cited herein are hereby incorporated by reference to the same extent as if each reference were individually and specifically indicated to be incorporated by reference and were set forth in its entirety herein.

INCORPORATION BY REFERENCE OF MATERIAL SUBMITTED IN THE PRIORITY APPLICATION

McDermott et al. Preclinical Efficacy of the Antibody-Drug Conjugate CLDN6-23-ADC for the Treatment of CLDN6-Positive Solid Tumors. Clin Cancer Res. 2023 Jun. 1; 29(11):2131-2143 (doi: 10.1158/1078-0432.CCR-22-2981. PMID: 36884217; PMCID: PMC10233360), which was filed as Appendix 1 in the U.S. Application No. 63/468,817 to which this application claims benefit of priority, is incorporated herein by reference in its entirety.

VARIATIONS

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein.

All methods described herein can be performed in any suitable order unless otherwise indicated herein or otherwise clearly contradicted by context. The use of any and all examples, or various language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Preferred embodiments of this disclosure are described herein, including the best mode known to the inventors for carrying out the disclosure. Variations of those preferred embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

```
                            SEQUENCE LISTING

Sequence total quantity: 537
SEQ ID NO: 1            moltype = AA  length = 220
FEATURE                 Location/Qualifiers
REGION                  1..220
                        note = NCBI / NP_067018.2, 2017-06-04
source                  1..220
                        mol_type = protein
                        organism = Homo sapiens
SEQUENCE: 1
MASAGMQILG VVLTLLGWVN GLVSCALPMW KVTAFIGNSI VVAQVVWEGL WMSCVVQSTG   60
QMQCKVYDSL LALPQDLQAA RALCVIALLV ALFGLLVYLA GAKCTTCVEE KDSKARLVLT  120
SGIVFVISGV LTLIPVCWTA HAIIRDFYNP LVAEAQKREL GASLYLGWAA SGLLLLGGGL  180
LCCTPSGGS QGPSHYMARY STSAPAISRG PSEYPTKNYV                         220

SEQ ID NO: 2            moltype = AA  length = 23
FEATURE                 Location/Qualifiers
source                  1..23
                        mol_type = protein
                        organism = Homo sapiens
SEQUENCE: 2
WTAHAIIRDF YNPLVAEAQK REL                                           23

SEQ ID NO: 3            moltype = AA  length = 13
FEATURE                 Location/Qualifiers
source                  1..13
                        mol_type = protein
                        organism = Homo sapiens
SEQUENCE: 3
TAHAIIRDFY NPL                                                      13

SEQ ID NO: 4            moltype = AA  length = 10
FEATURE                 Location/Qualifiers
source                  1..10
                        mol_type = protein
                        organism = Homo sapiens
SEQUENCE: 4
LVAEAQKREL                                                          10

SEQ ID NO: 5            moltype = AA  length = 220
FEATURE                 Location/Qualifiers
REGION                  1..220
```

```
                            note = NCBI / NP_001297.1, 2017-07-10
source                      1..220
                            mol_type = protein
                            organism = Homo sapiens
SEQUENCE: 5
MSMGLEITGT ALAVLGWLGT IVCCALPMWR VSAFIGSNII TSQNIWEGLW MNCVVQSTGQ    60
MQCKVYDSLL ALPQDLQAAR ALIVVAILLA AFGLLVALVG AQCTNCVQDD TAKAKITIVA   120
GVLFLLAALL TLVPVSWSAN TIIRDFYNPV VPEAQKREMG AGLYVGWAAA ALQLLGGALL   180
CCSCPPREKK YTATKVVYSA PRSTGPGASL GTGYDRKDYV                        220

SEQ ID NO: 6                moltype = AA   length = 209
FEATURE                     Location/Qualifiers
REGION                      1..209
                            note = NCBI / NP_001296.1, 2017-07-10
source                      1..209
                            mol_type = protein
                            organism = Homo sapiens
SEQUENCE: 6
MASMGLQVMG IALAVLGWLA VMLCCALPMW RVTAFIGSNI VTSQTIWEGL WMNCVVQSTG    60
QMQCKVYDSL LALPQDLQAA RALVIISIIV AALGVLLSVV GGKCTNCLED ESAKAKTMIV   120
AGVVFLLAGL MVIVPVSWTA HNIIQDFYNP LVASGQKREM GASLYVGWAA SGLLLLGGGL   180
LCCNCPPRTD KPYSAKYSAA RSAAASNYV                                    209

SEQ ID NO: 7                moltype = AA   length = 217
FEATURE                     Location/Qualifiers
REGION                      1..217
                            note = NCBI / NP_066192.1, 2017-04-15
source                      1..217
                            mol_type = protein
                            organism = Homo sapiens
SEQUENCE: 7
MASTGLELLG MTLAVLGWLG TLVSCALPLW KVTAFIGNSI VVAQVVWEGL WMSCVVQSTG    60
QMQCKVYDSL LALPQDLQAA RALCVIALLL ALLGLLVAIT GAQCTTCVED EGAKARIVLT   120
AGVILLLAGI LVLIPVCWTA HAIIQDFYNP LVAEALKREL GASLYLGWAA AALLMLGGGL   180
LCCTCPPPQV ERPRGPRLGY SIPSRSGASG LDKRDYV                           217

SEQ ID NO: 8                moltype = AA   length = 7
FEATURE                     Location/Qualifiers
REGION                      1..7
                            note = Synthetic peptide
source                      1..7
                            mol_type = protein
                            organism = synthetic construct
SEQUENCE: 8
SSVSSTY                                                              7

SEQ ID NO: 9                moltype =      length =
SEQUENCE: 9
000

SEQ ID NO: 10               moltype = AA   length = 9
FEATURE                     Location/Qualifiers
REGION                      1..9
                            note = Synthetic peptide
source                      1..9
                            mol_type = protein
                            organism = synthetic construct
SEQUENCE: 10
HQYHRSPLT                                                            9

SEQ ID NO: 11               moltype = AA   length = 8
FEATURE                     Location/Qualifiers
REGION                      1..8
                            note = Synthetic peptide
source                      1..8
                            mol_type = protein
                            organism = synthetic construct
SEQUENCE: 11
GYTFTTYT                                                             8

SEQ ID NO: 12               moltype = AA   length = 8
FEATURE                     Location/Qualifiers
REGION                      1..8
                            note = Synthetic peptide
source                      1..8
                            mol_type = protein
                            organism = synthetic construct
SEQUENCE: 12
INPSSGYT                                                             8
```

```
SEQ ID NO: 13            moltype = AA   length = 9
FEATURE                  Location/Qualifiers
REGION                   1..9
                         note = Synthetic peptide
source                   1..9
                         mol_type = protein
                         organism = synthetic construct
SEQUENCE: 13
ANGDYYVAY                                                                9

SEQ ID NO: 14            moltype = AA   length = 6
FEATURE                  Location/Qualifiers
REGION                   1..6
                         note = Synthetic peptide
source                   1..6
                         mol_type = protein
                         organism = synthetic construct
SEQUENCE: 14
ENIYSY                                                                   6

SEQ ID NO: 15            moltype =      length =
SEQUENCE: 15
000

SEQ ID NO: 16            moltype = AA   length = 9
FEATURE                  Location/Qualifiers
REGION                   1..9
                         note = Synthetic peptide
source                   1..9
                         mol_type = protein
                         organism = synthetic construct
SEQUENCE: 16
QHHYTVPWT                                                                9

SEQ ID NO: 17            moltype = AA   length = 8
FEATURE                  Location/Qualifiers
REGION                   1..8
                         note = Synthetic peptide
source                   1..8
                         mol_type = protein
                         organism = synthetic construct
SEQUENCE: 17
GFTFSDYW                                                                 8

SEQ ID NO: 18            moltype = AA   length = 10
FEATURE                  Location/Qualifiers
REGION                   1..10
                         note = Synthetic peptide
source                   1..10
                         mol_type = protein
                         organism = synthetic construct
SEQUENCE: 18
IRLKSDNYAT                                                              10

SEQ ID NO: 19            moltype = AA   length = 8
FEATURE                  Location/Qualifiers
REGION                   1..8
                         note = Synthetic peptide
source                   1..8
                         mol_type = protein
                         organism = synthetic construct
SEQUENCE: 19
NDGPPSGC                                                                 8

SEQ ID NO: 20            moltype = AA   length = 6
FEATURE                  Location/Qualifiers
REGION                   1..6
                         note = Synthetic peptide
source                   1..6
                         mol_type = protein
                         organism = synthetic construct
SEQUENCE: 20
ENIYSY                                                                   6

SEQ ID NO: 21            moltype =      length =
SEQUENCE: 21
000
```

```
SEQ ID NO: 22          moltype = AA   length = 9
FEATURE                Location/Qualifiers
REGION                 1..9
                       note = Synthetic peptide
source                 1..9
                       mol_type = protein
                       organism = synthetic construct
SEQUENCE: 22
QHHYTVPWT                                                                    9

SEQ ID NO: 23          moltype = AA   length = 8
FEATURE                Location/Qualifiers
REGION                 1..8
                       note = Synthetic peptide
source                 1..8
                       mol_type = protein
                       organism = synthetic construct
SEQUENCE: 23
GFTFSNYW                                                                     8

SEQ ID NO: 24          moltype = AA   length = 10
FEATURE                Location/Qualifiers
REGION                 1..10
                       note = Synthetic peptide
source                 1..10
                       mol_type = protein
                       organism = synthetic construct
SEQUENCE: 24
IRLKSDNYAT                                                                  10

SEQ ID NO: 25          moltype = AA   length = 8
FEATURE                Location/Qualifiers
REGION                 1..8
                       note = Synthetic peptide
source                 1..8
                       mol_type = protein
                       organism = synthetic construct
SEQUENCE: 25
NDGPPSGC                                                                     8

SEQ ID NO: 26          moltype = AA   length = 11
FEATURE                Location/Qualifiers
REGION                 1..11
                       note = Synthetic peptide
source                 1..11
                       mol_type = protein
                       organism = synthetic construct
SEQUENCE: 26
QSLVHSDGNT Y                                                                11

SEQ ID NO: 27          moltype =   length =
SEQUENCE: 27
000

SEQ ID NO: 28          moltype = AA   length = 9
FEATURE                Location/Qualifiers
REGION                 1..9
                       note = Synthetic peptide
source                 1..9
                       mol_type = protein
                       organism = synthetic construct
SEQUENCE: 28
SQSTHVPYT                                                                    9

SEQ ID NO: 29          moltype = AA   length = 8
FEATURE                Location/Qualifiers
REGION                 1..8
                       note = Synthetic peptide
source                 1..8
                       mol_type = protein
                       organism = synthetic construct
SEQUENCE: 29
GYTFTSYT                                                                     8

SEQ ID NO: 30          moltype = AA   length = 8
FEATURE                Location/Qualifiers
REGION                 1..8
                       note = Synthetic peptide
source                 1..8
```

```
                                     mol_type = protein
                                     organism = synthetic construct
SEQUENCE: 30
INPSSTYT                                                                        8

SEQ ID NO: 31           moltype = AA  length = 10
FEATURE                 Location/Qualifiers
REGION                  1..10
                        note = Synthetic peptide
source                  1..10
                        mol_type = protein
                        organism = synthetic construct
SEQUENCE: 31
SRGELGGFAY                                                                     10

SEQ ID NO: 32           moltype = AA  length = 11
FEATURE                 Location/Qualifiers
REGION                  1..11
                        note = Synthetic peptide
source                  1..11
                        mol_type = protein
                        organism = synthetic construct
SEQUENCE: 32
QSIVHSNGNT Y                                                                   11

SEQ ID NO: 33           moltype =     length =
SEQUENCE: 33
000

SEQ ID NO: 34           moltype = AA  length = 9
FEATURE                 Location/Qualifiers
REGION                  1..9
                        note = Synthetic peptide
source                  1..9
                        mol_type = protein
                        organism = synthetic construct
SEQUENCE: 34
FQGSHVPFT                                                                       9

SEQ ID NO: 35           moltype = AA  length = 8
FEATURE                 Location/Qualifiers
REGION                  1..8
                        note = Synthetic peptide
source                  1..8
                        mol_type = protein
                        organism = synthetic construct
SEQUENCE: 35
GYIFTHYI                                                                        8

SEQ ID NO: 36           moltype = AA  length = 8
FEATURE                 Location/Qualifiers
REGION                  1..8
                        note = Synthetic peptide
source                  1..8
                        mol_type = protein
                        organism = synthetic construct
SEQUENCE: 36
INPYNDGT                                                                        8

SEQ ID NO: 37           moltype = AA  length = 13
FEATURE                 Location/Qualifiers
REGION                  1..13
                        note = Synthetic peptide
source                  1..13
                        mol_type = protein
                        organism = synthetic construct
SEQUENCE: 37
ARYYGYPYYS MDY                                                                 13

SEQ ID NO: 38           moltype = AA  length = 12
FEATURE                 Location/Qualifiers
REGION                  1..12
                        note = Synthetic peptide
source                  1..12
                        mol_type = protein
                        organism = synthetic construct
SEQUENCE: 38
QSLLNSRTRK NY                                                                  12
```

| | | |
|---|---|---|
| SEQ ID NO: 39<br>SEQUENCE: 39<br>000 | moltype =   length = | |
| | | |
| SEQ ID NO: 40<br>FEATURE<br>REGION<br><br>source | moltype = AA   length = 8<br>Location/Qualifiers<br>1..8<br>note = Synthetic peptide<br>1..8<br>mol_type = protein<br>organism = synthetic construct | |
| SEQUENCE: 40<br>KQSYYLYT | | 8 |
| | | |
| SEQ ID NO: 41<br>FEATURE<br>REGION<br><br>source | moltype = AA   length = 9<br>Location/Qualifiers<br>1..9<br>note = Synthetic peptide<br>1..9<br>mol_type = protein<br>organism = synthetic construct | |
| SEQUENCE: 41<br>GYSITSGYY | | 9 |
| | | |
| SEQ ID NO: 42<br>FEATURE<br>REGION<br><br>source | moltype = AA   length = 7<br>Location/Qualifiers<br>1..7<br>note = Synthetic peptide<br>1..7<br>mol_type = protein<br>organism = synthetic construct | |
| SEQUENCE: 42<br>ISYDGGI | | 7 |
| | | |
| SEQ ID NO: 43<br>FEATURE<br>REGION<br><br>source | moltype = AA   length = 10<br>Location/Qualifiers<br>1..10<br>note = Synthetic peptide<br>1..10<br>mol_type = protein<br>organism = synthetic construct | |
| SEQUENCE: 43<br>ARFGKGAMDY | | 10 |
| | | |
| SEQ ID NO: 44<br>FEATURE<br>REGION<br><br>source | moltype = AA   length = 7<br>Location/Qualifiers<br>1..7<br>note = Synthetic peptide<br>1..7<br>mol_type = protein<br>organism = synthetic construct | |
| SEQUENCE: 44<br>SSVSSSY | | 7 |
| | | |
| SEQ ID NO: 45<br>SEQUENCE: 45<br>000 | moltype =   length = | |
| | | |
| SEQ ID NO: 46<br>FEATURE<br>REGION<br><br>source | moltype = AA   length = 9<br>Location/Qualifiers<br>1..9<br>note = Synthetic peptide<br>1..9<br>mol_type = protein<br>organism = synthetic construct | |
| SEQUENCE: 46<br>HQYHRSPPT | | 9 |
| | | |
| SEQ ID NO: 47<br>FEATURE<br>REGION<br><br>source | moltype = AA   length = 8<br>Location/Qualifiers<br>1..8<br>note = Synthetic peptide<br>1..8<br>mol_type = protein<br>organism = synthetic construct | |
| SEQUENCE: 47<br>GYSFTGYT | | 8 |
| | | |
| SEQ ID NO: 48 | moltype = AA   length = 8 | |

```
FEATURE              Location/Qualifiers
REGION               1..8
                     note = Synthetic peptide
source               1..8
                     mol_type = protein
                     organism = synthetic construct
SEQUENCE: 48
INPYNGGT                                                              8

SEQ ID NO: 49        moltype = AA  length = 12
FEATURE              Location/Qualifiers
REGION               1..12
                     note = Synthetic peptide
source               1..12
                     mol_type = protein
                     organism = synthetic construct
SEQUENCE: 49
ARGVYDYDGF TY                                                        12

SEQ ID NO: 50        moltype = AA  length = 11
FEATURE              Location/Qualifiers
REGION               1..11
                     note = Synthetic peptide
source               1..11
                     mol_type = protein
                     organism = synthetic construct
SEQUENCE: 50
QSLVHSDGNT Y                                                         11

SEQ ID NO: 51        moltype =    length =
SEQUENCE: 51
000

SEQ ID NO: 52        moltype = AA  length = 9
FEATURE              Location/Qualifiers
REGION               1..9
                     note = Synthetic peptide
source               1..9
                     mol_type = protein
                     organism = synthetic construct
SEQUENCE: 52
SQSTHVPYT                                                             9

SEQ ID NO: 53        moltype = AA  length = 8
FEATURE              Location/Qualifiers
REGION               1..8
                     note = Synthetic peptide
source               1..8
                     mol_type = protein
                     organism = synthetic construct
SEQUENCE: 53
GYTFTTYT                                                              8

SEQ ID NO: 54        moltype = AA  length = 8
FEATURE              Location/Qualifiers
REGION               1..8
                     note = Synthetic peptide
source               1..8
                     mol_type = protein
                     organism = synthetic construct
SEQUENCE: 54
INPRSGYS                                                              8

SEQ ID NO: 55        moltype = AA  length = 10
FEATURE              Location/Qualifiers
REGION               1..10
                     note = Synthetic peptide
source               1..10
                     mol_type = protein
                     organism = synthetic construct
SEQUENCE: 55
SRGELGGFAY                                                           10

SEQ ID NO: 56        moltype = AA  length = 6
FEATURE              Location/Qualifiers
REGION               1..6
                     note = Synthetic peptide
source               1..6
                     mol_type = protein
```

```
                        organism = synthetic construct
SEQUENCE: 56
QTIGTW                                                                            6

SEQ ID NO: 57           moltype =    length =
SEQUENCE: 57
000

SEQ ID NO: 58           moltype = AA   length = 9
FEATURE                 Location/Qualifiers
REGION                  1..9
                        note = Synthetic peptide
source                  1..9
                        mol_type = protein
                        organism = synthetic construct
SEQUENCE: 58
QQLYSIPRT                                                                         9

SEQ ID NO: 59           moltype = AA   length = 8
FEATURE                 Location/Qualifiers
REGION                  1..8
                        note = Synthetic peptide
source                  1..8
                        mol_type = protein
                        organism = synthetic construct
SEQUENCE: 59
GYRFTDYN                                                                          8

SEQ ID NO: 60           moltype = AA   length = 8
FEATURE                 Location/Qualifiers
REGION                  1..8
                        note = Synthetic peptide
source                  1..8
                        mol_type = protein
                        organism = synthetic construct
SEQUENCE: 60
INPNNGGT                                                                          8

SEQ ID NO: 61           moltype = AA   length = 10
FEATURE                 Location/Qualifiers
REGION                  1..10
                        note = Synthetic peptide
source                  1..10
                        mol_type = protein
                        organism = synthetic construct
SEQUENCE: 61
ARDYLYFFDC                                                                       10

SEQ ID NO: 62           moltype = AA   length = 11
FEATURE                 Location/Qualifiers
REGION                  1..11
                        note = Synthetic peptide
source                  1..11
                        mol_type = protein
                        organism = synthetic construct
SEQUENCE: 62
QSLVHSNGNT Y                                                                     11

SEQ ID NO: 63           moltype =    length =
SEQUENCE: 63
000

SEQ ID NO: 64           moltype = AA   length = 9
FEATURE                 Location/Qualifiers
REGION                  1..9
                        note = Synthetic peptide
source                  1..9
                        mol_type = protein
                        organism = synthetic construct
SEQUENCE: 64
SQITHVPYT                                                                         9

SEQ ID NO: 65           moltype = AA   length = 8
FEATURE                 Location/Qualifiers
REGION                  1..8
                        note = Synthetic peptide
source                  1..8
                        mol_type = protein
                        organism = synthetic construct
```

```
SEQUENCE: 65
GYTFTDYS                                                                        8

SEQ ID NO: 66           moltype = AA  length = 8
FEATURE                 Location/Qualifiers
REGION                  1..8
                        note = Synthetic peptide
source                  1..8
                        mol_type = protein
                        organism = synthetic construct
SEQUENCE: 66
ISTETGEP                                                                        8

SEQ ID NO: 67           moltype = AA  length = 10
FEATURE                 Location/Qualifiers
REGION                  1..10
                        note = Synthetic peptide
source                  1..10
                        mol_type = protein
                        organism = synthetic construct
SEQUENCE: 67
TRGLWSSFAY                                                                     10

SEQ ID NO: 68           moltype = AA  length = 10
FEATURE                 Location/Qualifiers
REGION                  1..10
                        note = Synthetic peptide
source                  1..10
                        mol_type = protein
                        organism = synthetic construct
SEQUENCE: 68
KSVSTSGYSY                                                                     10

SEQ ID NO: 69           moltype =     length =
SEQUENCE: 69
000

SEQ ID NO: 70           moltype = AA  length = 9
FEATURE                 Location/Qualifiers
REGION                  1..9
                        note = Synthetic peptide
source                  1..9
                        mol_type = protein
                        organism = synthetic construct
SEQUENCE: 70
QHSRELPLT                                                                       9

SEQ ID NO: 71           moltype = AA  length = 8
FEATURE                 Location/Qualifiers
REGION                  1..8
                        note = Synthetic peptide
source                  1..8
                        mol_type = protein
                        organism = synthetic construct
SEQUENCE: 71
GFTFSSFG                                                                        8

SEQ ID NO: 72           moltype = AA  length = 8
FEATURE                 Location/Qualifiers
REGION                  1..8
                        note = Synthetic peptide
source                  1..8
                        mol_type = protein
                        organism = synthetic construct
SEQUENCE: 72
ISSDSRTI                                                                        8

SEQ ID NO: 73           moltype = AA  length = 11
FEATURE                 Location/Qualifiers
REGION                  1..11
                        note = Synthetic peptide
source                  1..11
                        mol_type = protein
                        organism = synthetic construct
SEQUENCE: 73
ARDYGRTYEA Y                                                                   11

SEQ ID NO: 74           moltype = AA  length = 6
FEATURE                 Location/Qualifiers
```

```
REGION                  1..6
                        note = Synthetic peptide
source                  1..6
                        mol_type = protein
                        organism = synthetic construct
SEQUENCE: 74
QDIGGN                                                                         6

SEQ ID NO: 75           moltype =    length =
SEQUENCE: 75
000

SEQ ID NO: 76           moltype = AA   length = 9
FEATURE                 Location/Qualifiers
REGION                  1..9
                        note = Synthetic peptide
source                  1..9
                        mol_type = protein
                        organism = synthetic construct
SEQUENCE: 76
LQRNAYPLT                                                                      9

SEQ ID NO: 77           moltype = AA   length = 8
FEATURE                 Location/Qualifiers
REGION                  1..8
                        note = Synthetic peptide
source                  1..8
                        mol_type = protein
                        organism = synthetic construct
SEQUENCE: 77
GFTFSSYA                                                                       8

SEQ ID NO: 78           moltype = AA   length = 7
FEATURE                 Location/Qualifiers
REGION                  1..7
                        note = Synthetic peptide
source                  1..7
                        mol_type = protein
                        organism = synthetic construct
SEQUENCE: 78
IRSGGTT                                                                        7

SEQ ID NO: 79           moltype = AA   length = 12
FEATURE                 Location/Qualifiers
REGION                  1..12
                        note = Synthetic peptide
source                  1..12
                        mol_type = protein
                        organism = synthetic construct
SEQUENCE: 79
AKVGGNPYPM DY                                                                 12

SEQ ID NO: 80           moltype = AA   length = 7
FEATURE                 Location/Qualifiers
REGION                  1..7
                        note = Synthetic peptide
source                  1..7
                        mol_type = protein
                        organism = synthetic construct
SEQUENCE: 80
SSISSNY                                                                        7

SEQ ID NO: 81           moltype =    length =
SEQUENCE: 81
000

SEQ ID NO: 82           moltype = AA   length = 9
FEATURE                 Location/Qualifiers
REGION                  1..9
                        note = Synthetic peptide
source                  1..9
                        mol_type = protein
                        organism = synthetic construct
SEQUENCE: 82
QQGSSIPLT                                                                      9

SEQ ID NO: 83           moltype = AA   length = 8
FEATURE                 Location/Qualifiers
REGION                  1..8
```

```
                        note = Synthetic peptide
source                  1..8
                        mol_type = protein
                        organism = synthetic construct
SEQUENCE: 83
GYAFSNYL                                                                        8

SEQ ID NO: 84           moltype = AA  length = 8
FEATURE                 Location/Qualifiers
REGION                  1..8
                        note = Synthetic peptide
source                  1..8
                        mol_type = protein
                        organism = synthetic construct
SEQUENCE: 84
INPGSGGT                                                                        8

SEQ ID NO: 85           moltype = AA  length = 15
FEATURE                 Location/Qualifiers
REGION                  1..15
                        note = Synthetic peptide
source                  1..15
                        mol_type = protein
                        organism = synthetic construct
SEQUENCE: 85
ARSYFGRSYP YTMDY                                                               15

SEQ ID NO: 86           moltype = AA  length = 10
FEATURE                 Location/Qualifiers
REGION                  1..10
                        note = Synthetic peptide
source                  1..10
                        mol_type = protein
                        organism = synthetic construct
SEQUENCE: 86
QSVDYDGDNY                                                                     10

SEQ ID NO: 87           moltype =    length =
SEQUENCE: 87
000

SEQ ID NO: 88           moltype = AA  length = 9
FEATURE                 Location/Qualifiers
REGION                  1..9
                        note = Synthetic peptide
source                  1..9
                        mol_type = protein
                        organism = synthetic construct
SEQUENCE: 88
QQSNEDPFT                                                                       9

SEQ ID NO: 89           moltype = AA  length = 8
FEATURE                 Location/Qualifiers
REGION                  1..8
                        note = Synthetic peptide
source                  1..8
                        mol_type = protein
                        organism = synthetic construct
SEQUENCE: 89
GYTFTDYA                                                                        8

SEQ ID NO: 90           moltype = AA  length = 8
FEATURE                 Location/Qualifiers
REGION                  1..8
                        note = Synthetic peptide
source                  1..8
                        mol_type = protein
                        organism = synthetic construct
SEQUENCE: 90
ISTYSGNT                                                                        8

SEQ ID NO: 91           moltype = AA  length = 13
FEATURE                 Location/Qualifiers
REGION                  1..13
                        note = Synthetic peptide
source                  1..13
                        mol_type = protein
                        organism = synthetic construct
SEQUENCE: 91
```

```
ARRGDYSLYA MDY                                                                        13

SEQ ID NO: 92           moltype = AA   length = 12
FEATURE                 Location/Qualifiers
REGION                  1..12
                        note = Synthetic peptide
source                  1..12
                        mol_type = protein
                        organism = synthetic construct
SEQUENCE: 92
QSVLFSSNQK NY                                                                         12

SEQ ID NO: 93           moltype =      length =
SEQUENCE: 93
000

SEQ ID NO: 94           moltype = AA   length = 8
FEATURE                 Location/Qualifiers
REGION                  1..8
                        note = Synthetic peptide
source                  1..8
                        mol_type = protein
                        organism = synthetic construct
SEQUENCE: 94
HQYLSSRT                                                                              8

SEQ ID NO: 95           moltype = AA   length = 8
FEATURE                 Location/Qualifiers
REGION                  1..8
                        note = Synthetic peptide
source                  1..8
                        mol_type = protein
                        organism = synthetic construct
SEQUENCE: 95
GFTFSSFG                                                                              8

SEQ ID NO: 96           moltype = AA   length = 8
FEATURE                 Location/Qualifiers
REGION                  1..8
                        note = Synthetic peptide
source                  1..8
                        mol_type = protein
                        organism = synthetic construct
SEQUENCE: 96
ISSDSRTI                                                                              8

SEQ ID NO: 97           moltype = AA   length = 11
FEATURE                 Location/Qualifiers
REGION                  1..11
                        note = Synthetic peptide
source                  1..11
                        mol_type = protein
                        organism = synthetic construct
SEQUENCE: 97
ARDYGRTYEA Y                                                                          11

SEQ ID NO: 98           moltype = AA   length = 10
FEATURE                 Location/Qualifiers
REGION                  1..10
                        note = Synthetic peptide
source                  1..10
                        mol_type = protein
                        organism = synthetic construct
SEQUENCE: 98
ESVDNYGISF                                                                            10

SEQ ID NO: 99           moltype =      length =
SEQUENCE: 99
000

SEQ ID NO: 100          moltype = AA   length = 9
FEATURE                 Location/Qualifiers
REGION                  1..9
                        note = Synthetic peptide
source                  1..9
                        mol_type = protein
                        organism = synthetic construct
SEQUENCE: 100
QQSKEVPLT                                                                             9
```

```
SEQ ID NO: 101          moltype = AA   length = 8
FEATURE                 Location/Qualifiers
REGION                  1..8
                        note = Synthetic peptide
source                  1..8
                        mol_type = protein
                        organism = synthetic construct
SEQUENCE: 101
GFPFSSSA                                                                    8

SEQ ID NO: 102          moltype = AA   length = 7
FEATURE                 Location/Qualifiers
REGION                  1..7
                        note = Synthetic peptide
source                  1..7
                        mol_type = protein
                        organism = synthetic construct
SEQUENCE: 102
INSDGNT                                                                     7

SEQ ID NO: 103          moltype = AA   length = 13
FEATURE                 Location/Qualifiers
REGION                  1..13
                        note = Synthetic peptide
source                  1..13
                        mol_type = protein
                        organism = synthetic construct
SEQUENCE: 103
TRNGDYRYDE FAY                                                             13

SEQ ID NO: 104          moltype = AA   length = 7
FEATURE                 Location/Qualifiers
REGION                  1..7
                        note = Synthetic peptide
source                  1..7
                        mol_type = protein
                        organism = synthetic construct
SEQUENCE: 104
SSVSSSY                                                                     7

SEQ ID NO: 105          moltype =     length =
SEQUENCE: 105
000

SEQ ID NO: 106          moltype = AA   length = 9
FEATURE                 Location/Qualifiers
REGION                  1..9
                        note = Synthetic peptide
source                  1..9
                        mol_type = protein
                        organism = synthetic construct
SEQUENCE: 106
HQYHRSPPT                                                                   9

SEQ ID NO: 107          moltype = AA   length = 8
FEATURE                 Location/Qualifiers
REGION                  1..8
                        note = Synthetic peptide
source                  1..8
                        mol_type = protein
                        organism = synthetic construct
SEQUENCE: 107
GYTFTGYW                                                                    8

SEQ ID NO: 108          moltype = AA   length = 8
FEATURE                 Location/Qualifiers
REGION                  1..8
                        note = Synthetic peptide
source                  1..8
                        mol_type = protein
                        organism = synthetic construct
SEQUENCE: 108
INPSTGYT                                                                    8

SEQ ID NO: 109          moltype = AA   length = 12
FEATURE                 Location/Qualifiers
REGION                  1..12
                        note = Synthetic peptide
```

```
source                    1..12
                          mol_type = protein
                          organism = synthetic construct
SEQUENCE: 109
AREGITTVLV DY                                                                 12

SEQ ID NO: 110            moltype = AA  length = 12
FEATURE                   Location/Qualifiers
REGION                    1..12
                          note = Synthetic peptide
source                    1..12
                          mol_type = protein
                          organism = synthetic construct
SEQUENCE: 110
QSVLFSSNQK NY                                                                 12

SEQ ID NO: 111            moltype =   length =
SEQUENCE: 111
000

SEQ ID NO: 112            moltype = AA  length = 8
FEATURE                   Location/Qualifiers
REGION                    1..8
                          note = Synthetic peptide
source                    1..8
                          mol_type = protein
                          organism = synthetic construct
SEQUENCE: 112
HQYLSSRT                                                                       8

SEQ ID NO: 113            moltype = AA  length = 8
FEATURE                   Location/Qualifiers
REGION                    1..8
                          note = Synthetic peptide
source                    1..8
                          mol_type = protein
                          organism = synthetic construct
SEQUENCE: 113
GYSFTGYN                                                                       8

SEQ ID NO: 114            moltype = AA  length = 8
FEATURE                   Location/Qualifiers
REGION                    1..8
                          note = Synthetic peptide
source                    1..8
                          mol_type = protein
                          organism = synthetic construct
SEQUENCE: 114
IDPYYGGS                                                                       8

SEQ ID NO: 115            moltype = AA  length = 14
FEATURE                   Location/Qualifiers
REGION                    1..14
                          note = Synthetic peptide
source                    1..14
                          mol_type = protein
                          organism = synthetic construct
SEQUENCE: 115
ARERSGYVFS AMDY                                                               14

SEQ ID NO: 116            moltype = AA  length = 12
FEATURE                   Location/Qualifiers
REGION                    1..12
                          note = Synthetic peptide
source                    1..12
                          mol_type = protein
                          organism = synthetic construct
SEQUENCE: 116
QSVLFSSNQK NY                                                                 12

SEQ ID NO: 117            moltype =   length =
SEQUENCE: 117
000

SEQ ID NO: 118            moltype = AA  length = 8
FEATURE                   Location/Qualifiers
REGION                    1..8
                          note = Synthetic peptide
source                    1..8
```

```
                        mol_type = protein
                        organism = synthetic construct
SEQUENCE: 118
HQYLSSRT                                                                      8

SEQ ID NO: 119          moltype = AA   length = 8
FEATURE                 Location/Qualifiers
REGION                  1..8
                        note = Synthetic peptide
source                  1..8
                        mol_type = protein
                        organism = synthetic construct
SEQUENCE: 119
GYSFTGYT                                                                      8

SEQ ID NO: 120          moltype = AA   length = 8
FEATURE                 Location/Qualifiers
REGION                  1..8
                        note = Synthetic peptide
source                  1..8
                        mol_type = protein
                        organism = synthetic construct
SEQUENCE: 120
INPYNGVT                                                                      8

SEQ ID NO: 121          moltype = AA   length = 16
FEATURE                 Location/Qualifiers
REGION                  1..16
                        note = Synthetic peptide
source                  1..16
                        mol_type = protein
                        organism = synthetic construct
SEQUENCE: 121
TRDPLYYGYR DSTMDY                                                            16

SEQ ID NO: 122          moltype = AA   length = 11
FEATURE                 Location/Qualifiers
REGION                  1..11
                        note = Synthetic peptide
source                  1..11
                        mol_type = protein
                        organism = synthetic construct
SEQUENCE: 122
QSLVHSDGNT Y                                                                 11

SEQ ID NO: 123          moltype =    length =
SEQUENCE: 123
000

SEQ ID NO: 124          moltype = AA   length = 9
FEATURE                 Location/Qualifiers
REGION                  1..9
                        note = Synthetic peptide
source                  1..9
                        mol_type = protein
                        organism = synthetic construct
SEQUENCE: 124
SQSTHVPYT                                                                     9

SEQ ID NO: 125          moltype = AA   length = 8
FEATURE                 Location/Qualifiers
REGION                  1..8
                        note = Synthetic peptide
source                  1..8
                        mol_type = protein
                        organism = synthetic construct
SEQUENCE: 125
GYTFTSYT                                                                      8

SEQ ID NO: 126          moltype = AA   length = 8
FEATURE                 Location/Qualifiers
REGION                  1..8
                        note = Synthetic peptide
source                  1..8
                        mol_type = protein
                        organism = synthetic construct
SEQUENCE: 126
INPSSTYT                                                                      8
```

```
SEQ ID NO: 127          moltype = AA   length = 10
FEATURE                 Location/Qualifiers
REGION                  1..10
                        note = Synthetic peptide
source                  1..10
                        mol_type = protein
                        organism = synthetic construct
SEQUENCE: 127
SRGELGGFAY                                                                10

SEQ ID NO: 128          moltype = AA   length = 6
FEATURE                 Location/Qualifiers
REGION                  1..6
                        note = Synthetic peptide
source                  1..6
                        mol_type = protein
                        organism = synthetic construct
SEQUENCE: 128
QGIRGN                                                                    6

SEQ ID NO: 129          moltype =     length =
SEQUENCE: 129
000

SEQ ID NO: 130          moltype = AA   length = 9
FEATURE                 Location/Qualifiers
REGION                  1..9
                        note = Synthetic peptide
source                  1..9
                        mol_type = protein
                        organism = synthetic construct
SEQUENCE: 130
LQRNAYPLT                                                                 9

SEQ ID NO: 131          moltype = AA   length = 8
FEATURE                 Location/Qualifiers
REGION                  1..8
                        note = Synthetic peptide
source                  1..8
                        mol_type = protein
                        organism = synthetic construct
SEQUENCE: 131
GFTFSSFA                                                                  8

SEQ ID NO: 132          moltype = AA   length = 7
FEATURE                 Location/Qualifiers
REGION                  1..7
                        note = Synthetic peptide
source                  1..7
                        mol_type = protein
                        organism = synthetic construct
SEQUENCE: 132
IRSGGIT                                                                   7

SEQ ID NO: 133          moltype = AA   length = 13
FEATURE                 Location/Qualifiers
REGION                  1..13
                        note = Synthetic peptide
source                  1..13
                        mol_type = protein
                        organism = synthetic construct
SEQUENCE: 133
ARVSTATYYG MDY                                                            13

SEQ ID NO: 134          moltype = AA   length = 108
FEATURE                 Location/Qualifiers
REGION                  1..108
                        note = Synthetic peptide
source                  1..108
                        mol_type = protein
                        organism = synthetic construct
SEQUENCE: 134
QIVLTQSPAI MSASLGERVT MTCTASSSVS STYFHWYQQK PGSSPKLWIY STSNLASGVP          60
RRFSGSASGT SYSLTISSME AEDAATYYCH QYHRSPLTFG AGTKLELK                      108

SEQ ID NO: 135          moltype = AA   length = 116
FEATURE                 Location/Qualifiers
REGION                  1..116
                        note = Synthetic peptide
```

```
                        source          1..116
                                        mol_type = protein
                                        organism = synthetic construct
SEQUENCE: 135
QVQLQQSAAE LARPGASVKM SCKASGYTFT TYTMHWVKQR PGQGLEWIGF INPSSGYTDY    60
NQKFKDRTTL TADKSSSTVY MQLSSLTSED SAVYYCANGD YYVAYWGQGT LVTVSA       116

SEQ ID NO: 136          moltype = AA  length = 107
FEATURE                 Location/Qualifiers
REGION                  1..107
                        note = Synthetic peptide
source                  1..107
                        mol_type = protein
                        organism = synthetic construct
SEQUENCE: 136
DIQMTQSPAS LSASVGETVT ITCRISENIY SYLAWYQQKQ GKSPQLLVYN AKILVEGVPS    60
RFSGSGSGTQ FSLKINSLQP EDFGNYYCQH HYTVPWTFGG GTKLEIK                 107

SEQ ID NO: 137          moltype = AA  length = 117
FEATURE                 Location/Qualifiers
REGION                  1..117
                        note = Synthetic peptide
source                  1..117
                        mol_type = protein
                        organism = synthetic construct
SEQUENCE: 137
EVKLEESGGG LVQPGGSMKL SCVASGFTFS DYWMNWVRQS PEKGLEWVAQ IRLKSDNYAT    60
HYAESVKGRF TISRDDSKRS VYLQMNNLRA EDTGTYYCND GPPSGCWGQG TTLIVSS      117

SEQ ID NO: 138          moltype = AA  length = 107
FEATURE                 Location/Qualifiers
REGION                  1..107
                        note = Synthetic peptide
source                  1..107
                        mol_type = protein
                        organism = synthetic construct
SEQUENCE: 138
DIQMTQSPAS LSASVGETVT ITCRISENIY SYLAWYQQKQ GKSPQLLVYN AKILVEGVPS    60
RFSGSGSGTQ FSLKINSLQP EDFGNYYCQH HYTVPWTFGG GTKLEIK                 107

SEQ ID NO: 139          moltype = AA  length = 117
FEATURE                 Location/Qualifiers
REGION                  1..117
                        note = Synthetic peptide
source                  1..117
                        mol_type = protein
                        organism = synthetic construct
SEQUENCE: 139
EVKLEESGGG LVQPGGSMKL SCVASGFTFS NYWMNWVRQS PEKGLEWVAQ IRLKSDNYAT    60
HYAESVKGRF TISRDDSKRS VYLQMNNLRA EDTGTYYCND GPPSGCWGQG TTLIVSS      117

SEQ ID NO: 140          moltype = AA  length = 112
FEATURE                 Location/Qualifiers
REGION                  1..112
                        note = Synthetic peptide
source                  1..112
                        mol_type = protein
                        organism = synthetic construct
SEQUENCE: 140
DVVMTQTPLS LPVSLGDQAS ISCRSSQSLV HSDGNTYLNW YLQKPGQSPK LLIYKVSNRF    60
SGVPDRFSGS GSGTDFTLKI RRVEAEDLGV YFCSQSTHVP YTFGGGTKLE IK           112

SEQ ID NO: 141          moltype = AA  length = 117
FEATURE                 Location/Qualifiers
REGION                  1..117
                        note = Synthetic peptide
source                  1..117
                        mol_type = protein
                        organism = synthetic construct
SEQUENCE: 141
QVQLQQSGAE LARPGASVKM SCKASGYTFT SYTMHWIKQR PGQGQEWIGY INPSSTYTHY    60
IKKFKDKATL TADKSSSTAY MQLRSLTSED SAVYYCSRGE LGGFAYWGQG TLVTVSA      117

SEQ ID NO: 142          moltype = AA  length = 112
FEATURE                 Location/Qualifiers
REGION                  1..112
                        note = Synthetic peptide
source                  1..112
                        mol_type = protein
```

```
                        organism = synthetic construct
SEQUENCE: 142
DVLMTQTPLS LPVSLGDQPS ISCRSSQSIV HSNGNTYLDW YLQKPGQSPK LLIYKVSNRF    60
SGVPDRFSGS GSGTDFTLKI SRVEAEDLGV YYCFQGSHVP FTFGSGTRLE IK          112

SEQ ID NO: 143          moltype = AA   length = 120
FEATURE                 Location/Qualifiers
REGION                  1..120
                        note = Synthetic peptide
source                  1..120
                        mol_type = protein
                        organism = synthetic construct
SEQUENCE: 143
EVQLQQSGPE LVKPGASVKM SCKASGYIFT HYIMHWVKQK PGQGLEWIGC INPYNDGTKY    60
NEKFKGKATL TSDKSSSTAY MELSSLTSED SAVYYCARYY GYPYYSMDYW GQGTSVTVSS   120

SEQ ID NO: 144          moltype = AA   length = 112
FEATURE                 Location/Qualifiers
REGION                  1..112
                        note = Synthetic peptide
source                  1..112
                        mol_type = protein
                        organism = synthetic construct
SEQUENCE: 144
AIVMFQSPSS LVVSAGEKVT MSCKSSQSLL NSRTRKNYLA WYQQKPGQSP KLLIYWASTR    60
ESGVPDRFTG SGSGTDFTLT ISSVQAEDLA VYYCKQSYYL YTFGGGTKLE IK          112

SEQ ID NO: 145          moltype = AA   length = 117
FEATURE                 Location/Qualifiers
REGION                  1..117
                        note = Synthetic peptide
source                  1..117
                        mol_type = protein
                        organism = synthetic construct
SEQUENCE: 145
DVQLQESGPG LVKSSQSLSL TCSVTGYSIT SGYYWKWIRQ FPGNKLEWMG YISYDGGINY    60
NPSLKNRISI TRDTSKNQFF LKLNSVTTED TAKYYCARFG KGAMDYWGQG TSVTVSS     117

SEQ ID NO: 146          moltype = AA   length = 108
FEATURE                 Location/Qualifiers
REGION                  1..108
                        note = Synthetic peptide
source                  1..108
                        mol_type = protein
                        organism = synthetic construct
SEQUENCE: 146
QIVLTQSPAI MSASLGDRVT MTCTASSSVS SSYLHWYQQK PGSSPKLWIY STSNLASGVP    60
ARFSGSGSGT SYSLTISSME AEDAATYYCH QYHRSPPTFG SGTKLEIK               108

SEQ ID NO: 147          moltype = AA   length = 119
FEATURE                 Location/Qualifiers
REGION                  1..119
                        note = Synthetic peptide
source                  1..119
                        mol_type = protein
                        organism = synthetic construct
SEQUENCE: 147
EVQLQQSGPE LVKPGASMKI SCKASGYSFT GYTMNWVKQS HGKNLEWIGL INPYNGGTNY    60
NQKFKGKATL TVDKSSSTAY MELLSLTSED SAVYYCARGV YDYDGFTYWG QGTLVTVSA   119

SEQ ID NO: 148          moltype = AA   length = 112
FEATURE                 Location/Qualifiers
REGION                  1..112
                        note = Synthetic peptide
source                  1..112
                        mol_type = protein
                        organism = synthetic construct
SEQUENCE: 148
DVVMTQTPLS LPVSLGDQAS ISCRSSQSLV HSDGNTYLYW YLQKPGQSPK LLIYKVSNRF    60
SGVPDRFSGS GSGTDFTLKI SRVEAEDLGV YFCSQSTHVP YTFGGGTKLE IK          112

SEQ ID NO: 149          moltype = AA   length = 117
FEATURE                 Location/Qualifiers
REGION                  1..117
                        note = Synthetic peptide
source                  1..117
                        mol_type = protein
                        organism = synthetic construct
SEQUENCE: 149
```

```
QVQLQQSGAE LARPGASVKM SCKASGYTFT TYTMHWLKQR PGQGLEWIGY INPRSGYSNY    60
NQKFKDKATL TADKSSNTAY MQLNTLTSED SKVYYCSRGE LGGFAYWGQG TLVTVSA      117

SEQ ID NO: 150         moltype = AA   length = 107
FEATURE                Location/Qualifiers
REGION                 1..107
                       note = Synthetic peptide
source                 1..107
                       mol_type = protein
                       organism = synthetic construct
SEQUENCE: 150
DIQMTQSPAS QSASLGESVT ITCLASQTIG TWLAWYQQKP GKSPQLLIYA AASLADGVPS    60
RFSGSGSGTR FSFKISSLQA EDFVSYYCQQ LYSIPRTFGG GTKLEIK                 107

SEQ ID NO: 151         moltype = AA   length = 117
FEATURE                Location/Qualifiers
REGION                 1..117
                       note = Synthetic peptide
source                 1..117
                       mol_type = protein
                       organism = synthetic construct
SEQUENCE: 151
EVQLQQSGPE LVKPGASVKM SCKASGYRFT DYNMHWVKQS HGKSLEWIGY INPNNGGTNY    60
NQNFKGKATL TVNKSSSTAY MELRSLTSED SAAYYCARDY LYFFDCWGQG TTLTVSS      117

SEQ ID NO: 152         moltype = AA   length = 112
FEATURE                Location/Qualifiers
REGION                 1..112
                       note = Synthetic peptide
source                 1..112
                       mol_type = protein
                       organism = synthetic construct
SEQUENCE: 152
DVVMTQTPLS LPVSLGDQAS ISCRASQSLV HSNGNTYLHW FLQKPGQSPK LLIYKVSNRF    60
SGVPDRFSGS GSRTDFTLKI SRVEAEDLGV YFCSQITHVP YTFGGGTKLE IK           112

SEQ ID NO: 153         moltype = AA   length = 117
FEATURE                Location/Qualifiers
REGION                 1..117
                       note = Synthetic peptide
source                 1..117
                       mol_type = protein
                       organism = synthetic construct
SEQUENCE: 153
QIQLVQSGPA LKKPGETVKI SCKASGYTFT DYSMHWIKQA PGKGLKWMGW ISTETGEPTY    60
ADGFKGRFDF SLETSADTAY LSINNLTNED TATYFCTRGL WSSFAYWGQG TLVTVSA      117

SEQ ID NO: 154         moltype = AA   length = 111
FEATURE                Location/Qualifiers
REGION                 1..111
                       note = Synthetic peptide
source                 1..111
                       mol_type = protein
                       organism = synthetic construct
SEQUENCE: 154
DIVLTQSPAS LAVSLGQRAT ISCRASKSVS TSGYSYIHWY QQKPGQPPKL LIYLASNLES    60
GVPARFSGSG SGTDFTLNIH PVEEEDAATY YCQHSRELPL TFGAGTKLEL K            111

SEQ ID NO: 155         moltype = AA   length = 118
FEATURE                Location/Qualifiers
REGION                 1..118
                       note = Synthetic peptide
source                 1..118
                       mol_type = protein
                       organism = synthetic construct
SEQUENCE: 155
DVQLVESGGG LVQPRGSRKL SCAASGFTFS SFGMHWVRQA PEKGLEWVAY ISSDSRTIYY    60
ADTVKGRFTI SRDNPTNTLF LQMTSLRSED TAMYYCARDY GRTYEAYWGQ GTLVTVSA    118

SEQ ID NO: 156         moltype = AA   length = 107
FEATURE                Location/Qualifiers
REGION                 1..107
                       note = Synthetic peptide
source                 1..107
                       mol_type = protein
                       organism = synthetic construct
SEQUENCE: 156
DIQMIQSPSS MFASLGDRVS LSCRASQDIG GNLDWYQQKP GGTIKLLIYS TSNLNSGVPS    60
RFSGSGSGSD YSLTITSLES EDFADYYCLQ RNAYPLTFGA GTKLELK                 107
```

```
SEQ ID NO: 157            moltype = AA   length = 118
FEATURE                   Location/Qualifiers
REGION                    1..118
                          note = Synthetic peptide
source                    1..118
                          mol_type = protein
                          organism = synthetic construct
SEQUENCE: 157
EVKLMESGGD LVKPGGSLKL SCAASGFTFS SYAMSWVRQT PEKRLEWVAS IRSGGTTYYP     60
DSVKGRFTIS RDNARNILYL RMSSLRSEDT AIYYCAKVGG NPYPMDYWGQ GTSVTVSS     118

SEQ ID NO: 158            moltype = AA   length = 108
FEATURE                   Location/Qualifiers
REGION                    1..108
                          note = Synthetic peptide
source                    1..108
                          mol_type = protein
                          organism = synthetic construct
SEQUENCE: 158
EIVLTQSPTT MAASPGEKIT ITCSASSSIS SNYLHWYQQK PGFSPKLLIY RTSNLASGVP     60
ARFSGSGSGT SYSLTIGTME AEDVATYYCQ QGSSIPLTFG AGTKLELK                108

SEQ ID NO: 159            moltype = AA   length = 122
FEATURE                   Location/Qualifiers
REGION                    1..122
                          note = Synthetic peptide
source                    1..122
                          mol_type = protein
                          organism = synthetic construct
SEQUENCE: 159
QVQLQQSGAE LVRPGTSVKV SCKASGYAFS NYLIEWVKQR PGQGLEWIGV INPGSGGTNY     60
NEKFKGKATM TADKSSSTAY MHLSNLTSED SVVYFCARSY FGRSYPYTMD YWGQGTSVTV    120
SS                                                                  122

SEQ ID NO: 160            moltype = AA   length = 111
FEATURE                   Location/Qualifiers
REGION                    1..111
                          note = Synthetic peptide
source                    1..111
                          mol_type = protein
                          organism = synthetic construct
SEQUENCE: 160
DIVLTQSPAS LAVSLGQRAT ISCKASQSVD YDGDNYVNWY QQKVGQPPKL LISAASNLES     60
GIPARFSGSG SGTDFTLNIH PVEEEDAATY YCQQSNEDPF TFGSGTKLEI K             111

SEQ ID NO: 161            moltype = AA   length = 120
FEATURE                   Location/Qualifiers
REGION                    1..120
                          note = Synthetic peptide
source                    1..120
                          mol_type = protein
                          organism = synthetic construct
SEQUENCE: 161
QVQLQQSGPE LVRPGVSVKI SCKGSGYTFT DYAMHWVKQS HAKSLEWIGV ISTYSGNTNY     60
NQKFQDKATM TVDKSSSTAY MALARLTSDD SAIYYCARRG DYSLYAMDYW GQGTSVTVSS    120

SEQ ID NO: 162            moltype = AA   length = 112
FEATURE                   Location/Qualifiers
REGION                    1..112
                          note = Synthetic peptide
source                    1..112
                          mol_type = protein
                          organism = synthetic construct
SEQUENCE: 162
NIMMTQSPSS LAVSAGEKVT MSCKSSQSVL FSSNQKNYLA WYQQKPGQSP RLLIYWASTR     60
ESGVPDRFTG SGSGTDFTLT ISNVQAEDLA VYYCHQYLSS RTFGAGTKLE LK            112

SEQ ID NO: 163            moltype = AA   length = 118
FEATURE                   Location/Qualifiers
REGION                    1..118
                          note = Synthetic peptide
source                    1..118
                          mol_type = protein
                          organism = synthetic construct
SEQUENCE: 163
DVQLVESGGG LVQPRGSRKL SCAASGFTFS SFGMHWVRQA PEKGLEWVAY ISSDSRTIYY     60
ADTVKGRFTI SRDNPTNTLF LQMTSLRSED TAMYYCARDY GRTYEAYWGQ GTLVTVSA     118
```

```
SEQ ID NO: 164            moltype = AA  length = 111
FEATURE                   Location/Qualifiers
REGION                    1..111
                          note = Synthetic peptide
source                    1..111
                          mol_type = protein
                          organism = synthetic construct
SEQUENCE: 164
DIVLTQSPAS LALSLGQRAT ISCRASESVD NYGISFMNWF QQKPGQPPKL LIYAASNQGS    60
GVPARFSGSG SGTDFSLNIH PMEEDDTAMY FCQQSKEVPL TFGAGTKLEL K            111

SEQ ID NO: 165            moltype = AA  length = 119
FEATURE                   Location/Qualifiers
REGION                    1..119
                          note = Synthetic peptide
source                    1..119
                          mol_type = protein
                          organism = synthetic construct
SEQUENCE: 165
EVRLVESGGG LMQPGGSLKL PCAASGFPFS SSAMSWVRQT PEKRLEWVAS INSDGNTYYP    60
DSVKGRFTIS RDSARNILYL QMSSLRSEDT AMYYCTRNGD YRYDEFAYWG QGTLVTVSA    119

SEQ ID NO: 166            moltype = AA  length = 108
FEATURE                   Location/Qualifiers
REGION                    1..108
                          note = Synthetic peptide
source                    1..108
                          mol_type = protein
                          organism = synthetic construct
SEQUENCE: 166
QIVLTQSPAI MSASLGERVT MTCTASSSVS SSYLHWYQQK PGSSPKLWIY STSNLASGVP    60
ARFSGSGSGT SYSLTISSME AEDAATYYCH QYHRSPPTFG AGTKLELK                108

SEQ ID NO: 167            moltype = AA  length = 119
FEATURE                   Location/Qualifiers
REGION                    1..119
                          note = Synthetic peptide
source                    1..119
                          mol_type = protein
                          organism = synthetic construct
SEQUENCE: 167
QVQLQQSGAE LAKPGASVKM SCKASGYTFT GYWMHWVKQR PGQGLEWLGY INPSTGYTES    60
NQKFKDKATL TADKSSTTAY MQLRSLTPED SAVYYCAREG ITTVLVDYWG QGTTLTVSS    119

SEQ ID NO: 168            moltype = AA  length = 112
FEATURE                   Location/Qualifiers
REGION                    1..112
                          note = Synthetic peptide
source                    1..112
                          mol_type = protein
                          organism = synthetic construct
SEQUENCE: 168
NIMMTQSPSS LAVSAGEKVT MSCKSSQSVL FSSNQKNYLA WYQQKPGQSP RLLIYWASTR    60
ESGVPDRFTG SGSGTDFTLT ISNVQAEDLA VYYCHQYLSS RTFGAGTKLE LK            112

SEQ ID NO: 169            moltype = AA  length = 121
FEATURE                   Location/Qualifiers
REGION                    1..121
                          note = Synthetic peptide
source                    1..121
                          mol_type = protein
                          organism = synthetic construct
SEQUENCE: 169
QVQLKQSGPE LEKPGASVKI SCKASGYSFT GYNMNWVKQS NGKSLEWIGN IDPYYGGSTY    60
NQKFTGKATL TVDKSSTAY MQLKSLTSED SAVYYCARER SGYVFSAMDY WGQGTSVTVS   120
S                                                                   121

SEQ ID NO: 170            moltype = AA  length = 112
FEATURE                   Location/Qualifiers
REGION                    1..112
                          note = Synthetic peptide
source                    1..112
                          mol_type = protein
                          organism = synthetic construct
SEQUENCE: 170
NIMMTQSPSS LAVSAGEKVT MSCKSSQSVL FSSNQKNYLA WYQQKPGQSP RLLIYWASTR    60
ESGVPDRFTG SGSGTDFTLT ISNVQAEDLA VYYCHQYLSS RTFGAGTKLE LK            112

SEQ ID NO: 171            moltype = AA  length = 123
```

```
FEATURE                 Location/Qualifiers
REGION                  1..123
                        note = Synthetic peptide
source                  1..123
                        mol_type = protein
                        organism = synthetic construct
SEQUENCE: 171
EVQLQQSGPE LVKPGGSMKI SCKASGYSFT GYTMNWVKRS HGKNLEWIGL INPYNGVTTY    60
NQNFKGKATL AVDKSSSTAY MELLGLTSED SAVYYCTRDP LYYGYRDSTM DYWGQGTSVT   120
VSS                                                                 123

SEQ ID NO: 172          moltype = AA  length = 112
FEATURE                 Location/Qualifiers
REGION                  1..112
                        note = Synthetic peptide
source                  1..112
                        mol_type = protein
                        organism = synthetic construct
SEQUENCE: 172
DVVMTQTPLS LPVSLGDQAS ISCRSSQSLV HSDGNTYLNW YLQKPGQSPK LLIYKVSNRF    60
SGVPDRFSGS GSGTDFTLKI RRVEAEDLGV YFCSQSTHVP YTFGGGTKLE IK           112

SEQ ID NO: 173          moltype = AA  length = 117
FEATURE                 Location/Qualifiers
REGION                  1..117
                        note = Synthetic peptide
source                  1..117
                        mol_type = protein
                        organism = synthetic construct
SEQUENCE: 173
EVQLQQSGAE LARPGASVKM SCKASGYTFT SYTMHWIKQR PGQGQEWIGY INPSSTYTHY    60
IKKFKDKATL TADKSSSTAY MQLRSLTSED SAVYYCSRGE LGGFAYWGQG TLVTVSA     117

SEQ ID NO: 174          moltype = AA  length = 107
FEATURE                 Location/Qualifiers
REGION                  1..107
                        note = Synthetic peptide
source                  1..107
                        mol_type = protein
                        organism = synthetic construct
SEQUENCE: 174
DIQMIQSPSS MFASLGDRVS LSCRASQGIR GNLDWYQQKP GGTIKLLIYS TSILNSGVPS    60
RFSGSGSGSD YSLTITSLES EDFADYYCLQ RNAYPLTFGS GTKLELK                107

SEQ ID NO: 175          moltype = AA  length = 119
FEATURE                 Location/Qualifiers
REGION                  1..119
                        note = Synthetic peptide
source                  1..119
                        mol_type = protein
                        organism = synthetic construct
SEQUENCE: 175
EVKLVESGGG LMKPGGSLKL SCAASGFTFS SFALSWVRQT PEKRLEWVAS IRSGGITYHA    60
DSVKGRFTIS RDNAGNILYL QMNSLRSEDT AMYFCARVST ATYYGMDYWG QGTSVTVSS   119

SEQ ID NO: 176          moltype = AA  length = 219
FEATURE                 Location/Qualifiers
REGION                  1..219
                        note = NCBI / NP_061247.1, 2017-08-07
source                  1..219
                        mol_type = protein
                        organism = Mus musculus
SEQUENCE: 176
MASTGLQILG IVLTLLGWVN ALVSCALPMW KVTAFIGNSI VVAQMVWEGL WMSCVVQSTG    60
QMQCKVYDSL LALPQDLQAA RALCVVTLLI VLLGLLVYLA GAKCTTCVED RNSKSRLVLI   120
SGIIFVISGV LTLIPVCWTA HSIIQDFYNP LVADAQKREL GASLYLGWAA SGLLLLGGGL   180
LCCACSSGGT QGPRHYMACY STSVPHSRGP SEYPTKNYV                         219

SEQ ID NO: 177          moltype = AA  length = 80
FEATURE                 Location/Qualifiers
REGION                  1..80
                        note = Synthetic peptide
source                  1..80
                        mol_type = protein
                        organism = synthetic construct
SEQUENCE: 177
MASAGMQILG VVLTLLGWVN GLVSCALPMW KVTAFIGNSI VVAQVVWEGL WMSCVVQSTG    60
QMQCKVYDSL LALPQDLQAA                                                80
```

-continued

```
SEQ ID NO: 178         moltype = AA  length = 220
FEATURE                Location/Qualifiers
REGION                 1..220
                       note = Synthetic peptide
source                 1..220
                       mol_type = protein
                       organism = synthetic construct
SEQUENCE: 178
MASAGMQILG VVLTLLGWVN GLVSCALPMW KVTAFIGNSI VVAQVVWEGL WMSCVVQSTG   60
QMQCKVYDSL LALPQDLQAA RALCVIALLV ALFGLLVYLA GAKCTTCVEE KDSKARLVLT  120
SGIVFVISGV LTLIPVCWTA HAVIRDFYNP LVAEAQKREL GASLYLGWAA SGLLLLGGGL  180
LCCTCPSGGS QGPSHYMARY STSAPAISRG PSEYPTKNYV                       220

SEQ ID NO: 179         moltype = AA  length = 322
FEATURE                Location/Qualifiers
REGION                 1..322
                       note = Synthetic peptide
source                 1..322
                       mol_type = protein
                       organism = synthetic construct
SEQUENCE: 179
CAGATCGTGC TGACTCAGAG TCCTTCAATT ATGTCCGTGA GCCCAGGCGA GAAGGTCACC   60
ATCACATGCA GTGCCTCCAG CTCTGTCTCA TACATGCACT GGTTCCAGCA GAAGCCAGGG  120
ACCAGTCCCA AGCTGTGCAT CTACTCTACA TCGAACCTGG CCTCCGGAGT GCCCGCAAGG  180
TTTAGCGGTC GGGGCTCTGG AACTTCATAC TCCCTGACCA TCTCGCGGGT GGCCGCTGAG  240
GATGCAGCAA CATACTATTG CCAGCAGAGG TCCAATTATC CCCCTTGGAC ATTCGGCGGA  300
GGTACCAAAC TCGAGATTAA GC                                          322

SEQ ID NO: 180         moltype = AA  length = 351
FEATURE                Location/Qualifiers
REGION                 1..351
                       note = Synthetic peptide
source                 1..351
                       mol_type = protein
                       organism = synthetic construct
SEQUENCE: 180
GAAGTCCAGC TGCAGCAGTC TGGCCCTGAA CTGGTGAAGC CTGGCGCCAG CATGAAGATC   60
TCCTGCAAGG CCAGCGGCTA CTCCTTCACC GGCTATACAA TGAACTGGGT GAAGCAGTCC  120
CACGGCAAGA ATCTGGAGTG GATCGGCCTG ATCAACCCAT ACAATGGCGG CACCATCTAC  180
AACCAGAAGT TTAAGGGCAA GGCCACCCTG ACAGTGGACA AGAGCTCCTC TACCGCCTAC  240
ATGGAGCTGC TGTCTCTGAC AAGCGAGGAC TCCGCCGTGT ACTATTGCGC CCGGGACTAC  300
GGCTTCGTGC TGGACTATTG GGGCCAGGGC ACCACACTGA CAGTGAGCTC C           351

SEQ ID NO: 181         moltype = AA  length = 107
FEATURE                Location/Qualifiers
REGION                 1..107
                       note = Synthetic peptide
source                 1..107
                       mol_type = protein
                       organism = synthetic construct
SEQUENCE: 181
QIVLTQSPSI MSVSPGEKVT ITCSASSSVS YMHWFQQKPG TSPKLCIYST SNLASGVPAR   60
FSGRGSGTSY SLTISRVAAE DAATYYCQQR SNYPPWTFGG GTKLEIK                107

SEQ ID NO: 182         moltype = AA  length = 117
FEATURE                Location/Qualifiers
REGION                 1..117
                       note = Synthetic peptide
source                 1..117
                       mol_type = protein
                       organism = synthetic construct
SEQUENCE: 182
EVQLQQSGPE LVKPGASMKI SCKASGYSFT GYTMNWVKQS HGKNLEWIGL INPYNGGTIY   60
NQKFKGKATL TVDKSSSTAY MELLSLTSED SAVYYCARDY GFVLDYWGQG TTLTVSS     117

SEQ ID NO: 183         moltype = DNA  length = 324
FEATURE                Location/Qualifiers
misc_feature           1..324
                       note = Synthetic polynucleotide
source                 1..324
                       mol_type = other DNA
                       organism = synthetic construct
SEQUENCE: 183
gaaattgtgc tcacccagtc tccagcactc atggctgcat ctccagggga gaaggtcacc   60
atcacctgca gtgtcagctc aagtataagt tccagcaact tgcactggta ccagcagaag  120
tcaggaacct cccccaaact ctggatttat ggcacatcca acctggcttc tggagtccct  180
gttcgcttca gtggcagtgg atctgggacc tcttattctc tcacaatcag caacatggag  240
gctgaagatg ctgccactta ttactgtcaa cagtggagta gttacccaca cacgttcgga  300
gggggggacca agctggaaat aaaa                                        324
```

```
SEQ ID NO: 184           moltype = DNA  length = 378
FEATURE                  Location/Qualifiers
misc_feature             1..378
                         note = Synthetic polynucleotide
source                   1..378
                         mol_type = other DNA
                         organism = synthetic construct
SEQUENCE: 184
caggtccaaa tgcagcagtc tggagctgag ctggtaaggc ctgggacttc agtgaaggtg    60
tcctgcaagg cttctggata cgccttcact aattacttga tagagtgggt aaagcagagg   120
cctgacagg gccttgagtg gattggactg attaatcctg aagtggtgg tactaattac    180
aatgagaagt tcaagggcaa ggcaacactg actgcagaca atcctccac cactgcctac   240
atgcagctca gcagcctgac atctgatgac tctgcggttt atttctgtgc aagacggtcc   300
cctctaggga gttggatcta ctatgcttac gacggtgttg cttactgggg ccaagggact   360
ctggtcactg tctctgca                                                 378

SEQ ID NO: 185           moltype = AA  length = 108
FEATURE                  Location/Qualifiers
REGION                   1..108
                         note = Synthetic peptide
source                   1..108
                         mol_type = protein
                         organism = synthetic construct
SEQUENCE: 185
EIVLTQSPAL MAASPGEKVT ITCSVSSSIS SSNLHWYQQK SGTSPKLWIY GTSNLASGVP    60
VRFSGSGSGT SYSLTISNME AEDAATYYCQ QWSSYPHTFG GGTKLEIK               108

SEQ ID NO: 186           moltype = AA  length = 126
FEATURE                  Location/Qualifiers
REGION                   1..126
                         note = Synthetic peptide
source                   1..126
                         mol_type = protein
                         organism = synthetic construct
SEQUENCE: 186
QVQMQQSGAE LVRPGTSVKV SCKASGYAFT NYLIEWVKQR PGQGLEWIGL INPGSGGTNY    60
NEKFKGKATL TADKSSTTAY MQLSSLTSDD SAVYFCARRS PLGSWIYYAY DGVAYWGQGT   120
LVTVSA                                                              126

SEQ ID NO: 187           moltype = DNA  length = 645
FEATURE                  Location/Qualifiers
source                   1..645
                         mol_type = genomic DNA
                         organism = Mus musculus
SEQUENCE: 187
gatattgtgc taactcagtc tccagccacc ctgtctgtga ctccaggaaa tagcgtcagt    60
ctttcctgca gggccagcca agtattggc ggtaacctac actggtatca acaaaaatca   120
catgagtctc caaggcttct catcaagtat gcttcccagt ccatctctgg atcccctcc   180
aggttcagtg gcagtggatc agggacagat ttcactctca gtatcaacag tgtggagact   240
gaagattttg gaatgtattt ctgtcaacag agtaacagt ggcctacac gttcggaggg   300
gggaccaagc tggaaataaa acgggcagat gctgcaccaa ctgtatccat cttcccacca   360
tccagtgagc agttaacatc tggaggtgcc tcagtcgtgt gcttcttgaa caacttctac   420
cccaaagaca tcaatgtcaa gtggaagatt gatggcagtg aacgacaaaa tggcgtcctg   480
aacagttgga ctgatcagga cagcaaagac agcacctaca gcatgagcag cacccctcacg   540
ttgaccaagg acgagtatga acgacataaa agctatacct gtgaggccac tcacaagaca   600
tcaacttcac ccattgtcaa gagcttcaac aggaatgagt gttag                 645

SEQ ID NO: 188           moltype = DNA  length = 1335
FEATURE                  Location/Qualifiers
source                   1..1335
                         mol_type = genomic DNA
                         organism = Mus musculus
SEQUENCE: 188
gacgtgcagc ttcaggagtc aggacctagc ctcgtgaaac cttctcagac tctgtccctc    60
acctgttctg tcactggcga ctccatcacc agtgattact ggagctggat ccggaaattc   120
ccagggaata gacttgagta catggggtac gtaagctaca gtggtagcac ttactacaat   180
ccatctctca aaagtcgaat ctccatcacc cgagacacat ccaagaacca gtactacctg   240
gatttgaatt ctgtgactac tgaggacaca gccacatatt actgtgcaaa ctgggacgqt   300
gattactggg gccaagggac tctggtcact gtctcttcag cagctaaaac aacagcccca   360
tcggtctatc cactggcccc tgtgtgtgga gatacaactg ctcctcggt gactctagga   420
tgcctggtca aggttatttt ccctgagcca gtgaccttga cctggaactc tggatccctg   480
tccagtggtg tgcacacctt cccagctgtc ctgcagtctg acctctacac cctcagcagc   540
tcagtgactg taacctcgag cacctggccc agccagtcca tcacctgcaa tgtggcccac   600
ccggcaagca gcaccaaggt ggacaagaaa attgagccca gagggccac aatcaagccc   660
tgtcctccat gcaaatgccc agcacctaac ctcttgggtg gaccatccgt cttcatcttc   720
cctccaaaga tcaaggatgt actcatgatc tccctgagcc ccatagtcac atgtgtggtg   780
gtggatgtga gcgaggatga cccagatgtc cagatcagct ggtttgtgaa caacgtggaa   840
gtacacacag ctcagacaca aacccataga gaggattaca acagtactct ccgggtgtc   900
```

```
agtgccctcc ccatccagca ccaggactgg atgagtggca aggagttcaa atgcaaggtc    960
aacaacaaag acctcccagc gcccatcgag agaaccatct caaaacccaa agggtcagta   1020
agagctccac aggtatatgt cttgcctcca ccagaagaag agatgactaa gaaacaggtc   1080
actctgacct gcatggtcac agacttcatg cctgaagaca tttacgtgga gtggaccaac   1140
aacgggaaaa cagagctaaa ctacaagaac actgaaccag tcctggactc tgatggttct   1200
tacttcatgt acagcaagct gagagtggaa aagaagaact gggtggaaag aaatagctac   1260
tcctgttcag tggtccacga gggtctgcac aatcaccaca cgactaagag cttctcccgg   1320
actccgggta aatga                                                     1335

SEQ ID NO: 189         moltype = DNA   length = 8806
FEATURE                Location/Qualifiers
misc_feature           1..8806
                       note = Synthetic peptide
source                 1..8806
                       mol_type = other DNA
                       organism = synthetic construct
SEQUENCE: 189
aatgtagtct tatgcaatac tcttgtagtc ttgcaacatg gtaacgatga gttagcaaca     60
tgccttacaa ggagagaaaa agcaccgtgc atgccgattg gtggaagtaa ggtggtacga    120
tcgtgcctta ttaggaaggc aacagacggg tctgacatgg attggacgaa ccactgaatt    180
gccgcattgc agagatattg tatttaagtg cctagctcga tacataaacg ggtctctctg    240
gttagaccag atctgagcct gggagctctc tggctaacta gggaacccac tgcttaagcc    300
tcaataaagc ttgccttgag tgcttcaagt agtgtgtgcc cgtctgttgt gtgactctgg    360
taactagaga tccctcagac cctttttagt cagtgtggaa atctctagca gtggcgcccg    420
aacagggact tgaaagcgaa agggaaacca gaggagctct ctcgacgcag gactcggctt    480
gctgaagcgc gcacggcaag aggcgagggg cggcgactgg tgagtacgcc aaaaattttg    540
actagcggag gctagaagga gagagatggg tgcgagagcg tcagtattaa gcggggggaga   600
attagatcgc gatgggaaaa aattcggtta aggccagggg gaagaaaaaa atataaatta    660
aaacatatag tatgggcaag cagggagcta gaacgattcg cagttaatcc tggcctgtta    720
gaaacatcag aaggctgtag acaaatactg ggacaggtac aaccatccct tcagacagga    780
tcagaagaac ttagatcatt atataataca gtagcaaccc tctattgtgt gcatcaaagg    840
atagagataa aagacaccaa ggaagcttta gacaagatag aggaagagca aaacaaaagt    900
aagaccaccg cacagcaagc ggccgctgat cttcagacct ggaggaggag atatgaggga    960
caattggaga agtgaattat ataaatataa agtagtaaaa attgaaccat taggagtagc   1020
acccaccaag gcaaagagaa gagtggtgca gagagaaaaa agagcagtgg gaataggagc   1080
tttgttcctt gggttcttgg gagcagcagg aagcactatg ggcgcagcgt caatgacgct   1140
gacggtacag gccagacaat tattgtctgg tatagtgcag cagcagaaca atttgctgag   1200
ggctattgag gcgcaacagc atctgttgca actcacagtc tggggcatca agcagctcca   1260
ggcaagaatc ctggctgtgg aaagatacct aaaggatcaa cagctcctgg ggatttgggg   1320
ttgctctgga aaactcattt gcaccactgc tgtgccttgg aatgctagtt ggagtaataa   1380
atctctggaa cagatttgga atcacacgac ctggatggag tgggacagag aaattaacaa   1440
ttacacaagc ttaatacact ccttaattga agaatcgcaa aaccagcaag aaaagaatga   1500
acaagaatta ttggaattag ataaatgggc aagtttgtgg aattggttta acataacaaa   1560
ttggctgtgg tatataaaat tattcataat gatagtagga ggcttggtag gtttaagaat   1620
agtttttgct gtactttcta tagtgaatag agttaggcag ggatattcac cattatcgtt   1680
tcagacccac ctcccaaccc cgaggggacc cgacaggccc gaaggaatag aagaagaagg   1740
tggagagaga gacagagaca gatccattcg attagtgaac ggatctcgac ggtatcggtt   1800
aacttttaaa agaaaagggg ggattggggg gtacagtgca ggggaaagaa tagtagacat   1860
aatagcaaca gacatacaaa ctaaagaatt acaaaaacaa attacaaaaa ttcaaaattt   1920
tccgataagc ttgggagttc cgcgttacat aacttacggt aaatgcccg cctggctgac   1980
cgcccaacga ccccccgccc ttgacgtcaa taatgacgta tgttcccata gtaacgccaa   2040
tagggacttt ccattgacgt caatgggtgg agtatttacg gtaaactgcc cacttggcag   2100
tacatcaagt gtatcatatg ccaagtacgc cccctattga cgtcaatgac ggtaaatggc   2160
ccgcctggca ttatgcccag tacatgacct tatgggactt tcctacttgg cagtacatct   2220
acgtattagt catcgctatt accatggtga tgcggttttg gcagtacatc aatgggcgtg   2280
gatagcggtt tgactcacgg ggatttccaa gtctccaccc cattgacgtc aatgggagtt   2340
tgttttggca ccaaaatcaa cgggactttc caaaatgtcg taacaactcc gccccattga   2400
cgcaaatggg cggtaggcgt gtacggtggg aggtctatat aagcagagct cgtttagtga   2460
accgtcagat cgcctggaga cgccatccac gctgttttga cctccataga agacaccgac   2520
tctagaacta gtggatcccc cgggctcag gaattcgtcg actgatccg gtaccgagga   2580
gatctgccgc cgcgatcgcc ggcgcgccag atctcaagct taactagtta gcggaccgac   2640
gcgtacgcgc ccgctcgaga tgagcggggg cgaggagctg ttcgccggca tcgtgccgt   2700
gctgatcgag ctggacggcg acgtgcacgg ccacaagttc agcgtgcgcg gcgagggcga   2760
gggcgacgcc gactacggca agctggagat caagttcatc tgcaccaccg gcaagctgcc   2820
cgtgccctgg cccaccctgg tgaccaccct gctgtacggc atccagtgct cgcccgcta   2880
ccccgagcac atgaagatga cgacttcttc aagagcgcc atgcccgagg ctacatcca   2940
ggagcgcacc atccagttcc aggacgacgg caagtacaag acccgcgcg aggtgaagtt   3000
cgagggcgac accctggtga accgcatcga gctgaagggc aaggacttca aggaggacgg   3060
caacatcctg ggccacaagc tggagtacag cttcaacagc cacaacgtgt acatccgcgc   3120
cgacaaggcc aacaacggcc tggaggctaa cttcaagacc cgccacaaca tcggggcag   3180
cggcgtgcag ctgccgacc actaccgaca caacgtgccc ctgggcgacg gccccgtgct   3240
gatccccatc aaccactacc tgagcactca gaccaagatc agcaaggacc gcaacgaggc   3300
ccgcgaccac atggtgctcc tggagtcctt cagcgcctgc tgcacaccc acggcatgga   3360
cgagctgtac aaggacgagc tcagataagt taaacctgag tatcatcatc tagggccgca   3420
aattccgccc ctctcccccc ccctaacgtt actggccgaa gccgcttgga taaggccga   3480
tgtgcgtttg tctatatgtt attttccacc atattgccgt cttttggcaa tgtgagggcc   3540
cggaaacctg gccctgtctt cttgacgagc attcctaggg gtcttcccc tctcgccaaa   3600
ggaatgcaag gtctgttgaa tgtcgtgaag gaagcagttc ctctggaagc ttcttgaaga   3660
caaacaacgt ctgtagcgac cctttgcagg cagcggaacc ccccacctgg cgacaggtgc   3720
```

```
ctctgcggcc aaaagccacg tgtataagat acacctgcaa aggcggcaca accccagtgc  3780
cacgttgtga gttggatagt tgtgaaagag tcaaatggc tctcctcaag cgtattcaac   3840
aaggggctga aggatgccca gaaggtaccc cattgtatgg gatctgatct ggggcctcgg  3900
tgcacatgct ttacatgtgt ttagtcgagg ttaaaaaaac gtctaggccc cccgaaccac  3960
ggggacgtgg ttttcctttg aaaaacacga tgataagctt gccacaaccc acaaggagac  4020
gaccttccat gaccgagtac aagcccacgg tgccgctcgc cacccgcgac gacgtccccc  4080
gggccgtacg caccctcgcc gccgcgttcg ccgactaccc cgccacgcgc cacaccgtcg  4140
acccggaccg ccacatcgag cgggtcaccg agctgcaaga actcttcctc acgcgcgtcg  4200
ggctcgacat cggcaaggtg tgggtcgcgg acgacgcgc cgcggtggcg gtctggacca   4260
cgccggagag cgtcgaagcg ggggcggtgt tcgccgagat cggcccgcgc atggccgagt  4320
tgagcggttc ccggctggcc gcgcagcaac agatggaagg cctcctggcg ccgcaccggc  4380
ccaaggagcc cgcgtggttc ctggccaccg tcggcgtctc gcccgaccac cagggcaagg  4440
gtctgggcag cgccgtcgtg ctccccgagg tggaggcggc cgagcgcgcc ggggtgcccg  4500
ccttcctgga gacctccgcg ccccgcaacc tcccctttca gcagcggctc ggcttcaccg  4560
tcaccgccga cgtcgaggtg cccgaaggac cgcgcacctg gtgcatgacc gcaagcccg   4620
gtgcctgaaa ttagatcgat accgtcgaca atcaacctct ggattacaaa atttgtgaaa  4680
gattgactgg tattcttaac tatgttgctc cttttacgct atgtggatac gctgctttaa  4740
tgccttgtta tcatgctcat tgttcccgta tggctttcat tttctcctcc ttgtataaat  4800
cctggttgct gtctctttat gaggagttgt ggcccgttgt caggcaacgt ggcgtggtgt  4860
gcactgtgtt tgctgacgca accccactg gttgggcat tgccaccacc tgtcagctcc    4920
tttccgggac tttcgctttc cccctcccta ttgccacggc ggaactcatc gccgcctgcc  4980
ttgccgcgct ctggacaggg gctcggctgt tgggcactga caattccgtg gtgttgtcgg  5040
ggaagctgac gtcctttcca tggctgctcg cctgtgttgc cacctggatt ctgcgcggga  5100
cgtccttctg ctacgtccct tcggccctca atccagcgga ccttcttcc gcggcctgc    5160
tgccggctct gcggcctctt ccgcgtcttc gccttcgccc tcagacgagt cggatctccc  5220
tttgggccgc ctccccgcct gaatacgagc tcggtaccct taagaccaat gacttacaag  5280
gcagctgtag atcttagcca ctttttaaaa gaaaaggggg gactggaagg gctaattcac  5340
tcccaacgaa gacaagatct gctttttgct tgtactgggt ctctctggtt agaccagatc  5400
tgagcctggg agctctctgg ctaactaggg aacccactgc ttaagcctca ataaagcttg  5460
ccttgagtgc ttcaagtagt gtgtgcccgt ctgttgtgtg actctggtaa ctagagatcc  5520
ctcagaccct tttagtcagt gtggaaaatc tctagcagta gtagttcatg tcatcttatt  5580
attcagtatt tataacttgc aaagaaatga atatcagaga gtgagaggaa cttgtttatt  5640
gcagcttata atggttacaa ataaagcaat agcatcacaa atttcacaaa taaagcattt  5700
ttttcactgc attctagttg tggtttgtcc aaactcatca atgtatctta tcatgtctgg  5760
ctctagctat cccgccccta actccgccca tcccgcccct aactccgccc agttccgccc  5820
attctccgcc ccatggctga ctaatttttt ttatttatgc agaggccgag gccgcctcgg  5880
cctctgagct attccagaag tagtgaggag gcttttttgg aggcctaggg acgtacccaa  5940
ttcgccctat agtgagtcgt attacgcgcg ctcactggcc gtcgttttac aacgtcgtga  6000
ctgggaaaac cctggcgtta cccaacttaa tcgccttgca gcacatcccc ctttcgccag  6060
ctggcgtaat agcgaagagg cccgcaccga tcgcccttcc caacagttgc gcagcctgaa  6120
tggcgaatgg gacgcgccct gtagcggcgc attaagcgcg gcgggtgtgg tggttacgcg  6180
cagcgtgacc gctacacttg ccagcgccct agcgcccgct cctttcgctt tcttcccttc  6240
ctttctcgcc acgttcgccg gctttccccg tcaagctcta aatcgggggc tcccttaagg  6300
gttccgattt agtgctttac ggcacctcga ccccaaaaaa cttgattagg gtgatggttc  6360
acgtagtggg ccatcgccct gatagacggt ttttcgccct ttgacgttgg agtccacgtt  6420
ctttaatagt ggactcttgt tccaaactgg aacaacactc aaccctatct cggtctattc  6480
ttttgattta taaggggattt tgccgatttc ggcctattgg ttaaaaaatg agctgattta  6540
acaaaaattt aacgcgaatt ttaacaaaat attaacgttt acaatttccc aggtggcact  6600
tttcggggaa atgtgcgcgg aacccctatt tgtttatttt tctaaataca ttcaaatatg  6660
tatccgctca tgagacaata accctgataa atgcttcaat aatattgaaa aaggaagagt  6720
atgagtattc aacatttccg tgtcgccctt attcccttt ttgcggcatt ttgccttcct   6780
gttttgctc acccagaaac gctggtgaaa gtaaaagatg ctgaagatca gttgggtgca   6840
cgagtgggtt acatcgaact ggatctcaac agcggtaaga tccttgagag ttttcgcccc  6900
gaagaacgtt ttccaatgat gagcactttt aaagttctgc tatgtggcgc ggtattatcc  6960
cgtattgacg ccgggcaaga gcaactcggt cgccgcatac actattctca gaatgacttg  7020
gttgagtact caccagtcac agaaaagcat cttacgatg gcatgacagt aagagaatta   7080
tgcagtgctg ccataaccat gagtgataac actgcggcca acttactct gacaacgatc    7140
ggaggaccga aggagctaac cgcttttttg cacaacatgg gggatcatgt aactcgcctt  7200
gatcgttggg aaccggagct gaatgaagcc ataccaaacg acgagcgtga ccacacgatg  7260
cctgtagcaa tggcaacaac gttgcgcaaa ctattaactg gcgaactact tactctagct  7320
tcccggcaac aattaataga ctggatggag gcggataaag ttgcaggacc acttctgcgc  7380
tcggcccttc cggctggctg gtttattgct gataaatctg gagccggtga gcgtgggtct  7440
cgcggtatca ttgcagcact ggggccagat ggtaagccct cccgtatcgt agttatctac  7500
acgacgggga gtcaggcaac tatgatgaa cgaaatagac agatcgctga gataggtgcc   7560
tcactgatta gcattggta actgtcagac caagtttact catatatact ttagattgat   7620
ttaaaacttc attttttaatt taaaggatc taggtgaaga tccttttga taatctcatg    7680
accaaaatcc cttaacgtga gttttcgttc cactgagcgt cagaccccgt agaaaagatc  7740
aaaggatctt cttgagatcc ttttttttctg cgcgtaatct gctgcttgca aacaaaaaaa  7800
ccaccgctac cagcggtggt ttgtttgccg gatcaagagc taccaactct ttttccgaag  7860
gtaactggct tcagcagagc gcagatacca aatactgtcc ttctagtgta gccgtagtta  7920
ggccaccact tcaagaactc tgtagcaccg cctacatacc tcgctctgct aatcctgtta  7980
ccagtggctg ctgccagtgg cgataagtcg tgtcttaccg ggttggactc aagacgatag  8040
ttaccggata aggcgcagcg gtcgggctga acggggggtt cgtgcacaca gcccagcttg  8100
gagcgaacga cctacaccga actgagatac ctacagcgtga agcgccacg                8160
cttcccgaag ggagaaaggc ggacaggtat ccggtaagcg gcagggtcgg aacaggagag  8220
cgcacgaggg agcttccagg gggaaacgcc tggtatcttt atagtcctgt cgggtttcgc  8280
cacctctgac ttgagcgtcg atttttgtga tgctcgtcag gggggcggag cctatggaaa  8340
aacgccagca acgcggcctt tttacggttc ctggcctttt gctggccttt tgctcacatg  8400
ttctttcctg cgttatcccc tgattctgtg gataaccgta ttaccgcctt tgagtgagct  8460
```

```
gataccgctc gccgcagccg aacgaccgag cgcagcgagt cagtgagcga ggaagcggaa  8520
gagcgcccaa tacgcaaacc gcctctcccc gcgcgttggc cgattcatta atgcagctgg  8580
cacgacaggt ttcccgactg gaaagcgggc agtgagcgca acgcaattaa tgtgagttag  8640
ctcactcatt aggcacccca ggctttacac tttatgcttc cggctcgtat gttgtgtgga  8700
attgtgagcg gataacaatt tcacacagga aacagctatg accatgatta cgccaagcgc  8760
gcaattaacc ctcactaaag ggaacaaaag ctggagctgc aagctt                 8806
```

| | | |
|---|---|---|
| SEQ ID NO: 190 | moltype = AA length = 220 | |
| FEATURE | Location/Qualifiers | |
| REGION | 1..220 | |
| | note = Synthetic peptide | |
| VARIANT | 143 | |
| | note = Xaa can be any naturally occurring amino acid | |
| source | 1..220 | |
| | mol_type = protein | |
| | organism = synthetic construct | |

```
SEQUENCE: 190
MASAGMQILG VVLTLLGWVN GLVSCALPMW KVTAFIGNSI VVAQVVWEGL WMSCVVQSTG   60
QMQCKVYDSL LALPQDLQAA RALCVIALLV ALFGLLVYLA GAKCTTCVEE KDSKARLVLT  120
SGIVFVISGV LTLIPVCWTA HAXIRDFYNP LVAEAQKREL GASLYLGWAA SGLLLLGGGL  180
LCCTCPSGGS QGPSHYMARY STSAPAISRG PSEYPTKNYV                       220
```

| | | |
|---|---|---|
| SEQ ID NO: 191 | moltype = DNA length = 68 | |
| FEATURE | Location/Qualifiers | |
| misc_feature | 1..68 | |
| | note = Synthetic polynucleotide | |
| source | 1..68 | |
| | mol_type = other DNA | |
| | organism = synthetic construct | |

```
SEQUENCE: 191
cagaaactca tctcagaaga ggatctggca gcaaatgata tcctggatta caaggatgac   60
gacgataa                                                            68
```

| | | |
|---|---|---|
| SEQ ID NO: 192 | moltype = DNA length = 683 | |
| FEATURE | Location/Qualifiers | |
| misc_feature | 1..683 | |
| | note = NCBI / NM_021195.4, 2017-06-04, | |
| source | 1..683 | |
| | mol_type = genomic DNA | |
| | organism = Homo sapiens | |

```
SEQUENCE: 192
ccgcgatcgc catggcctct gccggaatgc agatcctggg agtcgtcctg cactgctgg    60
gctgggtgaa tggcctggtc tcctgtgccc tgcccatgtg gaaggtgacc gctttcatcg  120
gcaacagcat cgtggtggcc caggtggtgt gggagggcct gtggatgtcc tgcgtggtgc  180
agagcaccgg ccagatgcag tgcaaggtgt acgactcact gctggcgctg ccacaggacc  240
tgcaggctgc acgtgccctc tgtgtcatcg ccctccttgt ggccctgttc ggcttgctgg  300
tctaccttgc tggggccaag tgtaccacct gtgtggagga gaaggattcc aaggcccgcc  360
tggtgctcac ctctgggatt gtctttgtca tctcaggggt cctgacgcta atccccgtgt  420
gctggacggc gcatgccgtc atccggaact tctataaccc cctggtggct gaggcccaaa  480
agcgggagct gggggcctcc ctctacttgg gctgggcggc ctcaggcctt ttgttgctgg  540
gtgggggtt gctgtgctgc acttgccccct cggggggtc ccagggcccc agccattaca  600
tggcccgcta ctcaacatct gccccatgcca tctctcgggg gccctctgag tacccctacca  660
agaattacgt cacgcgtacg cgg                                          683
```

| | | |
|---|---|---|
| SEQ ID NO: 193 | moltype = DNA length = 677 | |
| FEATURE | Location/Qualifiers | |
| misc_feature | 1..677 | |
| | note = NCBI / NM_018777.4, 2017-08-07 | |
| source | 1..677 | |
| | mol_type = genomic DNA | |
| | organism = Mus musculus | |

```
SEQUENCE: 193
gccgcgatcg ccatggcctc tactggtctg caaatcttgg ggatcgtcct gaccctgctt   60
ggctgggtca acgcccctggt gtcctgtgcc ctgcccatgg gaaggtgac cgccttcatc  120
ggcaacagca tcgtcgtggc ccagatggtg tgggaggggc tgtggatgtc ctgtgtggtt  180
cagagcactg gccagatgca gtgcaaggtg tatgactcac tgttggcgct gccccaggac  240
ctgcaggctg ccagagccct ctgtgttgtc accctcctca ttgtcctgct ggcctgctc  300
gtgtacctgg ctggagccaa gtgcactacc tgtgtggaag ataggaactc caagtctcgt  360
ctggtgctca tctctggcat catctttgtc atttctggcc tcctgacgct cattcctgtc  420
tgctggactg cccactctat catccaggac ttctacaacc ccttggtggc tgatgctcaa  480
aagcgggagc tggggcctc cctctacctg gctgggcag cctcaggcct tttgctgctg  540
ggtgagggc tactatgctg cgcctgctct tctggaggga cccagggacc cagacattac  600
atggcctgct attctacatc tgtcccacat tctcggggac cctccgaata tcccaccaag  660
aattatgtga cgcgtac                                                  677
```

| | | |
|---|---|---|
| SEQ ID NO: 194 | moltype = DNA length = 683 | |
| FEATURE | Location/Qualifiers | |
| misc_feature | 1..683 | |
| | note = Synthetic polynucleotide | |

| | | |
|---|---|---|
| source | 1..683<br>mol_type = other DNA<br>organism = synthetic construct | |

SEQUENCE: 194

```
cgcgatcgcc atggcctctg ccggaatgca gatcctggga gtcgtcctga cactgctggg    60
ctgggtgaat ggcctggtct cctgtgccct gcccatgtgg aaggtgaccg ctttcatcgg   120
caacagcatc gtggtggccc aggtggtgtg ggagggcctg tggatgtcct gcgtggtgca   180
gagcaccggc cagatgcagt gcaaggtgta cgactcactg ctggcgctgc acaggacct    240
gcaggctgca cgtgccctct gtgtcatcgc cctccttgtg gccctgttcg gcttgctggt   300
ctaccttgct ggggccaagt gtaccacctg tgtggaggag aaggattcca aggcccgcct   360
ggtgctcacc tctgggattg tctttgtcat ctcaggggtc ctgacgctaa tccccgtgtg   420
ctggacggcg catgccatca tccgggactt ctataacccc ctggtggctg aggcccaaaa   480
gcgggagctg ggggcctccc tctacttggg ctgggcggcc tcaggccttt tgttgctggg   540
tggggggttg ctgtgctgca cttgcccctc gggggggtcc cagggcccca gccattacat   600
ggcccgctac tcaacatctg cccctgccat ctctcggggg ccctctgagt accctaccaa   660
gaattacgtc acgcgtacgc ggc                                           683
```

| | | |
|---|---|---|
| SEQ ID NO: 195<br>FEATURE<br>misc_feature | moltype = DNA   length = 672<br>Location/Qualifiers<br>1..672<br>note = NCBI / NM_020982.3, 2017-04-15 | |
| source | 1..672<br>mol_type = genomic DNA<br>organism = Homo sapiens | |

SEQUENCE: 195

```
gccgcgatcg ccatggcttc gaccggctta gaactgctgg gcatgaccct ggctgtgctg    60
ggctggctgg ggaccctggt gtcctgcgcc ctgcccctgt ggaaggtgac cgccttcatc   120
ggcaacagca tcgtggtggc ccaggtggtg tgggagggcc tgtggatgtc ctgcgtggtg   180
cagagcacgg gccagatgca gtgcaaggtg tacgactcac tgctggctct gccgcaggac   240
ctgcaggccg cacgtgccct ctgtgtcatt gcctcctgg tggcctcctg                300
gtggccatca caggtgccca gtgtaccacg tgtgtggagg acgaaggtgc caaggcccgt   360
atcgtgctca ccgcggggg catcctcctc ctcgccggca tcctggtgct catccctgtg   420
tgctggacgg cgcacgccat catccaggac ttctacaacc cctggtggc tgaggccctc   480
aagcgggagc tgggggcctc cctctacctg ggctgggcgg cggctgcact gcttatgctg   540
ggcgggggc tcctctgctg cacgtgcccc ccgcccagg tcgagcggcc ccgcggacct   600
cggctgggct actccatccc ctcccgctcg ggtgcatctg gactggacaa gagggactac   660
gtgacgcgta cg                                                       672
```

| | | |
|---|---|---|
| SEQ ID NO: 196<br>FEATURE<br>misc_feature | moltype = DNA   length = 651<br>Location/Qualifiers<br>1..651<br>note = NCBI / NM_001305.4, 2017-07-10 | |
| source | 1..651<br>mol_type = genomic DNA<br>organism = Homo sapiens | |

SEQUENCE: 196

```
ccgcgatcgc catggcctcc atggggctac aggtaatggg catcgcgctg gccgtcctgg    60
gctggctggc cgtcatgctg tgctgcgcgc tgcccatgtg gcgcgtgacg gccttcatcg   120
gcagcaacat tgtcacctcg cagaccatcg ggagggcct atggatgaac tgcgtggtgc   180
agagcaccgg ccagatgcag tgcaaggtgt acgactcgct gctggcactg ccgcaggacc   240
tgcaggccg ccgcgccctc gtcatcatca gcatccatcgt ggctgctctg ggcgtgctgc   300
tgtccgtggt gggggggcaag tgtaccaact gcctggagga tgaaagcgcc aaggccaaga   360
ccatgatcgt ggcgggcgtg gtgttcctgt tggccggcct tatggtgata gtgccggtgt   420
cctgacggc ccacaacatc atccaagact tctacaatcc gctggtggcc tccgggcaga   480
agcgggagat gggtgcctcg ctctacgtcg gctgggcgc ctccggactg ctgctccttg   540
gcggggggct gctttgctgc aactgtccac cccgcacaga caagccttac tccgccaagt   600
attctgctgc ccgctctgct gctgccagca actacgtgac gcgtacgcgg c             651
```

| | | |
|---|---|---|
| SEQ ID NO: 197<br>FEATURE<br>misc_feature | moltype = DNA   length = 680<br>Location/Qualifiers<br>1..680<br>note = NCBI / NM_001306.3, 2017-07-10 | |
| source | 1..680<br>mol_type = genomic DNA<br>organism = Homo sapiens | |

SEQUENCE: 197

```
gccgcgatcg ccatgtccat gggcctggag atcacgggca ccgcgctggc cgtgctgggc    60
tggctgggca ccatcgtgtg ctgcgcgttg cccatgtggc gcgtatcggc cttcatcggc   120
agcaacatca tcacgtcgca gaacatctgg agggcctgcg gatgaactg cgtggtgcag   180
agcaccggcc agatgcagtg caaggtgtac gactcgctgc tggcactgcc acaggacctt   240
caggcggccc gcgccctcat cgtggtggcc atcctgctgg ccgccttcgg gctgctagtg   300
gcgctggtgg gcgcccagtg caccaactgc gtgcaggacg acacggccaa ggccaagatc   360
accatcgtgt caggcgtgct gttccttctc gccgccctgc tcaccctcgt gccggtgtcc   420
tggtcggcca acaccattat ccgggacttc tacaaccctg tggtgccga ccgcagaag    480
cgcgagatgc gcgggggcct gtacgtgggc tgggcggccg cggcgctgca gctgctgggg   540
ggcgcgctgc tctgctgctc gtgtccccca cgcagaagaa agtacacggc caccaaggtc   600
gtctactccg cgccgcgctc caccggcccg ggagccagcc tgggcacagg ctacgaccgc   660
aaggactacg tcacgcgtac                                               680
```

```
SEQ ID NO: 198           moltype = AA  length = 214
FEATURE                  Location/Qualifiers
REGION                   1..214
                         note = Synthetic peptide
source                   1..214
                         mol_type = protein
                         organism = synthetic construct
SEQUENCE: 198
DIVLTQSPAT LSVTPGNSVS LSCRASQSIG GNLHWYQQKS HESPRLLIKY ASQSISGIPS    60
RFSGSGSGTD FTLSINSVET EDFGMYFCQQ SNSWPYTFGG GTKLEIKRAD AAPTVSIFPP   120
SSEQLTSGGA SVVCFLNNFY PKDINVKWKI DGSERQNGVL NSWTDQDSKD STYSMSSTLT   180
LTKDEYERHN SYTCEATHKT STSPIVKSFN RNEC                               214

SEQ ID NO: 199           moltype = AA  length = 444
FEATURE                  Location/Qualifiers
REGION                   1..444
                         note = Synthetic peptide
source                   1..444
                         mol_type = protein
                         organism = synthetic construct
SEQUENCE: 199
DVQLQESGPS LVKPSQTLSL TCSVTGDSIT SDYWSWIRKF PGNRLEYMGY VSYSGSTYYN    60
PSLKSRISIT RDTSKNQYYL DLNSVTTEDT ATYYCANWDG DYWGQGTLVT VSSAAKTTAP   120
SVYPLAPVCG DTTGSSVTLG CLVKGYFPEP VTLTWNSGSL SSGVHTFPAV LQSDLYTLSS   180
SVTVTSSTWP SQSITCNVAH PASSTKVDKK IEPRGPTIKP CPPCKCPAPN LLGGPSVFIF   240
PPKIKDVLMI SLSPIVTCVV VDVSEDDPDV QISWFVNNVE VHTAQTQTHR EDYNSTLRVV   300
SALPIQHQDW MSGKEFKCKV NNKDLPAPIE RTISKPKGSV RAPQVYVLPP PEEEMTKKQV   360
TLTCMVTDFM PEDIYVEWTN NGKTELNYKN TEPVLDSDGS YFMYSKLRVE KKNWVERNSY   420
SCSVVHEGLH NHHTTKSFSR TPGK                                          444

SEQ ID NO: 200           moltype = AA  length = 220
FEATURE                  Location/Qualifiers
REGION                   1..220
                         note = Synthetic peptide
VARIANT                  143
                         note = Xaa can be any naturally occurring amino acid
source                   1..220
                         mol_type = protein
                         organism = synthetic construct
SEQUENCE: 200
MASAGMQILG VVLTLLGWVN GLVSCALPMW KVTAFIGNSI VVAQVVWEGL WMSCVVQSTG    60
QMQCKVYDSL LALPQDLQAA RALCVIALLV ALFGLLVYLA GAKCTTCVEE KDSKARLVLT   120
SGIVFVISGV LTLIPVCWTA HAXIRDFYNP LVAEAQKREL GASLYLGWAA SGLLLLGGGL   180
LCCTCPSGGS QGPSHYMARY STSAPAISRG PSEYPTKNYV                         220

SEQ ID NO: 201           moltype = AA  length = 220
FEATURE                  Location/Qualifiers
REGION                   1..220
                         note = Synthetic peptide
VARIANT                  143
                         note = Xaa can be any naturally occurring amino acid
source                   1..220
                         mol_type = protein
                         organism = synthetic construct
SEQUENCE: 201
MASAGMQILG VVLTLLGWVN GLVSCALPMW KVTAFIGNSI VVAQVVWEGL WMSCVVQSTG    60
QMQCKVYDSL LALPQDLQAA RALCVIALLV ALFGLLVYLA GAKCTTCVEE KDSKARLVLT   120
SGIVFVISGV LTLIPVCWTA HAXIRDFYNP LVAEAQKREL GASLYLGWAA SGLLLLGGGL   180
LCCTCPSGGS QGPSHYMARY STSAPAISRG PSEYPTKNYV                         220

SEQ ID NO: 202           moltype = AA  length = 220
FEATURE                  Location/Qualifiers
REGION                   1..220
                         note = human CLDN6
VARIANT                  143
                         note = X is I or V
source                   1..220
                         mol_type = protein
                         organism = Homo sapiens
SEQUENCE: 202
MASAGMQILG VVLTLLGWVN GLVSCALPMW KVTAFIGNSI VVAQVVWEGL WMSCVVQSTG    60
QMQCKVYDSL LALPQDLQAA RALCVIALLV ALFGLLVYLA GAKCTTCVEE KDSKARLVLT   120
SGIVFVISGV LTLIPVCWTA HAXIRDFYNP LVAEAQKREL GASLYLGWAA SGLLLLGGGL   180
LCCTCPSGGS QGPSHYMARY STSAPAISRG PSEYPTKNYV                         220

SEQ ID NO: 203           moltype =     length =
SEQUENCE: 203
000
```

```
SEQ ID NO: 204          moltype =    length =
SEQUENCE: 204
000

SEQ ID NO: 205          moltype =    length =
SEQUENCE: 205
000

SEQ ID NO: 206          moltype =    length =
SEQUENCE: 206
000

SEQ ID NO: 207          moltype =    length =
SEQUENCE: 207
000

SEQ ID NO: 208          moltype = DNA  length = 21
FEATURE                 Location/Qualifiers
misc_feature            1..21
                        note = Synthetic polynucleotide
source                  1..21
                        mol_type = other DNA
                        organism = synthetic construct
SEQUENCE: 208
tccagtgtaa gttccactta c                                               21

SEQ ID NO: 209          moltype =    length =
SEQUENCE: 209
000

SEQ ID NO: 210          moltype = DNA  length = 27
FEATURE                 Location/Qualifiers
misc_feature            1..27
                        note = Synthetic polynucleotide
source                  1..27
                        mol_type = other DNA
                        organism = synthetic construct
SEQUENCE: 210
caccagtatc atcgttcccc gctcacg                                         27

SEQ ID NO: 211          moltype = DNA  length = 24
FEATURE                 Location/Qualifiers
misc_feature            1..24
                        note = Synthetic polynucleotide
source                  1..24
                        mol_type = other DNA
                        organism = synthetic construct
SEQUENCE: 211
ggctacacct ttactaccta cacg                                            24

SEQ ID NO: 212          moltype = DNA  length = 24
FEATURE                 Location/Qualifiers
misc_feature            1..24
                        note = Synthetic polynucleotide
source                  1..24
                        mol_type = other DNA
                        organism = synthetic construct
SEQUENCE: 212
attaatccta gcagtggata tact                                            24

SEQ ID NO: 213          moltype = DNA  length = 27
FEATURE                 Location/Qualifiers
misc_feature            1..27
                        note = Synthetic polynucleotide
source                  1..27
                        mol_type = other DNA
                        organism = synthetic construct
SEQUENCE: 213
gcaaacgggg attactacgt cgcttac                                         27

SEQ ID NO: 214          moltype = DNA  length = 18
FEATURE                 Location/Qualifiers
misc_feature            1..18
                        note = Synthetic polynucleotide
source                  1..18
                        mol_type = other DNA
                        organism = synthetic construct
SEQUENCE: 214
gagaatattt acagttat                                                   18
```

```
SEQ ID NO: 215          moltype =    length =
SEQUENCE: 215
000

SEQ ID NO: 216          moltype = DNA   length = 27
FEATURE                 Location/Qualifiers
misc_feature            1..27
                        note = Synthetic polynucleotide
source                  1..27
                        mol_type = other DNA
                        organism = synthetic construct
SEQUENCE: 216
caacatcatt atactgttcc gtggacg                                    27

SEQ ID NO: 217          moltype = DNA   length = 24
FEATURE                 Location/Qualifiers
misc_feature            1..24
                        note = Synthetic polynucleotide
source                  1..24
                        mol_type = other DNA
                        organism = synthetic construct
SEQUENCE: 217
ggtttcactt tcagtgatta ctgg                                       24

SEQ ID NO: 218          moltype = DNA   length = 30
FEATURE                 Location/Qualifiers
misc_feature            1..30
                        note = Synthetic polynucleotide
source                  1..30
                        mol_type = other DNA
                        organism = synthetic construct
SEQUENCE: 218
attagattga aatctgataa ttatgcaaca                                 30

SEQ ID NO: 219          moltype = DNA   length = 24
FEATURE                 Location/Qualifiers
misc_feature            1..24
                        note = Synthetic polynucleotide
source                  1..24
                        mol_type = other DNA
                        organism = synthetic construct
SEQUENCE: 219
aatgatggcc ccccctcggg gtgt                                       24

SEQ ID NO: 220          moltype = DNA   length = 18
FEATURE                 Location/Qualifiers
misc_feature            1..18
                        note = Synthetic polynucleotide
source                  1..18
                        mol_type = other DNA
                        organism = synthetic construct
SEQUENCE: 220
gagaatattt acagttat                                              18

SEQ ID NO: 221          moltype =    length =
SEQUENCE: 221
000

SEQ ID NO: 222          moltype = DNA   length = 27
FEATURE                 Location/Qualifiers
misc_feature            1..27
                        note = Synthetic polynucleotide
source                  1..27
                        mol_type = other DNA
                        organism = synthetic construct
SEQUENCE: 222
caacatcatt atactgttcc gtggacg                                    27

SEQ ID NO: 223          moltype = DNA   length = 24
FEATURE                 Location/Qualifiers
misc_feature            1..24
                        note = Synthetic polynucleotide
source                  1..24
                        mol_type = other DNA
                        organism = synthetic construct
SEQUENCE: 223
ggattcactt tcagtaatta ctgg                                       24
```

```
SEQ ID NO: 224          moltype = DNA   length = 30
FEATURE                 Location/Qualifiers
misc_feature            1..30
                        note = Synthetic polynucleotide
source                  1..30
                        mol_type = other DNA
                        organism = synthetic construct
SEQUENCE: 224
attagattga aatctgataa ttatgcaaca                                         30

SEQ ID NO: 225          moltype = DNA   length = 24
FEATURE                 Location/Qualifiers
misc_feature            1..24
                        note = Synthetic polynucleotide
source                  1..24
                        mol_type = other DNA
                        organism = synthetic construct
SEQUENCE: 225
aatgatggcc cccctcggg gtgt                                                24

SEQ ID NO: 226          moltype = DNA   length = 33
FEATURE                 Location/Qualifiers
misc_feature            1..33
                        note = Synthetic polynucleotide
source                  1..33
                        mol_type = other DNA
                        organism = synthetic construct
SEQUENCE: 226
cagagccttg tacacagtga tggaaacacc tat                                     33

SEQ ID NO: 227          moltype =       length =
SEQUENCE: 227
000

SEQ ID NO: 228          moltype = DNA   length = 27
FEATURE                 Location/Qualifiers
misc_feature            1..27
                        note = Synthetic polynucleotide
source                  1..27
                        mol_type = other DNA
                        organism = synthetic construct
SEQUENCE: 228
tctcaaagta cacatgttcc ttacacg                                            27

SEQ ID NO: 229          moltype = DNA   length = 24
FEATURE                 Location/Qualifiers
misc_feature            1..24
                        note = Synthetic polynucleotide
source                  1..24
                        mol_type = other DNA
                        organism = synthetic construct
SEQUENCE: 229
ggctacacct ttactagcta cacg                                               24

SEQ ID NO: 230          moltype = DNA   length = 24
FEATURE                 Location/Qualifiers
misc_feature            1..24
                        note = Synthetic polynucleotide
source                  1..24
                        mol_type = other DNA
                        organism = synthetic construct
SEQUENCE: 230
attaatccta gcagtactta tact                                               24

SEQ ID NO: 231          moltype = DNA   length = 30
FEATURE                 Location/Qualifiers
misc_feature            1..30
                        note = Synthetic polynucleotide
source                  1..30
                        mol_type = other DNA
                        organism = synthetic construct
SEQUENCE: 231
tcaagagggg aactgggagg gtttgcttac                                         30

SEQ ID NO: 232          moltype = DNA   length = 33
FEATURE                 Location/Qualifiers
misc_feature            1..33
                        note = Synthetic polynucleotide
source                  1..33
```

```
                        mol_type = other DNA
                        organism = synthetic construct
SEQUENCE: 232
cagagcattg tacatagtaa tggaaacacc tat                                    33

SEQ ID NO: 233          moltype =    length =
SEQUENCE: 233
000

SEQ ID NO: 234          moltype = DNA   length = 27
FEATURE                 Location/Qualifiers
misc_feature            1..27
                        note = Synthetic polynucleotide
source                  1..27
                        mol_type = other DNA
                        organism = synthetic construct
SEQUENCE: 234
tttcaaggtt cacatgttcc attcacg                                           27

SEQ ID NO: 235          moltype = DNA   length = 24
FEATURE                 Location/Qualifiers
misc_feature            1..24
                        note = Synthetic polynucleotide
source                  1..24
                        mol_type = other DNA
                        organism = synthetic construct
SEQUENCE: 235
ggatacatat tcactcacta tatt                                              24

SEQ ID NO: 236          moltype = DNA   length = 24
FEATURE                 Location/Qualifiers
misc_feature            1..24
                        note = Synthetic polynucleotide
source                  1..24
                        mol_type = other DNA
                        organism = synthetic construct
SEQUENCE: 236
attaatcctt acaatgatgg tact                                              24

SEQ ID NO: 237          moltype = DNA   length = 39
FEATURE                 Location/Qualifiers
misc_feature            1..39
                        note = Synthetic polynucleotide
source                  1..39
                        mol_type = other DNA
                        organism = synthetic construct
SEQUENCE: 237
gcaagatact acggctaccc ttactattct atggactac                              39

SEQ ID NO: 238          moltype = DNA   length = 36
FEATURE                 Location/Qualifiers
misc_feature            1..36
                        note = Synthetic polynucleotide
source                  1..36
                        mol_type = other DNA
                        organism = synthetic construct
SEQUENCE: 238
cagagtctgc tcaacagtag aacccgaaag aactac                                 36

SEQ ID NO: 239          moltype =    length =
SEQUENCE: 239
000

SEQ ID NO: 240          moltype = DNA   length = 24
FEATURE                 Location/Qualifiers
misc_feature            1..24
                        note = Synthetic polynucleotide
source                  1..24
                        mol_type = other DNA
                        organism = synthetic construct
SEQUENCE: 240
aagcaatctt attatctgta cacg                                              24

SEQ ID NO: 241          moltype = DNA   length = 27
FEATURE                 Location/Qualifiers
misc_feature            1..27
                        note = Synthetic polynucleotide
source                  1..27
                        mol_type = other DNA
```

```
                        organism = synthetic construct
SEQUENCE: 241
ggctactcca tcaccagtgg ttattac                                              27

SEQ ID NO: 242          moltype = DNA   length = 21
FEATURE                 Location/Qualifiers
misc_feature            1..21
                        note = Synthetic polynucleotide
source                  1..21
                        mol_type = other DNA
                        organism = synthetic construct
SEQUENCE: 242
atcagctacg atggtggcat t                                                    21

SEQ ID NO: 243          moltype = DNA   length = 30
FEATURE                 Location/Qualifiers
misc_feature            1..30
                        note = Synthetic polynucleotide
source                  1..30
                        mol_type = other DNA
                        organism = synthetic construct
SEQUENCE: 243
gcaagatttg gtaaggggc tatggactac                                            30

SEQ ID NO: 244          moltype = DNA   length = 21
FEATURE                 Location/Qualifiers
misc_feature            1..21
                        note = Synthetic polynucleotide
source                  1..21
                        mol_type = other DNA
                        organism = synthetic construct
SEQUENCE: 244
tcaagtgtaa gttccagtta c                                                    21

SEQ ID NO: 245          moltype =    length =
SEQUENCE: 245
000

SEQ ID NO: 246          moltype = DNA   length = 27
FEATURE                 Location/Qualifiers
misc_feature            1..27
                        note = Synthetic polynucleotide
source                  1..27
                        mol_type = other DNA
                        organism = synthetic construct
SEQUENCE: 246
caccagtatc atcgttcccc acccacg                                              27

SEQ ID NO: 247          moltype = DNA   length = 24
FEATURE                 Location/Qualifiers
misc_feature            1..24
                        note = Synthetic polynucleotide
source                  1..24
                        mol_type = other DNA
                        organism = synthetic construct
SEQUENCE: 247
ggttactcat tcactggcta cacc                                                 24

SEQ ID NO: 248          moltype = DNA   length = 24
FEATURE                 Location/Qualifiers
misc_feature            1..24
                        note = Synthetic polynucleotide
source                  1..24
                        mol_type = other DNA
                        organism = synthetic construct
SEQUENCE: 248
attaatcctt acaatggtgg tact                                                 24

SEQ ID NO: 249          moltype = DNA   length = 36
FEATURE                 Location/Qualifiers
misc_feature            1..36
                        note = Synthetic polynucleotide
source                  1..36
                        mol_type = other DNA
                        organism = synthetic construct
SEQUENCE: 249
gcaagagggg tctatgatta cgacggattt acttac                                    36

SEQ ID NO: 250          moltype = DNA   length = 33
```

```
FEATURE                 Location/Qualifiers
misc_feature            1..33
                        note = Synthetic polynucleotide
source                  1..33
                        mol_type = other DNA
                        organism = synthetic construct
SEQUENCE: 250
cagagccttg tacacagtga tggaaacacc tat                                    33

SEQ ID NO: 251          moltype =    length =
SEQUENCE: 251
000

SEQ ID NO: 252          moltype = DNA   length = 27
FEATURE                 Location/Qualifiers
misc_feature            1..27
                        note = Synthetic polynucleotide
source                  1..27
                        mol_type = other DNA
                        organism = synthetic construct
SEQUENCE: 252
tctcaaagta cacatgttcc ttacacg                                           27

SEQ ID NO: 253          moltype = DNA   length = 24
FEATURE                 Location/Qualifiers
misc_feature            1..24
                        note = Synthetic polynucleotide
source                  1..24
                        mol_type = other DNA
                        organism = synthetic construct
SEQUENCE: 253
ggctacacct ttactaccta cacg                                              24

SEQ ID NO: 254          moltype = DNA   length = 24
FEATURE                 Location/Qualifiers
misc_feature            1..24
                        note = Synthetic polynucleotide
source                  1..24
                        mol_type = other DNA
                        organism = synthetic construct
SEQUENCE: 254
attaatcctc gcagtggtta tagt                                              24

SEQ ID NO: 255          moltype = DNA   length = 30
FEATURE                 Location/Qualifiers
misc_feature            1..30
                        note = Synthetic polynucleotide
source                  1..30
                        mol_type = other DNA
                        organism = synthetic construct
SEQUENCE: 255
tcaagagggg aactgggagg gtttgcttac                                        30

SEQ ID NO: 256          moltype = DNA   length = 18
FEATURE                 Location/Qualifiers
misc_feature            1..18
                        note = Synthetic polynucleotide
source                  1..18
                        mol_type = other DNA
                        organism = synthetic construct
SEQUENCE: 256
cagaccattg gtacatgg                                                     18

SEQ ID NO: 257          moltype =    length =
SEQUENCE: 257
000

SEQ ID NO: 258          moltype = DNA   length = 27
FEATURE                 Location/Qualifiers
misc_feature            1..27
                        note = Synthetic polynucleotide
source                  1..27
                        mol_type = other DNA
                        organism = synthetic construct
SEQUENCE: 258
caacaacttt acagtattcc tcggacg                                           27

SEQ ID NO: 259          moltype = DNA   length = 24
FEATURE                 Location/Qualifiers
```

```
misc_feature              1..24
                          note = Synthetic polynucleotide
source                    1..24
                          mol_type = other DNA
                          organism = synthetic construct
SEQUENCE: 259
ggatacagat tcactgacta caac                                                  24

SEQ ID NO: 260            moltype = DNA  length = 24
FEATURE                   Location/Qualifiers
misc_feature              1..24
                          note = Synthetic polynucleotide
source                    1..24
                          mol_type = other DNA
                          organism = synthetic construct
SEQUENCE: 260
attaaccta acaatggtgg tact                                                   24

SEQ ID NO: 261            moltype = DNA  length = 30
FEATURE                   Location/Qualifiers
misc_feature              1..30
                          note = Synthetic polynucleotide
source                    1..30
                          mol_type = other DNA
                          organism = synthetic construct
SEQUENCE: 261
gcaagagatt acttgtactt ctttgactgc                                            30

SEQ ID NO: 262            moltype = DNA  length = 33
FEATURE                   Location/Qualifiers
misc_feature              1..33
                          note = Synthetic polynucleotide
source                    1..33
                          mol_type = other DNA
                          organism = synthetic construct
SEQUENCE: 262
cagagccttg tacacagtaa tggaaacacc tat                                        33

SEQ ID NO: 263            moltype =     length =
SEQUENCE: 263
000

SEQ ID NO: 264            moltype = DNA  length = 27
FEATURE                   Location/Qualifiers
misc_feature              1..27
                          note = Synthetic polynucleotide
source                    1..27
                          mol_type = other DNA
                          organism = synthetic construct
SEQUENCE: 264
tctcaaatta cacatgttcc gtacacg                                               27

SEQ ID NO: 265            moltype = DNA  length = 24
FEATURE                   Location/Qualifiers
misc_feature              1..24
                          note = Synthetic polynucleotide
source                    1..24
                          mol_type = other DNA
                          organism = synthetic construct
SEQUENCE: 265
ggttatacct tcacagacta ttca                                                  24

SEQ ID NO: 266            moltype = DNA  length = 24
FEATURE                   Location/Qualifiers
misc_feature              1..24
                          note = Synthetic polynucleotide
source                    1..24
                          mol_type = other DNA
                          organism = synthetic construct
SEQUENCE: 266
ataagcactg agactggtga gcca                                                  24

SEQ ID NO: 267            moltype = DNA  length = 30
FEATURE                   Location/Qualifiers
misc_feature              1..30
                          note = Synthetic polynucleotide
source                    1..30
                          mol_type = other DNA
                          organism = synthetic construct
```

```
SEQUENCE: 267
actagaggtc tatggtcctc gtttgcttac                                                30

SEQ ID NO: 268          moltype = DNA  length = 30
FEATURE                 Location/Qualifiers
misc_feature            1..30
                        note = Synthetic polynucleotide
source                  1..30
                        mol_type = other DNA
                        organism = synthetic construct
SEQUENCE: 268
aaaagtgtca gtacatctgg ctatagttat                                                30

SEQ ID NO: 269          moltype =   length =
SEQUENCE: 269
000

SEQ ID NO: 270          moltype = DNA  length = 27
FEATURE                 Location/Qualifiers
misc_feature            1..27
                        note = Synthetic polynucleotide
source                  1..27
                        mol_type = other DNA
                        organism = synthetic construct
SEQUENCE: 270
cagcacagta gggagcttcc gctcacg                                                   27

SEQ ID NO: 271          moltype = DNA  length = 24
FEATURE                 Location/Qualifiers
misc_feature            1..24
                        note = Synthetic polynucleotide
source                  1..24
                        mol_type = other DNA
                        organism = synthetic construct
SEQUENCE: 271
ggattcactt tcagtagctt tgga                                                      24

SEQ ID NO: 272          moltype = DNA  length = 24
FEATURE                 Location/Qualifiers
misc_feature            1..24
                        note = Synthetic polynucleotide
source                  1..24
                        mol_type = other DNA
                        organism = synthetic construct
SEQUENCE: 272
attagtagtg acagtaggac catc                                                      24

SEQ ID NO: 273          moltype = DNA  length = 33
FEATURE                 Location/Qualifiers
misc_feature            1..33
                        note = Synthetic polynucleotide
source                  1..33
                        mol_type = other DNA
                        organism = synthetic construct
SEQUENCE: 273
gcaagagact acggtagaac ctacgaggct tac                                            33

SEQ ID NO: 274          moltype = DNA  length = 18
FEATURE                 Location/Qualifiers
misc_feature            1..18
                        note = Synthetic polynucleotide
source                  1..18
                        mol_type = other DNA
                        organism = synthetic construct
SEQUENCE: 274
caggacattg gaggaaat                                                             18

SEQ ID NO: 275          moltype =   length =
SEQUENCE: 275
000

SEQ ID NO: 276          moltype = DNA  length = 27
FEATURE                 Location/Qualifiers
misc_feature            1..27
                        note = Synthetic polynucleotide
source                  1..27
                        mol_type = other DNA
                        organism = synthetic construct
SEQUENCE: 276
```

```
ctacagcgta atgcgtatcc gctcact                                    27

SEQ ID NO: 277          moltype = DNA  length = 24
FEATURE                 Location/Qualifiers
misc_feature            1..24
                        note = Synthetic polynucleotide
source                  1..24
                        mol_type = other DNA
                        organism = synthetic construct
SEQUENCE: 277
ggattcactt tcagtagtta tgcc                                       24

SEQ ID NO: 278          moltype = DNA  length = 21
FEATURE                 Location/Qualifiers
misc_feature            1..21
                        note = Synthetic polynucleotide
source                  1..21
                        mol_type = other DNA
                        organism = synthetic construct
SEQUENCE: 278
attagaagtg gtggtaccac c                                          21

SEQ ID NO: 279          moltype = DNA  length = 36
FEATURE                 Location/Qualifiers
misc_feature            1..36
                        note = Synthetic polynucleotide
source                  1..36
                        mol_type = other DNA
                        organism = synthetic construct
SEQUENCE: 279
gcaaaagtgg gcggtaaccc ctatcctatg gactac                          36

SEQ ID NO: 280          moltype = DNA  length = 21
FEATURE                 Location/Qualifiers
misc_feature            1..21
                        note = Synthetic polynucleotide
source                  1..21
                        mol_type = other DNA
                        organism = synthetic construct
SEQUENCE: 280
tcaagtataa gttccaatta c                                          21

SEQ ID NO: 281          moltype =      length =
SEQUENCE: 281
000

SEQ ID NO: 282          moltype = DNA  length = 27
FEATURE                 Location/Qualifiers
misc_feature            1..27
                        note = Synthetic polynucleotide
source                  1..27
                        mol_type = other DNA
                        organism = synthetic construct
SEQUENCE: 282
cagcagggta gtagtatacc gctcacg                                    27

SEQ ID NO: 283          moltype = DNA  length = 24
FEATURE                 Location/Qualifiers
misc_feature            1..24
                        note = Synthetic polynucleotide
source                  1..24
                        mol_type = other DNA
                        organism = synthetic construct
SEQUENCE: 283
ggatacgcct tcagtaatta cttg                                       24

SEQ ID NO: 284          moltype = DNA  length = 24
FEATURE                 Location/Qualifiers
misc_feature            1..24
                        note = Synthetic polynucleotide
source                  1..24
                        mol_type = other DNA
                        organism = synthetic construct
SEQUENCE: 284
attaatcctg gaagtggtgg tact                                       24

SEQ ID NO: 285          moltype = DNA  length = 45
FEATURE                 Location/Qualifiers
misc_feature            1..45
```

```
                        note = Synthetic polynucleotide
source                  1..45
                        mol_type = other DNA
                        organism = synthetic construct
SEQUENCE: 285
gcaagatcat acttcggtag aagctacccc tatactatgg actac            45

SEQ ID NO: 286          moltype = DNA  length = 30
FEATURE                 Location/Qualifiers
misc_feature            1..30
                        note = Synthetic polynucleotide
source                  1..30
                        mol_type = other DNA
                        organism = synthetic construct
SEQUENCE: 286
caaagtgttg attatgatgg tgataattat                             30

SEQ ID NO: 287          moltype =   length =
SEQUENCE: 287
000

SEQ ID NO: 288          moltype = DNA  length = 27
FEATURE                 Location/Qualifiers
misc_feature            1..27
                        note = Synthetic polynucleotide
source                  1..27
                        mol_type = other DNA
                        organism = synthetic construct
SEQUENCE: 288
cagcaaagta atgaggatcc attcacg                                27

SEQ ID NO: 289          moltype = DNA  length = 24
FEATURE                 Location/Qualifiers
misc_feature            1..24
                        note = Synthetic polynucleotide
source                  1..24
                        mol_type = other DNA
                        organism = synthetic construct
SEQUENCE: 289
ggctacacat tcactgatta tgct                                   24

SEQ ID NO: 290          moltype = DNA  length = 24
FEATURE                 Location/Qualifiers
misc_feature            1..24
                        note = Synthetic polynucleotide
source                  1..24
                        mol_type = other DNA
                        organism = synthetic construct
SEQUENCE: 290
attagtacat actctggtaa taca                                   24

SEQ ID NO: 291          moltype = DNA  length = 39
FEATURE                 Location/Qualifiers
misc_feature            1..39
                        note = Synthetic polynucleotide
source                  1..39
                        mol_type = other DNA
                        organism = synthetic construct
SEQUENCE: 291
gcaagaaggg gcgattacag cctctatgct atggactac                   39

SEQ ID NO: 292          moltype = DNA  length = 36
FEATURE                 Location/Qualifiers
misc_feature            1..36
                        note = Synthetic polynucleotide
source                  1..36
                        mol_type = other DNA
                        organism = synthetic construct
SEQUENCE: 292
caaagtgttt tattcagttc aaatcagaaa aactac                      36

SEQ ID NO: 293          moltype =   length =
SEQUENCE: 293
000

SEQ ID NO: 294          moltype = DNA  length = 24
FEATURE                 Location/Qualifiers
misc_feature            1..24
                        note = Synthetic polynucleotide
```

```
                        source          1..24
                                        mol_type = other DNA
                                        organism = synthetic construct
SEQUENCE: 294
catcaatacc tctcctcgcg cacg                                              24

SEQ ID NO: 295          moltype = DNA  length = 24
FEATURE                 Location/Qualifiers
misc_feature            1..24
                        note = Synthetic polynucleotide
source                  1..24
                        mol_type = other DNA
                        organism = synthetic construct
SEQUENCE: 295
ggattcactt tcagtagctt tgga                                              24

SEQ ID NO: 296          moltype = DNA  length = 24
FEATURE                 Location/Qualifiers
misc_feature            1..24
                        note = Synthetic polynucleotide
source                  1..24
                        mol_type = other DNA
                        organism = synthetic construct
SEQUENCE: 296
attagtagtg acagtaggac catc                                              24

SEQ ID NO: 297          moltype = DNA  length = 33
FEATURE                 Location/Qualifiers
misc_feature            1..33
                        note = Synthetic polynucleotide
source                  1..33
                        mol_type = other DNA
                        organism = synthetic construct
SEQUENCE: 297
gcaagagact acggtagaac ctacgaggct tac                                    33

SEQ ID NO: 298          moltype = DNA  length = 30
FEATURE                 Location/Qualifiers
misc_feature            1..30
                        note = Synthetic polynucleotide
source                  1..30
                        mol_type = other DNA
                        organism = synthetic construct
SEQUENCE: 298
gaaagtgttg ataattatgg cattagtttt                                        30

SEQ ID NO: 299          moltype =    length =
SEQUENCE: 299
000

SEQ ID NO: 300          moltype = DNA  length = 27
FEATURE                 Location/Qualifiers
misc_feature            1..27
                        note = Synthetic polynucleotide
source                  1..27
                        mol_type = other DNA
                        organism = synthetic construct
SEQUENCE: 300
cagcaaagta aggaggttcc gctcacg                                           27

SEQ ID NO: 301          moltype = DNA  length = 24
FEATURE                 Location/Qualifiers
misc_feature            1..24
                        note = Synthetic polynucleotide
source                  1..24
                        mol_type = other DNA
                        organism = synthetic construct
SEQUENCE: 301
ggattcccctt tcagtagctc tgcc                                             24

SEQ ID NO: 302          moltype = DNA  length = 21
FEATURE                 Location/Qualifiers
misc_feature            1..21
                        note = Synthetic polynucleotide
source                  1..21
                        mol_type = other DNA
                        organism = synthetic construct
SEQUENCE: 302
attaatagtg atggtaacac c                                                 21
```

```
SEQ ID NO: 303          moltype = DNA  length = 39
FEATURE                 Location/Qualifiers
misc_feature            1..39
                        note = Synthetic polynucleotide
source                  1..39
                        mol_type = other DNA
                        organism = synthetic construct
SEQUENCE: 303
acaagaaacg gggactatag gtacgacgag tttgcttac                               39

SEQ ID NO: 304          moltype = DNA  length = 21
FEATURE                 Location/Qualifiers
misc_feature            1..21
                        note = Synthetic polynucleotide
source                  1..21
                        mol_type = other DNA
                        organism = synthetic construct
SEQUENCE: 304
tcaagtgtaa gttccagtta c                                                 21

SEQ ID NO: 305          moltype =   length =
SEQUENCE: 305
000

SEQ ID NO: 306          moltype = DNA  length = 27
FEATURE                 Location/Qualifiers
misc_feature            1..27
                        note = Synthetic polynucleotide
source                  1..27
                        mol_type = other DNA
                        organism = synthetic construct
SEQUENCE: 306
caccagtatc atcgttcccc acccacg                                           27

SEQ ID NO: 307          moltype = DNA  length = 24
FEATURE                 Location/Qualifiers
misc_feature            1..24
                        note = Synthetic polynucleotide
source                  1..24
                        mol_type = other DNA
                        organism = synthetic construct
SEQUENCE: 307
ggctacacct ttactggcta ctgg                                              24

SEQ ID NO: 308          moltype = DNA  length = 24
FEATURE                 Location/Qualifiers
misc_feature            1..24
                        note = Synthetic polynucleotide
source                  1..24
                        mol_type = other DNA
                        organism = synthetic construct
SEQUENCE: 308
attaatccta gcactggtta tact                                              24

SEQ ID NO: 309          moltype = DNA  length = 36
FEATURE                 Location/Qualifiers
misc_feature            1..36
                        note = Synthetic polynucleotide
source                  1..36
                        mol_type = other DNA
                        organism = synthetic construct
SEQUENCE: 309
gcaagagagg ggattactac tgtgctggtt gactac                                 36

SEQ ID NO: 310          moltype = DNA  length = 36
FEATURE                 Location/Qualifiers
misc_feature            1..36
                        note = Synthetic polynucleotide
source                  1..36
                        mol_type = other DNA
                        organism = synthetic construct
SEQUENCE: 310
caaagtgttt tattcagttc aaatcagaaa aactac                                 36

SEQ ID NO: 311          moltype =   length =
SEQUENCE: 311
000
```

```
SEQ ID NO: 312         moltype = DNA  length = 24
FEATURE                Location/Qualifiers
misc_feature           1..24
                       note = Synthetic polynucleotide
source                 1..24
                       mol_type = other DNA
                       organism = synthetic construct
SEQUENCE: 312
catcaatacc tctcctcgcg cacg                                              24

SEQ ID NO: 313         moltype = DNA  length = 24
FEATURE                Location/Qualifiers
misc_feature           1..24
                       note = Synthetic polynucleotide
source                 1..24
                       mol_type = other DNA
                       organism = synthetic construct
SEQUENCE: 313
ggttactctt tcactggcta caat                                              24

SEQ ID NO: 314         moltype = DNA  length = 24
FEATURE                Location/Qualifiers
misc_feature           1..24
                       note = Synthetic polynucleotide
source                 1..24
                       mol_type = other DNA
                       organism = synthetic construct
SEQUENCE: 314
attgatcctt actatggtgg ttct                                              24

SEQ ID NO: 315         moltype = DNA  length = 42
FEATURE                Location/Qualifiers
misc_feature           1..42
                       note = Synthetic polynucleotide
source                 1..42
                       mol_type = other DNA
                       organism = synthetic construct
SEQUENCE: 315
gcaagagaga ggtcgggcta cgttttctct gctatggact ac                          42

SEQ ID NO: 316         moltype = DNA  length = 36
FEATURE                Location/Qualifiers
misc_feature           1..36
                       note = Synthetic polynucleotide
source                 1..36
                       mol_type = other DNA
                       organism = synthetic construct
SEQUENCE: 316
caaagtgttt tattcagttc aaatcagaaa aactac                                 36

SEQ ID NO: 317         moltype =     length =
SEQUENCE: 317
000

SEQ ID NO: 318         moltype = DNA  length = 24
FEATURE                Location/Qualifiers
misc_feature           1..24
                       note = Synthetic polynucleotide
source                 1..24
                       mol_type = other DNA
                       organism = synthetic construct
SEQUENCE: 318
catcaatacc tctcctcgcg cacg                                              24

SEQ ID NO: 319         moltype = DNA  length = 24
FEATURE                Location/Qualifiers
misc_feature           1..24
                       note = Synthetic polynucleotide
source                 1..24
                       mol_type = other DNA
                       organism = synthetic construct
SEQUENCE: 319
ggttactcat tcactggcta cacc                                              24

SEQ ID NO: 320         moltype = DNA  length = 24
FEATURE                Location/Qualifiers
misc_feature           1..24
                       note = Synthetic polynucleotide
source                 1..24
```

```
                                    mol_type = other DNA
                                    organism = synthetic construct
SEQUENCE: 320
attaatcctt acaatggtgt tact                                                  24

SEQ ID NO: 321          moltype = DNA   length = 48
FEATURE                 Location/Qualifiers
misc_feature            1..48
                        note = Synthetic polynucleotide
source                  1..48
                        mol_type = other DNA
                        organism = synthetic construct
SEQUENCE: 321
acaagagatc ccctttacta cggctacagg gactctacta tggactac                        48

SEQ ID NO: 322          moltype = DNA   length = 33
FEATURE                 Location/Qualifiers
misc_feature            1..33
                        note = Synthetic polynucleotide
source                  1..33
                        mol_type = other DNA
                        organism = synthetic construct
SEQUENCE: 322
cagagccttg tacacagtga tggaaacacc tat                                        33

SEQ ID NO: 323          moltype =    length =
SEQUENCE: 323
000

SEQ ID NO: 324          moltype = DNA   length = 27
FEATURE                 Location/Qualifiers
misc_feature            1..27
                        note = Synthetic polynucleotide
source                  1..27
                        mol_type = other DNA
                        organism = synthetic construct
SEQUENCE: 324
tctcaaagta cacatgttcc ttacacg                                               27

SEQ ID NO: 325          moltype = DNA   length = 24
FEATURE                 Location/Qualifiers
misc_feature            1..24
                        note = Synthetic polynucleotide
source                  1..24
                        mol_type = other DNA
                        organism = synthetic construct
SEQUENCE: 325
ggctacacct ttactagcta cacg                                                  24

SEQ ID NO: 326          moltype = DNA   length = 24
FEATURE                 Location/Qualifiers
misc_feature            1..24
                        note = Synthetic polynucleotide
source                  1..24
                        mol_type = other DNA
                        organism = synthetic construct
SEQUENCE: 326
attaatccta gcagtacgta tact                                                  24

SEQ ID NO: 327          moltype = DNA   length = 30
FEATURE                 Location/Qualifiers
misc_feature            1..30
                        note = Synthetic polynucleotide
source                  1..30
                        mol_type = other DNA
                        organism = synthetic construct
SEQUENCE: 327
tcaagagggg aactgggagg gtttgcttac                                            30

SEQ ID NO: 328          moltype = DNA   length = 18
FEATURE                 Location/Qualifiers
misc_feature            1..18
                        note = Synthetic polynucleotide
source                  1..18
                        mol_type = other DNA
                        organism = synthetic construct
SEQUENCE: 328
cagggcatta gaggtaat                                                         18
```

```
SEQ ID NO: 329          moltype =    length =
SEQUENCE: 329
000

SEQ ID NO: 330          moltype = DNA   length = 27
FEATURE                 Location/Qualifiers
misc_feature            1..27
                        note = Synthetic polynucleotide
source                  1..27
                        mol_type = other DNA
                        organism = synthetic construct
SEQUENCE: 330
ctacagcgta atgcgtatcc tctcacg                                        27

SEQ ID NO: 331          moltype = DNA   length = 24
FEATURE                 Location/Qualifiers
misc_feature            1..24
                        note = Synthetic polynucleotide
source                  1..24
                        mol_type = other DNA
                        organism = synthetic construct
SEQUENCE: 331
ggattcactt tcagtagttt tgcc                                           24

SEQ ID NO: 332          moltype = DNA   length = 21
FEATURE                 Location/Qualifiers
misc_feature            1..21
                        note = Synthetic polynucleotide
source                  1..21
                        mol_type = other DNA
                        organism = synthetic construct
SEQUENCE: 332
attagaagtg gtggtattac c                                              21

SEQ ID NO: 333          moltype = DNA   length = 39
FEATURE                 Location/Qualifiers
misc_feature            1..39
                        note = Synthetic polynucleotide
source                  1..39
                        mol_type = other DNA
                        organism = synthetic construct
SEQUENCE: 333
gcaagagtta gtacggctac gtactatggt atggactac                           39

SEQ ID NO: 334          moltype = DNA   length = 325
FEATURE                 Location/Qualifiers
misc_feature            1..325
                        note = Synthetic polynucleotide
source                  1..325
                        mol_type = other DNA
                        organism = synthetic construct
SEQUENCE: 334
caaattgttc tcacccagtc tccagcaatc atgtctgcat ctctagggga acgggtcacc    60
atgacctgca ctgccagctc cagtgtaagt tccacttact tcactggta ccaacagaag    120
ccaggatcct cccccaaaact ctggatttat agcacatcca acctggcttc tggagtccca   180
cgtcgcttca gtggcagtgc gtctgggacc tcttactctc tcacaatcag cagcatggag   240
gctgaagatg ctgccactta ttattgccac cagtatcatc gttccccgct cacgttcggt   300
gctgggacca agctggagct gaaac                                          325

SEQ ID NO: 335          moltype = DNA   length = 349
FEATURE                 Location/Qualifiers
misc_feature            1..349
                        note = Synthetic polynucleotide
source                  1..349
                        mol_type = other DNA
                        organism = synthetic construct
SEQUENCE: 335
caggtccagc tgcagcagtc tgcagctgaa ctggcaagac ctggggcctc agtgaagatg    60
tcctgcaagg cttctggcta cacctttact acctacacga tgcactgggt aaaacagagg    120
cctggacagg gtctggaatg gattggatta ttaatccta gcagtggata tactgactac    180
aatcagaagt tcaaggacag gaccacattg actgcagaca aatcctccag cacagtctac    240
atgcaactga gtagcctgac atctgaggac tctgcggtct attactgtgc aaacggggat    300
tactacgtcg cttactgggg ccaagggact ctggtcactg tctctgcag                349

SEQ ID NO: 336          moltype = DNA   length = 322
FEATURE                 Location/Qualifiers
misc_feature            1..322
                        note = Synthetic polynucleotide
source                  1..322
```

```
                       mol_type = other DNA
                       organism = synthetic construct
SEQUENCE: 336
gacatccaga tgactcagtc tccagcctcc ctatctgcat ctgtgggaga aactgtcacc    60
atcacatgtc gaataagcga gaatatttac agttatttag catggtatca gcagaaacag   120
ggaaaatctc ctcagctcct ggtctataat gcaaaaatct tagtagaagg tgtgccatca   180
aggttcagtg gcagtggatc aggcacacag ttttctctga agatcaacag cctgcagcct   240
gaagattttg ggaattatta ctgtcaacat cattatactg ttccgtggac gttcggtgga   300
ggcaccaaac tggaaatcaa ac                                            322

SEQ ID NO: 337         moltype = DNA   length = 352
FEATURE                Location/Qualifiers
misc_feature           1..352
                       note = Synthetic polynucleotide
source                 1..352
                       mol_type = other DNA
                       organism = synthetic construct
SEQUENCE: 337
gaagtgaagc ttgaggagtc tggaggaggc ttggtgcaac ctggaggatc catgaaactc    60
tcctgtgttg cctctggttt cactttcagt gattactgga tgaactgggt ccgccagtct   120
ccagagaagg ggcttgaatg ggttgctcaa attagattga aatctgataa ttatgcaaca   180
cattatgcgg agtctgtgaa agggaggttc accatctcaa gagatgattc caaaagaagt   240
gtctacctgc aaatgaacaa cttaaggggct gaagacactg gaacttatta ctgcaatgat   300
ggccccccct cggggtgttg gggccaaggc accactctca tagtctcctc ag           352

SEQ ID NO: 338         moltype = DNA   length = 322
FEATURE                Location/Qualifiers
misc_feature           1..322
                       note = Synthetic polynucleotide
source                 1..322
                       mol_type = other DNA
                       organism = synthetic construct
SEQUENCE: 338
gacatccaga tgactcagtc tccagcctcc ctatctgcat ctgtgggaga aactgtcacc    60
atcacatgtc gaataagtga gaatatttac agttatttag catggtatca gcagaaacag   120
ggaaaatctc ctcagctcct ggtctataat gcaaaaatct tagtagaagg tgtgccatca   180
aggttcagtg gcagtggatc aggcacacag ttttctctga agatcaacag cctgcagcct   240
gaagattttg ggaattatta ctgtcaacat cattatactg ttccgtggac gttcggtgga   300
ggcaccaaac tggaaatcaa ac                                            322

SEQ ID NO: 339         moltype = DNA   length = 352
FEATURE                Location/Qualifiers
misc_feature           1..352
                       note = Synthetic polynucleotide
source                 1..352
                       mol_type = other DNA
                       organism = synthetic construct
SEQUENCE: 339
gaagtgaagc ttgaggagtc tggaggaggc ttggtgcaac ctggaggatc catgaaactc    60
tcctgtgttg cctctggatt cactttcagt aattactgga tgaactgggt ccgccagtct   120
ccagagaagg ggcttgaatg ggttgctcaa attagattga aatctgataa ttatgcaaca   180
cattatgcgg agtctgtgaa agggaggttc accatctcaa gagatgattc caaaagaagt   240
gtctacctgc aaatgaacaa cttaaggggct gaagacactg gaacttatta ctgcaatgat   300
ggccccccct cggggtgttg gggccaaggc accactctca tagtctcctc ag           352

SEQ ID NO: 340         moltype = DNA   length = 337
FEATURE                Location/Qualifiers
misc_feature           1..337
                       note = Synthetic polynucleotide
source                 1..337
                       mol_type = other DNA
                       organism = synthetic construct
SEQUENCE: 340
gatgttgtga tgacccaaac tccactctcc ctgcctgtca gtcttggaga tcaagcctcc    60
atctcttgca gatctagtca gagccttgta cacagtgatg gaaacaccta tttaaattgg   120
tacctgcaga agccaggcca gtctccaaag ctcctgatct acaaagtttc caaccgtttt   180
tctggggtcc cagacaggtt cagtggcagt ggatcaggga cagatttcac actcaagatc   240
aggagagtgg aggctgagga tctgggagtt tatttctgct ctcaaagtac acatgttcct   300
tacacgttcg gagggggac caagctggaa ataaaac                             337

SEQ ID NO: 341         moltype = DNA   length = 352
FEATURE                Location/Qualifiers
misc_feature           1..352
                       note = Synthetic polynucleotide
source                 1..352
                       mol_type = other DNA
                       organism = synthetic construct
SEQUENCE: 341
caggtccagt tgcagcagtc tggggctgaa ctggcaagac ctggggcctc agtgaagatg    60
```

```
tcctgcaagg cttctggcta cacctttact agctacacga tgcactggat aaaacagaga   120
cctggacagg gtcaggaatg gattggatac attaatccta gcagtactta tactcattac   180
attaagaaat tcaaggacaa ggccacattg actgcagaca atcctccag cacagcctac    240
atgcaactgc gcagcctgac atctgaggac tctgcagtct attactgttc aagaggggaa   300
ctgggagggt tgcttactg gggccaaggg actctggtca ctgtctctgc ag            352

SEQ ID NO: 343          moltype = DNA   length = 361
FEATURE                 Location/Qualifiers
misc_feature            1..361
                        note = Synthetic polynucleotide
source                  1..361
                        mol_type = other DNA
                        organism = synthetic construct
SEQUENCE: 342
gatgttttga tgacccaaac tccactctcc ctgcctgtca gtcttggaga tcaaccctcc   60
atctcttgca gatctagtca gagcattgta catagtaatg gaaacaccta tttagattgg   120
tacctgcaga accaggcca gtctccaaag ctcctgatca caaagtttc caaccgattt    180
tctggggtcc cagacaggtt cagtggcagt ggatcaggga cagattcac actcaagatc   240
agcagagtgg aggctgagga tctgggagtt tattactgct ttcaaggttc acatgttcca   300
ttcacgttcg gctcggggac aaggttggaa ataaaac                            337

SEQ ID NO: 343          moltype = DNA   length = 361
FEATURE                 Location/Qualifiers
misc_feature            1..361
                        note = Synthetic polynucleotide
source                  1..361
                        mol_type = other DNA
                        organism = synthetic construct
SEQUENCE: 343
gaagtccagc tgcagcagtc tggacctgag ctggtaaagc ctggggcttc agtgaagatg   60
tcctgcaagg cttctggata catattcact cactatatta tgcactgggt gaagcagaag   120
cctgggcagg gccttgagtg gattggatgt attaatcctt acaatgatgg tactaagtac   180
aatgagaagt tcaaaggcaa ggccacactg acttcagaca atcctccag cacagcctac   240
atggagctca gcagcctgac ctctgaggac tctgcggtct attactgtgc aagatactac   300
ggctacccctt actattctat ggactactgg ggtcaaggaa ccctcagtcac cgtctcctca   360
g                                                                    361

SEQ ID NO: 344          moltype = DNA   length = 337
FEATURE                 Location/Qualifiers
misc_feature            1..337
                        note = Synthetic polynucleotide
source                  1..337
                        mol_type = other DNA
                        organism = synthetic construct
SEQUENCE: 344
gccattgtga tgttccagtc tccatcctcc ctggttgtgt cagcaggaga gaaggtcact   60
atgagctgca aatccagtca gagtctgctc aacagtgaa cccgaaagaa ctacttggct   120
tggtaccagc agaaaccagg gcagtctcct aaactgctga tctactgggc atccactagg   180
gaatctgggg tccctgatcg cttcacaggc agtggatctg gacagattt cactctcacc   240
atcagcagtg tgcaggctga agacctggca gtttattact gcaagcaatc ttattatctg   300
tacacgttcg gaggggggac caagctggaa ataaaac                            337

SEQ ID NO: 345          moltype = DNA   length = 352
FEATURE                 Location/Qualifiers
misc_feature            1..352
                        note = Synthetic polynucleotide
source                  1..352
                        mol_type = other DNA
                        organism = synthetic construct
SEQUENCE: 345
gatgtgcagc ttcaggagtc aggacctggc ctcgtgaaat cttctcagtc tctgtctctc   60
acctgctctg tcactggcta ctccatcacc agtggttatt actggaaatg gatccggcag   120
tttccaggaa acaaactgga atggatgggc tacatcagct acgatggtgg cattaactac   180
aacccatctc tcaaaaatcg aatctccatc actcgtgaca ccaagtttc                240
ctgaagttga attctgtgac tactgaggac acagccaaat attactgtgc aagatttggt   300
aagggggcta tggactactg gggtcaagga acctcagtca ccgtctcctc ag            352

SEQ ID NO: 346          moltype = DNA   length = 325
FEATURE                 Location/Qualifiers
misc_feature            1..325
                        note = Synthetic polynucleotide
source                  1..325
                        mol_type = other DNA
                        organism = synthetic construct
SEQUENCE: 346
caaattgttc tcacccagtc tccagcaatc atgtctgcat ctctggggga ccgggtcacc   60
atgacctgca ctgccagctc aagtgtaagt tccagttact gcactggta ccagcagaag   120
ccaggatcct cccccaaaact ctggatttat agcacatcca acctggcttc tggagtccca   180
gctcgcttca gtggcagtgg gtctgggacc tcttactctc tcacaatcag cagcatgag   240
```

```
gctgaagatg ctgccactta ttactgccac cagtatcatc gttccccacc cacgttcggc    300
tcggggacaa agttggaaat aaaac                                          325

SEQ ID NO: 347          moltype = DNA  length = 358
FEATURE                 Location/Qualifiers
misc_feature            1..358
                        note = Synthetic polynucleotide
source                  1..358
                        mol_type = other DNA
                        organism = synthetic construct
SEQUENCE: 347
gaggtccagc tgcaacagtc tggacctgag ctggtgaagc ctggagcttc aatgaagata    60
tcctgcaagg cttctggtta ctcattcact ggctacacca tgaactgggt gaagcagagc    120
catggaaaga accttgagtg gattggactt attaatcctt acaatggtgg tactaactac    180
aaccagaagt tcaagggcaa ggccacatta actgtagaca agtcatccag cacagcctac    240
atggagctcc tcagtctgac atctgaggac tctgcagtct attactgtgc aagaggggtc    300
tatgattacg acggatttac ttactggggc caagggactc tggtcactgt ctctgcag     358

SEQ ID NO: 348          moltype = DNA  length = 337
FEATURE                 Location/Qualifiers
misc_feature            1..337
                        note = Synthetic polynucleotide
source                  1..337
                        mol_type = other DNA
                        organism = synthetic construct
SEQUENCE: 348
gatgttgtga tgacccaaac tccactctcc ctgcctgtca gtcttggaga tcaagcctcc    60
atctcttgca gatctagtca gagccttgta cacagtgatg gaaacaccta tttatattgg    120
tacctgcaga agccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tatttctgct ctcaaagtac acatgttcct    300
tacacgttcg gaggggggac caagctggaa ataaaac                             337

SEQ ID NO: 349          moltype = DNA  length = 352
FEATURE                 Location/Qualifiers
misc_feature            1..352
                        note = Synthetic polynucleotide
source                  1..352
                        mol_type = other DNA
                        organism = synthetic construct
SEQUENCE: 349
caggtccagc tgcagcagtc tggggctgaa ctggcaagac ctggggcctc agtgaagatg    60
tcctgcaagg cttctggcta cacctttact acctacgtga tgcactggtt aaaacagagg    120
cctggacagg gtctggaatg gattggatac attaatcctc gcagtggtta tagtaattac    180
aatcagaagt tcaaggacaa ggccacattg actgcagaca gtcctccaa cacagcctac    240
atgcaactga cacccctgac atctgaggac tctaaagtct attactgttc aagagggaa    300
ctgggagggt ttgcttactg gggccaaggg actctggtca ctgtctctgc ag           352

SEQ ID NO: 350          moltype = DNA  length = 322
FEATURE                 Location/Qualifiers
misc_feature            1..322
                        note = Synthetic polynucleotide
source                  1..322
                        mol_type = other DNA
                        organism = synthetic construct
SEQUENCE: 350
gacattcaga tgacccagtc tcctgcctcc cagtctgcat ctctgggaga aagtgtcacc    60
atcacatgcc tggcaagtca gaccattggt acatggttag catggtatca gcagaaacca    120
gggaaatctc ctcagctcct gatttatgct gcagccagct ggcagatgg ggtcccatca    180
aggttcagtg gtagtggatc tggcacaaga ttttctttca agatcagcag cctacaggct    240
gaagattttg taagttatta ctgtcaacaa ctttacagta ttccctcgga cgttcggtgga    300
ggcaccaagc tggaaatcaa ac                                             322

SEQ ID NO: 351          moltype = DNA  length = 352
FEATURE                 Location/Qualifiers
misc_feature            1..352
                        note = Synthetic polynucleotide
source                  1..352
                        mol_type = other DNA
                        organism = synthetic construct
SEQUENCE: 351
gaggtccagc tgcaacagtc tggacctgag ctggtgaagc ctggggcttc agtgaagatg    60
tcctgcaagg cttctggata cagattcact gactacaaca tgcactgggt gaagcagagc    120
catggaaaga gccttgagtg gattggatat attaaccta acaatggtgg tactaactac    180
aaccaaaact tcaagggcaa ggccacattg actgtgaaca gtcctccag cacagcctac    240
atggagctcc gcagcctgac atcggaggat tctgcagcct attactgtgc aagagattac    300
ttgtactttct tgactgctgg ggccaaggc accactctca cagtctcctc ag           352

SEQ ID NO: 352          moltype = DNA  length = 337
```

```
FEATURE                 Location/Qualifiers
misc_feature            1..337
                        note = Synthetic polynucleotide
source                  1..337
                        mol_type = other DNA
                        organism = synthetic construct
SEQUENCE: 352
gatgttgtga tgacccaaac tccactctcc ctgcctgtca gtcttggaga tcaagcctcc    60
atctcttgca gagctagtca gagccttgta cacagtaatg gaaacaccta tttacattgg   120
ttcctgcaga agccaggcca gtctccaaag ctcctgatct acaaagtttc caaccgattt   180
tctggggtcc cagacaggtt cagtggcagt ggatcacgga cagatttcac actcaagatc   240
agcagagtgg aggctgagga tctgggagtt tatttctgct ctcaaattac acatgttccg   300
tacacgttcg gagggggac caagctggaa ataaaac                              337

SEQ ID NO: 353          moltype = DNA  length = 352
FEATURE                 Location/Qualifiers
misc_feature            1..352
                        note = Synthetic polynucleotide
source                  1..352
                        mol_type = other DNA
                        organism = synthetic construct
SEQUENCE: 353
caaatccagt tggtgcagtc tggacctgcg ctgaagaagc ctggagagac agtcaagatc    60
tcctgcaagg cttctggtta taccttcaca gactattcaa tgcactggat aaagcaggct   120
ccaggaaagg gtttaaagtg gatgggctgg ataagcactg agactggtga gccaacatat   180
gcagatggct tcaagggacg gtttgacttc tctttggaaa cctgcgcga cactgcctat   240
ttgtccatca acaacctcac aaatgaggac acggctacat atttctgtac tagaggtcta   300
tggtcctcgt ttgcttactg gggccaaggg actctggtca ctgtctctgc ag           352

SEQ ID NO: 354          moltype = DNA  length = 334
FEATURE                 Location/Qualifiers
misc_feature            1..334
                        note = Synthetic polynucleotide
source                  1..334
                        mol_type = other DNA
                        organism = synthetic construct
SEQUENCE: 354
gacattgtgc tgacacagtc tcctgcttcc ttagctgtat ctctggggca gagggccacc    60
atctcatgca gggccagcaa aagtgtcagt acatctggct atagttatat acactggtac   120
caacagaaac caggacagcc acccaaactc ctcatctatc ttgcatccaa cctagaatct   180
ggggtccctg ccaggttcag tggcagtggg tctgggacag acttcaccct caacatccat   240
cctgtggagg aggaggatgc tgcaacctat tactgtcagc acagtaggga gcttccgctc   300
acgttcggtc tgggaccaa gctggagctg aaac                                334

SEQ ID NO: 355          moltype = DNA  length = 355
FEATURE                 Location/Qualifiers
misc_feature            1..355
                        note = Synthetic polynucleotide
source                  1..355
                        mol_type = other DNA
                        organism = synthetic construct
SEQUENCE: 355
gatgtgcagc tggtggagtc tgggggaggc ttggtgcagc ctagagggtc ccggaaactc    60
tcctgtgcag cctctggatt cactttcagt agctttggaa tgcactgggt tcgtcaggct   120
ccagagaagg ggctggagtg ggtcgcatac attagtagta cagtaggac catctattat   180
gcagacacag tgaagggccg attcaccatc tccagagaca atcccacgaa caccctgttc   240
ctgcaaatga ccagtctcag gtctgaggac acggccatgt attactgtgc aagagactac   300
ggtagaacct acgaggctta ctggggccaa gggactctgg tcactgtctc tgcag         355

SEQ ID NO: 356          moltype = DNA  length = 322
FEATURE                 Location/Qualifiers
misc_feature            1..322
                        note = Synthetic polynucleotide
source                  1..322
                        mol_type = other DNA
                        organism = synthetic construct
SEQUENCE: 356
gacatccaga tgattcagtc tccatcgtcc atgtttgcct ctctgggaga cagagtcagt    60
ctctcttgtc gggctagtca ggacattgga ggaaatttag actggtatca gcagaaacca   120
ggtggaacta ttaaactcct gatctactcc acatccaatt taaattctgg tgtcccatca   180
aggttcagtg gcagtgggtc tgggtcagat tattctctca ccatcaccag cctgagtct   240
gaagattttg cagactatta ctgtctacag cgtaatgcgt atccgctcac tttcggtgct   300
gggaccaagc tggagctgaa ac                                            322

SEQ ID NO: 357          moltype = DNA  length = 355
FEATURE                 Location/Qualifiers
misc_feature            1..355
                        note = Synthetic polynucleotide
source                  1..355
```

```
                        mol_type = other DNA
                        organism = synthetic construct
SEQUENCE: 357
gaagtgaaac tgatggagtc tggggagac ttagtgaagc ctggagggtc cctgaaactc    60
tcctgtgcag cctctggatt cacttttcagt agttatgcca tgtcttgggt tcgccagact  120
ccagagaaga ggctggagtg ggtcgcgtcc attagaagtg gtggtaccac ctactatcca   180
gacagtgtga agggccgatt caccatctcc agagataatg ccaggaacat cctgtacctg   240
cgaatgagta gtctgaggtc tgaggacacg gccatatatt actgtgcaaa agtgggcggt   300
aaccctatc ctatggacta ctgggtcaa ggaacctcag tcaccgtctc ctcag          355

SEQ ID NO: 358          moltype = DNA   length = 325
FEATURE                 Location/Qualifiers
misc_feature            1..325
                        note = Synthetic polynucleotide
source                  1..325
                        mol_type = other DNA
                        organism = synthetic construct
SEQUENCE: 358
gaaattgtgc tcacccagtc tccaaccacc atggctgcat ctcccgggga gaagatcact    60
atcacctgca gtgccagctc aagtataagt tccaattact tgcattggta tcagcagaag   120
ccaggattct cccctaaact cttgatttat aggacatcca atctggcttc tggagtccca   180
gctcgcttca gtggcagtgg gtctgggacc tcttactctc tcacaattgg caccatggag   240
gctgaagatg ttgccactta ctactgccag caggtagta gtataccgct cacgttcggt   300
gctgggacca agctggagct gaaac                                         325

SEQ ID NO: 359          moltype = DNA   length = 367
FEATURE                 Location/Qualifiers
misc_feature            1..367
                        note = Synthetic polynucleotide
source                  1..367
                        mol_type = other DNA
                        organism = synthetic construct
SEQUENCE: 359
caggtccagc tgcagcagtc tggagctgag ctggtaaggc ctggggcttc agtgaaggtg    60
tcctgcaagg cttctggata cgccttcagt aattacttga tagagtgggt taagcagagg   120
cctggacagg gccttgagtg gattggagtg attaatcctg gaagtggtgg tactaactac   180
aatgagaagt tcaagggcaa ggcaacaatg actgcagaca atcctccag cactgcctac   240
atgcacctca gcaacctgac atctgaggac tctgtggtct atttctgtgc aagatcatac   300
ttcggtagaa gctacccta tactatggac tactgggtc aaggaacctc agtcaccgtc     360
tcctcag                                                             367

SEQ ID NO: 360          moltype = DNA   length = 334
FEATURE                 Location/Qualifiers
misc_feature            1..334
                        note = Synthetic polynucleotide
source                  1..334
                        mol_type = other DNA
                        organism = synthetic construct
SEQUENCE: 360
gatattgtgc tgacccaatc tccagcttct ttggctgtgt ctctagggca gagggccacc    60
atctcctgca aggccagcca aagtgttgat tatgatggtg ataattatgt gaactggtac   120
caacagaaag taggacagcc acccaaactc ctcatctctg ctgcatccaa tctagaatct   180
gggatcccag ccaggtttag tggcagtggg tctgggacag acttcacccct caacatccat   240
cctgtggagg aggaggatgc tgcaacctat tactgtcagc aaagtaatga ggatccattc   300
acgttcggct cggggacaaa gttggaaata aaac                               334

SEQ ID NO: 361          moltype = DNA   length = 361
FEATURE                 Location/Qualifiers
misc_feature            1..361
                        note = Synthetic polynucleotide
source                  1..361
                        mol_type = other DNA
                        organism = synthetic construct
SEQUENCE: 361
caggtccagc tgcagcagtc tgggcctgag ctggtgaggc ctggggtctc agtgaagatt    60
tcctgcaagg gttccggcta cacattcact gattatgcta tgcactgggt gaagcagagt   120
catgcaaaga gtctagagtg gattggagtt attagtacat actctggtaa tacaaactac   180
aaccagaagt tcaggacaa ggccaccatg actgtagaca atcctccag cacagcctat    240
atggcacttg ccagattgac atctgacgat tctgccatct attactgtgc aagagggggc   300
gattacagcc tctatgctat ggactactgg ggtcaaggaa cctcagtcac cgtctcctca   360
g                                                                   361

SEQ ID NO: 362          moltype = DNA   length = 337
FEATURE                 Location/Qualifiers
misc_feature            1..337
                        note = Synthetic polynucleotide
source                  1..337
                        mol_type = other DNA
                        organism = synthetic construct
```

```
SEQUENCE: 362
aacattatga tgacacagtc gccatcatct ctggctgtgt ctgcaggaga aaaggtcact   60
atgagctgta agtccagtca aagtgtttta ttcagttcaa atcagaaaaa ctacttggcc  120
tggtaccagc agaaaccagg gcagtctcct agactgctga tctactgggc atccactagg  180
gaatctgggt tccctgatcg cttcacaggc agtggatctg ggacagattt tactcttacc  240
atcagcaatg ttcaagctga agacctggca gtttattact gtcatcaata cctctcctcg  300
cgcacgttcg gtgctgggac caagctggag ctgaaac                           337

SEQ ID NO: 363            moltype = DNA   length = 355
FEATURE                   Location/Qualifiers
misc_feature              1..355
                          note = Synthetic polynucleotide
source                    1..355
                          mol_type = other DNA
                          organism = synthetic construct
SEQUENCE: 363
gatgtgcagc tggtggagtc tgggggaggc ttggtgcagc ctagagggtc ccggaaactc   60
tcctgtgcag cctctggatt cactttcagt agctttgcaa tgcactgggt tcgtcaggct  120
ccagagaagg ggctggagtg ggtcgcatac attagtagtg acagtaggac catctattat  180
gcagacacag tgaagggccg attcaccatc tccagagaca atcccacgaa caccctgttc  240
ctgcaaatga ccagtctcag gtctgaggac acggccatgt attactgtgc aagagactac  300
ggtagaacct acgaggctta ctggggccaa gggactctgg tcactgtctc tgcag        355

SEQ ID NO: 364            moltype = DNA   length = 334
FEATURE                   Location/Qualifiers
misc_feature              1..334
                          note = Synthetic polynucleotide
source                    1..334
                          mol_type = other DNA
                          organism = synthetic construct
SEQUENCE: 364
gacattgtgc tgacccaatc tccagcttct ttggctctgt ctctaggca gagggccacc   60
atctcctgca gagccagcga aagtgttgat aattatggca ttagttttat gaactggttc  120
caacagaaac ccggacagcc acccaaactc ctcatcatg ctgcatccaa ccaaggatcc  180
ggggtccctg ccaggtttag tggcagtggg tctgggacag acttcagcct caacatccat  240
cctatggagg aggatgatac tgcaatgtat ttctgtcagc aaagtaagga ggttccgctc  300
acgttcggtg ctgggaccaa gctggagctg aaac                              334

SEQ ID NO: 365            moltype = DNA   length = 358
FEATURE                   Location/Qualifiers
misc_feature              1..358
                          note = Synthetic polynucleotide
source                    1..358
                          mol_type = other DNA
                          organism = synthetic construct
SEQUENCE: 365
gaagtgaggc tggtggagtc tgggggaggc ttgatgcagc ctggagggtc cctgaaactc   60
ccctgtgcag cctctggatt cccttcagt agctctgcca tgtcttgggt tcgccagact  120
ccagagaaga ggctggagtg ggtcgcatcc attaatagtg atggtaacac ctactatccc  180
gacagtgtga agggccgatt caccatctcc agagatagtg ccaggaacat cctgtacctc  240
caaatgagca gtctgaggtc tgaggacacg gccatgtatt actgtacaag aaacggggac  300
tataggtacg acgagtttgc ttactggggc caagggactc tggtcactgt ctctgcag    358

SEQ ID NO: 366            moltype = DNA   length = 325
FEATURE                   Location/Qualifiers
misc_feature              1..325
                          note = Synthetic polynucleotide
source                    1..325
                          mol_type = other DNA
                          organism = synthetic construct
SEQUENCE: 366
caaattgttc tcacccagtc tccagcaatc atgtctgcat ctctagggga acgggtcacc   60
atgacctgca ctgccagctc aagtgtaagt tccagttact gcactggta ccagcagaag  120
ccaggatcct cccccaaact ctggatttat agcacatcca acctggcttc tggagtccca  180
gctcgcttca gtggcagtgg gtctgggacc tcttactctc tcacaatcag cagcatggag  240
gctgaagatg ctgccactta ttactgccac cagtatcatc gttccccacc cacgttcgga  300
gctgggacca agctggagct gaaac                                        325

SEQ ID NO: 367            moltype = DNA   length = 358
FEATURE                   Location/Qualifiers
misc_feature              1..358
                          note = Synthetic polynucleotide
source                    1..358
                          mol_type = other DNA
                          organism = synthetic construct
SEQUENCE: 367
caggtccagc tcagcagtc tggggctgaa ctggcaaaac tggggcctc agtgaagatg    60
tcctgcaagg cttctggcta caccttract ggctactgga tgcactgggt aaaacagagg  120
cctggacagg gtctggaatg gcttggatac attaatccta gcactggtta tactgagtcc  180
```

```
aatcagaagt tcaaggacaa ggccacattg actgcagaca aatcctccac cacagcctac    240
atgcaactga gaagcctgac acctgaggac tctgcagtct attactgtgc aagagagggg    300
attactactg tgctggttga ctactggggc caaggcacca ctctcacagt ctcctcag     358

SEQ ID NO: 368         moltype = DNA   length = 337
FEATURE                Location/Qualifiers
misc_feature           1..337
                       note = Synthetic polynucleotide
source                 1..337
                       mol_type = other DNA
                       organism = synthetic construct
SEQUENCE: 368
aacattatga tgacacagtc gccatcatct ctggctgtgt ctgcaggaga aaaggtcact    60
atgagctgta agtccagtca aagtgtttta ttcagttcaa atcagaaaaa ctacttggcc    120
tggtaccagc agaaaccagg gcagtctcct agactgctga tctactgggc atccactagg    180
gaatctggtg tccctgatcg cttcacaggc agtggatctg ggacagattt tactcttacc    240
atcagcaatg ttcaagctga agacctggca gtttattact gtcatcaata cctctcctcg    300
cgcacgttcg gtgctgggac caagctggag ctgaaac                              337

SEQ ID NO: 369         moltype = DNA   length = 364
FEATURE                Location/Qualifiers
misc_feature           1..364
                       note = Synthetic polynucleotide
source                 1..364
                       mol_type = other DNA
                       organism = synthetic construct
SEQUENCE: 369
caggtgcagc tgaagcagtc tggacctgag ctggagaagc ctggcgcttc agtgaagata    60
tcctgcaagg cttctggtta ctctttcact ggctacaata tgaactgggt gaagcagagc    120
aatgggaaga gccttgagtg gattggaaat attgatcctt actatggtgg ttctacctac    180
aaccagaagt tcacgggcaa ggccacattg actgtagaca aatcctccag cacagcctac    240
atgcagctca gagcctgaca tctgaggac tctgcagtgt attactgtgc aagagagagg    300
tcgggctacg ttttctctgc tatggactac tggggtcaag gaacctcagt caccgtctcc    360
tcag                                                                  364

SEQ ID NO: 370         moltype = DNA   length = 337
FEATURE                Location/Qualifiers
misc_feature           1..337
                       note = Synthetic polynucleotide
source                 1..337
                       mol_type = other DNA
                       organism = synthetic construct
SEQUENCE: 370
aacattatga tgacacagtc gccatcatct ctggctgtgt ctgcaggaga aaaggtcact    60
atgagctgta agtccagtca aagtgtttta ttcagttcaa atcagaaaaa ctacttggcc    120
tggtaccagc agaaaccagg gcagtctcct agactgctga tctactgggc atccactagg    180
gaatctggtg tccctgatcg cttcacaggc agtggatctg ggacagattt tactcttacc    240
atcagcaatg ttcaagctga agacctggca gtttattact gtcatcaata cctctcctcg    300
cgcacgttcg gtgctgggac caagctggag ctgaaac                              337

SEQ ID NO: 371         moltype = DNA   length = 370
FEATURE                Location/Qualifiers
misc_feature           1..370
                       note = Synthetic polynucleotide
source                 1..370
                       mol_type = other DNA
                       organism = synthetic construct
SEQUENCE: 371
gaggtccagc tgcaacagtc tggacctgag ctggtgaagc ctggaggttc aatgaagata    60
tcctgcaagg cttctggtta ctcattcact ggctacacca tgaactgggt gaagcggagc    120
catggaaaga accttgagtg gattggactt attaatcctt acaatggtgt tactacctac    180
aaccagaact tcaagggcaa ggccacatta gctgtagaca gtcatccag cacagcctac    240
atggagctcc tcggtctgac atctgaggac tctgcagtct attactgtac aagagatccc    300
ctttactacg gctacaggga ctctactatg gactactggg gtcaaggaac ctcagtcacc    360
gtctcctcag                                                            370

SEQ ID NO: 372         moltype = DNA   length = 337
FEATURE                Location/Qualifiers
misc_feature           1..337
                       note = Synthetic polynucleotide
source                 1..337
                       mol_type = other DNA
                       organism = synthetic construct
SEQUENCE: 372
gatgttgtga tgacccaaac tccactctcc ctgcctgtca gtcttggaga tcaagcctcc    60
atctcttgca gatctagtca gagccttgta cacagtgatg gaaacaccta tttaaattgg    120
tacctgcaga agccaggcca gtctccaaag ctcctgatct acaaagtttc caaccgtttt    180
tctggggtcc cagacaggtt cagtggcagt ggatcaggga cagatttcac actcaagatc    240
aggagagtgg aggctgagga tctgggagtt tatttctgct ctcaaagtac acatgttcct    300
```

```
tacacgttcg gagggggac caagctggaa ataaaac                              337

SEQ ID NO: 373            moltype = DNA   length = 352
FEATURE                   Location/Qualifiers
misc_feature              1..352
                          note = Synthetic polynucleotide
source                    1..352
                          mol_type = other DNA
                          organism = synthetic construct
SEQUENCE: 373
gaggtccagc tgcagcagtc tggggctgaa ctggcaagac ctggggcctc agtgaagatg    60
tcctgcaagg cttctggcta caccttact agctacacga tgcactggat aaaacagaga    120
cctggacagg gtcaggaatg gattggatac attaatccta gcagtacgta tactcattac   180
attaagaagt tcaaggacaa ggccacattg actgcagaca aatcctccag cacagcctac   240
atgcaactgc gcagcctgac atctgaggac tctgcagtct attactgttc aagaggggaa   300
ctgggagggt ttgcttactg gggccaaggg actctggtca ctgtctctgc ag           352

SEQ ID NO: 374            moltype = DNA   length = 322
FEATURE                   Location/Qualifiers
misc_feature              1..322
                          note = Synthetic polynucleotide
source                    1..322
                          mol_type = other DNA
                          organism = synthetic construct
SEQUENCE: 374
gacatccaga tgattcagtc tccatcgtcc atgtttgcct ctctgggaga cagagtcagt    60
ctctcttgtc gggctagtca gggcattaga ggtaatttag actggtatca gcagaaacca   120
ggtggaacta ttaaactcct gatctactcc acatccattt taaattctgg tgtcccatca   180
aggttcagtg gcagtgggtc tgggtcagat tattctctca ccatcaccag cctagagtct   240
gaagattttg cagactatta ctgtctacag cgtaatgcgt atcctctcac gttcggttct   300
gggaccaagc tggagctgaa ac                                             322

SEQ ID NO: 375            moltype = DNA   length = 358
FEATURE                   Location/Qualifiers
misc_feature              1..358
                          note = Synthetic polynucleotide
source                    1..358
                          mol_type = other DNA
                          organism = synthetic construct
SEQUENCE: 375
gaagtgaagt tggtggagtc tgggggaggc ttaatgaagc ctggagggtc cctgaaactc    60
tcctgtgcgg cctctggatt cactttcagt agttttgcct tgtcttgggt tcgccagact   120
ccagagaaga ggctggagtg ggtcgcatcc attagagtg gtggtattac ctaccatgca    180
gacagtgtga agggccgatt caccatctcc agagataatg ccgggaacat cctgtacctg   240
caaatgaaca gtctgaggtc tgaggacacg gccatgtatt tctgtgcaag agttagtacg   300
gctacgtact atggtatgga ctactgggt caaggaacct cagtcaccgt ctcctcag      358

SEQ ID NO: 376            moltype = AA    length = 116
FEATURE                   Location/Qualifiers
REGION                    1..116
                          note = Synthetic peptide
source                    1..116
                          mol_type = protein
                          organism = synthetic construct
SEQUENCE: 376
QVQLVQSGAE VKKPGASVKV SCKASGYTFT TYTMHWVRQA PGQGLEWMGF INPSSGYTDY    60
AQKFQGRVTM TRDTSTSTVY MELSSLRSED TAVYYCARGD YVAYWGQGT LVTVSS         116

SEQ ID NO: 377            moltype = AA    length = 116
FEATURE                   Location/Qualifiers
REGION                    1..116
                          note = Synthetic peptide
source                    1..116
                          mol_type = protein
                          organism = synthetic construct
SEQUENCE: 377
QVQLVQSGAE VKKPGASVKV SCKASGYTFT TYTMHWVRQA PGQGLEWMGF INPSSGYTDY    60
AQKFQGRVTM TADTSTSTVY MELSSLRSED TAVYYCANGD YVAYWGQGT LVTVSS         116

SEQ ID NO: 378            moltype = AA    length = 116
FEATURE                   Location/Qualifiers
REGION                    1..116
                          note = Synthetic peptide
source                    1..116
                          mol_type = protein
                          organism = synthetic construct
SEQUENCE: 378
QVQLVQSGAE VKKPGASVKM SCKASGYTFT TYTMHWVRQA PGQGLEWIGF INPSSGYTDY    60
AQKFQGRVTL TADTSTSTVY MELSSLRSED TAVYYCANGD YVAYWGQGT LVTVSS         116
```

```
SEQ ID NO: 379          moltype = AA  length = 116
FEATURE                 Location/Qualifiers
REGION                  1..116
                        note = Synthetic peptide
source                  1..116
                        mol_type = protein
                        organism = synthetic construct
SEQUENCE: 379
QVQLVQSGAE VKKPGASVKM SCKASGYTFT TYTMHWVRQA PGQGLEWIGF INPSSGYTDY    60
AQKFQGRVTL TADKSTSTVY MELSSLRSED TAVYYCANGD YVVAYWGQGT LVTVSS       116

SEQ ID NO: 380          moltype = AA  length = 108
FEATURE                 Location/Qualifiers
REGION                  1..108
                        note = Synthetic peptide
source                  1..108
                        mol_type = protein
                        organism = synthetic construct
SEQUENCE: 380
DIQMTQSPSS LSASVGDRVT ITCTASSSVS STYFHWYQQK PGKAPKLLIY STSNLASGVP    60
SRFSGSGSGT DFTLTISSLQ PEDFATYYCH QYHRSPLTFG QGTKLEIK                108

SEQ ID NO: 381          moltype = AA  length = 108
FEATURE                 Location/Qualifiers
REGION                  1..108
                        note = Synthetic peptide
source                  1..108
                        mol_type = protein
                        organism = synthetic construct
SEQUENCE: 381
DIQMTQSPSS LSASVGDRVT ITCTASSSVS STYFHWYQQK PGKAPKLLIY STSNLASGVP    60
SRFSGSGSGT DYTLTISSLQ PEDFATYYCH QYHRSPLTFG QGTKLEIK                108

SEQ ID NO: 382          moltype = AA  length = 108
FEATURE                 Location/Qualifiers
REGION                  1..108
                        note = Synthetic peptide
source                  1..108
                        mol_type = protein
                        organism = synthetic construct
SEQUENCE: 382
DIQLTQSPSS LSASVGDRVT MTCTASSSVS STYFHWYQQK PGKAPKLLIY STSNLASGVP    60
SRFSGSGSGT DYTLTISSMQ PEDAATYYCH QYHRSPLTFG QGTKLEIK                108

SEQ ID NO: 383          moltype = AA  length = 108
FEATURE                 Location/Qualifiers
REGION                  1..108
                        note = Synthetic peptide
source                  1..108
                        mol_type = protein
                        organism = synthetic construct
SEQUENCE: 383
DIQLTQSPSS LSASVGDRVT MTCTASSSVS STYFHWYQQK PGKAPKLWIY STSNLASGVP    60
SRFSGSGSGT DYTLTISSMQ PEDAATYYCH QYHRSPLTFG QGTKLEIK                108

SEQ ID NO: 384          moltype = AA  length = 117
FEATURE                 Location/Qualifiers
REGION                  1..117
                        note = Synthetic peptide
source                  1..117
                        mol_type = protein
                        organism = synthetic construct
SEQUENCE: 384
EVQLLESGGG LVQPGGSLRL SCAASGFTFS NYWMNWVRQA PGKGLEWVSQ IRLKSDNYAT    60
HYADSVKGRF TISRDNSKNT LYLQMNSLRA EDTAVYYCAK GPPSGCWGQG TLVTVSS      117

SEQ ID NO: 385          moltype = AA  length = 117
FEATURE                 Location/Qualifiers
REGION                  1..117
                        note = Synthetic peptide
source                  1..117
                        mol_type = protein
                        organism = synthetic construct
SEQUENCE: 385
EVQLLESGGG LVQPGGSMRL SCAASGFTFS NYWMNWVRQA PGKGLEWVAQ IRLKSDNYAT    60
HYADSVKGRF TISRDDSKNT VYLQMNSLRA EDTGVYYCND GPPSGCWGQG TLLTVSS      117

SEQ ID NO: 386          moltype = AA  length = 117
```

```
FEATURE                 Location/Qualifiers
REGION                  1..117
                        note = Synthetic peptide
source                  1..117
                        mol_type = protein
                        organism = synthetic construct
SEQUENCE: 386
EVQLLESGGG LVQPGGSMRL SCAASGFTFS NYWMNWVRQA PGKGLEWVAQ IRLKSDNYAT    60
HYADSVKGRF TISRDDSKNT VYLQMNSLRA EDTGVYYCND GPPSGYWGQG TLLTVSS     117

SEQ ID NO: 387          moltype = AA  length = 117
FEATURE                 Location/Qualifiers
REGION                  1..117
                        note = Synthetic peptide
source                  1..117
                        mol_type = protein
                        organism = synthetic construct
SEQUENCE: 387
EVQLLESGGG LVQPGGSMRL SCAASGFTFS NYWMNWVRQA PGKGLEWVAQ IRLKSDNYAT    60
HYADSVKGRF TISRDDSKNT VYLQMNSLRA EDTGVYYCND GPPSGSWGQG TLLTVSS     117

SEQ ID NO: 388          moltype = AA  length = 107
FEATURE                 Location/Qualifiers
REGION                  1..107
                        note = Synthetic peptide
source                  1..107
                        mol_type = protein
                        organism = synthetic construct
SEQUENCE: 388
DIQMTQSPSS LSASVGDRVT ITCRISENIY SYLAWYQQKP GKAPKLLIYN AKILVEGVPS    60
RFSGSGSGTD FTLTISSLQP EDFATYYCQH HYTVPWTFGQ GTKLEIK                107

SEQ ID NO: 389          moltype = AA  length = 107
FEATURE                 Location/Qualifiers
REGION                  1..107
                        note = Synthetic peptide
source                  1..107
                        mol_type = protein
                        organism = synthetic construct
SEQUENCE: 389
DIQMTQSPSS LSASVGDRVT ITCRISENIY SYLAWYQQKP GKAPKLLVYN AKILVEGVPS    60
RFSGSGSGTD FTLTISSLQP EDFGTYYCQH HYTVPWTFGQ GTKLEIK                107

SEQ ID NO: 390          moltype = AA  length = 107
FEATURE                 Location/Qualifiers
REGION                  1..107
                        note = Synthetic peptide
source                  1..107
                        mol_type = protein
                        organism = synthetic construct
SEQUENCE: 390
DIQMTQSPSS LSASVGDRVT ITCRISENIY SYLAWYQQKP GKAPKLLVYN AKSLVEGVPS    60
RFSGSGSGTD FTLTISSLQP EDFGTYYCQH HYTVPWTFGQ GTKLEIK                107

SEQ ID NO: 391          moltype = AA  length = 117
FEATURE                 Location/Qualifiers
REGION                  1..117
                        note = Synthetic peptide
source                  1..117
                        mol_type = protein
                        organism = synthetic construct
SEQUENCE: 391
QVQLVQSGAE VKKPGASVKV SCKASGYTFT SYTMHWVRQA PGQGLEWMGY INPSSTYTHY    60
AQKFQGRVTM TRDTSTSTVY MELSSLRSED TAVYYCARGE LGGFAYWGQG TLVTVSS     117

SEQ ID NO: 392          moltype = AA  length = 117
FEATURE                 Location/Qualifiers
REGION                  1..117
                        note = Synthetic peptide
source                  1..117
                        mol_type = protein
                        organism = synthetic construct
SEQUENCE: 392
QVQLVQSGAE VKKPGASVKV SCKASGYTFT SYTMHWVRQA PGQGLEWMGY INPSSTYTHY    60
AQKFQGRVTM TADTSTSTVY MELSSLRSED TAVYYCSRGE LGGFAYWGQG TLVTVSS     117

SEQ ID NO: 393          moltype = AA  length = 117
FEATURE                 Location/Qualifiers
REGION                  1..117
```

|   |   |
|---|---|
|   | note = Synthetic peptide |
| source | 1..117 |
|   | mol_type = protein |
|   | organism = synthetic construct |

SEQUENCE: 393
QVQLVQSGAE VKKPGASVKM SCKASGYTFT SYTMHWIRQA PGQGLEWIGY INPSSTYTHY  60
AQKFQGRATL TADTSTSTAY MELSSLRSED TAVYYCSRGE LGGFAYWGQG TLVTVSS    117

| SEQ ID NO: 394 | moltype = AA   length = 117 |
|---|---|
| FEATURE | Location/Qualifiers |
| REGION | 1..117 |
|   | note = Synthetic peptide |
| source | 1..117 |
|   | mol_type = protein |
|   | organism = synthetic construct |

SEQUENCE: 394
QVQLVQSGAE VKKPGASVKM SCKASGYTFT SYTMHWIRQA PGQGQEWIGY INPSSTYTHY  60
AQKFQGRATL TADTSTSTAY MELSSLRSED TAVYYCSRGE LGGFAYWGQG TLVTVSS    117

| SEQ ID NO: 395 | moltype = AA   length = 117 |
|---|---|
| FEATURE | Location/Qualifiers |
| REGION | 1..117 |
|   | note = Synthetic peptide |
| source | 1..117 |
|   | mol_type = protein |
|   | organism = synthetic construct |

SEQUENCE: 395
QVQLVQSGAE VKKPGASVKM SCKASGYTFT SYTMHWIRQA PGQGLEWIGY INPSSTYTHY  60
AQKFQGRATL TADKSTSTAY MELSSLRSED TAVYYCSRGE LGGFAYWGQG TLVTVSS    117

| SEQ ID NO: 396 | moltype = AA   length = 117 |
|---|---|
| FEATURE | Location/Qualifiers |
| REGION | 1..117 |
|   | note = Synthetic peptide |
| source | 1..117 |
|   | mol_type = protein |
|   | organism = synthetic construct |

SEQUENCE: 396
QVQLVQSGAE VKKPGASVKM SCKASGYTFT SYTMHWIRQA PGQGQEWIGY INPSSTYTHY  60
AQKFQGRATL TADKSTSTAY MELSSLRSED TAVYYCSRGE LGGFAYWGQG TLVTVSS    117

| SEQ ID NO: 397 | moltype = AA   length = 112 |
|---|---|
| FEATURE | Location/Qualifiers |
| REGION | 1..112 |
|   | note = Synthetic peptide |
| source | 1..112 |
|   | mol_type = protein |
|   | organism = synthetic construct |

SEQUENCE: 397
DVVMTQSPLS LPVTLGQPAS ISCRSSQSLV HSDGNTYLNW FQQRPGQSPR RLIYKVSNRF  60
SGVPDRFSGS GSGTDFTLKI SRVEAEDVGV YYCSQSTHVP YTFGQGTKLE IK         112

| SEQ ID NO: 398 | moltype = AA   length = 112 |
|---|---|
| FEATURE | Location/Qualifiers |
| REGION | 1..112 |
|   | note = Synthetic peptide |
| source | 1..112 |
|   | mol_type = protein |
|   | organism = synthetic construct |

SEQUENCE: 398
DVVMTQSPLS LPVTLGQPAS ISCRSSQSLV HSDGNTYLNW YQQRPGQSPR LLIYKVSNRF  60
SGVPDRFSGS GSGTDFTLKI SRVEAEDVGV YYCSQSTHVP YTFGQGTKLE IK         112

| SEQ ID NO: 399 | moltype = AA   length = 112 |
|---|---|
| FEATURE | Location/Qualifiers |
| REGION | 1..112 |
|   | note = Synthetic peptide |
| source | 1..112 |
|   | mol_type = protein |
|   | organism = synthetic construct |

SEQUENCE: 399
DVVMTQSPLS LPVTLGQPAS ISCRSSQSLV HSEGNTYLNW YQQRPGQSPR LLIYKVSNRF  60
SGVPDRFSGS GSGTDFTLKI SRVEAEDVGV YYCSQSTHVP YTFGQGTKLE IK         112

| SEQ ID NO: 400 | moltype = AA   length = 112 |
|---|---|
| FEATURE | Location/Qualifiers |
| REGION | 1..112 |
|   | note = Synthetic peptide |
| source | 1..112 |

```
                        mol_type = protein
                        organism = synthetic construct
SEQUENCE: 400
DVVMTQSPLS LPVTLGQPAS ISCRSSQSLV HSSGNTYLNW YQQRPGQSPR LLIYKVSNRF    60
SGVPDRFSGS GSGTDFTLKI SRVEAEDVGV YYCSQSTHVP YTFGQGTKLE IK           112

SEQ ID NO: 401          moltype = AA  length = 112
FEATURE                 Location/Qualifiers
REGION                  1..112
                        note = Synthetic peptide
source                  1..112
                        mol_type = protein
                        organism = synthetic construct
SEQUENCE: 401
DVVMTQSPLS LPVTLGQPAS ISCRSSQSLV HSEGSTYLNW YQQRPGQSPR LLIYKVSNRF    60
SGVPDRFSGS GSGTDFTLKI SRVEAEDVGV YYCSQSTHVP YTFGQGTKLE IK           112

SEQ ID NO: 402          moltype = AA  length = 112
FEATURE                 Location/Qualifiers
REGION                  1..112
                        note = Synthetic peptide
source                  1..112
                        mol_type = protein
                        organism = synthetic construct
SEQUENCE: 402
DVVMTQSPLS LPVTLGQPAS ISCRSSQSLV HSSGSTYLNW YQQRPGQSPR LLIYKVSNRF    60
SGVPDRFSGS GSGTDFTLKI SRVEAEDVGV YYCSQSTHVP YTFGQGTKLE IK           112

SEQ ID NO: 403          moltype = AA  length = 117
FEATURE                 Location/Qualifiers
REGION                  1..117
                        note = Synthetic peptide
source                  1..117
                        mol_type = protein
                        organism = synthetic construct
SEQUENCE: 403
QVQLVQSGAE VKKPGASVKV SCKASGYRFT DYNMHWVRQA PGQGLEWMGY INPNNGGTNY    60
AQKFQGRVTM TRDTSTSTVY MELSSLRSED TAVYYCARDY LYFFDCWGQG TLVTVSS      117

SEQ ID NO: 404          moltype = AA  length = 117
FEATURE                 Location/Qualifiers
REGION                  1..117
                        note = Synthetic peptide
source                  1..117
                        mol_type = protein
                        organism = synthetic construct
SEQUENCE: 404
QVQLVQSGAE VKKPGASVKV SCKASGYRFT DYNMHWVRQA PGQGLEWMGY INPNNGGTNY    60
AQKFQGRVTM TVDTSTSTVY MELSSLRSED TAVYYCARDY LYFFDCWGQG TLVTVSS      117

SEQ ID NO: 405          moltype = AA  length = 117
FEATURE                 Location/Qualifiers
REGION                  1..117
                        note = Synthetic peptide
source                  1..117
                        mol_type = protein
                        organism = synthetic construct
SEQUENCE: 405
QVQLVQSGAE VKKPGASVKM SCKASGYRFT DYNMHWVRQA PGQGLEWIGY INPNNGGTNY    60
AQKFQGRATL TVDTSTSTAY MELSSLRSED TAVYYCARDY LYFFDCWGQG TLLTVSS      117

SEQ ID NO: 406          moltype = AA  length = 117
FEATURE                 Location/Qualifiers
REGION                  1..117
                        note = Synthetic peptide
source                  1..117
                        mol_type = protein
                        organism = synthetic construct
SEQUENCE: 406
QVQLVQSGAE VKKPGASVKM SCKASGYRFT DYNMHWVRQA PGQGLEWIGY INPNNGGTNY    60
AQKFQGRATL TVDKSTSTAY MELSSLRSED TAVYYCARDY LYFFDCWGQG TLLTVSS      117

SEQ ID NO: 407          moltype = AA  length = 117
FEATURE                 Location/Qualifiers
REGION                  1..117
                        note = Synthetic peptide
source                  1..117
                        mol_type = protein
                        organism = synthetic construct
```

```
SEQUENCE: 407
QVQLVQSGAE VKKPGASVKM SCKASGYRFT DYNMHWVRQA PGQGLEWIGY INPNNGGTNY    60
AQKFQGRATL TVNKSTSTAY MELSSLRSED TAVYYCARDY LYFFDCWGQG TLLTVSS      117

SEQ ID NO: 408           moltype = AA   length = 117
FEATURE                  Location/Qualifiers
REGION                   1..117
                         note = Synthetic peptide
source                   1..117
                         mol_type = protein
                         organism = synthetic construct
SEQUENCE: 408
QVQLVQSGAE VKKPGASVKM SCKASGYRFT DYNMHWVRQA PGQGLEWIGY INPNNGGTNY    60
AQKFQGRATL TVNTSTSTAY MELSSLRSED TAVYYCARDY LYFFDCWGQG TLLTVSS      117

SEQ ID NO: 409           moltype = AA   length = 107
FEATURE                  Location/Qualifiers
REGION                   1..107
                         note = Synthetic peptide
source                   1..107
                         mol_type = protein
                         organism = synthetic construct
SEQUENCE: 409
DIQMTQSPSS LSASVGDRVT ITCLASQTIG TWLAWYQQKP GKAPKLLIYA AASLADGVPS    60
RFSGSGSGTD FTLTISSLQP EDFATYYCQQ LYSIPRTFGQ GTKLEIK                 107

SEQ ID NO: 410           moltype = AA   length = 107
FEATURE                  Location/Qualifiers
REGION                   1..107
                         note = Synthetic peptide
source                   1..107
                         mol_type = protein
                         organism = synthetic construct
SEQUENCE: 410
DIQMTQSPSS LSASVGDRVT ITCLASQTIG TWLAWYQQKP GKAPKLLIYA AASLADGVPS    60
RFSGSGSGTD FTFTISSLQP EDFVTYYCQQ LYSIPRTFGQ GTKLEIK                 107

SEQ ID NO: 411           moltype = AA   length = 107
FEATURE                  Location/Qualifiers
REGION                   1..107
                         note = Synthetic peptide
source                   1..107
                         mol_type = protein
                         organism = synthetic construct
SEQUENCE: 411
DIQMTQSPSS LSASVGDRVT ITCRASQTIG TWLAWYQQKP GKAPKLLIYA AASLADGVPS    60
RFSGSGSGTD FTFTISSLQP EDFVTYYCQQ LYSIPRTFGQ GTKLEIK                 107

SEQ ID NO: 412           moltype = AA   length = 118
FEATURE                  Location/Qualifiers
REGION                   1..118
                         note = Synthetic peptide
source                   1..118
                         mol_type = protein
                         organism = synthetic construct
SEQUENCE: 412
EVQLVESGGG LVQPGGSLRL SCAASGFTFS SFGMHWVRQA PGKGLEWVSY ISSDSRTIYY    60
ADSVKGRFTI SRDNAKNSLY LQMNSLRAED TAVYYCARDY GRTYEAYWGQ GTLVTVSS     118

SEQ ID NO: 413           moltype = AA   length = 118
FEATURE                  Location/Qualifiers
REGION                   1..118
                         note = Synthetic peptide
source                   1..118
                         mol_type = protein
                         organism = synthetic construct
SEQUENCE: 413
EVQLVESGGG LVQPGGSLRL SCAASGFTFS SFGMHWVRQA PGKGLEWVAY ISSDSRTIYY    60
ADSVKGRFTI SRDNAKNSLY LQMNSLRAED TAVYYCARDY GRTYEAYWGQ GTLVTVSS     118

SEQ ID NO: 414           moltype = AA   length = 111
FEATURE                  Location/Qualifiers
REGION                   1..111
                         note = Synthetic peptide
source                   1..111
                         mol_type = protein
                         organism = synthetic construct
SEQUENCE: 414
DIVMTQSPDS LAVSLGERAT INCRASKSVS TSGYSYIHWY QQKPGQPPKL LIYLASNLES    60
```

```
GVPDRFSGSG SGTDFTLTIS SLQAEDVAVY YCQHSRELPL TFGQGTKLEI K            111

SEQ ID NO: 415              moltype = AA   length = 111
FEATURE                     Location/Qualifiers
REGION                      1..111
                            note = Synthetic peptide
source                      1..111
                            mol_type = protein
                            organism = synthetic construct
SEQUENCE: 415
DIVLTQSPDS LAVSLGERAT INCRASKSVS TSGYSYIHWY QQKPGQPPKL LIYLASNLES   60
GVPDRFSGSG SGTDFTLTIS SVQAEDVAVY YCQHSRELPL TFGQGTKLEL K            111

SEQ ID NO: 416              moltype = AA   length = 121
FEATURE                     Location/Qualifiers
REGION                      1..121
                            note = Synthetic peptide
source                      1..121
                            mol_type = protein
                            organism = synthetic construct
SEQUENCE: 416
QVQLVQSGAE VKKPGASVKV SCKASGYSFT GYNMNWVRQA PGQGLEWMGN IDPYYGGSTY   60
AQKFQGRVTM TRDTSTSTVY MELSSLRSED TAVYYCARER SGYVFSAMDY WGQGTLVTVS   120
S                                                                   121

SEQ ID NO: 417              moltype = AA   length = 121
FEATURE                     Location/Qualifiers
REGION                      1..121
                            note = Synthetic peptide
source                      1..121
                            mol_type = protein
                            organism = synthetic construct
SEQUENCE: 417
QVQLVQSGAE VKKPGASVKV SCKASGYSFT GYNMNWVRQA PGQGLEWMGN IDPYYGGSTY   60
AQKFQGRVTM TVDTSTSTVY MELSSLRSED TAVYYCARER SGYVFSAMDY WGQGTLVTVS   120
S                                                                   121

SEQ ID NO: 418              moltype = AA   length = 121
FEATURE                     Location/Qualifiers
REGION                      1..121
                            note = Synthetic peptide
source                      1..121
                            mol_type = protein
                            organism = synthetic construct
SEQUENCE: 418
QVQLVQSGAE VKKPGASVKI SCKASGYSFT GYNMNWVRQA PGQGLEWIGN IDPYYGGSTY   60
AQKFQGRATL TVDTSTSTAY MELSSLRSED TAVYYCARER SGYVFSAMDY WGQGTLVTVS   120
S                                                                   121

SEQ ID NO: 419              moltype = AA   length = 121
FEATURE                     Location/Qualifiers
REGION                      1..121
                            note = Synthetic peptide
source                      1..121
                            mol_type = protein
                            organism = synthetic construct
SEQUENCE: 419
QVQLVQSGAE VKKPGASVKI SCKASGYSFT GYNMNWVRQA PGQGLEWIGN IDPYYGGSTY   60
AQKFQGRATL TVDKSTSTAY MELSSLRSED TAVYYCARER SGYVFSAMDY WGQGTLVTVS   120
S                                                                   121

SEQ ID NO: 420              moltype = AA   length = 112
FEATURE                     Location/Qualifiers
REGION                      1..112
                            note = Synthetic peptide
source                      1..112
                            mol_type = protein
                            organism = synthetic construct
SEQUENCE: 420
DIVMTQSPDS LAVSLGERAT INCKSSQSVL FSSNQKNYLA WYQQKPGQPP KLLIYWASTR   60
ESGVPDRFSG SGSGTDFTLT ISSLQAEDVA VYYCHQYLSS RTFGQGTKLE IK           112

SEQ ID NO: 421              moltype = AA   length = 112
FEATURE                     Location/Qualifiers
REGION                      1..112
                            note = Synthetic peptide
source                      1..112
                            mol_type = protein
                            organism = synthetic construct
```

```
SEQUENCE: 421
DIVMTQSPDS LAVSLGERVT MNCKSSQSVL FSSNQKNYLA WYQQKPGQPP KLLIYWASTR    60
ESGVPDRFSG SGSGTDFTLT ISSVQAEDVA VYYCHQYLSS RTFGQGTKLE IK          112

SEQ ID NO: 422          moltype = AA  length = 117
FEATURE                 Location/Qualifiers
REGION                  1..117
                        note = Synthetic peptide
source                  1..117
                        mol_type = protein
                        organism = synthetic construct
SEQUENCE: 422
EVQLLESGGG LVQPGGSMRL SCAASGFTFS NYWMNWVRQA PGKGLEWVAQ IRLKSDNYAT    60
HYADSVKGRF TISRDDSKNT VYLQMNSLRA EDTGVYYCND GPPSGAWGQG TLLTVSS     117

SEQ ID NO: 423          moltype = AA  length = 117
FEATURE                 Location/Qualifiers
REGION                  1..117
                        note = Synthetic peptide
source                  1..117
                        mol_type = protein
                        organism = synthetic construct
SEQUENCE: 423
QVQLVQSGAE VKKPGASVKV SCKASGYTFT SYTMHWVRQA PGQGLEWMGY INPSSTYTHY    60
IKKFKDRVTM TADTSTSTVY MELSSLRSED TAVYYCSRGE LGGFAYWGQG TLVTVSS     117

SEQ ID NO: 424          moltype = AA  length = 117
FEATURE                 Location/Qualifiers
REGION                  1..117
                        note = Synthetic peptide
source                  1..117
                        mol_type = protein
                        organism = synthetic construct
SEQUENCE: 424
QVQLVQSGAE VKKPGASVKM SCKASGYTFT SYTMHWIRQA PGQGLEWIGY INPSSTYTHY    60
IKKFKDRATL TADTSTSTAY MELSSLRSED TAVYYCSRGE LGGFAYWGQG TLVTVSS     117

SEQ ID NO: 425          moltype = AA  length = 117
FEATURE                 Location/Qualifiers
REGION                  1..117
                        note = Synthetic peptide
source                  1..117
                        mol_type = protein
                        organism = synthetic construct
SEQUENCE: 425
QVQLVQSGAE VKKPGASVKM SCKASGYTFT SYTMHWIRQA PGQGQEWIGY INPSSTYTHY    60
IKKFKDRATL TADTSTSTAY MELSSLRSED TAVYYCSRGE LGGFAYWGQG TLVTVSS     117

SEQ ID NO: 426          moltype = AA  length = 117
FEATURE                 Location/Qualifiers
REGION                  1..117
                        note = Synthetic peptide
source                  1..117
                        mol_type = protein
                        organism = synthetic construct
SEQUENCE: 426
QVQLVQSGAE VKKPGASVKM SCKASGYTFT SYTMHWIRQA PGQGLEWIGY INPSSTYTHY    60
IKKFKDRATL TADKSTSTAY MELSSLRSED TAVYYCSRGE LGGFAYWGQG TLVTVSS     117

SEQ ID NO: 427          moltype = AA  length = 117
FEATURE                 Location/Qualifiers
REGION                  1..117
                        note = Synthetic peptide
source                  1..117
                        mol_type = protein
                        organism = synthetic construct
SEQUENCE: 427
QVQLVQSGAE VKKPGASVKM SCKASGYTFT SYTMHWIRQA PGQGEWIGY INPSSTYTHY     60
IKKFKDRATL TADKSTSTAY MELSSLRSED TAVYYCSRGE LGGFAYWGQG TLVTVSS     117

SEQ ID NO: 428          moltype = AA  length = 116
FEATURE                 Location/Qualifiers
REGION                  1..116
                        note = Synthetic peptide
VARIANT                 5
                        note = Xaa can be any naturally occurring amino acid
VARIANT                 8
                        note = Xaa can be any naturally occurring amino acid
VARIANT                 11..13
```

```
VARIANT         20
                note = Xaa can be any naturally occurring amino acid
VARIANT         31
                note = Xaa can be any naturally occurring amino acid
VARIANT         33
                note = Xaa can be any naturally occurring amino acid
VARIANT         35
                note = Xaa can be any naturally occurring amino acid
VARIANT         38
                note = Xaa can be any naturally occurring amino acid
VARIANT         40
                note = Xaa can be any naturally occurring amino acid
VARIANT         48
                note = Xaa can be any naturally occurring amino acid
VARIANT         50
                note = Xaa can be any naturally occurring amino acid
VARIANT         55
                note = Xaa can be any naturally occurring amino acid
VARIANT         57
                note = Xaa can be any naturally occurring amino acid
VARIANT         59
                note = Xaa can be any naturally occurring amino acid
VARIANT         61
                note = Xaa can be any naturally occurring amino acid
VARIANT         65..68
                note = Xaa can be any naturally occurring amino acid
VARIANT         70
                note = Xaa can be any naturally occurring amino acid
VARIANT         72
                note = Xaa can be any naturally occurring amino acid
VARIANT         74..76
                note = Xaa can be any naturally occurring amino acid
VARIANT         79..80
                note = Xaa can be any naturally occurring amino acid
VARIANT         82
                note = Xaa can be any naturally occurring amino acid
VARIANT         87
                note = Xaa can be any naturally occurring amino acid
VARIANT         90..91
                note = Xaa can be any naturally occurring amino acid
VARIANT         98
                note = Xaa can be any naturally occurring amino acid
VARIANT         101
                note = Xaa can be any naturally occurring amino acid
VARIANT         116
                note = Xaa can be any naturally occurring amino acid
source          1..116
                mol_type = protein
                organism = synthetic construct
SEQUENCE: 428
QVQLXQSXAE XXXPGASVKX SCKASGYTFT XYXMXWVXQX PGQGLEWXGX INPSXGXTXY    60
XQKFXXXXTX TXDXSXSTXX MXLSSLXSEX XAVYYCAXGD XYVAYWGQGT LVTVSX      116

SEQ ID NO: 429          moltype = AA   length = 116
FEATURE                 Location/Qualifiers
REGION                  1..116
                note = Synthetic peptide
VARIANT         20
                note = Xaa can be any naturally occurring amino acid
VARIANT         31
                note = Xaa can be any naturally occurring amino acid
VARIANT         35
                note = Xaa can be any naturally occurring amino acid
VARIANT         48
                note = Xaa can be any naturally occurring amino acid
VARIANT         50
                note = Xaa can be any naturally occurring amino acid
VARIANT         59
                note = Xaa can be any naturally occurring amino acid
VARIANT         67
                note = Xaa can be any naturally occurring amino acid
VARIANT         70
                note = Xaa can be any naturally occurring amino acid
VARIANT         74
                note = Xaa can be any naturally occurring amino acid
VARIANT         79
                note = Xaa can be any naturally occurring amino acid
VARIANT         98
```

```
                         note = Xaa can be any naturally occurring amino acid
VARIANT                  101
                         note = Xaa can be any naturally occurring amino acid
source                   1..116
                         mol_type = protein
                         organism = synthetic construct
SEQUENCE: 429
QVQLVQSGAE VKKPGASVKX SCKASGYTFT XYTMXWVRQA PGQGLEWXGX INPSSGYTXY    60
AQKFQGXVTX TADXSTSTXY MELSSLRSED TAVYYCAXGD XYVAYWGQGT LVTVSS       116

SEQ ID NO: 430           moltype = AA  length = 108
FEATURE                  Location/Qualifiers
REGION                   1..108
                         note = Synthetic peptide
VARIANT                  1
                         note = Xaa can be any naturally occurring amino acid
VARIANT                  3..4
                         note = Xaa can be any naturally occurring amino acid
VARIANT                  9..11
                         note = Xaa can be any naturally occurring amino acid
VARIANT                  15
                         note = Xaa can be any naturally occurring amino acid
VARIANT                  17
                         note = Xaa can be any naturally occurring amino acid
VARIANT                  21
                         note = Xaa can be any naturally occurring amino acid
VARIANT                  24
                         note = Xaa can be any naturally occurring amino acid
VARIANT                  27
                         note = Xaa can be any naturally occurring amino acid
VARIANT                  29
                         note = Xaa can be any naturally occurring amino acid
VARIANT                  32
                         note = Xaa can be any naturally occurring amino acid
VARIANT                  34..35
                         note = Xaa can be any naturally occurring amino acid
VARIANT                  43..44
                         note = Xaa can be any naturally occurring amino acid
VARIANT                  48
                         note = Xaa can be any naturally occurring amino acid
VARIANT                  51..56
                         note = Xaa can be any naturally occurring amino acid
VARIANT                  61
                         note = Xaa can be any naturally occurring amino acid
VARIANT                  67
                         note = Xaa can be any naturally occurring amino acid
VARIANT                  71..73
                         note = Xaa can be any naturally occurring amino acid
VARIANT                  79..81
                         note = Xaa can be any naturally occurring amino acid
VARIANT                  84
                         note = Xaa can be any naturally occurring amino acid
VARIANT                  90..91
                         note = Xaa can be any naturally occurring amino acid
VARIANT                  93..96
                         note = Xaa can be any naturally occurring amino acid
VARIANT                  101
                         note = Xaa can be any naturally occurring amino acid
VARIANT                  107
                         note = Xaa can be any naturally occurring amino acid
source                   1..108
                         mol_type = protein
                         organism = synthetic construct
SEQUENCE: 430
XIXXTQSPXX XSASXGXRVT TCXASXSXS SXYXXWYQQK PGXXPKLXIY XXXXXXSGVP     60
XRFSGSXSGT XXXLTISSXX XEDXATYYCX XYXXXXLTFG XGTKLEXK                 108

SEQ ID NO: 431           moltype = AA  length = 108
FEATURE                  Location/Qualifiers
REGION                   1..108
                         note = Synthetic peptide
VARIANT                  4
                         note = Xaa can be any naturally occurring amino acid
VARIANT                  21
                         note = Xaa can be any naturally occurring amino acid
VARIANT                  32
                         note = Xaa can be any naturally occurring amino acid
VARIANT                  34
                         note = Xaa can be any naturally occurring amino acid
```

| | | |
|---|---|---|
| VARIANT | 48 | |
| | note = Xaa can be any naturally occurring amino acid | |
| VARIANT | 51 | |
| | note = Xaa can be any naturally occurring amino acid | |
| VARIANT | 53 | |
| | note = Xaa can be any naturally occurring amino acid | |
| VARIANT | 61 | |
| | note = Xaa can be any naturally occurring amino acid | |
| VARIANT | 67 | |
| | note = Xaa can be any naturally occurring amino acid | |
| VARIANT | 79 | |
| | note = Xaa can be any naturally occurring amino acid | |
| VARIANT | 84 | |
| | note = Xaa can be any naturally occurring amino acid | |
| VARIANT | 91 | |
| | note = Xaa can be any naturally occurring amino acid | |
| VARIANT | 93 | |
| | note = Xaa can be any naturally occurring amino acid | |
| source | 1..108 | |
| | mol_type = protein | |
| | organism = synthetic construct | |

SEQUENCE: 431

```
DIQXTQSPSS LSASVGDRVT XTCTASSSVS SXYXHWYQQK PGKAPKLXIY XTXNLASGVP    60
XRFSGSXSGT DYTLTISSXQ PEDXATYYCH XYXRSPLTFG QGTKLEIK              108
```

| | | |
|---|---|---|
| SEQ ID NO: 432 | moltype = AA length = 117 | |
| FEATURE | Location/Qualifiers | |
| REGION | 1..117 | |
| | note = Synthetic peptide | |
| VARIANT | 3 | |
| | note = Xaa can be any naturally occurring amino acid | |
| VARIANT | 5 | |
| | note = Xaa can be any naturally occurring amino acid | |
| VARIANT | 18..19 | |
| | note = Xaa can be any naturally occurring amino acid | |
| VARIANT | 23 | |
| | note = Xaa can be any naturally occurring amino acid | |
| VARIANT | 31 | |
| | note = Xaa can be any naturally occurring amino acid | |
| VARIANT | 33 | |
| | note = Xaa can be any naturally occurring amino acid | |
| VARIANT | 35 | |
| | note = Xaa can be any naturally occurring amino acid | |
| VARIANT | 40 | |
| | note = Xaa can be any naturally occurring amino acid | |
| VARIANT | 42 | |
| | note = Xaa can be any naturally occurring amino acid | |
| VARIANT | 49..50 | |
| | note = Xaa can be any naturally occurring amino acid | |
| VARIANT | 52..59 | |
| | note = Xaa can be any naturally occurring amino acid | |
| VARIANT | 61 | |
| | note = Xaa can be any naturally occurring amino acid | |
| VARIANT | 64 | |
| | note = Xaa can be any naturally occurring amino acid | |
| VARIANT | 76 | |
| | note = Xaa can be any naturally occurring amino acid | |
| VARIANT | 79..81 | |
| | note = Xaa can be any naturally occurring amino acid | |
| VARIANT | 87 | |
| | note = Xaa can be any naturally occurring amino acid | |
| VARIANT | 94..95 | |
| | note = Xaa can be any naturally occurring amino acid | |
| VARIANT | 99 | |
| | note = Xaa can be any naturally occurring amino acid | |
| VARIANT | 106 | |
| | note = Xaa can be any naturally occurring amino acid | |
| VARIANT | 112 | |
| | note = Xaa can be any naturally occurring amino acid | |
| VARIANT | 114 | |
| | note = Xaa can be any naturally occurring amino acid | |
| source | 1..117 | |
| | mol_type = protein | |
| | organism = synthetic construct | |

SEQUENCE: 432

```
EVXLXESGGG LVQPGGSXXL SCXASGFTFS XYXMXWVRQX PXKGLEWVXX IXXXXXXXXT    60
XYAXSVKGRF TISRDXSKXX XYLQMNXLRA EDTXXYYCXD GPPSGXWGQG TXLXVSS    117
```

SEQ ID NO: 433      moltype = AA length = 117

```
FEATURE                 Location/Qualifiers
REGION                  1..117
                        note = Synthetic peptide
VARIANT                 31
                        note = Xaa can be any naturally occurring amino acid
VARIANT                 35
                        note = Xaa can be any naturally occurring amino acid
VARIANT                 50
                        note = Xaa can be any naturally occurring amino acid
VARIANT                 55
                        note = Xaa can be any naturally occurring amino acid
VARIANT                 79
                        note = Xaa can be any naturally occurring amino acid
VARIANT                 99
                        note = Xaa can be any naturally occurring amino acid
VARIANT                 106
                        note = Xaa can be any naturally occurring amino acid
source                  1..117
                        mol_type = protein
                        organism = synthetic construct
SEQUENCE: 433
EVQLLESGGG LVQPGGSMRL SCAASGFTFS XYWMXWVRQA PGKGLEWVAX IRLKXDNYAT   60
HYADSVKGRF TISRDDSKXT VYLQMNSLRA EDTGVYYCXD GPPSGXWGQG TLLTVSS    117

SEQ ID NO: 434          moltype = AA  length = 107
FEATURE                 Location/Qualifiers
REGION                  1..107
                        note = Synthetic peptide
VARIANT                 9
                        note = Xaa can be any naturally occurring amino acid
VARIANT                 17..18
                        note = Xaa can be any naturally occurring amino acid
VARIANT                 25
                        note = Xaa can be any naturally occurring amino acid
VARIANT                 27..28
                        note = Xaa can be any naturally occurring amino acid
VARIANT                 30
                        note = Xaa can be any naturally occurring amino acid
VARIANT                 34
                        note = Xaa can be any naturally occurring amino acid
VARIANT                 40
                        note = Xaa can be any naturally occurring amino acid
VARIANT                 43
                        note = Xaa can be any naturally occurring amino acid
VARIANT                 45
                        note = Xaa can be any naturally occurring amino acid
VARIANT                 48
                        note = Xaa can be any naturally occurring amino acid
VARIANT                 50
                        note = Xaa can be any naturally occurring amino acid
VARIANT                 52..53
                        note = Xaa can be any naturally occurring amino acid
VARIANT                 55..56
                        note = Xaa can be any naturally occurring amino acid
VARIANT                 70
                        note = Xaa can be any naturally occurring amino acid
VARIANT                 72
                        note = Xaa can be any naturally occurring amino acid
VARIANT                 74
                        note = Xaa can be any naturally occurring amino acid
VARIANT                 76
                        note = Xaa can be any naturally occurring amino acid
VARIANT                 84..85
                        note = Xaa can be any naturally occurring amino acid
VARIANT                 90..91
                        note = Xaa can be any naturally occurring amino acid
VARIANT                 93..94
                        note = Xaa can be any naturally occurring amino acid
VARIANT                 97
                        note = Xaa can be any naturally occurring amino acid
VARIANT                 100
                        note = Xaa can be any naturally occurring amino acid
source                  1..107
                        mol_type = protein
                        organism = synthetic construct
SEQUENCE: 434
DIQMTQSPXS LSASVGXXVT ITCRXSXXIX SYLXWYQQKX GKXPXLLXYX AXXLXXGVPS   60
RFSGSGSGTX FXLXIXSLQP EDFXXYYCQX XYXXPWXFGX GTKLEIK              107
```

```
SEQ ID NO: 435               moltype = AA  length = 107
FEATURE                      Location/Qualifiers
REGION                       1..107
                             note = Synthetic peptide
VARIANT                      25
                             note = Xaa can be any naturally occurring amino acid
VARIANT                      34
                             note = Xaa can be any naturally occurring amino acid
VARIANT                      48
                             note = Xaa can be any naturally occurring amino acid
VARIANT                      53
                             note = Xaa can be any naturally occurring amino acid
VARIANT                      55
                             note = Xaa can be any naturally occurring amino acid
VARIANT                      84..85
                             note = Xaa can be any naturally occurring amino acid
VARIANT                      90
                             note = Xaa can be any naturally occurring amino acid
VARIANT                      93
                             note = Xaa can be any naturally occurring amino acid
source                       1..107
                             mol_type = protein
                             organism = synthetic construct
SEQUENCE: 435
DIQMTQSPSS LSASVGDRVT ITCRXSENIY SYLXWYQQKP GKAPKLLXYN AKXLXEGVPS   60
RFSGSGSGTD FTLTISSLQP EDFXXYYCQX HYXVPWTFGQ GTKLEIK                107

SEQ ID NO: 436               moltype = AA  length = 117
FEATURE                      Location/Qualifiers
REGION                       1..117
                             note = Synthetic peptide
VARIANT                      5
                             note = Xaa can be any naturally occurring amino acid
VARIANT                      11..13
                             note = Xaa can be any naturally occurring amino acid
VARIANT                      20
                             note = Xaa can be any naturally occurring amino acid
VARIANT                      29
                             note = Xaa can be any naturally occurring amino acid
VARIANT                      31
                             note = Xaa can be any naturally occurring amino acid
VARIANT                      33
                             note = Xaa can be any naturally occurring amino acid
VARIANT                      37..38
                             note = Xaa can be any naturally occurring amino acid
VARIANT                      40
                             note = Xaa can be any naturally occurring amino acid
VARIANT                      45
                             note = Xaa can be any naturally occurring amino acid
VARIANT                      48
                             note = Xaa can be any naturally occurring amino acid
VARIANT                      50
                             note = Xaa can be any naturally occurring amino acid
VARIANT                      55..57
                             note = Xaa can be any naturally occurring amino acid
VARIANT                      59
                             note = Xaa can be any naturally occurring amino acid
VARIANT                      61..62
                             note = Xaa can be any naturally occurring amino acid
VARIANT                      65..68
                             note = Xaa can be any naturally occurring amino acid
VARIANT                      70
                             note = Xaa can be any naturally occurring amino acid
VARIANT                      72
                             note = Xaa can be any naturally occurring amino acid
VARIANT                      74
                             note = Xaa can be any naturally occurring amino acid
VARIANT                      76
                             note = Xaa can be any naturally occurring amino acid
VARIANT                      79
                             note = Xaa can be any naturally occurring amino acid
VARIANT                      82
                             note = Xaa can be any naturally occurring amino acid
VARIANT                      84
                             note = Xaa can be any naturally occurring amino acid
VARIANT                      87
                             note = Xaa can be any naturally occurring amino acid
VARIANT                      91
                             note = Xaa can be any naturally occurring amino acid
```

```
VARIANT              97
                     note = Xaa can be any naturally occurring amino acid
VARIANT              101
                     note = Xaa can be any naturally occurring amino acid
VARIANT              117
                     note = Xaa can be any naturally occurring amino acid
source               1..117
                     mol_type = protein
                     organism = synthetic construct
SEQUENCE: 436
QVQLXQSGAE XXXPGASVKX SCKASGYTXT XYXMHWXXQX PGQGXEWXGX INPSXXXTXY   60
XXKFXXXXTX TXDXSXSTXY MXLXSLXSED XAVYYCXRGE XGGFAYWGQG TLVTVSX     117

SEQ ID NO: 437       moltype = AA  length = 117
FEATURE              Location/Qualifiers
REGION               1..117
                     note = Synthetic peptide
VARIANT              20
                     note = Xaa can be any naturally occurring amino acid
VARIANT              29
                     note = Xaa can be any naturally occurring amino acid
VARIANT              31
                     note = Xaa can be any naturally occurring amino acid
VARIANT              37
                     note = Xaa can be any naturally occurring amino acid
VARIANT              45
                     note = Xaa can be any naturally occurring amino acid
VARIANT              48
                     note = Xaa can be any naturally occurring amino acid
VARIANT              56
                     note = Xaa can be any naturally occurring amino acid
VARIANT              59
                     note = Xaa can be any naturally occurring amino acid
VARIANT              61..62
                     note = Xaa can be any naturally occurring amino acid
VARIANT              65..66
                     note = Xaa can be any naturally occurring amino acid
VARIANT              68
                     note = Xaa can be any naturally occurring amino acid
VARIANT              70
                     note = Xaa can be any naturally occurring amino acid
VARIANT              74
                     note = Xaa can be any naturally occurring amino acid
VARIANT              79
                     note = Xaa can be any naturally occurring amino acid
VARIANT              84
                     note = Xaa can be any naturally occurring amino acid
VARIANT              97
                     note = Xaa can be any naturally occurring amino acid
VARIANT              101
                     note = Xaa can be any naturally occurring amino acid
source               1..117
                     mol_type = protein
                     organism = synthetic construct
SEQUENCE: 437
QVQLVQSGAE VKKPGASVKX SCKASGYTXT XYTMHWXRQA PGQGXEWXGY INPSSXYTXY   60
XXKFXXRXTX TADXSTSTXY MELXSLRSED TAVYYCXRGE XGGFAYWGQG TLVTVSS     117

SEQ ID NO: 438       moltype = AA  length = 112
FEATURE              Location/Qualifiers
REGION               1..112
                     note = Synthetic peptide
VARIANT              7
                     note = Xaa can be any naturally occurring amino acid
VARIANT              14
                     note = Xaa can be any naturally occurring amino acid
VARIANT              17..18
                     note = Xaa can be any naturally occurring amino acid
VARIANT              31
                     note = Xaa can be any naturally occurring amino acid
VARIANT              33
                     note = Xaa can be any naturally occurring amino acid
VARIANT              39
                     note = Xaa can be any naturally occurring amino acid
VARIANT              41..42
                     note = Xaa can be any naturally occurring amino acid
VARIANT              44
                     note = Xaa can be any naturally occurring amino acid
VARIANT              50..51
```

-continued

```
VARIANT         55
                note = Xaa can be any naturally occurring amino acid
VARIANT         57
                note = Xaa can be any naturally occurring amino acid
VARIANT         81
                note = Xaa can be any naturally occurring amino acid
VARIANT         88
                note = Xaa can be any naturally occurring amino acid
VARIANT         92
                note = Xaa can be any naturally occurring amino acid
VARIANT         94..96
                note = Xaa can be any naturally occurring amino acid
VARIANT         99..100
                note = Xaa can be any naturally occurring amino acid
VARIANT         105
                note = Xaa can be any naturally occurring amino acid
source          1..112
                mol_type = protein
                organism = synthetic construct
SEQUENCE: 438
DVVMTQXPLS LPVXLGXXAS ISCRSSQSLV XSXGNTYLXW XXQXPGQSPX XNPSXTXTHY     60
SGVPDRFSGS GSGTDFTLKI XRVEAEDXGV YXCXXXTHXX YTFGXGTKLE IK           112

SEQ ID NO: 439          moltype = AA  length = 112
FEATURE                 Location/Qualifiers
REGION                  1..112
                        note = Synthetic peptide
VARIANT         33
                note = Xaa can be any naturally occurring amino acid
VARIANT         39
                note = Xaa can be any naturally occurring amino acid
VARIANT         55
                note = Xaa can be any naturally occurring amino acid
VARIANT         57
                note = Xaa can be any naturally occurring amino acid
VARIANT         81
                note = Xaa can be any naturally occurring amino acid
VARIANT         95..96
                note = Xaa can be any naturally occurring amino acid
source          1..112
                mol_type = protein
                organism = synthetic construct
SEQUENCE: 439
DVVMTQSPLS LPVTLGQPAS ISCRSSQSLV HSXGNTYLXW YQQRPGQSPR LLIYXVXNRF     60
SGVPDRFSGS GSGTDFTLKI XRVEAEDVGV YYCSXXTHVP YTFGQGTKLE IK           112

SEQ ID NO: 440          moltype = AA  length = 120
FEATURE                 Location/Qualifiers
REGION                  1..120
                        note = Synthetic peptide
VARIANT         5
                note = Xaa can be any naturally occurring amino acid
VARIANT         9
                note = Xaa can be any naturally occurring amino acid
VARIANT         11..12
                note = Xaa can be any naturally occurring amino acid
VARIANT         20
                note = Xaa can be any naturally occurring amino acid
VARIANT         38
                note = Xaa can be any naturally occurring amino acid
VARIANT         40..41
                note = Xaa can be any naturally occurring amino acid
VARIANT         43..44
                note = Xaa can be any naturally occurring amino acid
VARIANT         48
                note = Xaa can be any naturally occurring amino acid
VARIANT         61
                note = Xaa can be any naturally occurring amino acid
VARIANT         65
                note = Xaa can be any naturally occurring amino acid
VARIANT         67..68
                note = Xaa can be any naturally occurring amino acid
VARIANT         70
                note = Xaa can be any naturally occurring amino acid
VARIANT         72
                note = Xaa can be any naturally occurring amino acid
VARIANT         74
                note = Xaa can be any naturally occurring amino acid
```

```
VARIANT             76
                    note = Xaa can be any naturally occurring amino acid
VARIANT             79
                    note = Xaa can be any naturally occurring amino acid
VARIANT             82
                    note = Xaa can be any naturally occurring amino acid
VARIANT             84
                    note = Xaa can be any naturally occurring amino acid
VARIANT             87
                    note = Xaa can be any naturally occurring amino acid
VARIANT             91
                    note = Xaa can be any naturally occurring amino acid
VARIANT             116
                    note = Xaa can be any naturally occurring amino acid
source              1..120
                    mol_type = protein
                    organism = synthetic construct
SEQUENCE: 440
QVQLXQSGXE XXKPGASVKX SCKASGYSFT GYNMNWVXQX XGXXLEWXGN IDPYYGGSTY    60
XQKFXGXXTX TXDXSXSTXY MXLXSLXSED XAVYYCARER SGYVFSAMDY WGQGTXVTVS   120

SEQ ID NO: 441          moltype = AA  length = 120
FEATURE                 Location/Qualifiers
REGION                  1..120
                        note = Synthetic peptide
VARIANT                 20
                        note = Xaa can be any naturally occurring amino acid
VARIANT                 48
                        note = Xaa can be any naturally occurring amino acid
VARIANT                 68
                        note = Xaa can be any naturally occurring amino acid
VARIANT                 70
                        note = Xaa can be any naturally occurring amino acid
VARIANT                 79
                        note = Xaa can be any naturally occurring amino acid
source                  1..120
                        mol_type = protein
                        organism = synthetic construct
SEQUENCE: 441
QVQLVQSGAE VKKPGASVKX SCKASGYSFT GYNMNWVRQA PGQGLEWXGN IDPYYGGSTY    60
AQKFQGRXTX TRDTSTSTXY MELSSLRSED TAVYYCARER SGYVFSAMDY WGQGTLVTVS   120

SEQ ID NO: 442          moltype = AA  length = 112
FEATURE                 Location/Qualifiers
REGION                  1..112
                        note = Synthetic peptide
VARIANT                 1
                        note = Xaa can be any naturally occurring amino acid
VARIANT                 3
                        note = Xaa can be any naturally occurring amino acid
VARIANT                 9
                        note = Xaa can be any naturally occurring amino acid
VARIANT                 15
                        note = Xaa can be any naturally occurring amino acid
VARIANT                 18..19
                        note = Xaa can be any naturally occurring amino acid
VARIANT                 21..22
                        note = Xaa can be any naturally occurring amino acid
VARIANT                 49
                        note = Xaa can be any naturally occurring amino acid
VARIANT                 51
                        note = Xaa can be any naturally occurring amino acid
VARIANT                 69
                        note = Xaa can be any naturally occurring amino acid
VARIANT                 78
                        note = Xaa can be any naturally occurring amino acid
VARIANT                 84
                        note = Xaa can be any naturally occurring amino acid
VARIANT                 93
                        note = Xaa can be any naturally occurring amino acid
VARIANT                 105
                        note = Xaa can be any naturally occurring amino acid
VARIANT                 111
                        note = Xaa can be any naturally occurring amino acid
source                  1..112
                        mol_type = protein
                        organism = synthetic construct
SEQUENCE: 442
XIXMTQSPXS LAVSXGEXXT XXCKSSQSVL FSSNQKNYLA WYQQKPGQXP XLLIYWASTR    60
```

```
ESGVPDRFXG SGSGTDFXLT ISSXQAEDVA VYXCHQYLSS RTFGXGTKLE XK          112

SEQ ID NO: 443          moltype = AA   length = 112
FEATURE                 Location/Qualifiers
REGION                  1..112
                        note = Synthetic peptide
VARIANT                 19
                        note = Xaa can be any naturally occurring amino acid
VARIANT                 21
                        note = Xaa can be any naturally occurring amino acid
VARIANT                 84
                        note = Xaa can be any naturally occurring amino acid
source                  1..112
                        mol_type = protein
                        organism = synthetic construct
SEQUENCE: 443
DIVMTQSPDS LAVSLGERXT XNCKSSQSVL FSSNQKNYLA WYQQKPGQPP KLLIYWASTR  60
ESGVPDRFSG SGSGTDFTLT ISSXQAEDVA VYYCHQYLSS RTFGQGTKLE IK          112

SEQ ID NO: 444          moltype = AA   length = 117
FEATURE                 Location/Qualifiers
REGION                  1..117
                        note = Synthetic peptide
VARIANT                 1
                        note = Xaa can be any naturally occurring amino acid
VARIANT                 5
                        note = Xaa can be any naturally occurring amino acid
VARIANT                 9
                        note = Xaa can be any naturally occurring amino acid
VARIANT                 11..12
                        note = Xaa can be any naturally occurring amino acid
VARIANT                 20
                        note = Xaa can be any naturally occurring amino acid
VARIANT                 38
                        note = Xaa can be any naturally occurring amino acid
VARIANT                 40..41
                        note = Xaa can be any naturally occurring amino acid
VARIANT                 43..44
                        note = Xaa can be any naturally occurring amino acid
VARIANT                 48
                        note = Xaa can be any naturally occurring amino acid
VARIANT                 61
                        note = Xaa can be any naturally occurring amino acid
VARIANT                 63
                        note = Xaa can be any naturally occurring amino acid
VARIANT                 65
                        note = Xaa can be any naturally occurring amino acid
VARIANT                 67
                        note = Xaa can be any naturally occurring amino acid
VARIANT                 69..70
                        note = Xaa can be any naturally occurring amino acid
VARIANT                 72..74
                        note = Xaa can be any naturally occurring amino acid
VARIANT                 76
                        note = Xaa can be any naturally occurring amino acid
VARIANT                 79
                        note = Xaa can be any naturally occurring amino acid
VARIANT                 84
                        note = Xaa can be any naturally occurring amino acid
VARIANT                 87
                        note = Xaa can be any naturally occurring amino acid
VARIANT                 91
                        note = Xaa can be any naturally occurring amino acid
VARIANT                 93
                        note = Xaa can be any naturally occurring amino acid
VARIANT                 112..113
                        note = Xaa can be any naturally occurring amino acid
source                  1..117
                        mol_type = protein
                        organism = synthetic construct
SEQUENCE: 444
XVQLXQSGXE XXKPGASVKX SCKASGYRFT DYNMHWVXQX XGXXLEWXGY INPNNGGTNY  60
XQXFXGXVXX TXXXSXSTXY MELXSLXSED XAXYYCARDY LYFFDCWGQG TXXTVSS     117

SEQ ID NO: 445          moltype = AA   length = 107
FEATURE                 Location/Qualifiers
REGION                  1..107
                        note = Synthetic peptide
VARIANT                 9
```

|  |  |
|---|---|
| VARIANT | 11 |
|  | note = Xaa can be any naturally occurring amino acid |
| VARIANT | 15 |
|  | note = Xaa can be any naturally occurring amino acid |
| VARIANT | 17..18 |
|  | note = Xaa can be any naturally occurring amino acid |
| VARIANT | 43 |
|  | note = Xaa can be any naturally occurring amino acid |
| VARIANT | 45 |
|  | note = Xaa can be any naturally occurring amino acid |
| VARIANT | 70 |
|  | note = Xaa can be any naturally occurring amino acid |
| VARIANT | 72..74 |
|  | note = Xaa can be any naturally occurring amino acid |
| VARIANT | 80 |
|  | note = Xaa can be any naturally occurring amino acid |
| VARIANT | 84..85 |
|  | note = Xaa can be any naturally occurring amino acid |
| VARIANT | 100 |
|  | note = Xaa can be any naturally occurring amino acid |
| source | 1..107 |
|  | mol_type = protein |
|  | organism = synthetic construct |

SEQUENCE: 445
DIQMTQSPXS XSASXGXXVT ITCLASQTIG TWLAWYQQKP GKXPXLLIYA AASLADGVPS    60
RFSGSGSGTX FXXXISSLQX EDFXXYYCQQ LYSIPRTFGX GTKLEIK                 107

| SEQ ID NO: 446 | moltype = AA   length = 107 |
|---|---|
| FEATURE | Location/Qualifiers |
| REGION | 1..107 |
|  | note = Synthetic peptide |
| VARIANT | 1 |
|  | note = Xaa can be any naturally occurring amino acid |
| VARIANT | 15 |
|  | note = Xaa can be any naturally occurring amino acid |
| VARIANT | 18..19 |
|  | note = Xaa can be any naturally occurring amino acid |
| VARIANT | 42 |
|  | note = Xaa can be any naturally occurring amino acid |
| VARIANT | 49 |
|  | note = Xaa can be any naturally occurring amino acid |
| VARIANT | 63 |
|  | note = Xaa can be any naturally occurring amino acid |
| VARIANT | 75..76 |
|  | note = Xaa can be any naturally occurring amino acid |
| VARIANT | 78 |
|  | note = Xaa can be any naturally occurring amino acid |
| VARIANT | 80 |
|  | note = Xaa can be any naturally occurring amino acid |
| VARIANT | 84 |
|  | note = Xaa can be any naturally occurring amino acid |
| VARIANT | 88 |
|  | note = Xaa can be any naturally occurring amino acid |
| VARIANT | 93 |
|  | note = Xaa can be any naturally occurring amino acid |
| source | 1..107 |
|  | mol_type = protein |
|  | organism = synthetic construct |

SEQUENCE: 446
XVQLVESGGG LVQPXGSXXL SCAASGFTFS SFGMHWVRQA PXKGLEWVXY ISSDSRTIYY    60
ADXVKGRFTI SRDNXXNXLX LQMXSLRXED TAXYYCARDY GRTYEAY                 107

| SEQ ID NO: 447 | moltype = AA   length = 111 |
|---|---|
| FEATURE | Location/Qualifiers |
| REGION | 1..111 |
|  | note = Synthetic peptide |
| VARIANT | 4 |
|  | note = Xaa can be any naturally occurring amino acid |
| VARIANT | 9 |
|  | note = Xaa can be any naturally occurring amino acid |
| VARIANT | 17 |
|  | note = Xaa can be any naturally occurring amino acid |
| VARIANT | 22 |
|  | note = Xaa can be any naturally occurring amino acid |
| VARIANT | 64 |
|  | note = Xaa can be any naturally occurring amino acid |
| VARIANT | 78 |
|  | note = Xaa can be any naturally occurring amino acid |

```
VARIANT            80..84
                   note = Xaa can be any naturally occurring amino acid
VARIANT            87
                   note = Xaa can be any naturally occurring amino acid
VARIANT            89
                   note = Xaa can be any naturally occurring amino acid
VARIANT            104
                   note = Xaa can be any naturally occurring amino acid
VARIANT            110
                   note = Xaa can be any naturally occurring amino acid
source             1..111
                   mol_type = protein
                   organism = synthetic construct
SEQUENCE: 447
DIVXTQSPXS LAVSLGXRAT IXCRASKSVS TSGYSYIHWY QQKPGQPPKL LIYLASNLES   60
GVPXRFSGSG SGTDFTLXIX XXXXEDXAXY YCQHSRELPL TFGXGTKLEX K           111

SEQ ID NO: 448     moltype = AA  length = 111
FEATURE            Location/Qualifiers
REGION             1..111
                   note = Synthetic peptide
VARIANT            4
                   note = Xaa can be any naturally occurring amino acid
VARIANT            82
                   note = Xaa can be any naturally occurring amino acid
VARIANT            110
                   note = Xaa can be any naturally occurring amino acid
source             1..111
                   mol_type = protein
                   organism = synthetic construct
SEQUENCE: 448
DIVXTQSPDS LAVSLGERAT INCRASKSVS TSGYSYIHWY QQKPGQPPKL LIYLASNLES   60
GVPDRFSGSG SGTDFTLTIS SXQAEDVAVY YCQHSRELPL TFGQGTKLEX K           111

SEQ ID NO: 449     moltype = AA  length = 7
FEATURE            Location/Qualifiers
REGION             1..7
                   note = Synthetic peptide
VARIANT            6
                   note = Xaa is T, V, F, or D
source             1..7
                   mol_type = protein
                   organism = synthetic construct
SEQUENCE: 449
SSVSSXY                                                              7

SEQ ID NO: 450     moltype =    length =
SEQUENCE: 450
000

SEQ ID NO: 451     moltype = AA  length = 9
FEATURE            Location/Qualifiers
REGION             1..9
                   note = Synthetic peptide
VARIANT            2
                   note = Xaa is Q, H or S
VARIANT            4
                   note = Xaa is H, Y, Q, or S
source             1..9
                   mol_type = protein
                   organism = synthetic construct
SEQUENCE: 451
HXYXRSPLT                                                            9

SEQ ID NO: 452     moltype = AA  length = 7
FEATURE            Location/Qualifiers
REGION             1..7
                   note = Synthetic peptide
VARIANT            5
                   note = Xaa is T, V, D, or S
source             1..7
                   mol_type = protein
                   organism = synthetic construct
SEQUENCE: 452
YTFTXYT                                                              7

SEQ ID NO: 453     moltype = AA  length = 9
FEATURE            Location/Qualifiers
REGION             1..9
```

```
                        note = Synthetic peptide
VARIANT                 2
                        note = Xaa is N, Q, H, D, S, R, or A
source                  1..9
                        mol_type = protein
                        organism = synthetic construct
SEQUENCE: 453
AXGDYYVAY                                                                        9

SEQ ID NO: 454          moltype = AA  length = 9
FEATURE                 Location/Qualifiers
REGION                  1..9
                        note = Synthetic peptide
VARIANT                 2
                        note = Xaa is H, Q, S, or T
VARIANT                 5
                        note = Xaa is T, S, N, or G
source                  1..9
                        mol_type = protein
                        organism = synthetic construct
SEQUENCE: 454
QXHYXVPWT                                                                        9

SEQ ID NO: 455          moltype = AA  length = 7
FEATURE                 Location/Qualifiers
REGION                  1..7
                        note = Synthetic peptide
VARIANT                 5
                        note = Xaa is N, S, R, q, s, or a
VARIANT                 7
                        note = Xaa is w, h, y, or f
source                  1..7
                        mol_type = protein
                        organism = synthetic construct
SEQUENCE: 455
FTFSXYX                                                                          7

SEQ ID NO: 456          moltype = AA  length = 10
FEATURE                 Location/Qualifiers
REGION                  1..10
                        note = Synthetic peptide
VARIANT                 5
                        note = Xaa is S, N, A, or T
VARIANT                 7
                        note = Xaa is Q, S,A, or N
source                  1..10
                        mol_type = protein
                        organism = synthetic construct
SEQUENCE: 456
IRLKXDXYAT                                                                      10

SEQ ID NO: 457          moltype = AA  length = 8
FEATURE                 Location/Qualifiers
REGION                  1..8
                        note = Synthetic peptide
VARIANT                 1
                        note = Xaa is N, D, A, or T
VARIANT                 8
                        note = Xaa is S, T, A, C, Y
source                  1..8
                        mol_type = protein
                        organism = synthetic construct
SEQUENCE: 457
XDGPPSGX                                                                         8

SEQ ID NO: 458          moltype = AA  length = 11
FEATURE                 Location/Qualifiers
REGION                  1..11
                        note = Synthetic peptide
VARIANT                 7
                        note = Xaa is D, N, E, Q, S, or A
VARIANT                 9
                        note = Xaa is Q, S, A, D, or N
source                  1..11
                        mol_type = protein
                        organism = synthetic construct
SEQUENCE: 458
QSLVHSXGXT Y                                                                    11
```

```
SEQ ID NO: 459         moltype =    length =
SEQUENCE: 459
000

SEQ ID NO: 460         moltype = AA  length = 9
FEATURE                Location/Qualifiers
REGION                 1..9
                       note = Synthetic peptide
VARIANT                2
                       note = Xaa is Q, H, or T
VARIANT                3
                       note = Xaa is S, G, T, or D
source                 1..9
                       mol_type = protein
                       organism = synthetic construct
SEQUENCE: 460
SXXTHVPYT                                                                9

SEQ ID NO: 461         moltype = AA  length = 9
FEATURE                Location/Qualifiers
REGION                 1..9
                       note = Synthetic peptide
VARIANT                3
                       note = Xaa is F, Y, S, or T
VARIANT                5
                       note = Xaa is S, T, Y , or D
source                 1..9
                       mol_type = protein
                       organism = synthetic construct
SEQUENCE: 461
YTXTXYTMH                                                                9

SEQ ID NO: 462         moltype = AA  length = 8
FEATURE                Location/Qualifiers
REGION                 1..8
                       note = Synthetic peptide
VARIANT                2
                       note = Xaa is Q, S, A, or N
VARIANT                6
                       note = Xaa is T, S, V, D, or G
source                 1..8
                       mol_type = protein
                       organism = synthetic construct
SEQUENCE: 462
IXPSSXYT                                                                 8

SEQ ID NO: 463         moltype = AA  length = 10
FEATURE                Location/Qualifiers
REGION                 1..10
                       note = Synthetic peptide
VARIANT                1
                       note = Xaa is S, A, T, or V
VARIANT                5
                       note = Xaa is L, V, or F
source                 1..10
                       mol_type = protein
                       organism = synthetic construct
SEQUENCE: 463
XRGEXGGFAY                                                              10

SEQ ID NO: 464         moltype = AA  length = 6
FEATURE                Location/Qualifiers
REGION                 1..6
                       note = Synthetic peptide
VARIANT                6
                       note = Xaa is W, H, Y, or F
source                 1..6
                       mol_type = protein
                       organism = synthetic construct
SEQUENCE: 464
QTIGYX                                                                   6

SEQ ID NO: 465         moltype = AA  length = 8
FEATURE                Location/Qualifiers
REGION                 1..8
                       note = Synthetic peptide
VARIANT                3
                       note = Xaa is R or T
VARIANT                8
```

|  |  |  |
|---|---|---|
| source | note = Xaa is N, Q, S, or A<br>1..8<br>mol_type = protein<br>organism = synthetic construct | |
| SEQUENCE: 465<br>GYXFTDYX | | 8 |
| SEQ ID NO: 466<br>FEATURE<br>REGION | moltype = AA  length = 8<br>Location/Qualifiers<br>1..8<br>note = Synthetic peptide | |
| VARIANT | 2<br>note = Xaa is N, Q, S, or A | |
| VARIANT | 4<br>note = Xaa is N, Q, S, or A | |
| VARIANT | 5<br>note = Xaa is N, Q, S, or A | |
| source | 1..8<br>mol_type = protein<br>organism = synthetic construct | |
| SEQUENCE: 466<br>IXPXXGGT | | 8 |
| SEQ ID NO: 467<br>FEATURE<br>REGION | moltype = AA  length = 8<br>Location/Qualifiers<br>1..8<br>note = Synthetic peptide | |
| VARIANT | 8<br>note = Xaa is C, Y, S, or A | |
| source | 1..8<br>mol_type = protein<br>organism = synthetic construct | |
| SEQUENCE: 467<br>DYLYFFDX | | 8 |
| SEQ ID NO: 468<br>FEATURE<br>REGION | moltype = AA  length = 8<br>Location/Qualifiers<br>1..8<br>note = Synthetic peptide | |
| VARIANT | 4<br>note = Xaa is D, E, S, or A | |
| source | 1..8<br>mol_type = protein<br>organism = synthetic construct | |
| SEQUENCE: 468<br>ISSXSRTI | | 8 |
| SEQ ID NO: 469<br>FEATURE<br>REGION | moltype = AA  length = 9<br>Location/Qualifiers<br>1..9<br>note = Synthetic peptide | |
| source | 1..9<br>mol_type = protein<br>organism = synthetic construct | |
| SEQUENCE: 469<br>DYGRTYEAY | | 9 |
| SEQ ID NO: 470<br>FEATURE<br>REGION | moltype = AA  length = 12<br>Location/Qualifiers<br>1..12<br>note = Synthetic peptide | |
| VARIANT | 8<br>note = Xaa is Q, S, A, D, or N | |
| VARIANT | 11<br>note = Xaa is Q, S, A, D, or N | |
| source | 1..12<br>mol_type = protein<br>organism = synthetic construct | |
| SEQUENCE: 470<br>QSVLFSSXQK XY | | 12 |
| SEQ ID NO: 471<br>SEQUENCE: 471<br>000 | moltype =   length = | |
| SEQ ID NO: 472<br>FEATURE<br>REGION | moltype = AA  length = 8<br>Location/Qualifiers<br>1..8<br>note = Synthetic peptide | |

```
VARIANT                  8
                         note = Xaa is N, Q, S, or A
source                   1..8
                         mol_type = protein
                         organism = synthetic construct
SEQUENCE: 472
GYSFTFYX                                                                 8

SEQ ID NO: 473           moltype = AA  length = 8
FEATURE                  Location/Qualifiers
REGION                   1..8
                         note = Synthetic peptide
VARIANT                  2
                         note = Xaa is A, S, E, or D
source                   1..8
                         mol_type = protein
                         organism = synthetic construct
SEQUENCE: 473
IXPYYGGS                                                                 8

SEQ ID NO: 474           moltype = AA  length = 12
FEATURE                  Location/Qualifiers
REGION                   1..12
                         note = Synthetic peptide
source                   1..12
                         mol_type = protein
                         organism = synthetic construct
SEQUENCE: 474
ERSGYVFSAM DY                                                           12

SEQ ID NO: 475           moltype = AA  length = 8
FEATURE                  Location/Qualifiers
REGION                   1..8
                         note = Synthetic peptide
VARIANT                  2
                         note = Xaa is Q, S, A, or N
source                   1..8
                         mol_type = protein
                         organism = synthetic construct
SEQUENCE: 475
IXPSSGYT                                                                 8

SEQ ID NO: 476           moltype = AA  length = 6
FEATURE                  Location/Qualifiers
REGION                   1..6
                         note = Synthetic peptide
VARIANT                  2
                         note = Xaa is Q, S, A, D, or N
source                   1..6
                         mol_type = protein
                         organism = synthetic construct
SEQUENCE: 476
EXIYSY                                                                   6

SEQ ID NO: 477           moltype =     length =
SEQUENCE: 477
000

SEQ ID NO: 478           moltype = AA  length = 116
FEATURE                  Location/Qualifiers
REGION                   1..116
                         note = Synthetic peptide
VARIANT                  20
                         note = Xaa is M or V
VARIANT                  31
                         note = Xaa is T, V, D, or S
VARIANT                  48
                         note = Xaa is I or M
VARIANT                  52
                         note = Xaa is Q, S, A, or N
VARIANT                  70
                         note = Xaa is L or M
VARIANT                  74
                         note = Xaa is T or K
VARIANT                  98
                         note = Xaa is N, Q, H, D, S, R, or A
source                   1..116
                         mol_type = protein
                         organism = synthetic construct
```

```
SEQUENCE: 478
QVQLVQSGAE VKKPGASVKX SCKASGYTFT XYTMHWVRQA PGQGLEWXGF IXPSSGYTDY    60
AQKFQGRVTX TADXSTSTVY MELSSLRSED TAVYYCAXGD YVAYWGQGT LVTVSS        116

SEQ ID NO: 479          moltype = AA  length = 108
FEATURE                 Location/Qualifiers
REGION                  1..108
                        note = Synthetic peptide
VARIANT                 4
                        note = Xaa is L or M
VARIANT                 21
                        note = Xaa is M or I
VARIANT                 32
                        note = Xaa is T, V, F, or D
VARIANT                 48
                        note = Xaa is W or L
VARIANT                 51
                        note = Xaa is S, t, Q or A
VARIANT                 53
                        note = Xaa is S,T, D or Q
VARIANT                 79
                        note = Xaa is M or L
VARIANT                 84
                        note = Xaa is A or F
VARIANT                 91
                        note = Xaa is Q, H or S
VARIANT                 93
                        note = Xaa is H, Y, Q, or S
source                  1..108
                        mol_type = protein
                        organism = synthetic construct
SEQUENCE: 479
DIQXTQSPSS LSASVGDRVT XTCTASSSVS SXYFHWYQQK PGKAPKLXIY XTXNLASGVP    60
SRFSGSGSGT DYTLTISSXQ PEDXATYYCH XYXRSPLTFG QGTKLEIK                108

SEQ ID NO: 480          moltype = AA  length = 117
FEATURE                 Location/Qualifiers
REGION                  1..117
                        note = Synthetic peptide
VARIANT                 31
                        note = Xaa is N, S, R, Q or A
VARIANT                 33
                        note = Xaa is W, H, Y or F
VARIANT                 55
                        note = Xaa is S, N, A, or T
VARIANT                 57
                        note = Xaa is Q, S, A, or N
VARIANT                 99
                        note = Xaa is N, D, or T
VARIANT                 106
                        note = Xaa is S, T, A, C, or Y
source                  1..117
                        mol_type = protein
                        organism = synthetic construct
SEQUENCE: 480
EVQLLESGGG LVQPGGSMRL SCAASGFTFS XYXMNWVRQA PGKGLEWVAQ IRLKXDXYAT    60
HYADSVKGRF TISRDDSKNT VYLQMNSLRA EDTGVYYCXD GPPSGXWGQG TLLTVSS      117

SEQ ID NO: 481          moltype = AA  length = 107
FEATURE                 Location/Qualifiers
REGION                  1..107
                        note = Synthetic peptide
VARIANT                 28
                        note = Xaa is Q, S, A, D, or N
VARIANT                 48
                        note = Xaa is V or I
VARIANT                 50
                        note = Xaa is S, T, Q or A
VARIANT                 84
                        note = Xaa is G or A
VARIANT                 90
                        note = Xaa is H, Q, S or T
VARIANT                 93
                        note = Xaa is T, S, N, or G
source                  1..107
                        mol_type = protein
                        organism = synthetic construct
SEQUENCE: 481
DIQMTQSPSS LSASVGDRVT ITCRISEXIY SYLAWYQQKP GKAPKLLXYX AKILVEGVPS    60
```

```
RFSGSGSGTD FTLTISSLQP EDFXTYYCQX HYXVPWTFGQ GTKLEIK                  107

SEQ ID NO: 482         moltype = AA  length = 117
FEATURE                Location/Qualifiers
REGION                 1..117
                       note = Synthetic peptide
VARIANT                20
                       note = Xaa is M or V
VARIANT                29
                       note = Xaa is F, Y, S or T
VARIANT                31
                       note = Xaa is S, T, Y, or D
VARIANT                37
                       note = Xaa is I or V
VARIANT                45
                       note = Xaa is Q or L
VARIANT                48
                       note = Xaa is I or M
VARIANT                52
                       note = Xaa is Q, S, A, or N
VARIANT                56
                       note = Xaa is T, S, V, D or G
VARIANT                61
                       note = Xaa is I or A
VARIANT                62
                       note = Xaa is K or Q
VARIANT                65
                       note = Xaa is K or Q
VARIANT                66
                       note = Xaa is D or G
VARIANT                68
                       note = Xaa is A or V
VARIANT                70
                       note = Xaa is L or M
VARIANT                74
                       note = Xaa is T or K
VARIANT                79
                       note = Xaa is A or V
VARIANT                97
                       note = Xaa is S, A, T, or V
VARIANT                101
                       note = Xaa is L, V, or F
source                 1..117
                       mol_type = protein
                       organism = synthetic construct
SEQUENCE: 482
QVQLVQSGAE VKKPGASVKX SCKASGYTXT XYTMHWXRQA PGQGXEWXGY IXPSSXYTHY    60
XXKFXXRXTX TADXSTSTXY MELSSLRSED TAVYYCXRGE XGGFAYWGQG TLVTVSS      117

SEQ ID NO: 483         moltype = AA  length = 112
FEATURE                Location/Qualifiers
REGION                 1..112
                       note = Synthetic peptide
VARIANT                33
                       note = Xaa is D, N, E, Q, S, or A
VARIANT                35
                       note = Xaa is Q, S, A, D, or N
VARIANT                55
                       note = Xaa is K, Q, or R
VARIANT                57
                       note = Xaa is S, T, or V
VARIANT                95
                       note = Xaa is Q, H, or T
VARIANT                96
                       note = Xaa is S, G, T, or D
source                 1..112
                       mol_type = protein
                       organism = synthetic construct
SEQUENCE: 483
DVVMTQSPLS LPVTLGQPAS ISCRSSQSLV HSDGXTYLNW YQQRPGQSPR LLIYXVXNRF    60
SGVPDRFSGS GSGTDFTLKI SRVEAEDVGV YYCSXXTHVP YTFGQGTKLE IK           112

SEQ ID NO: 484         moltype = AA  length = 121
FEATURE                Location/Qualifiers
REGION                 1..121
                       note = Synthetic peptide
VARIANT                20
                       note = Xaa is I or V
VARIANT                33
```

```
                           note = Xaa is N, Q, S, or A
VARIANT                    48
                           note = Xaa is I or M
VARIANT                    52
                           note = Xaa is A, S, E or D
VARIANT                    68
                           note = Xaa is A or V
VARIANT                    70
                           note = Xaa is L or M
VARIANT                    79
                           note = Xaa is A or V
source                     1..121
                           mol_type = protein
                           organism = synthetic construct
SEQUENCE: 484
QVQLVQSGAE VKKPGASVKX SCKASGYSFT GYXMNWVRQA PGQGLEWXGN IXPYYGGSTY    60
AQKFQGRXTX TVDTSTSTXY MELSSLRSED TAVYYCARER SGYVFSAMDY WGQGTLVTVS   120
S                                                                  121

SEQ ID NO: 485             moltype = AA  length = 112
FEATURE                    Location/Qualifiers
REGION                     1..112
                           note = Synthetic peptide
VARIANT                    19
                           note = Xaa is V or A
VARIANT                    21
                           note = Xaa is M or I
VARIANT                    34
                           note = Xaa is Q, S, A, D, or N
VARIANT                    37
                           note = Xaa is Q, S, A, D, or N
VARIANT                    56
                           note = Xaa is H, Y, F, or W
VARIANT                    84
                           note = Xaa is V or L
source                     1..112
                           mol_type = protein
                           organism = synthetic construct
SEQUENCE: 485
DIVMTQSPDS LAVSLGERXT XNCKSSQSVL FSSXQKXYLA WYQQKPGQPP KLLIYXASTR    60
ESGVPDRFSG SGSGTDFTLT ISSXQAEDVA VYYCHQYLSS RTFGQGTKLE IK           112

SEQ ID NO: 486             moltype = AA  length = 118
FEATURE                    Location/Qualifiers
REGION                     1..118
                           note = Synthetic peptide
VARIANT                    54
                           note = Xaa is D, E, S, or A
source                     1..118
                           mol_type = protein
                           organism = synthetic construct
SEQUENCE: 486
EVQLVESGGG LVQPGGSLRL SCAASGFTFS SFGMHWVRQA PGKGLEWVAY ISSXSRTIYY    60
ADSVKGRFTI SRDNAKNSLY LQMNSLRAED TAVYYCARDY GRTYEAYWGQ GTLVTVSS    118

SEQ ID NO: 487             moltype = AA  length = 111
FEATURE                    Location/Qualifiers
REGION                     1..111
                           note = Synthetic peptide
VARIANT                    4
                           note = Xaa is M or L
VARIANT                    82
                           note = Xaa is V or L
VARIANT                    110
                           note = Xaa is I or L
source                     1..111
                           mol_type = protein
                           organism = synthetic construct
SEQUENCE: 487
DIVXTQSPDS LAVSLGERAT INCRASKSVS TSGYSIHWY QQKPGQPPKL LIYLASNLES     60
GVPDRFSGSG SGTDFTLTIS SXQAEDVAVY YCQHSRELPL TFGQGTKLEI K            111

SEQ ID NO: 488             moltype = AA  length = 117
FEATURE                    Location/Qualifiers
REGION                     1..117
                           note = Synthetic peptide
VARIANT                    28
                           note = Xaa is R or T
VARIANT                    33
```

```
                         note = Xaa is N, Q, S or A
VARIANT                  52
                         note = Xaa is N, Q, S or A
VARIANT                  54
                         note = Xaa is N, Q, S or A
VARIANT                  55
                         note = Xaa is N, Q, S, or A
VARIANT                  106
                         note = Xaa is C, Y, S, or A
source                   1..117
                         mol_type = protein
                         organism = synthetic construct
SEQUENCE: 488
QVQLVQSGAE VKKPGASVKM SCKASGYXFT DYXMHWVRQA PGQGLEWIGY IXPXXGGTNY    60
AQKFQGRATL TVDTSTSTAY MELSSLRSED TAVYYCARDY LYFFDXWGQG TLLTVSS      117

SEQ ID NO: 489           moltype = AA  length = 107
FEATURE                  Location/Qualifiers
REGION                   1..107
                         note = Synthetic peptide
VARIANT                  24
                         note = Xaa is L or R
VARIANT                  32
                         note = Xaa is W, H, Y, or F
source                   1..107
                         mol_type = protein
                         organism = synthetic construct
SEQUENCE: 489
DIQMTQSPSS LSASVGDRVT ITCLASQTIG TXLAWYQQKP GKAPKLLIYA AASLADGVPS    60
RFSGSGSGTD FTFTISSLQP EDFVTYYCQQ LYSIPRTFGQ GTKLEIK                 107

SEQ ID NO: 490           moltype = AA  length = 117
FEATURE                  Location/Qualifiers
REGION                   1..117
                         note = Synthetic Polypeptide
source                   1..117
                         mol_type = protein
                         organism = synthetic construct
SEQUENCE: 490
EVQLLESGGG LVQPGGSMRL SCAASGFTFS NYWMNWVRQA PGKGLEWIAQ IRLKSDNYAT    60
HYTDSVKGRF TISRDDSKRT VYLQMNSLRA EDTGTYYCSD GPPSGSWGQG TLLTVSS      117

SEQ ID NO: 491           moltype = AA  length = 117
FEATURE                  Location/Qualifiers
REGION                   1..117
                         note = Synthetic Polypeptide
source                   1..117
                         mol_type = protein
                         organism = synthetic construct
SEQUENCE: 491
EVQLLESGGG LVQPGGSMRL SCAASGFTFS NYWMNWVRQA PGKGLEWIAQ IRLKSDNYAT    60
HYADSVKGRF TISRDDSKRT VYLQMNSLRA EDTGTYYCSD GPPSGSWGQG TLLTVSS      117

SEQ ID NO: 492           moltype = AA  length = 117
FEATURE                  Location/Qualifiers
REGION                   1..117
                         note = Synthetic Polypeptide
source                   1..117
                         mol_type = protein
                         organism = synthetic construct
SEQUENCE: 492
EVQLLESGGG LVQPGGSMRL SCAASGFTFS NYWMNWVRQA PGKGLEWIAQ IRLKSDNYVT    60
HYTDSVKGRF TISRDDSKRT VYLQMNSLRA EDTGIYYCSD GPPSGSWGQG TLLTVSS      117

SEQ ID NO: 493           moltype = AA  length = 117
FEATURE                  Location/Qualifiers
REGION                   1..117
                         note = Synthetic Polypeptide
source                   1..117
                         mol_type = protein
                         organism = synthetic construct
SEQUENCE: 493
EVQLLESGGG LVQPGGSMRL SCAASGFTFS NYWMNWVRQA PGKGLEWIAQ IRLKSDNYAT    60
HYTDSVKGRF TISRDDSKST VYLQMNSLRA EDTGTYYCND GPPSGSWGQG TLLTVSS      117

SEQ ID NO: 494           moltype = AA  length = 117
FEATURE                  Location/Qualifiers
REGION                   1..117
                         note = Synthetic Polypeptide
```

```
source                    1..117
                          mol_type = protein
                          organism = synthetic construct
SEQUENCE: 494
EVQLLESGGG LVQPGGSMRL SCAASGFTFS NYWMNWVRQA PGKGLEWLAQ IRLKSDNYAT    60
HYTDSVKGRF TISRDDSKRT VYLQMNSLRA EDTGIYYCSD GPPSGSWGQG TLLTVSS      117

SEQ ID NO: 495            moltype = AA  length = 117
FEATURE                   Location/Qualifiers
REGION                    1..117
                          note = Synthetic Polypeptide
source                    1..117
                          mol_type = protein
                          organism = synthetic construct
SEQUENCE: 495
EVQLLESGGG LVQPGGSMRL SCAASGFTFS NYWMNWVRQA PGKGLEWLAQ IRLKSDNYVT    60
HYADSVKGRF TISRDDSKRT VYLQMNSLRA EDTGTYYCND GPPSGSWGQG TLLTVSS      117

SEQ ID NO: 496            moltype = AA  length = 116
FEATURE                   Location/Qualifiers
REGION                    1..116
                          note = Synthetic Polypeptide
source                    1..116
                          mol_type = protein
                          organism = synthetic construct
SEQUENCE: 496
QVQLVQSGAE VKKPGASVKM SCKASGYTFT TYTIHWVRQA PGQGLEWIGF INPSSGYTEY    60
AQKFQGRVTL TADKSTSTVY MELSSLRSED TAVYFCANGD YVVAYWGQGT LVTVSS       116

SEQ ID NO: 497            moltype = AA  length = 116
FEATURE                   Location/Qualifiers
REGION                    1..116
                          note = Synthetic Polypeptide
source                    1..116
                          mol_type = protein
                          organism = synthetic construct
SEQUENCE: 497
QVQLVQSGAE VKKPGASVKM SCKASGYTFT TYTMHWVRQA PGQGLEWIGV INPSSGYTEY    60
AQKFQGRVTL TADKSTSTVY MELSSLRSED TAVYFCANGD YVVGYWGQGT LVTVSS       116

SEQ ID NO: 498            moltype = AA  length = 116
FEATURE                   Location/Qualifiers
REGION                    1..116
                          note = Synthetic Polypeptide
source                    1..116
                          mol_type = protein
                          organism = synthetic construct
SEQUENCE: 498
QVQLVQSGAE VKKPGASVKM SCKASGYTFT TYTIHWVRQA PGQGLEWIGV INPSSGYTDY    60
AQKFQGRVTL TADKSTSTVY MELSSLRSED TAVYFCANGD YVVGYWGQGT LVTVSS       116

SEQ ID NO: 499            moltype = AA  length = 116
FEATURE                   Location/Qualifiers
REGION                    1..116
                          note = Synthetic Polypeptide
source                    1..116
                          mol_type = protein
                          organism = synthetic construct
SEQUENCE: 499
QVQLVQSGAE VKKPGASVKM SCKASGYTFT TYTMHWVRQA PGQGLEWIGF INPSSGYTEY    60
AQKFQGRVTL TADKSTSTVY MELSSLRSED TAVYYCANGD YVVGYWGQGT LVTVSS       116

SEQ ID NO: 500            moltype = AA  length = 116
FEATURE                   Location/Qualifiers
REGION                    1..116
                          note = Synthetic Polypeptide
source                    1..116
                          mol_type = protein
                          organism = synthetic construct
SEQUENCE: 500
QVQLVQSGAE VKKPGASVKM SCKASGYTFT TYTIHWVRQA PGQGLEWIGV INPSSGYTEY    60
AQKFQGRVTL TADKSTSTVY MELSSLRSED TAVYFCANGD YVVAYWGQGT LVTVSS       116

SEQ ID NO: 501            moltype = AA  length = 116
FEATURE                   Location/Qualifiers
REGION                    1..116
                          note = Synthetic Polypeptide
source                    1..116
                          mol_type = protein
```

```
                              organism = synthetic construct
SEQUENCE: 501
QVQLVQSGAE VKKPGASVKM SCKASGYTFT TYTMHWVRQA PGQGLEWIGF INPSSGYTEY    60
AQKFQGRVTL TADKSTSTVY MELSSLRSED TAVYFCANGD YVGYWGQGT LVTVSS        116

SEQ ID NO: 502           moltype = AA   length = 117
FEATURE                  Location/Qualifiers
REGION                   1..117
                         note = Synthetic Polypeptide
VARIANT                  48
                         note = Xaa is any aliphatic amino acid, optionally Ile or
                          Leu
VARIANT                  59
                         note = Xaa is any aliphatic amino acid, optionally, Ala or
                          Val
VARIANT                  63
                         note = Xaa is any aliphatic or any amino acid with a polar
                          side chain, optionally, Ala or Thr
VARIANT                  79
                         note = Xaa is any basic amino acid or any amino acid with a
                          polar side chain, optionally Arg or Ser
VARIANT                  95
                         note = Xaa is any aliphatic amino acid or any amino acid
                          with a polar side chain, optionally, Thr or Ile
VARIANT                  99
                         note = Xaa is any acidic amino acid or any amino acid with
                          a polar side chain, optionally, Ser or Asn
source                   1..117
                         mol_type = protein
                         organism = synthetic construct
SEQUENCE: 502
EVQLLESGGG LVQPGGSMRL SCAASGFTFS NYWMNWVRQA PGKGLEWXAQ IRLKSDNYXT    60
HYXDSVKGRF TISRDDSKXT VYLQMNSLRA EDTGXYYCXD GPPSGSWGQG TLLTVSS      117

SEQ ID NO: 503           moltype = AA   length = 116
FEATURE                  Location/Qualifiers
REGION                   1..116
                         note = Synthetic Polypeptide
VARIANT                  34
                         note = Xaa is any aliphatic amino acid or any amino acid
                          comprising a sulfur containing side chain; optionally, Ile
                          or Met
VARIANT                  50
                         note = Xaa is any aliphatic amino acid or any aromatic
                          amino acid, optionally, Phe or Val
VARIANT                  59
                         note = Xaa is any acidic amino acid, optionally, Glu or Asp
VARIANT                  95
                         note = Xaa is any aromatic amino acid, optionally, Phe or
                          Tyr
VARIANT                  104
                         note = Xaa is any aliphatic amino acid, optionally, Gly or
                          Ala
source                   1..116
                         mol_type = protein
                         organism = synthetic construct
SEQUENCE: 503
QVQLVQSGAE VKKPGASVKM SCKASGYTFT TYTXHWVRQA PGQGLEWIGX INPSSGYTXY    60
AQKFQGRVTL TADKSTSTVY MELSSLRSED TAVYXCANGD YVXYWGQGT LVTVSS        116

SEQ ID NO: 504           moltype = AA   length = 8
FEATURE                  Location/Qualifiers
REGION                   1..8
                         note = Synthetic Polypeptide
source                   1..8
                         mol_type = protein
                         organism = synthetic construct
SEQUENCE: 504
GYTFTTYT                                                              8

SEQ ID NO: 505           moltype = AA   length = 8
FEATURE                  Location/Qualifiers
REGION                   1..8
                         note = Synthetic Polypeptide
source                   1..8
                         mol_type = protein
                         organism = synthetic construct
SEQUENCE: 505
INPSSGYT                                                              8
```

```
SEQ ID NO: 506         moltype = AA   length = 9
FEATURE                Location/Qualifiers
REGION                 1..9
                       note = Synthetic Polypeptide
VARIANT                8
                       note = Xaa is any aliphatic amino acid, optionally, Gly or
                        Ala
source                 1..9
                       mol_type = protein
                       organism = synthetic construct
SEQUENCE: 506
ANGDYYVXY                                                                       9

SEQ ID NO: 507         moltype = AA   length = 8
FEATURE                Location/Qualifiers
REGION                 1..8
                       note = Synthetic Polypeptide
source                 1..8
                       mol_type = protein
                       organism = synthetic construct
SEQUENCE: 507
GFTFSNYW                                                                        8

SEQ ID NO: 508         moltype = AA   length = 10
FEATURE                Location/Qualifiers
REGION                 1..10
                       note = Synthetic Polypeptide
VARIANT                9
                       note = Xaa is any aliphatic amino acid, optionally, Ala or
                        Val
source                 1..10
                       mol_type = protein
                       organism = synthetic construct
SEQUENCE: 508
IRLKSDNYXT                                                                      10

SEQ ID NO: 509         moltype = AA   length = 8
FEATURE                Location/Qualifiers
REGION                 1..8
                       note = Synthetic Polypeptide
VARIANT                1
                       note = Xaa is any acidic amino acid or any amino acid with
                        a polar side chain, optionally, Ser or Asn
source                 1..8
                       mol_type = protein
                       organism = synthetic construct
SEQUENCE: 509
XDGPPSGS                                                                        8

SEQ ID NO: 510         moltype = AA   length = 117
FEATURE                Location/Qualifiers
REGION                 1..117
                       note = Synthetic Polypeptide
source                 1..117
                       mol_type = protein
                       organism = synthetic construct
SEQUENCE: 510
EVKLEESGGG LVQPGGSMKL SCVASGFTFS NYWMNWVRQS PEKGLEWVAQ IRLKSDNYAT              60
HYAESVKGRF TISRDDSKSS VYLQMNNLRA EDTGIYYCND GPPSGCWGQG TTLTVSS                 117

SEQ ID NO: 511         moltype = AA   length = 107
FEATURE                Location/Qualifiers
REGION                 1..107
                       note = Synthetic Polypeptide
source                 1..107
                       mol_type = protein
                       organism = synthetic construct
SEQUENCE: 511
DIQMTQSPAS LSASVGETVT ITCRASENIY SYLAWYQQKQ GKSPQLLVYN AKILVEGVPS              60
RFSGSGSGTQ FSLKINSLQP EDFGNYYCQH HYTVPWTFGG GTKLEIK                            107

SEQ ID NO: 512         moltype = AA   length = 108
FEATURE                Location/Qualifiers
REGION                 1..108
                       note = Synthetic Polypeptide
source                 1..108
                       mol_type = protein
                       organism = synthetic construct
```

```
SEQUENCE: 512
QIVLTQSPAI MSASLGERVT MTCTASSSVS SSYLHWYQQK PGSSPKLWIY STSNLASGVP    60
ARFSGSGSGT SYSLTISSME AEDAATYYCH QYHRSPLTFG AGTKLELK              108

SEQ ID NO: 513          moltype = AA  length = 116
FEATURE                 Location/Qualifiers
REGION                  1..116
                        note = Synthetic Polypeptide
source                  1..116
                        mol_type = protein
                        organism = synthetic construct
SEQUENCE: 513
QVQLQQSAAE LARPGASVKM SCKASGYTFT SYTMHWVKQR PGQGLEWIGF INPSSGYTDY    60
NQKFKDKTTL TADKSSSTAY MQLSSLTSED SAVYYCANGD YYVAYWGQGT LVTVSA      116

SEQ ID NO: 514          moltype = AA  length = 10
FEATURE                 Location/Qualifiers
REGION                  1..10
                        note = Synthetic
source                  1..10
                        mol_type = protein
                        organism = synthetic construct
SEQUENCE: 514
GYTFTEYTMH                                                          10

SEQ ID NO: 515          moltype = AA  length = 10
FEATURE                 Location/Qualifiers
REGION                  1..10
                        note = Synthetic
source                  1..10
                        mol_type = protein
                        organism = synthetic construct
SEQUENCE: 515
GVNPNSGDTS                                                          10

SEQ ID NO: 516          moltype = AA  length = 13
FEATURE                 Location/Qualifiers
REGION                  1..13
                        note = Synthetic
source                  1..13
                        mol_type = protein
                        organism = synthetic construct
SEQUENCE: 516
PGGYDVGYYA MDY                                                      13

SEQ ID NO: 517          moltype = AA  length = 11
FEATURE                 Location/Qualifiers
REGION                  1..11
                        note = Synthetic
source                  1..11
                        mol_type = protein
                        organism = synthetic construct
SEQUENCE: 517
RASQDINNYL N                                                        11

SEQ ID NO: 518          moltype = AA  length = 7
FEATURE                 Location/Qualifiers
REGION                  1..7
                        note = Synthetic
source                  1..7
                        mol_type = protein
                        organism = synthetic construct
SEQUENCE: 518
FTSRLHS                                                             7

SEQ ID NO: 519          moltype = AA  length = 9
FEATURE                 Location/Qualifiers
REGION                  1..9
                        note = Synthetic
source                  1..9
                        mol_type = protein
                        organism = synthetic construct
SEQUENCE: 519
QQGYPLPWT                                                           9

SEQ ID NO: 520          moltype = AA  length = 10
FEATURE                 Location/Qualifiers
REGION                  1..10
                        note = Synthetic
```

```
source                          1..10
                                mol_type = protein
                                organism = synthetic construct
SEQUENCE: 520
GYTFTEYTMH                                                                    10

SEQ ID NO: 521                  moltype = AA   length = 10
FEATURE                         Location/Qualifiers
REGION                          1..10
                                note = Synthetic
source                          1..10
                                mol_type = protein
                                organism = synthetic construct
SEQUENCE: 521
GVNPNSGDTS                                                                    10

SEQ ID NO: 522                  moltype = AA   length = 13
FEATURE                         Location/Qualifiers
REGION                          1..13
                                note = Synthetic
source                          1..13
                                mol_type = protein
                                organism = synthetic construct
SEQUENCE: 522
PGGYDVGYYA MDY                                                                13

SEQ ID NO: 523                  moltype = AA   length = 11
FEATURE                         Location/Qualifiers
REGION                          1..11
                                note = Synthetic
source                          1..11
                                mol_type = protein
                                organism = synthetic construct
SEQUENCE: 523
RASQDINNYL N                                                                  11

SEQ ID NO: 524                  moltype = AA   length = 7
FEATURE                         Location/Qualifiers
REGION                          1..7
                                note = Synthetic
source                          1..7
                                mol_type = protein
                                organism = synthetic construct
SEQUENCE: 524
STSRLHS                                                                        7

SEQ ID NO: 525                  moltype = AA   length = 9
FEATURE                         Location/Qualifiers
REGION                          1..9
                                note = Synthetic
source                          1..9
                                mol_type = protein
                                organism = synthetic construct
SEQUENCE: 525
QQGYPLPWT                                                                      9

SEQ ID NO: 526                  moltype = AA   length = 10
FEATURE                         Location/Qualifiers
REGION                          1..10
                                note = Synthetic
source                          1..10
                                mol_type = protein
                                organism = synthetic construct
SEQUENCE: 526
GYTFTEYTMH                                                                    10

SEQ ID NO: 527                  moltype = AA   length = 10
FEATURE                         Location/Qualifiers
REGION                          1..10
                                note = Synthetic
source                          1..10
                                mol_type = protein
                                organism = synthetic construct
SEQUENCE: 527
GVNPNSGDTS                                                                    10

SEQ ID NO: 528                  moltype = AA   length = 13
FEATURE                         Location/Qualifiers
REGION                          1..13
```

```
                         note = Synthetic
source                   1..13
                         mol_type = protein
                         organism = synthetic construct
SEQUENCE: 528
PGGYDVGYYA MDY                                                              13

SEQ ID NO: 529           moltype = AA  length = 11
FEATURE                  Location/Qualifiers
REGION                   1..11
                         note = Synthetic
source                   1..11
                         mol_type = protein
                         organism = synthetic construct
SEQUENCE: 529
RASQDINNYL N                                                                11

SEQ ID NO: 530           moltype = AA  length = 7
FEATURE                  Location/Qualifiers
REGION                   1..7
                         note = Synthetic
source                   1..7
                         mol_type = protein
                         organism = synthetic construct
SEQUENCE: 530
FTSRLHS                                                                      7

SEQ ID NO: 531           moltype = AA  length = 9
FEATURE                  Location/Qualifiers
REGION                   1..9
                         note = Synthetic
source                   1..9
                         mol_type = protein
                         organism = synthetic construct
SEQUENCE: 531
QQGYPLPWT                                                                    9

SEQ ID NO: 532           moltype = AA  length = 10
FEATURE                  Location/Qualifiers
REGION                   1..10
                         note = Synthetic
source                   1..10
                         mol_type = protein
                         organism = synthetic construct
SEQUENCE: 532
GYTFTEYTMH                                                                  10

SEQ ID NO: 533           moltype = AA  length = 10
FEATURE                  Location/Qualifiers
REGION                   1..10
                         note = Synthetic
source                   1..10
                         mol_type = protein
                         organism = synthetic construct
SEQUENCE: 533
GVNPNSGDTS                                                                  10

SEQ ID NO: 534           moltype = AA  length = 13
FEATURE                  Location/Qualifiers
REGION                   1..13
                         note = Synthetic
source                   1..13
                         mol_type = protein
                         organism = synthetic construct
SEQUENCE: 534
PGGYDVGYYA MDY                                                              13

SEQ ID NO: 535           moltype = AA  length = 11
FEATURE                  Location/Qualifiers
REGION                   1..11
                         note = Synthetic
source                   1..11
                         mol_type = protein
                         organism = synthetic construct
SEQUENCE: 535
RASQDINNYL N                                                                11

SEQ ID NO: 536           moltype = AA  length = 7
FEATURE                  Location/Qualifiers
```

```
REGION              1..7
                    note = Synthetic
source              1..7
                    mol_type = protein
                    organism = synthetic construct
SEQUENCE: 536
STSRLHS                                                                          7

SEQ ID NO: 537      moltype = AA  length = 9
FEATURE             Location/Qualifiers
REGION              1..9
                    note = Synthetic
source              1..9
                    mol_type = protein
                    organism = synthetic construct
SEQUENCE: 537
QQGYPLPWT                                                                        9
```

What is claimed is:

1. A method for inhibiting a solid tumor expressing claudin-6 (CLDN6) in a human subject, comprising administering to the human subject an effective amount of a composition comprising conjugates of a CLDN6-specific antigen-binding protein covalently bound to heterologous moieties of structural formula (II):

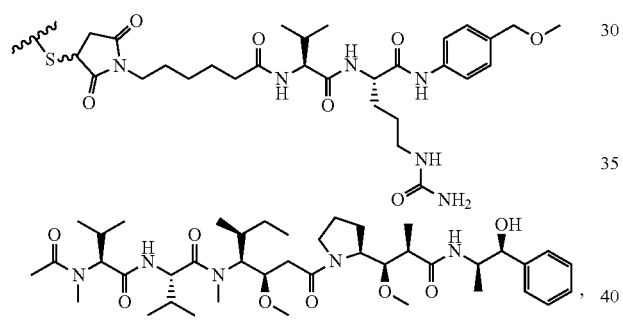

(II)

wherein

is a bond and a sulfur atom of the CLDN6-specific antigen-binding protein;

the CLDN6-specific antigen-binding protein comprises an antibody that binds CLDN6 or antigen-binding fragment thereof comprising:
(i) HC CDR1 having a sequence GFTFSNYW (SEQ ID NO: 23);
(ii) HC CDR2 having a sequence IRLKSDNYAT (SEQ ID NO: 24),
(iii) HC CDR3 having a sequence NDGPPSGS (SEQ ID NO: 457),
(iv) LC CDR1 having a sequence ENIYSY (SEQ ID NO: 20),
(v) LC CDR2 having a sequence NAK, and
(vi) LC CDR3 having a sequence QHHYTVPWT (SEQ ID NO: 22);
a first plurality of the conjugates are bound to four heterologous moieties of structural formula (II);
at least about 95% of the first plurality of conjugates are structurally homogenous;
the average number of heterologous moieties per CLDN6-specific antigen-binding protein in the composition is about 3.5 to about 4;
the effective amount is in a range of about 2.4 mg/kg to 4.0 mg/kg; and
a dose normalized $C_{max}$ value for unbound circulating monomethyl auristatin E (MMAE) is less than about 35 µg/mL per mg of the conjugate after administration of the composition, thereby minimizing toxicity in the subject and inhibiting the solid tumor.

2. The method of claim 1, wherein the dose normalized $C_{max}$ value for unbound circulating MMAE is less than about 30 pg/mL per mg.

3. The method of claim 2, wherein the dose normalized $C_{max}$ value for unbound circulating MMAE is less than about 25 pg/mL per mg.

4. The method of claim 3, wherein the dose normalized $C_{max}$ value for unbound circulating MMAE is less than about 20 µg/mL per mg.

5. The method of claim 4, wherein the dose normalized $C_{max}$ value for unbound circulating MMAE is less than about 15 µg/mL per mg.

6. The method of claim 5, wherein the dose normalized $C_{max}$ value for unbound circulating MMAE is less than about 10 µg/mL per mg.

7. The method of claim 1, wherein the effective amount is about 3 mg/kg.

8. The method of claim 1, wherein the effective amount is about 3.6 mg/kg.

9. The method of claim 1, wherein the effective amount is about 4 mg/kg.

10. The method of claim 1, wherein the solid tumor is an ovarian tumor.

11. The method of claim 1, wherein the solid tumor is a bladder tumor.

12. The method of claim 1, wherein the solid tumor is a testicular tumor.

13. The method of claim 1, wherein the solid tumor is an endometrial tumor.

14. The method of claim 1, wherein the effective amount is in the range of about 2.4 mg/kg to 3.0 mg/kg.

15. The method of claim 1, wherein the effective amount is in the range of about 3 mg/kg to about 3.6 mg/kg.

16. The method of claim 1, wherein the composition is administered intravenously.

17. The method of claim 1, wherein the average number of heterologous moieties per CLDN6-specific antigen-binding protein in the composition is about 3.6 to about 3.9, or about 3.7 to about 3.8.

18. The method of claim 1, wherein, in the first plurality of conjugates, the heterologous moieties are covalently conjugated at unpaired cysteine residues of the CLDN6-specific antigen-binding protein.

19. The method of claim 1, wherein, in the first plurality of conjugates, the heterologous moieties are covalently conjugated at cysteine residues resulting from cleavage of the heavy chain-light chain interchain disulfide bonds of the CLDN6-specific antigen-binding protein.

20. The method of claim 1, wherein about 95%, about 96%, about 97%, or about 98% of the first plurality of conjugates are structurally homogenous.

21. The method of claim 1, wherein at a $C_{max}$ after administration, percent of unbound circulating MMAE in serum is less than about 0.007% $C_{max}$ of total CLDN6-specific antigen-binding proteins.

22. The method of claim 1, wherein at a $C_{max}$ after administration, percent of unbound circulating MMAE in serum is less than about 0.005% $C_{max}$ of total CLDN6-specific antigen-binding proteins.

23. The method of claim 1, wherein at a $C_{max}$ after administration, percent of unbound circulating MMAE in serum is less than about 0.018% $C_{max}$ of the conjugate.

24. The method of claim 1, wherein at a $C_{max}$ after administration, percent of unbound circulating MMAE in serum is less than about 0.01% $C_{max}$ of the conjugate.

25. The method of claim 1, wherein at a $C_{max}$ after administration, percent of unbound circulating MMAE in serum is less than about 0.007% $C_{max}$ of the conjugate.

26. The method of claim 1, wherein the effective amount of the composition is administered once every 1-4 weeks, once every 2-4 weeks, or once every 3 weeks.

27. The method of any one of the preceding claims, wherein the method further comprises, prior to administration of the composition, administering a granulocyte-colony stimulating factor (G-CSF) to the subject.

* * * * *

UNITED STATES PATENT AND TRADEMARK OFFICE
CERTIFICATE OF CORRECTION

| | |
|---|---|
| PATENT NO. | : 12,403,202 B2 |
| APPLICATION NO. | : 18/674612 |
| DATED | : September 2, 2025 |
| INVENTOR(S) | : Dennis Slamon et al. |

Page 1 of 1

It is certified that error appears in the above-identified patent and that said Letters Patent is hereby corrected as shown below:

In the Claims

In Claim 1, at Column 235, Line 45, replace " \ " with -- \S--.

In Claim 1, at Column 236, Lines 27-28, replace "35 µg/mL" with --35 pg/mL--.

In Claim 4, at Column 236, Line 40, replace "20 µg/mL" with --20 pg/mL--.

In Claim 5, at Column 236, Line 43, replace "15 µg/mL" with --15 pg/mL--.

In Claim 6, at Column 236, Line 46, replace "10 µg/mL" with --10 pg/mL--.

Signed and Sealed this
Tenth Day of February, 2026

John A. Squires
*Director of the United States Patent and Trademark Office*